US008486693B2

(12) United States Patent
Park et al.

(10) Patent No.: US 8,486,693 B2
(45) Date of Patent: Jul. 16, 2013

(54) MODIFIED DENDRITIC CELLS HAVING ENHANCED SURVIVAL AND IMMUNOGENICITY AND RELATED COMPOSITIONS AND METHODS

(71) Applicants: Dongsu Park, Houston, TX (US); David Spencer, Houston, TX (US); Natalia Lapteva, Houston, TX (US)

(72) Inventors: Dongsu Park, Houston, TX (US); David Spencer, Houston, TX (US); Natalia Lapteva, Houston, TX (US)

(73) Assignee: Bellicum Pharmaceuticals, Inc., Houston, TX (US)

( * ) Notice: Subject to any disclaimer, the term of this patent is extended or adjusted under 35 U.S.C. 154(b) by 0 days.

(21) Appl. No.: 13/622,501

(22) Filed: Sep. 19, 2012

(65) Prior Publication Data
US 2013/0130386 A1    May 23, 2013

Related U.S. Application Data

(63) Continuation of application No. 12/301,021, filed as application No. PCT/US2007/069586 on May 23, 2007, now abandoned.

(60) Provisional application No. 60/803,025, filed on May 23, 2006.

(51) Int. Cl.
*C12N 5/00* (2006.01)
*C12N 5/07* (2010.01)
*C12N 5/0784* (2010.01)
*C12N 5/10* (2006.01)

(52) U.S. Cl.
USPC ........... 435/325; 435/355; 435/362; 435/363; 424/93.1; 424/93.21

(58) Field of Classification Search
USPC ......... 435/325, 355, 362, 363, 388; 424/93.1, 424/93.21, 172.1
See application file for complete search history.

(56) References Cited

U.S. PATENT DOCUMENTS

| | | | |
|---|---|---|---|
| 3,817,827 A | 6/1974 | Charles et al. |
| 3,850,752 A | 11/1974 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,376,110 A | 3/1983 | David et al. |
| 4,452,901 A | 6/1984 | Gordon et al. |
| 4,469,863 A | 9/1984 | Ts'o et al. |
| 4,683,195 A | 7/1987 | Mullis et al. |
| 4,683,202 A | 7/1987 | Mullis |
| 4,727,138 A | 2/1988 | Goeddel et al. |
| 4,738,927 A | 4/1988 | Taniguchi et al. |
| 4,762,791 A | 8/1988 | Goeddel et al. |
| 4,810,643 A | 3/1989 | Souza |
| 4,892,743 A | 1/1990 | Leibowitz et al. |
| 4,965,188 A | 10/1990 | Mullis et al. |
| 4,965,195 A | 10/1990 | Namen et al. |
| 4,966,843 A | 10/1990 | McCormick et al. |
| 4,987,071 A | 1/1991 | Cech et al. |
| 4,999,291 A | 3/1991 | Souza |
| 5,017,691 A | 5/1991 | Lee et al. |
| 5,093,246 A | 3/1992 | Cech et al. |
| 5,116,742 A | 5/1992 | Cech et al. |
| 5,223,409 A | 6/1993 | Ladner et al. |
| 5,232,841 A | 8/1993 | Hashimoto et al. |
| 5,238,317 A | 8/1993 | Bohmer et al. |
| 5,268,273 A | 12/1993 | Buckholz |
| 5,389,529 A | 2/1995 | Panayotatos et al. |
| 5,470,719 A | 11/1995 | Meng et al. |
| 5,530,101 A | 6/1996 | Queen et al. |
| 5,541,306 A | 7/1996 | Agrawal et al. |
| 5,546,821 A | 8/1996 | Brackett |
| 5,614,622 A | 3/1997 | Iyer et al. |
| 5,637,683 A | 6/1997 | Usher et al. |
| 5,637,684 A | 6/1997 | Cook et al. |
| 5,656,493 A | 8/1997 | Mullis et al. |
| 5,700,922 A | 12/1997 | Cook |
| 5,707,622 A | 1/1998 | Fong et al. |
| 5,712,114 A | 1/1998 | Mankovich et al. |
| 5,717,083 A | 2/1998 | Cook et al. |
| 5,719,262 A | 2/1998 | Buchardt et al. |
| 5,739,308 A | 4/1998 | Kandimalla et al. |
| 5,739,314 A | 4/1998 | Roy et al. |
| 5,766,891 A | 6/1998 | Shuman |

(Continued)

FOREIGN PATENT DOCUMENTS

| | | |
|---|---|---|
| EP | 0423980 | 7/2000 |
| WO | WO 85/02862 | 7/1985 |

(Continued)

OTHER PUBLICATIONS

Akbergenov et al., "ART-1, a sequence element complementary to an internal 18S rRNA segment, enhances translation efficiency in plants when present in the leader or intercistronic region of mRNAs." Nucleic Acids Res. Jan. 12, 2004;32(1):239-247.
Allison AC., "Immunological adjuvants and their modes of action." Arch Immunol Ther Exp (Warsz). 1997;45(2-3):141-147.
Allshire R., "Molecular biology. RNAi and heterochromatin—a hushed-up affair." Science. Sep. 13, 2002;297(5588):1818-1819.
Altmann et al., "Cotransfection of ICAM-1 and HLA-DR reconstitutes human antigen-presenting cell function in mouse L cells." Nature. Apr. 6, 1989;338(6215):512-514.

(Continued)

*Primary Examiner* — Maria Leavitt
(74) *Attorney, Agent, or Firm* — Grant Anderson LLP

(57) ABSTRACT

Modified antigen presenting cells provided herein have improved lifespan and immunogenicity compared to unmodified antigen presenting cells, and are useful for immunotherapy. The modified antigen presenting cells express an altered protein kinase, referred to herein as "Akt." The altered Akt associates with the cell membrane with greater frequency than unaltered Akt, and is referred to herein as "membrane-targeted Akt."

24 Claims, 15 Drawing Sheets

U.S. PATENT DOCUMENTS

| | | | |
|---|---|---|---|
| 5,773,601 A | 6/1998 | Agrawal | |
| 5,788,963 A | 8/1998 | Murphy et al. | |
| 5,846,818 A | 12/1998 | Robinson et al. | |
| 5,849,589 A | 12/1998 | Tedder et al. | |
| 5,851,756 A | 12/1998 | Steinman et al. | |
| 5,886,165 A | 3/1999 | Kandimalla et al. | |
| 5,888,732 A | 3/1999 | Hartley et al. | |
| 5,929,226 A | 7/1999 | Padmapriya et al. | |
| 5,932,474 A | 8/1999 | Tsien et al. | |
| 5,955,599 A | 9/1999 | Iyer et al. | |
| 5,962,674 A | 10/1999 | Iyer et al. | |
| 5,977,296 A | 11/1999 | Nielsen et al. | |
| 5,990,296 A | 11/1999 | Pastan et al. | |
| 5,994,126 A | 11/1999 | Steinman et al. | |
| 5,994,524 A | 11/1999 | Matsushima et al. | |
| 6,008,378 A | 12/1999 | Tsien et al. | |
| 6,017,527 A | 1/2000 | Maraskovsky et al. | |
| 6,054,271 A | 4/2000 | Tsien et al. | |
| 6,099,842 A | 8/2000 | Pastan et al. | |
| 6,117,992 A | 9/2000 | Iyer | |
| 6,140,482 A | 10/2000 | Iyer et al. | |
| 6,143,557 A | 11/2000 | Hartley et al. | |
| 6,171,861 B1 | 1/2001 | Hartley et al. | |
| 6,245,894 B1 | 6/2001 | Matsushima et al. | |
| 6,270,969 B1 | 8/2001 | Hartley et al. | |
| 6,277,608 B1 | 8/2001 | Hartley et al. | |
| 6,288,302 B1 | 9/2001 | Yu et al. | |
| 6,342,221 B1 | 1/2002 | Thorpe et al. | |
| 6,451,579 B1 | 9/2002 | Jessee et al. | |
| 6,720,140 B1 | 4/2004 | Hartley et al. | |
| 2002/0007051 A1 | 1/2002 | Cheo et al. | |
| 2002/0123479 A1 | 9/2002 | Song et al. | |
| 2003/0083373 A1 | 5/2003 | Tsien et al. | |
| 2003/0143672 A1 | 7/2003 | Tangri et al. | |
| 2003/0144204 A1 | 7/2003 | Spencer | |
| 2004/0014956 A1 | 1/2004 | Woolf et al. | |
| 2004/0033213 A1 | 2/2004 | Walker et al. | |
| 2004/0115174 A1 | 6/2004 | Gilboa et al. | |
| 2004/0209836 A1 | 10/2004 | Spencer et al. | |
| 2004/0229229 A1 | 11/2004 | Cheo et al. | |
| 2005/0049197 A1 | 3/2005 | Sette et al. | |
| 2005/0271676 A1 | 12/2005 | Sette et al. | |
| 2006/0009409 A1 | 1/2006 | Woolf | |
| 2006/0084136 A1 | 4/2006 | Kudlicki et al. | |
| 2006/0093617 A1 | 5/2006 | Buyse et al. | |
| 2010/0196336 A1 | 8/2010 | Park et al. | |
| 2011/0033920 A1 | 2/2011 | Hartley et al. | |

FOREIGN PATENT DOCUMENTS

| | | |
|---|---|---|
| WO | WO 85/04188 | 9/1985 |
| WO | WO 90/06370 | 6/1990 |
| WO | WO 94/04680 | 3/1994 |
| WO | WO 94/10300 | 5/1994 |
| WO | WO 95/16099 | 6/1995 |
| WO | WO 96/19497 | 6/1996 |
| WO | WO 97/24447 | 7/1997 |
| WO | WO 99/07409 | 2/1999 |
| WO | WO 99/21013 | 4/1999 |
| WO | WO 99/32619 | 7/1999 |
| WO | WO 00/01846 | 1/2000 |
| WO | WO 00/44895 | 8/2000 |
| WO | WO 00/44914 | 8/2000 |
| WO | WO 00/56746 | 9/2000 |
| WO | WO 00/75372 | 12/2000 |
| WO | WO 01/14398 | 3/2001 |
| WO | WO 01/29058 | 4/2001 |
| WO | WO 01/36646 | 5/2001 |
| WO | WO 2007/137300 | 11/2007 |

OTHER PUBLICATIONS

Altschul et al. "Basic local alignment search tool," J Mol Biol. Oct. 5, 1990; 215(3):403-410.

Altschul et al. "Gapped BLAST and PSI-BLAST: a new generation of protein database search programs," Nucleic Acids Res. Sep. 1, 1997; (17):3389-3402.

Anantha et al., "Porphyrin binding to quadrupled T4G4." Biochemistry. Mar. 3, 1998;37(9):2709-2714.

Arcone et al., "Identification of sequences responsible for acute-phase induction of human C-reacitve protein." Nucleic Acids Res. Apr. 15, 1988; 16(8):3195-3207.

Ausubel et al., "Current Protocols in Molecular Biology" (1995).

Barnea et al., "Analysis of endogenous peptides bound by soluble MHC class I molecules: a novel approach for identifying tumor-specific antigens." Eur J Immunol. Jan. 2002;32(1):213-222.

Bartel DP, Szostak JW., "Isolation of new ribozymes from a large pool of random sequences." Science. Sep. 10, 1993;261(5127):1411-1418.

Bartel et al., "Elimination of false positives that arise in using the two-hybrid system." Biotechniques. Jun. 1993;14(6):920-924.

Bass BL., "RNA interference. The short answer." Nature. May 24, 2001;411 (6836):428-429.

Bayer et al., "On the mode of liposome-cell interactions. Biotin-conjugated lipids as ultrastructural probes." Biochim Biophys Acta. Feb. 2, 1979;550(3):464-473.

Benvenisty N, Reshef L., "Direct introduction of genes into rats and expression of the genes." Proc Natl Acad Sci USA. Dec. 1986;83(24):9551-9555.

Berzofsky et al., "Progress on new vaccine strategies for the immunotherapy and prevention of cancer." J Clin Invest. Jun. 2004;113(11):1515-1525.

Bishop et al., "High-dose therapy and peripheral blood progenitor cell transplantation: effects of recombinant human granulocyte-macrophage colony-stimulating factor on the autograft." Blood. Jan. 15, 1994;83(2):610-616.

Blau et al., "A proliferation switch for genetically modified cells." Proc Natl Acad Sci USA. Apr. 1, 1997;94(7):3076-3081.

Bos JL., "ras oncogenes in human cancer: a review." Cancer Res. Sep. 1, 1989;49(17):4682-4689.

Bowen-Pope et al., "Production of platelet-derived growth factor-like molecules and reduced expression of platelet-derived growth factor receptors accompany transformation by a wide spectrum of agents." Proc Natl Acad Sci USA. Apr. 1984;81(8):2396-2400.

Brakenhoff et al., "Molecular cloning and expression of hybridoma growth factor in *Escherichia coli*." J Immunol. Dec. 15, 1987;139(12):4116-4121.

Brooks et al., "Human lymphocyte markers defined by antibodies derived from somatic cell hybrids. I. A hybridoma secreting antibody against a marker specific for human B lymphocytes." Clin Exp Immunol. Feb. 1980;39(2):477-485.

Brown et al., "Protein antigens of normal and malignant human cells identified by immunoprecipitation with monoclonal antibodies." J Biol Chem. Jun. 10, 1980;255(11):4980-4983.

Capone et al., "Amber, ochre and opal suppressor tRNA genes derived from a human serine tRNA gene." EMBO J. Jan. 1985;4(1):213-21.

Carell et al., "A Solution-Phase Screening Procedure for the Isolation of Active Compounds from a Library of Molecules," Angew. Chem. Int. Ed. Engl. 33:2061(1994).

Caux et al., "Activation of human dendritic cells through CD40 cross-linking." J Exp Med. Oct. 1, 1994;180(4):1263-1272.

Chatterjee et al., "Strategies for efficient gene transfer into hematopoietic cells. The use of adeno-associated virus vectors in gene therapy." Ann N Y Acad Sci. Dec. 29, 1995;770:79-90.

Chen C., Okayama H., "High-efficiency transformation of mammalian cells by plasmid DNA." Mol Cell Biol. Aug. 1987;7(8):2745-2752.

Chiba et al., "Mutations in the p53 gene are frequent in primary, resected non-small cell lung cancer. Lung cancer study group." Oncogene. Oct. 1990;5(10):1603-1610.

Cho et al., "An unnatural biopolymer." Science. Sep. 3, 1993;261(5126):1303-1305.

Coffin JM., "Molecular mechanisms of nucleic acid integration." J Med Virol. May 1990;31(1):43-49.

Couper et al., "A general method for the construction of recombinant *vaccinia* viruses expressing multiple foreign genes." Gene. Aug. 15, 1988;68(1):1-10.

Cull et al., "Screening for receptor ligands using large libraries of peptides linked to the C terminus of the lac repressor." Proc Natl Acad Sci USA. Mar. 1, 1992;89(5):1865-1869.

Cwirla et al., "Peptides on phage: a vast library of peptides for identifying ligands." Proc Natl Acad Sci USA. Aug. 1990;87(16):6378-6382.

Dermime et al., "Cancer vaccines and immunotherapy." Br Med Bull. 2002;62:149-162.

Devlin et al., "Random peptide libraries: a source of specific protein binding molecules." Science. Jul. 27, 1990;49(4967):404-406.

DeWitt et al., "'Diversomers': an approach to nonpeptide, nonoligomeric chemical diversity." Proc Natl Acad Sci USA. Aug. 1, 1993;90(15):6909-6913.

Dubensky et al., "Direct transfection of viral and plasmid DNA into the liver or spleen of mice." Proc Natl Acad Sci USA. Dec. 1984;81(23):7529-7533.

Dudley ME, Rosenberg SA., "Adoptive-cell-transfer therapy for the treatment of patients with cancer." Nat Rev Cancer. Sep. 2003;3(9):666-675.

Eggertsson et al., "Transfer ribonucleic acid-mediated suppression of termination codons in Escherichia coli." Microbiol Rev. Sep. 1988;52(3):354-374.

Elbashir et al., "Duplexes of 21-nucleotide RNAs mediate RNA interference in cultured mammalian cells." Nature. May 24, 2001;411(6836):494-498.

Erb et al., "Recursive deconvolution of combinatorial chemical libraries." Proc Natl Acad Sci USA. Nov. 22, 1994;91(24):11422-11426.

Faktor et al., "The identification of hepatitis B virus X gene responsive elements reveals functional similarity of X and HTLV-I tax." Oncogene. Jun. 1990;5(6):867-872.

Familletti et al., "A convenient and rapid cytopathic effect inhibition assay for interferon." Methods Enzymol. 1981;78(Pt A):387-394.

Fechheimer et al., "Transfection of mammalian cells with plasmid DNA by scrape loading and sonication loading." Proc Natl Acad Sci USA. Dec. 1987;84(23):8463-8467.

Felici et al., "Selection of antibody ligands from a large library of oligopeptides expressed on a multivalent exposition vector." J Mol Biol. Nov. 20, 1991;222(2):301-310.

Ferrari et al., "Second-strand synthesis is a rate-limiting step for efficient transduction by recombinant adeno-assocated virus vectors." J Virol. May 1996;70(5):3227-3234.

Finter et al., "The use of interferon-alpha in virus infections." Drugs. Nov. 1991;42(5):749-765.

Fisher et al., "A novel adenovirus-adeno-associated virus hybrid vector that displays efficient rescue and delivery of the AAV genome," Hum Gen Ther, Nov. 10, 1996;8(17):2079-2087.

Flotte et al., "Expression of the cystic fibrosis transmembrane conductance regulator from a novel adeno-associated virus promoter." J Biol Chem. Feb. 15, 1993;268(5):3781-3790.

Flotte TR, Carter BJ. "Adeno-associated virus vectors for gene therapy." Gene Ther. Aug. 1995;2(6):357-362.

Fodor et al., "Multiplexed biochemical assays with biological chips." Nature. Aug. 5, 1993;364(6437):555-556.

Fraley et al., "Entrapment of a bacterial plasmid in phospholipid vesicles: potential for gene transfer." Proc Natl Acad Sci USA. Jul. 1979;76(7):3348-3352.

Freeman et al., "B7, a new member of the Ig superfamily with unique expression on activated and neoplastic B cells." J Immunol. Oct. 15, 1989;143(8):2714-2722.

Freshney et al., Culture of Animal Cells, 3rd Ed. 1993.

Freudenthal PS, Steinman RM., "The distinct surface of human blood dendritic cells, as observed after an improved isolation method." Proc Natl Acad Sci USA. Oct. 1990;87(19):7698-7702.

Galbiati et al. "N-terminal fatty acylation of the alpha-subunit of the G-protein Gi1: only the myristoylated protein is a substrate for palmitoylation," Biochem J. Nov. 1, 1994;303(Pt 3):697-700.

Gallie DR., "The 5'-leader of tobacco mosaic virus promotes translation through enhanced recruitment of eIF4F." Nucleic Acids Res. Aug. 1, 2002;30(15):3401-3411.

Gallie et al., "The 5'-leader sequence of tobacco mosaic virus RNA enhances the expression of foreign gene transcripts in vitro and in vivo." Nucleic Acids Res. Apr. 24, 1987;15(8):3257-3273.

Gallop et al., "Applications of combinatorial technologies to drug discovery. 1. Background and peptide combinatorial libraries." J Med Chem. 1004 Apr. 29;37(9):1233-1251.

Gansbacher et al., "Interleukin 2 gene transfer into tumor cells abrogates tumorigenicity and induces protective immunity." J Exp Med. Oct. 1, 1990;172(4):1217-1224.

Gansbacher et al., "Retroviral vector-mediated gamma-interferon gene transfer into tumor cells generates potent and long lasting anti-tumor immunity." Cancer Res. Dec. 15, 1990;50(24):7820-7825.

Gauthier-Campbell et al. "Regulation of dendritic branching and filopodia formation in hippocampal neurons by specific acylated protein motifs," Mol Biol Cell May 2004; 15(5):2205-2217.

Gautier et al., Alpha-DNA. IV: Alpha-anomeric and beta-anomeric tetrathymidylates covalently linked to intercalating oxazolopyridocarbazole. Synthesis, physicochemical properties and poly (rA) binding. Nucleic Acids Res. Aug. 25, 1987;15(16):6625-6641.

Golumbek et al., "Treatment of established renal cancer by tumor cells engineered to secrete interleukin-4." Science. Nov. 1, 1991;254(5032):713-716.

Goodman et al., "Recombinant adeno-associated virus-mediated gene transfer into hematopoietic progenitor cells," Blood, Sep. 1, 1994,;84(5):1492-1500.

Gopal TV., "Gene transfer method for transient gene expression, stable transformation, and cotransformation of suspension cell cultures." Mol Cell Biol. May 1985;5(5):1188-1190.

Gossen and Bujard, "Tight control of gene expression in mammalian cells by tetracycline-responsive promoters," PNAS, Jun. 15, 1992,;89(12)5547-5551.

Gossen et al., "Transcriptional activation by tetracyclines in mammalian cells." Science. Jun. 23, 1995;268(5218):1766-1769.

Graham FL, Van Der Eb AJ., "A new technique for the assay of infectivity of human adenovirus 5 DNA." Virology. Apr. 1973;52(2)456-467.

Gubler et al., "Coexpression of two distinct genes is required to generate secreted bioactive cytotoxic lymphocyte maturation factor." Proc Natl Acad Sci USA. May 15, 1991;88(10):4143-4147.

Guha et al., "Lipopolysaccharide activation of the MEK-ERK1/2 pathway in human monocytic cells mediates tissue factor and tumor necrosis factor alpha expression by inducing Elk-1 phosphorylation and Egr-1 expression." Blood. Sep. 1, 2001;98(5):1429-1439.

Hall et al., "Establishment and maintenance of a heterochromatin domain." Science. Sep. 27, 2002;297(5590):2232-2237.

Harland R, Weintraub H., "Translation of mRNA injected into Xenopus oocytes is specifically inhibited by antisense RNA." J Cell Biol. Sep. 1985;101(3):1094-1099.

Haselhoff J, Gerlach WL., "Simple RNA enzymes with new and highly specific endoribonuclease activities." Nature. Aug. 18, 1988;334(6183):585-591.

Hay et al., "Replication of adenovirus mini-chromosomes.", J Mol Biol. Jun. 5, 1984;175(4):493-510.

Hearing et al., "Identification of a repeated sequence element required for efficient encapsidation of the adenovirus type 5 chromosome." J Virol. Aug. 1987; 61(8):2555-2558.

Hearing P., Shenk T., "Functional analysis of the nucleotide sequence surrounding the cap site for adenovirus type 5 region E1A messenger RNAs." J Mol Biol. Jul. 15, 1983; 167(4):809-822.

Helene C., "The anti-gene strategy: control of gene expression by triplex-forming-oligonucleotides." Anticancer Drug Des. Dec. 1991;6(6):569-584.

Helene et al., "Control of gene expression by triple helix-forming oligonucleotides. The antigene strategy." Ann N Y Acad Sci. Oct. 28, 1992;660:27-36.

Ho et al., "Dimeric ligands define a role for transcriptional activation domains in reinitiation." Nature Aug. 29, 1996;382(6594):822-826.

Holsinger et al., "Signal transduction in T lymphocytes using a conditional allele of Sos." Proc Natl Acad Sci USA Oct. 10, 1995;92(21):9810-9814.

Houghten et al., "Generation and use of synthetic peptide combinatorial libraries for basic research and drug discovery." Nature. Nov. 7, 1991;354(6348):84-86.

Houghten et al., "The use of synthetic peptide combinatorial libraries for the identification of bioactive peptides." Biotechniques. Sep. 1992;13(3):412-421.

Hutvagner G, Zamore PD., "A microRNA in a multiple-turnover RNAi enzyme complex." Science. Sep. 20, 2002;297(5589):2056-2060.

Inaba et al., "Generation of large numbers of dendritic cells from mouse bone marrow cultures suplemented with granulocyte/macrophage colony-stimulating factor." J Exp Med. Dec. 1, 1992;176(6):1693-1702.

Inaba et al., "Identification of proliferating dendritic cell precursors in mouse blood." J Exp Med. May 1, 1992;175(5):1157-1167.

Inaba et al., "Isolation of dendritic cells." Curr Protoc Immunol. May 2001;Chapter 3:Unit 3.7, Coico et al., eds. 1998.

Inoue et al., "Sequence-dependent hydrolysis of RNA using modified oligonucleotide splints and RNase H." FEBS Lett. May 11, 1987;215(2):327-330.

Inoue et al., "Synthesis and hybridization studies on two complementary nona(2'-O-mtehyl)ribonucleotides." Nucleic Acids Res. Aug. 11, 1987;15(15):6131-6148.

International Preliminary Report on Patentability mailed: Dec. 11, 2008, for International Application No. PCT/US2007/069586, filed: May 23, 2007 and published as: WO 07/137300 on: Nov. 29, 2007.

International Search Report and Written Opinion mailed: Mar. 27, 2008, for International Application No. PCT/US2007/069586, filed: May 23, 2007 and published as: WO 07/137300 on: Nov. 29, 2007.

Invitrogen F13512 Brochure "PCR Cloning with TOPO Technology, Miminze planning, guarantee success," 2004 Downloaded from: www.invitrogen.com/downloads/F-13512_Topo_Flyer.pdf.

Invitrogen TOPO Cloning Technology Brochure "Direct your Cloning Future," 2003 Downloaded from: www.invitrogen.com/contents/sfs/brochures/710_021849%20_B_TOPOCloning_bro.pdf.

Iwabuchi et al., "Use of the two-hybrid system to identify the domain of p53 involved in oligomerization." Oncogene. Jun. 1993;8(6):1693-1696.

Jackson et al., "Internal initiation of translation in eukaryotes: the picornavirus paradigm and beyond." RNA. Dec. 1995; 1(10):985-1000.

Jayaraman et al., "Enhancement of in vivo cell-mediated immune responses by three distinct cytokines." J Immunol. Feb. 1, 1990;144(3):942-951.

Jenuein T., "Molecular biology. An RNA-guided pathway for the epigenome." Science. Sep. 27, 2002;297(5590):2215-2218.

Johnson et al., "Synthesis and biological evaluation of a new class of vaccine adjuvants: aminoalkyl glucosaminide 4-phosphates (AGPs)." Bioorg Med Chem Lett. Aug. 2, 1999;9(15):2273-2278.

Kageyama et al., "Differing utilization of homologous transcription initiation sites of rat K and T kininogen genes under inflammation condition." J Biol Chem Feb. 15, 1987;262(5):2345-2351.

Kaneda et al., "Introduction and expression of the human insulin gene in adult rat liver." J Biol Chem. Jul. 25, 1989;264(21):12126-12129.

Kaplitt et al., "Long-term gene expression and phenotypic correction using adeno-associated virus vectors in the mammalian brain." Nat Genet. Oct. 1994;8(2):148-154.

Karupiah et al., Elevated natural killer call responses in mice infected with recombinant *Vaccinia* virus encoding murine IL-2. J Immunol. Jan. 1, 1990;144(1):290-298.

Kato et al., "Expression of hepatitis B virus surface antigen in adult rat liver. Co-introduction of DNA and nuclear protein by a simplified liposome method," J Biol Chem. Feb. 25, 1991;266(6):3361-3364.

Katome et al., "Use of RNA interference-mediated gene silencing and adenoviral overexpression to elucidate the roles of AKT/protein kinase B isoforms in insulin actions." J Biol Chem. Jul. 25, 2003;278(30):28312-28323.

Kessler et al., "Gene delivery to skeletal muscle results in sustained expression and systemic delivery of a therapeutic protein." Proc Natl Acad Sci USA. Nov. 26, 1996;93(24):14082-14087.

Klein et al., "High-velocity microprojectiles for delivering nucleic acids into living cells", Letters to Nature, vol. 327,pp. 70-73, May 1987.

Koeberl et al., "Persistent expression of hman clotting factor IX from mouse liver after intravenous injection of adeno-associated virus vectors." Proc Natl Acad Sci USA. Feb. 18, 1997;94(4):1426-1431.

Kohler G, Milstein C., "Continuous cultures of fused cells secreting antibody of predefined specificity." Nature. Aug. 7, 1975;256(5517):495-497.

Kohn et al., "Construction and Characterization of a conditionally active version of the serine/threonine kinase Akt." J. Biol. Chem, May 8, 1998 273(19): 11937-11943.

Krissansen et al., "Chromosomal locations of the gene coding for the CD3 (T3) gamma subunit of the human and mouse CD3/T-cell antigen receptor complexes." Immunogenetics. 1987;26(4-5):258-266.

Lam et al., "A new type of synthetic peptide library for identifying ligand-binding activity." Nature. Nov. 7, 1991;354(6348):82-84.

Lam KS., "Application of combinatorial library methods in cancer research and drug discovery." Anticancer Drug Des. Apr. 1997;12(3):145-167.

Landy A., "Mechanistic and structural complexity in the site-specific recombination pathways of Int and FLP." Curr Opin Genet Dev. Oct. 1993;3(5):699-707.

Leo et al., "Partition coefficients and their uses." Chem Rev. Dec. 1971;71(6):525-616.

Levrero et al., "Hepatitis B virus and hepatocellular carcinome: a possible role for the viral transactivators." Ital J Gastroenterol. Dec. 1991;23(9):576-583.

Li et al., "A novel conditional Akt 'survival switch' reversibly protects cells from apoptosis." Gene Ther. Feb. 2002;9(4):233-244.

Lotze and Thomson, Dendritic Cells, 2nd Edition, Academic Press, 2001.

Luo et al, "Oligomerization activates c-Raf-1 through a Ras-dependent mechanism." Nature. Sep. 12, 1996;383(6596):181-185.

Lutz et al., "An advanced culture method for generating large quantities of highly pure dendritic cells from mouse bone marrow." J Immunol Methods. Feb. 1, 1999;223(1):77-92.

Macatonia et al, "Suppression of immune response by dendritic cells infected with HIV." Immunology. Jul. 1989;67(3):285-289.

MacCorkle et al., "Synthetic activation of caspases: artificial death switches," Proc Natl Acad Sci USA Mar. 31, 1998;95(7):3655-3660.

Madura et al., "N-recognin/Ubc2 interactions in the N-end rule pathway." J Biol Chem. Jun. 5, 1993;268(16):12046-12054.

Maher LJ III., "DNA triple-helix formation: an approach to artificial gene repressors?" Bioessays. Dec. 1992; 14(12):807-815.

Mahvi et al., "DNA cancer vaccines: a gene gun approach." Immunol Cell Biol. Oct. 1997;75(5):456-460.

Maio et al., "Modulation by cytokines of HLA antigens, intercellular adhesion molecule 1 and high molecular weight melanoma associated antigen expression and of immune lysis of clones derived from the melanoma cell line MeM 50-10." Cancer Immunol Immunother. 1989;30(1):34-42.

Mann et al., "Construction of a retrovirus packaging mutant and its use to produce helper-free defective retrovirus," Cell. May 1983;33(1):153-159.

Mannino RJ, Gould-Fogerite S., "Liposome mediated gene transfer." Biotechniques. Jul.-Aug. 1988;6(7):682-690.

Markowicz S, Engleman EG., "Granulocyte-macrophage colony-stimulating factor promotes differentiation and survival of human peripheral blood dendritic cells in vitro." J Clin Invest. Mar. 1990;85(3):955-961.

Martinez et al., "Single-stranded antisense siRNAs guide target RNA cleavage in RNAi." Cell. Sep. 6, 2002;110(5):563-574.

Matthews DJ, Wells JA., "Substrate phage: selection of protease substrates by monovalent phage display." Science. May 21, 1993;260(5111):1113-1117.

McCown et al., "Differential and persistent expression patterns of CNS gene transfer by adeno-associated virus (AAV) vector." Brain Res. Mar. 25, 1996;713(12):99-107.

McManus et al., "Gene silencing using micro-RNA designed hairpins." RNA. Jun. 2002;8(6):842-850.

Merrifield, "Solid Phase Peptide Synthesis. I. The Synthesis of a Tetrapeptide," J. Am. Chem. Soc. 85:2149-2156(1963).

Mignone et al., "Untranslated regions of mRNAs." Genome Biol. 2002;3(3): reviews0004.1-0001.10.

Mignone et al., "UTRdb and UTRsite: a collection of sequences and regulatory motifs of the untranslated regions of eukaryotic mRNAs." Nucleic Acids Res. Jan. 1, 2005;33(Database issue):D141-146.

Miller et al., "The Abl-related gene (Arg) requires its F-actin-microtubule cross-linking activity to regulate lamellipodial dynaics during fibroblast adhesion." J Cell Biol. May 10, 2004;165(3):407-419.

Mizukami et al., "Adeno-associated virus type 2 binds to a 150-kilodalton cell membrane glycoprotein," Virology. Mar. 1, 1996;217(1):124-130.

Myers et al. "Optimal alignments in linear space," Comput Appl Biosci. Mar. 1988;4(1):11-17.

Nagata et al., "Synthesis in E. coli of a polypeptide with human leukocyte interferon activity." Nature. Mar. 27, 1980;284(5754):316-320.

Nelson et al., "Simultaneous detection of multiple nucleic acid targets in a homogeneous format." Biochemistry. Jun. 25, 1996;35(25):8429-8438.

Nestle et al., "Vaccination of melanoma patients with peptide- or tumor lystate-pulsed dendritic cells." Nat Med. Mar. 1998;4(3):328-332.

Nicolas JF, Rubenstein JL., "Retroviural vectors." Biotechnology. 1988;10:493-513.

Nicolau C, Sene C., "Liposome-mediated DNA transfer in eukaryotic cells. Dependence of the transfer efficiency upon the type of liposomes used and the host cell cycle stage." Biochim Biophys Acta. Oct. 11, 1982;721(2):185-190.

Nicolau et al., "Liposomes as carriers for in vivo gene transfer and expression." Methods Enzymol. 1987;149:157-176.

Nikitina et al., "Versatile prostate cancer treatment with inducible caspase and interleukin-12." Cancer Res. May 15, 2005;65(10):4309-4319.

Nissim et al., "Antibody fragments from a 'single pot' phage display library as immunochemical reagents." EMBO J. Feb. 1, 1994;13(3):692-698.

Nopora A, Brocker T., "Bcl-2 controls dendritic cell longevity in vivo." J Immunol. Sep. 15, 2002;169(6):3006-3014.

O'Doherty et al., "Dendritic cells freshly isolated from human blood express CD4 and mature into typical immunostimulatory dendritic cells after culture in monocyte-conditioned medium." J Exp Med. Sep. 1, 1993;178(3):1067-1076.

Oliviero et al. "The human haptoglobin gene: transcriptional regulation during development and acute phase induction." EMBO J. Jul. 1987;6(7):1905-1912.

Pal-Bhadra et al., "Heterochromatic silencing HP1 localization in Drosophila are dependent on the RNAi machinery." Science. Jan. 30, 2004;303(5658):669-672.

Park et al., "An essential role for Akt1 in dendritic cell function and tumor immunotherapy." Nat Biotechnol. Dec. 2006;24(12):1581-1590.

Parnes et al., "Mouse beta 2-microglobulin cDNA clones: a screening procedure for cDNA clones corresponding to rare mRNAs." Proc Natl Acad Sci USA. Apr. 1981;78(4):2253-2257.

Paskind et al., "Dependence of moloney murine leukemia virus production on cell growth." Virology. Sep. 1975; 67(1):242-248.

Paulous et al., "Comparison of the capacity of different viral internal ribosome entry segments to direct translation initiation in poly(A)-dependent reticulocyte lysates." Nucleic Acids Res. Jan. 15, 2003;31(2):722-733.

Perez-Diez et al., Cell Mol Life Sci. Feb. 2002;59(2):230-240.

Ping et al., "Altered Beta-adrenergic receptor signaling in heart failure, in vivo gene transfer via adeno and adeno-assocated virus." Microcirculation. Jun. 1996;3(2):225-228.

Plant et al., "Generic liposome reagent for immunoassays." Anal Biochem. Feb. 1, 1989;176(2):420-426.

Poli et al., "Interleukin 6 induces a liver-specific nuclear protein that binds to the promoter of acute-phase genes." Proc Natl Acad Sci USA Nov. 1989; 86(21):8202-8206.

Pollock et al., "Regulation of gene expression with synthetic dimerizers." Methods Enzymol 1999;306:263-81.

Potter et al., "Enhancer-dependent expression of human kappa immunoglobulin genes introduced into mouse pre-B lymphocytes by electroporation." Proc Natl Acad Sci USA. Nov. 1984; 81(22):7161-7165.

Powis et al., "Restoration of antigen presentation to the mutant cell line RMA-S by an MHC-linked transporter." Nature. Dec. 19-26, 1991;354(6354):528-531.

Prowse et al., "Hepatocyte-stimulating factor, beta 2 interferon, and interleukin-1 enhance expression of the rat alpha 1-acid glycoprotein gene via a distal upstream regulatory region." Mol Cell Biol Jan. 1988;8(1):42-51.

Qu X, Chaires JB., "Analysis of drug-DNA binding data." Methods Enzymol. 2000;321:353-369.

Radford et al., The American Society of Hepatology 9:2008, 1991.

Radler et al., "Structure of DNA-cationic liposome complexes: DNA intercalation in multilamellar membranes in distinct interhelical packing regimes." Science. Feb. 7, 1997;275(5301):810-814.

Radvanyi L., "Discovery and immunologic validation of ew antigens for therapeutic cancer vaccines." Int Arch Allergy Immunol. Feb. 2004;133(2):179-197.

Raines et al., "Platelet-derived growth factor. I. High yield purification and evidence for multiple forms." J Biol Chem. May 10, 1982;257(9):5154-5160.

Reinhart BJ, Bartel DP., "Small RNAs corresponding to centromere heterochromatic repeats." Science. Sep. 13, 2002;297(5588):1831.

Razzaq et al., "Regulation of the T-Cell receptor signaling by membrane microdomains," Immunology, Dec. 2004, 113(4): 413-426.

Reinhart et al., "MicroRNAs in plants." Genes Dev. Jul. 1, 2002;16(13):1616-1626.

Renan MJ., "Cancer genes: current status, future prospects, and applications in radiotherapy/oncology." Radiother Oncol. Nov. 1990; 19(3):197-218.

Rippe et al., "DNA-mediated gene transfer into adult rat hepatocytes in primary culture." Mol Cell Biol. Feb. 1990;10(2):689-695.

Rivera et al., "A humanized system for pharmacologic control of gene expression." Nat Med Sep. 1996;2(9):1028-1032.

Rivnay et al., "Use of avidin-biotin technology for liposome targeting." Methods Enzymol. 1987;149:119-123.

Ron et al., "Angiotensinogen gene-inducible enhancer-binding protein 1, a member of a new family of large nuclear proteins that recognize nuclear factor kappa B-binding sites through a zinc finger motif." Mol Cell Biol May 1991;11(5):2887-2895.

Rosenberg SA., "A new era for cancer immunotherapy based on the genes that encode cancer antigens." Immunity. Mar. 1999;10(3):281-287.

Roux et al., "A versatile and potentially general approach to the targeting of specific cell types by retroviruses: application to the infection of human cells by means of major histocompatibility complex class I and class II antigens by mouse ecotropic murine leukemia virus-derived viruses." Proc Natl Acad Sci USA. Dec. 1989;86(23)L9079-9083.

Sambrook et al., "Molecular Cloning: A Laboratory Manual, 2d Ed." (Cold Spring Harbor Laboratory Press, 1989.

Samulski et al., "A recombinant plasmid from which an infectious adeno-associated virus genome can be excised in vitro and its use to study viral replication." J Virol. Oct. 1987;61(10):3093-3101.

Sauer B., "Site-specific recombination: developments and applications." Curr Opin Biotechnol. Oct. 1994;5(5):521-527.

Savoldo et al., "Autologous Epstein-Barr virus (EBV)-specific cytotoxic T cells for the treatment of persistent active EBV infection." Blood. Dec. 1, 2002;100(12):4059-4066.

Scatchar, "The Attractions of Proteins for Small Molecules and Ions," Ann. N.Y. Acad. Sci. 51:660, 1949.

Scheicher et al., "Dendritic cells from mouse bone marrow: in vitro differentiation using low doses of recombinant granulocyte-macrophate colony-stimulating factor." J Immunol Methods. Oct. 2, 1992;154(2):253-264.

Schirle et al., "Identification of tumor-associated MHC class I gands by a novel T cell-independent approach." Eur J Immunol. Aug. 2000;30(8):2216-2225.

Schwarz et al., "Evidence that siRNAs function as guides, not prmers, in the Drosophila and human RNAi pathways." Mol Cell. Sep. 2002;10(3):537-548.

Scott JK, Smith GP., "Searching for peptide ligands with epitope library." Science. Jul. 27, 1990;249(4967):386-390.

Seif et al., "Stable antiviruval expression in BALB/c 3T3 cells carrying a beta interferon sequence behind a major histocompatibility complex promoter fragment." J Virol. Feb. 1991;65(2):664-671.

Sekiguchi et al., "Requirements for noncovalent binding of *vaccinia* topoisomerase I to duplex DNA." Nucleic Acids Res. Dec. 11, 1994;22(24):5360-5365.

Shaloiko et al., "Effective non-viral leader for cap-independent translation in a eukaryotic cell-free system." Biotechnology and Bioengineering. vol. 88, Issue 6, pp. 730-739, Dec. 20, 2004.

Shuman S., "Site-specific interaction of vaccinia virus topoisomerase I with duplex DNA. Minimal DNA substrate for strand cleavage in vitro." J Biol Chem. Jun. 15, 1991;266(17):11372-11379.

Simmons et al., "ICAM, an adhesion ligand of LFA-1, is homologous to the neural cell adhesion molecule NCAM." Nature. Feb. 18, 1988;331(6157):624-627.

Singer SJ., "Intercellular communication and cell-cell adhesion." Science. Mar. 27, 1992;255(5052):1671-1677.

Spencer et al. "Controlling programmed cell death with a cyclophilin-cyclosporin-based chemical inducer of dimerization," Chem Biol. Sep. 1996; 3(9):731-738.

Spencer et al. "Controlling signal transduction with synthetic ligands," Science. Nov. 12, 1993;262(5136):1019-1024.

Spencer et al., "A general strategy for producing conditional alleles of Src-like tyrosine kinases." Proc Natl Acad Sci USA Oct. 10, 1995;92(21):9805-9809.

Steinman RM., "The dendritic cell system and its role in immunogenicity." Annu Rev Immunol. 1991;9:271-296.

StGroth & Scheidegger, "Production of Monoclonal Antibodies: Strategies and Tactics." J Immunol Methods 35:1-21 (1980).

Szoka et al., "Fluorescence studies on the mechanism of liposome-cell interactions in vitro." Biochim Biophys Acta. Jul. 16, 1980;600(1):1-18.

Tag-On-Demand Gateway Vector Instruction Manual, Version C, Dec. 6, 2004.

Tag-On-Demand Supressor Supernatant Instruction Manual, Version B, Jun. 6, 2003.

Temin HM., "Retroviruses and evolution." Cell Biophys. Dec. 1986;9(1-2):9-16.

Tepper et al., "Murine interleukin-4 displays potent anti-tumor activity in vivo." Cell. May 5, 1989;57(3):503-512.

Thurner et al., "Generation of large numbers of fully mature and stable dendritic cells from leukapheresis products for clinical application." J Immunol Methods. Feb. 1, 1999;223(1):1-15.

Tibbetts C., "Viral DNA sequences from incomplete particles of human adenovirus type 7." Cell. Sep. 1977;12(1):243-249.

Tjalsma et al., "Signal peptide-dependent protein transport in *Bacillus subtilis*: a genome-based survey of the secretome." Microbiol Mol Biol Rev. Sep. 2000;64(3):515-547.

Stauss et al., "Tumor Antigens Recognized by T Cells and Antibodies," CRC Press, 2003.

Tur-Kaspa et al., "Use of electroporation to introduce biologically active foreign genes into primary rat hepatocytes." Mol Cell Biol. Feb. 1986;6(2):716-718.

Twu et al., "Hepatitis B virus X gene can transactivate heterologous viral sequences." Proc Natl Acad Sci USA. Mar. 1989;86(6):2046-2050.

Verdel et al., "RNAi-mediated targeting of heterochromatin by the RITS complex." Science. Jan. 30, 2004;303(5658):672-676.

Vinals et al., "Using in silico transcriptomics to search for tumor-associated antigens for immunotherapy." Vaccine. Mar. 21, 2001;19(17-19):2607-2614.

Volpe et al., "Regulation of heterochromatic silencing and histone H3 lysine-9 methylation by RNAi." Science. Sep. 13, 2002;297(5588):1833-1837.

Wallner et al., "Primary structure of lymphocyte function-associated antigen 3 (LFA-3). The ligand of the T lymphocyte CD2 glycoprotein." J Exp Med. Oct. 1, 1987;166(4):923-932.

Wang, Lei., "Expanding the Genetic Code of *Escherichia coli*." IUPAC Prize for Young Chemists—2003 Honorable Mention Essay.

Wang et al., Proc Natl Acad Sci USA. Nov. 1987;84(22):7851-7855.

Watanabe et al., "Exogenous expression of mouse interferon gamma cDNA in mouse neurobastoma C1300 cells results in reduced tumorigenicity by augmented anti-tumor immunity." Proc Natl Acad Sci USA. Dec. 1989; 86(23): 9456-9460.

Watt et al., "Human prostate-specific antigen: structural and functional similarity with serine proteases." Proc Natl Acad USA. May 1986;83(10):3166-3170.

Weber et al., "immunotherapy of a murine tumor with interleukin 2. Increased sensitivity after MHC class I gene transfection." J Exp Med. Dec. 1, 1987;166(6):1716-1733.

Wilcheck M, Bayer EA., "The avidin-biotin complex in bioanalytical applications." Anal Biochem, May 15, 1988;171(1):1-32.

Wilson et al., "A 58-base-pair region of the human C3 gene confers synergistic inducibility by interleukin-1 and interleukin-6." Mol Cell Biol. Dec. 1990;10(12):6181-6191.

Wolf et al., "Cloning of cDNA for natural killer cell stimulatory factor, a heterodimeric cytokine with multiple biologic effects on T and natural killer cells." J Immunol. May 1, 1991;146(9):3074-3081.

Wong et al., "Appearance of beta-lactamase activity in animal cells upon liposome-mediated gene transfer," Gene Jul. 1980;10(2):87-94.

Wu GY, Wu CH., "Receptor-mediated gene delivery and expression in vivo." J Biol Chem Oct. 15, 1988;263(29):14621-14624.

Wu GY, Wu CH., "Receptor-mediated in vitro gene transformation by a soluble DNA carrier system." J Biol Chem, Apr. 5, 1987;262(10):4429-4432.

Xiao et al., "Efficient long-term gene transfer into muscle tissue of immunocompetent mice by adeno-associated virus vector." J Virol. Nov. 1996; 70(11):8098-8108.

Xie et al., "Adenovirus-mediated tissue-targeted expression of a caspase-9-based artificial death switch for the treatment of prostate cancer." Cancer Res. Sep. 15, 2001;61(18):6795-6804.

Yang et al., "In vivo and in vitro gene transfer to mammalian somatic cells by particle bombardment," Proc Natl Acad Sci U S A. Dec. 1990;87(24):9568-9572.

Zamore et al., "RNAi: double-stranded RNA directs the ATP-dependent cleavage of mRNA at 21 to 23 nucleotide intervals." Cell. Mar. 31, 2000;101(1):25-33.

Zechner et al., "Recominant human cachectin/tumor necrosis factor but not interleukin-1 alpha downregulates lipoprotein lipase gene expression at the transcriptional level in mouse 3T3-L1 adipocytes." Mol Cell Biol Jun. 1988;8(6):2394-2401.

Zeis et al., "Generation of cytotoxic responses in mise and human individuals against hematological malignancies using survivin-RNA-transfected dendritic cells." J Immunol. Jun. 1, 2003;170(11):5391-5397.

Zervos et al., "Mxi1, a protein that specifically interacts with max to bind Myc-Max recognition sites." Cell. Jan. 29, 1993;72(2):223-232.

Zlatkine et al. "Retargeting of cytosolic proteins to the plasma membrane by the Lck protein tyrosine kinase dual acylation motif." J Cell Sci Mar. 1997; 110(Pt 5): 673-679.

Zuckermann et al., "Discovery of nanomolar ligands for 7-transmembrane G-protein coupled receptors from a diverse N-(substituted)glycine peptoid library." J Med Chem Aug. 19, 1994;37(17):2678-2685.

MODIFIED DENDRITIC CELLS HAVING ENHANCED SURVIVAL AND IMMUNOGENICITY AND RELATED COMPOSITIONS AND METHODS

RELATED PATENT APPLICATIONS

This patent application is a continuation application of U.S. patent application Ser. No. 12/301,021, filed on Jun. 4, 2009, naming Park et al. as inventors, now abandoned, which is a national stage of international patent application no. PCT/US2007/069586, filed on May 23, 2007, naming Park et al. as inventors, which claims the benefit of U.S. provisional patent application No. 60/803,025, filed on May 23, 2006, entitled "Modified Dendritic Cells Having Enhanced Survival and Immunogenicity and Related Compositions and Methods," naming Park et al. as inventors. The entire content of the foregoing patent applications is incorporated herein by reference, including all text, tables, and drawings.

GOVERNMENT SUPPORT

This invention was made in part with government support under Grant No. DAMD17-03-1-0156 awarded by the Department of Defense. The government has certain rights in this invention.

FIELD OF THE INVENTION

The invention pertains generally to immunotherapy, and more specifically to antigen-presenting cells.

BACKGROUND

Immunotherapy treatments generally involve inducing an immune response against a disease-associated antigen in a subject by sensitizing the subject's immune system to the antigen. The immune response often is induced by a vaccine that bears the antigen. Upon treatment with the vaccine, the immune system attacks cells bearing the antigen, which leads to a therapeutic effect. The immunity induced by vaccines depends largely on the efficiency of the antigen presenting cells (APC) that process and present the antigen. Dendritic cells (DCs) are APCs that can be responsible for vaccine efficacy by capturing and processing antigen and stimulating T cell immunity. It is possible to generate ex vivo functional DCs from a subject's peripheral blood monocytes or CD34 haemopoietic stem cells. In ex vivo approaches, dendritic cells generated from a patient's peripheral blood monocytes or CD34 haemopoietic stem cells can be loaded with a disease-associated antigen and reinfused into the patient with the aim of generating effective anti-disease immunity.

SUMMARY

Dendritic cells (DCs) are potent antigen-presenting cells (APCs), justifying their widespread use in vaccination protocols for the treatment of various malignancies. The lifespan of activated DCs is limited to only a few days in draining lymph nodes and phagocytosis or "reprocessing" of antigens from dying DCs to immature APCs can lead to tolerance. The limited lifespan of DCs therefore has been a shortcoming of immunotherapy.

Modified DCs provided herein have improved lifespan and immunogenicity, and are useful for immunotherapy. The modified DCs express an altered protein kinase, referred to herein as "protein kinase B" or "Akt." The altered Akt associates with cell membranes with greater frequency than unaltered Akt, and is referred to herein as "membrane-targeted Akt."

Thus, provided herein is a dendritic cell which comprises a nucleotide sequence that encodes a membrane-targeted Akt protein. The dendritic cell (DC) often originates from a mammal, including, for example, a rodent, (e.g., rat, mouse, rabbit, hamster, guinea pig), dog, cat, ungulate, fish, avian, monkey, ape or human. DCs often are isolated from a subject (e.g., a human) and then cultured ex vivo under conditions suitable for maintaining DCs for one or more days.

The membrane-targeted Akt protein comprises a mammalian Akt protein or a fragment thereof. A fragment often includes the protein kinase catalytic domain of Akt, and sometimes does not include the N-terminal pleckstrin homology (PH) domain of native Akt Amino acid sequences of mammalian Akt proteins or fragments are known, and sometimes the amino acid sequence is a mouse or a human Akt protein, a fragment thereof, a substantially identical variant of the foregoing. A human Akt protein may have the amino acid sequence encoded by SEQ ID NO: 2, 3, or 4, or a substantially identical variant thereof. An Akt protein fragment may have a portion of the amino acid sequence encoded by SEQ ID NO: 2, 3, or 4 or a substantially identical variant thereof, and in some embodiments, the fragment has the amino acid sequence of SEQ ID NO: 6 (i.e., encoded by SEQ ID NO: 5).

In certain embodiments, the membrane-targeted Akt protein is in association with a membrane association region, the latter of which can increase the frequency with which the Akt protein is in association with a cell membrane or portion thereof. In some embodiments, the membrane-targeted Akt interacts with (e.g., binds with) affinity and selectivity to membrane rafts in cells. The term "in association" as used herein with respect to an Akt region and a membrane association region refers to covalent or non-covalent association of the membrane association region to an Akt protein or fragment. The N- or C-terminus of an Akt protein or fragment may be covalently linked to a membrane association region, and a membrane association region may be linked to a non-terminal portion of an Akt protein or fragment. A protein having an Akt protein region and a membrane association region may be referred to as a "fusion protein" or "chimeric protein." In certain embodiments, an Akt chimeric protein does not include a heterologous multimerization region, such as a region that binds to a FK506 molecule or analog thereof, and in such embodiments, the chimeric protein can be constitutively active. An Akt protein or fragment component may be non-covalently associated with a membrane association region component via a complementary member of a binding pair linked to each component. The membrane association region and the Akt protein or fragment in the membrane-targeted Akt often are homologous (e.g., each are a human amino acid sequence), and sometimes are heterologous (e.g., one is a human amino acid sequence and the other is a mouse amino acid sequence).

A membrane association region often is an amino acid fragment of a native mammalian protein, or a substantially identical sequence thereof. Membrane association regions include, for example, acylation regions, transmembrane proteins, and transmembrane protein fragments. Acylation regions are capable of being linked to one or more acyl moieties. For example a dual acylation region is capable of being linked to two acyl moieties. In certain embodiments, the acylation region is from a protein kinase, such as Fyn, Lck or Src, for example, which can be myristoylated and may be linked to the N-terminus of the Akt protein or fragment. In some embodiments, the acylation region comprises a cys-alaala sequence, and sometimes the region is from a G-protein, which can be linked to the C-terminus of the Akt protein or fragment.

The nucleotide sequence that encodes the membrane-targeted Akt can be incorporated in the dendritic cell in a variety of manners. For example, one or more copies of the nucleotide sequence may be stably inserted into the dendritic cell genomic DNA by random insertion or by non-random insertion (e.g., knock-in), or the nucleotide sequence may be non-stably inserted in the dendritic cell (e.g., in plasmid DNA). For embodiments in which (a) an Akt protein or fragment-binding partner component and (b) a membrane association region-binding partner component, are expressed in a dendritic cell, each component may be expressed from a nucleotide sequence in functional association with a common promoter or from different promoters.

Modified dendritic cells comprising a nucleotide sequence that expresses a membrane-targeted Akt generally (a) survive longer on average than counterpart dendritic cells that do not include the nucleotide sequence, (b) present a greater amount of antigen on average than cells that do not include the nucleotide sequence, and (c) are more immunogenic on average than cells that do not include the nucleotide sequence. Processes for assessing dendritic cell survival periods and antigen presentation and immunogenicity are well known to the person of ordinary skill in the art.

A modified dendritic cell described herein sometimes is provided in a composition comprising components suitable for administering the dendritic cell to a subject. For example, dendritic cells can be mixed with Toll-like receptor (TLR) ligands that can increase DC activation locally, such as monophosphoryl lipid A (TLR4 ligand), imiquimod (TLR7/8 ligand), unmethylated CpG oligonucleotides (TLR9 ligand), and others. Additional activation ligands, such as those found in monocyte-conditioned media "maturation cocktail" also can be included. Thus, included is a non-human organism, sometimes a mammalian organism, comprising a modified dendritic cell described herein.

Also provided are methods for preparing a modified dendritic cell, which comprises: contacting a dendritic cell with a nucleic acid having a nucleotide sequence that encodes a membrane-targeted Akt protein, whereby the modified dendritic cell survives longer on average than dendritic cells that do not include the nucleotide sequence. The resulting modified dendritic cell often presents a greater amount of antigen on average than cells that do not include the nucleotide sequence, and the resulting modified dendritic cell is more immunogenic on average than cells that do not include the nucleic acid. The nucleic acid sometimes is isolated from a source (e.g., a cell or virus) before contacting the dendritic cell with the nucleic acid, and sometimes the nucleic acid is within a virus and is delivered to the dendritic cell by contacting the cell with the virus, whereby the virus inserts the nucleic acid into the cell.

In some embodiments, the modified dendritic cell is contacted with an antigen or antigen precursor. Any antigen or precursor suitable for immunotherapy can be utilized, such as an antigen expressed more frequently in cancer cells than in non-cancer cells, for example. The antigen may result from contacting the modified dendritic cell with prostate specific membrane antigen (PSMA) or a fragment thereof. In certain embodiments, the modified dendritic cell is contacted with a PSMA fragment having the amino acid sequence of SEQ ID NO: 10 (e.g., encoded by the nucleotide sequence of SEQ ID NO: 9).

Provided also are methods for loading a modified dendritic cell with an antigen, comprising: contacting a modified dendritic cell with an antigen or antigen precursor, where the modified dendritic cell expresses a membrane-targeted Akt protein, whereby the modified dendritic cell is loaded with the antigen. The antigen can be delivered as a purified protein or purified fragment, or by a viral or non-viral sequence. Also provided are methods for manufacturing a virus having a nucleotide sequence that encodes a membrane-targeted Akt protein, which comprise: transfecting a producer cell with a virus having a nucleotide sequence that encodes a membrane-targeted Akt; and isolating the virus produced by the cells.

Also provided are isolated membrane-targeted Akt proteins. For example, included is a protein comprising: (a) a mammalian Akt portion lacking a pleckstrin homology (PH) domain; and (b) a dual acylation portion, or (c) a membrane protein or membrane protein fragment. Portion (a) may be covalently linked or non-covalently linked to portion (b) or portion (c). In certain embodiments, portion (a) is non-covalently linked to portion (b) or portion (c) by components of a binding pair linked to each of portion (a) and portion (b) or (c). In certain embodiments, the dual acylation portion is from a protein kinase, such as Fyn, Lck or Src, for example. In certain embodiments, the dual acylation region comprises two acyl moieties, where one or both of the acyl moieties may be selected from the group consisting of myristoyl, geranyl, farnesyl and prenyl. The acylation region may comprise a cys-ala-ala sequence, and may be from a G-protein. In some embodiments, the dual acylation portion is identical to or substantially identical to the amino acid sequence of SEQ ID NO: 8. The acylation portion, membrane protein or membrane protein fragment may be linked to the N-terminus or C-terminus of the Akt portion. The mammalian Akt portion may be identical to or substantially identical to mouse Akt, or a fragment thereof, or may be identical to or substantially identical to human Akt, or a fragment thereof. In certain embodiments, the mammalian Akt portion is identical to or substantially identical to the amino acid sequence encoded by the nucleotide sequence of SEQ ID NO: 6, or a fragment thereof. Also provided is an antibody or antibody fragment that specifically binds to a membrane-targeted Akt protein.

In some embodiments, a membrane-targeted Akt protein may include one or more multimerization regions (e.g., one, two, three, four or more multimerization regions), and one or more multimerization regions may be located at the N-terminus of the chimeric protein, within the protein (e.g., between an Akt region and a membrane association region), or at the C-terminus of the protein. A multimeriation region often is heterologous to other regions of the membrane-targeted Akt protein (i.e., the nucleic acid encoding the multimerization region is not linked in vivo to a nucleic acid sequence encoding the Akt protein or the acylation region). A multimerization region may be covalently linked or non-covalently linked to a membrane-targeted Akt protein. An example of a multimerization region is an amino acid sequence that binds to a FK506 molecule or analog thereof. A membrane-targeted Akt protein containing a multimerization region can be referred to as an "inducible membrane-targeted Akt protein." In certain embodiments, a membrane-targeted does not contain a multimerization region or a heterologous multimerization region. A membrane-targeted Akt protein not containing a multimerization region or heterologous multimerization region can be referred to as a "constitutively active membrane-targeted Akt protein."

Provided also is a nucleic acid which comprises a nucleotide sequence that encodes a membrane-targeted Akt protein described herein. In certain embodiments, the nucleic acid comprises a promoter operably linked to the nucleotide sequence. The promoter sometimes is constitutively active, at times is inducible, and can be from a virus. The nucleic acid in some embodiments comprises one or more nucleotide sequences from a virus, and in certain embodiments, the nucleic acid is derived from a virus. Any suitable virus capable of expressing a protein in cells, and optionally replicating in cells, can be utilized, such as adenovirus.

Also provided is a cell which comprises a nucleic acid described herein. The cell can be an antigen presenting cell, such as a dendritic cell for example, and the cell sometimes is a human cell. The cell containing the nucleic acid often (a) survives longer on average than a counterpart cell that does not include the nucleic acid (i.e., the same type of cell that does not contain the nucleic acid), (b) presents a greater amount of antigen on average than a counterpart cell that does not include the nucleic acid, and/or (c) is more immunogenic on average than a cell that does not include the nucleic acid. In the cell, the membrane-associated Akt protein encoded by the nucleic acid can be in association with a raft membrane with higher frequency than other portions of the cell membrane, in certain embodiments.

Provided also is a method for inducing an immune response against an antigen, which comprises contacting a dendritic cell that expresses a membrane-targeted Akt protein with an antigen or antigen precursor; and administering the dendritic cell to a subject; whereby the immune response against the antigen is induced. Also included is a method for detecting an immune response against an antigen, which comprises: contacting a dendritic cell that expresses a membrane-targeted Akt protein with an antigen; administering the dendritic cell to a subject; and detecting the immune response. Provided in addition is a method for reducing cell proliferation in a subject, which comprises: contacting a dendritic cell that expresses a membrane-targeted Akt protein with an antigen produced in proliferating cells; and administering the dendritic cell to a subject; whereby cell proliferation is reduced. In certain methods, the antigen or a fragment thereof sometimes is co-administered to the subject (e.g., before, during or after administration of the dendritic cell). Administration of the dendritic cell and/or antigen may be pulsed (e.g., administered multiple times over a period of time (e.g., within a day, once every five days). Also provided is a method for inhibiting tumor growth in a subject, which comprises: contacting a dendritic cell that expresses a membrane-targeted Akt protein with an antigen produced by cells in a tumor; and administering the dendritic cell to a subject having a tumor; whereby tumor growth is inhibited.

Also provided is a kit which comprises a nucleic acid comprising a nucleotide sequence that encodes a membrane-targeted Akt protein described herein. In certain embodiments, the nucleic acid is packaged in a virus, and sometimes the virus is an adenovirus, such as a replication deficient adenovirus. In some embodiments, the kit comprises one or more transfection components for inserting the nucleic acid into a dendritic cell. A kit may comprise an antigen, and/or a second nucleic acid that encodes an antigen. Some kits comprise instructions, or directions to obtain instructions (e.g., obtained from a website), for preparing a dendritic cell with the nucleic acid comprising a nucleotide sequence that encodes the membrane-targeted Akt.

Also provided is an isolated nucleic acid which comprises a nucleotide sequence that encodes a protein containing: a first region comprising a human Akt sequence lacking a pleckstrin homology (PH) domain; and a second region linked to the N-terminus of the Akt sequence comprising two or more acylation sites. In certain embodiments, the second region comprises a Gly-Cys-Xaa-Cys-sequence, and sometimes the second region is about 5 to about 25 amino acids in length and from the N-terminus of the nucleic acid kinase Fyn, Yes or Lck. The second region sometimes comprises two acyl moieties, such as a myristoyl and palmitoyl region, for example. In certain embodiments, the Akt sequence is identical to or substantially identical to a fragment of an amino acid sequence encoded by SEQ ID NO: 2, 3, or 4. Sometimes the Akt sequence is identical to or substantially identical to the amino acid sequence of SEQ ID NO: 6, and at times the Akt sequence is identical to or substantially identical to an amino acid sequence encoded by SEQ ID NO: 5. In certain embodiments, the second region is identical to or substantially identical to the amino acid sequence encoded by SEQ ID NO: 7 (from Fyn). Provided also is an adenovirus which comprises the nucleotide sequence of any one of the preceding aspects. Also provided is a cell which comprises the nucleotide sequence of any one of the preceding aspects. In some embodiments the cell is a human antigen presenting cell, such as a human dendritic cell. In certain embodiments, the cell has been contacted with an antigen, such as a prostate specific membrane antigen or fragment thereof (e.g., SEQ ID NO: 10).

Also provided is a method for inducing an immune response, which comprises: (a) contacting a dendritic cell from a human subject with an antigen; (b) contacting the dendritic cell with a nucleic acid that comprises a nucleotide sequence that encodes a protein containing: a first region comprising a human Akt sequence lacking a pleckstrin homology (PH) domain; and a second region linked to the N-terminus of the Akt sequence comprising two or more acylation sites; and administering the dendritic cell after steps (a) and (b) to the subject, whereby an immune response is induced. The immune response often is or includes an antigen-specific CTL response, and sometimes the antigen is a prostate specific membrane antigen or fragment thereof (e.g., SEQ ID NO: 10). Provided also is a method for inducing an immune response, which comprises: (a) contacting a dendritic cell from a human subject with an antigen; (b) contacting the dendritic cell with a nucleic acid that comprises a nucleotide sequence that encodes a protein containing: a first region comprising a human Akt sequence lacking a pleckstrin homology (PH) domain; and a second region linked to the N-terminus of the AU sequence comprising two or more acylation sites; and proliferating in vitro antigen-specific CTLs against the dendritic cell after steps (a) and (b), whereby an immune response is induced. In certain embodiments the CTLs are administered to the subject, and sometimes the antigen is a prostate specific membrane antigen or fragment thereof (e.g., SEQ ID NO: 10).

These and other embodiments are described hereafter in the Detailed Description and in the Claims.

DETAILED DESCRIPTION

Akt Molecules

Figure 1:
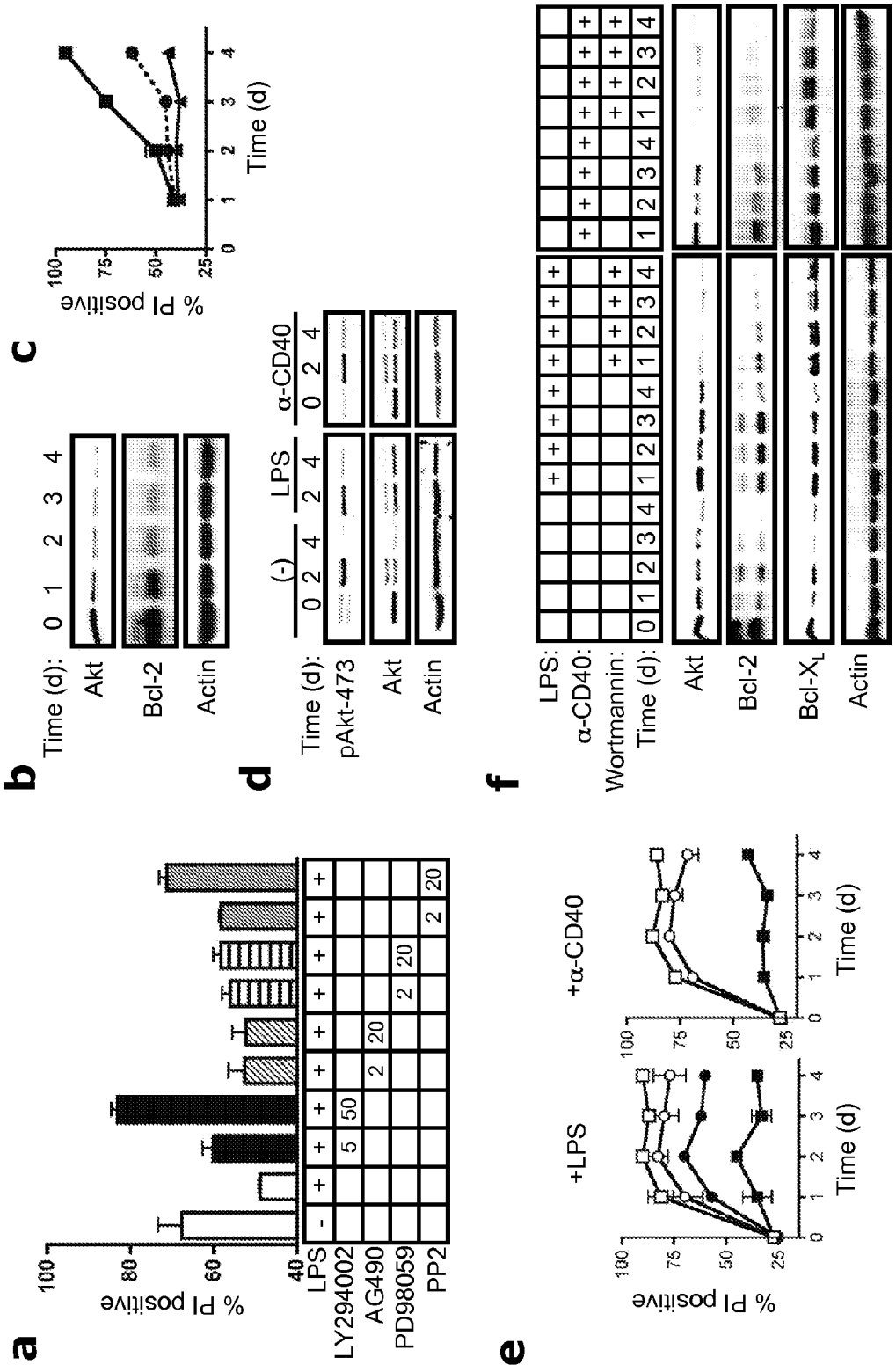
FIGS. 1A to 1F show LPS and CD40 prevent DC death by blocking the down-regulation of Akt and Bcl-2.

The term "Akt molecule" refers to a molecule, such as a protein, polypeptide, nucleic acid or expression vector, for example, comprising a native Akt sequence, or fragment thereof or substantially identical variant of the foregoing. An Akt molecule often is capable of enhancing antigen presenting cell longevity and immunogenicity when expressed in an antigen presenting cell in such a manner that it is membrane-targeted, and constitutively active in certain embodiments. An Akt molecule also may include other portions in addition to the Akt sequence, and in such embodiments, the Akt sequence in the Akt molecule sometimes is referred to herein as an "Akt portion" or "Akt region." Additional sequences that may be included optionally in an Akt molecule are described herein, such as a membrane association sequence and/or a multimerization sequence, for example.

An Akt sequence may be a native Akt sequence, a fragment of an Akt sequence or a substantially identical variant of the foregoing. An Akt sequence often is mammalian (e.g., mouse or human), or a fragment or variant sequence thereof. Examples of native polynucleotide sequences that encode Akt polypeptides include, but are not limited to, SEQ ID NO: 1 (mouse Akt1), SEQ ID NO: 2 (human Akt1), SEQ ID NO: 2 (human Akt2), SEQ ID NO: 4 (human Akt3), and Akt homologs from other species, often mammals, and including Akt oncogenic viral sequences.

As noted above, Akt sequences include Akt fragment sequences. An AKT fragment sequence may lack one or more nucleotides, amino acids or regions, the latter of which may be a functional region or domain. An Akt fragment sequence can include one or more functional regions, and may lack one or more functional regions compared to a native Akt sequence. Functional regions include a pleckstrin homology (PH) domain (e.g., from about position 6 to about position 107 in human AKT1), a serine/threonine protein kinase catalytic region (e.g., from about position 149 to about position 408 in human AKT1) and a catalytic domain extension region (e.g., from about position 409 to about position 476 in human AKT1). Where an Akt fragment sequence includes one or more functional regions, the region may be flanked on each side by a native amino acid sequence from a native Akt sequence. In certain embodiments, an Akt amino acid fragment sequence is 10 or more, 15 or more, 20 or more, 25 or more, 50 or more, 100 or more, 200 or more, 300 or more, 400 or more or 450 or more amino acids from a native Akt protein. An Akt molecule often includes an Akt protein kinase catalytic domain, and therefore often is capable of catalyzing Ser/Thr protein phosphorylation. An Akt fragment can exclude a PH domain or includes a modified PH domain. A modified PH domain may be truncated or mutated, generated by using standard mutagenesis, insertions, deletions, or substitutions, and the modified form may or may not be functional. Examples of Akt nucleic acids lacking a functional PH domain sequence have the nucleotide sequences of SEQ ID NO: 5 (mouse Akt) and SEQ ID NO: 6 (human Akt).

Akt sequences include homologs, alternative transcripts, alleles, functionally equivalent fragments, variants, and analogs of native Akt sequences (e.g., nucleotide sequences described herein). The term "substantially identical variant" as used herein refers to a nucleotide or amino acid sequence sharing sequence identity to a nucleotide sequence or amino acid sequence of Akt or another molecule described herein (e.g., membrane association region). Included are nucleotide sequences or amino acid sequences 55% or more, 60% or more, 65% or more, 70% or more, 75% or more, 80% or more, 85% or more, 90% or more, 95% or more (each sometimes within a 1%, 2%, 3% or 4% variability) identical to a nucleotide sequence or encoded amino acid sequence described herein, or has one to ten nucleotide or amino acid substitutions. One test for determining whether two nucleotide sequences or amino acids sequences are substantially identical is to determine the percent of identical nucleotide sequences or amino acid sequences shared.

Calculations of sequence identity can be performed as follows. Sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is sometimes 30% or more, 40% or more, 50% or more, often 60% or more, and more often 70% or more, 80% or more, 90% or more, or 100% of the length of the reference sequence. The nucleotides or amino acids at corresponding nucleotide or polypeptide positions, respectively, are then compared among the two sequences. When a position in the first sequence is occupied by the same nucleotide or amino acid as the corresponding position in the second sequence, the nucleotides or amino acids are deemed to be identical at that position. The percent identity between the two sequences is a function of the number of identical positions shared by the sequences, taking into account the number of gaps, and the length of each gap, introduced for optimal alignment of the two sequences. Comparison of sequences and determination of percent identity between two sequences can be accomplished using a mathematical algorithm. Percent identity between two amino acid or nucleotide sequences can be determined using the algorithm of Meyers & Miller, CABIOS 4: 11-17 (1989), which has been incorporated into the ALIGN program (version 2.0), using a PAM120 weight residue table, a gap length penalty of 12 and a gap penalty of 4. Also, percent identity between two amino acid sequences can be determined using the Needleman & Wunsch, J. Mol. Biol. 48: 444-453 (1970) algorithm which has been incorporated into the GAP program in the GCG software package (available at the http address www.gcg.com), using either a Blossum 62 matrix or a PAM250 matrix, and a gap weight of 16, 14, 12, 10, 8, 6, or 4 and a length weight of 1, 2, 3, 4, 5, or 6. Percent identity between two nucleotide sequences can be determined using the GAP program in the GCG software package (available at http address www.gcg.com), using a NWSgapdna.CMP matrix and a gap weight of 40, 50, 60, 70, or 80 and a length weight of 1, 2, 3, 4, 5, or 6. A set of parameters often used is a Blossum 62 scoring matrix with a gap open penalty of 12, a gap extend penalty of 4, and a frameshift gap penalty of 5.

Another manner for determining whether two nucleic acids are substantially identical is to assess whether a polynucleotide homologous to one nucleic acid will hybridize to the other nucleic acid under stringent conditions. As use herein, the term "stringent conditions" refers to conditions for hybridization and washing. Stringent conditions are known to those skilled in the art and can be found in Current Protocols in Molecular Biology, John Wiley & Sons, N.Y., 6.3.1-6.3.6 (1989). Aqueous and non-aqueous methods are described in that reference and either can be used. An example of stringent hybridization conditions is hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions is hybridization in 6× sodium chloride/sodium citrate (SSC) at about 45° C., followed by one or more washes in 0.2×SSC, 0.1% SDS at 60° C. Often, stringent hybridization conditions are hybridization in 6× sodium chloride/sodium citrate (SSC) at about 45° C., followed by one or more washes in 0.2×SSC, 0.1% SDS at 65° C. More often, stringency conditions are 0.5M sodium phosphate, 7% SDS at 65° C., followed by one or more washes at 0.2×SSC, 1% SDS at 65° C.

An example of a substantially identical nucleotide sequence to a base nucleotide sequence described herein is one that has a different nucleotide sequence but still encodes the same amino acid sequence encoded by the base nucleotide sequence. Another example is a nucleotide sequence that encodes a protein having an amino acid sequence 70% or more identical to, sometimes 75% or more, 80% or more, or 85% or more identical to, and often 90% to 99% identical to an amino acid sequence encoded by the base nucleotide sequence.

Nucleotide sequences and encoded amino acid sequences described herein can be used as "query sequences" to perform a search against public databases to identify other family members or related sequences, for example. Such searches can be performed using the NBLAST and XBLAST programs (version 2.0) of Altschul et al., J. Mol. Biol. 215: 403-10 (1990). BLAST nucleotide searches can be performed with the NBLAST program, score=100, wordlength=12 to obtain nucleotide sequences homologous to nucleotide sequences described herein. BLAST polypeptide searches can be performed with the XBLAST program, score=50, wordlength=3 to obtain amino acid sequences homologous to those encoded by nucleotide sequences described herein. To obtain gapped alignments for comparison purposes, Gapped BLAST can be utilized as described in Altschul et al., Nucleic Acids Res. 25(17): 3389-3402 (1997). When utilizing BLAST and Gapped BLAST programs, default parameters of the respective programs (e.g., XBLAST and NBLAST) can be used (see the http World Wide Web address ncbi.nlm.nih.gov). Thus, a protein having a substantially identical amino acid sequence to (i) an amino acid sequence described herein or (ii) an amino acid sequence encoded by a nucleotide sequence described herein, identified by a query sequence search can be considered a substantially identical sequence.

Substantially identical nucleotide sequences may include altered codons for enhancing expression of an amino acid sequence in a particular expression system. One or more codons may be altered, and sometimes 10% or more or 20% or more of the codons are altered for optimized expression in an expression system that may include bacteria (e.g., E. coli), yeast (e.g., S. cervesiae), human (e.g., 293 cells or antigen presenting cells), insect, or rodent (e.g., hamster) cells (e.g., antigen presenting cells).

An Akt protein, polypeptide or fragment variant can include one or more amino acid substitutions, deletions or insertions. Any amino acid may be substituted by a conservative or non-conservative substitution. For example, phosphorylatable amino acids (e.g., serine, threonine or tyrosine) in an Akt protein or fragment may be modified (e.g., deleted or substituted with an amino acid that cannot be phosphorylated).

An Akt protein, polypeptide or fragment variant may contain one or more unnatural amino acids. Unnatural amino acids include but are not limited to D-isomer amino acids, ornithine, diaminobutyric acid, norleucine, pyrylalanine, thienylalanine, naphthylalanine and phenylglycine, alpha and alpha-disubstituted amino acids, N-alkyl amino acids, lactic acid, halide derivatives of natural amino acids such as trifluorotyrosine, p-Cl-phenylalanine, p-Br-phenylalanine, p-1-phenylalanine, L-allyl-glycine, beta-alanine, L-alpha-amino butyric acid, L-gamma-amino butyric acid, L-alpha-amino isobutyric acid, L-epsilon-amino caproic acid, 7-amino heptanoic acid, L-methionine sulfone, L-norleucine, L-norvaline, p-nitro-L-phenylalanine, L-hydroxyproline, L-thioproline, methyl derivatives of phenylalanine (Phe) such as 4-methyl-Phe, pentamethyl-Phe, L-Phe (4-amino), L-Tyr (methyl), L-Phe (4-isopropyl), L-Tic (1,2,3,4-tetrahydroisoquinoline-3-carboxyl acid), L-diaminopropionic acid, L-Phe (4-benzyl), 2,4-diaminobutyric acid, 4-aminobutyric acid (gamma-Abu), 2-amino butyric acid (alpha-Abu), 6-amino hexanoic acid (epsilon-Ahx), 2-amino isobutyric acid (Aib), 3-amino propionic acid, ornithine, norleucine, norvaline, hydroxyproline, sarcosine, citrulline, homocitrulline, cysteic acid, t-butylglycine, t-butylalanine, an amino acid derivitized with a heavy atom or heavy isotope (e.g., Au, deuterium, 15N; useful for synthesizing protein applicable to X-ray crystallographic structural analysis or nuclear magnetic resonance analysis), phenylglycine, cyclohexylalanine, fluoroamino acids, designer amino acids such as beta-methyl amino acids, Ca-methyl amino acids, Na-methyl amino acids, naphthyl alanine, and the like.

Membrane Association Regions

Molecules in association with cell membranes contain certain regions that facilitate the membrane association, and such regions can be incorporated into or associated with a protein containing an Akt sequence to generate membrane-targeted Akt molecules (e.g., AU chimeras). For example, some proteins contain sequences at the N-terminus or C-terminus that are acylated, and these acyl moieties facilitate membrane association. Such sequences are recognized by acyltransferases and often conform to a particular sequence motif. Certain acylation motifs are capable of being modified with a single acyl moiety and others are capable of being modified with multiple acyl moieties. For example, the N-terminal sequence of the protein kinase Src can comprise a single myristoyl moiety. Dual acylation regions are located within the N-terminal regions of certain protein kinases (e.g., Yes, Fyn, Lck) and G-protein alpha subunits. Such dual acylation regions often are located within the first eighteen amino acids of such proteins, and conform to the sequence motif Met-Gly-Cys-Xaa-Cys (SEQ ID NO: 11), where the Met is cleaved, the Gly is N-acylated and one of the Cys residues is S-acylated. The Gly often is myristoylated and a Cys can be palmitoylated. Acylation regions conforming to the sequence motif Cys-Ala-Ala-Xaa (so called "CAAX boxes"), which can modified with C15 or C10 isoprenyl moieties, from the C-terminus of G-protein gamma subunits and other proteins (e.g., http World Wide Web address ebi.ac.uk/interpro/DisplayIproEntry?ac=IPR001230) also can be utilized. These and other acylation motifs are known to the person of ordinary skill in the art (e.g., Gauthier-Campbell et al., Molecular Biology of the Cell 15: 2205-2217 (2004); Glabati et al., Biochem. J. 303: 697-700 (1994) and Zlakine et al., J. Cell Science 110: 673-679 (1997)), and can be incorporated in Akt molecules to induce membrane localization. In certain embodiments, a native sequence from a protein containing an acylation motif can be linked to an Akt protein. For example, in some embodiments, an N-terminal portion of Lck, Fyn or Yes or a G-protein alpha subunit, such as the first twenty-five N-terminal amino acids or fewer from such proteins (e.g., about 5 to about 20 amino acids, about 10 to about 19 amino acids, or about 15 to about 19 amino acids of the native sequence with optional mutations), may be linked to the N-terminus of an Akt protein (e.g., a Fyn fragment-AU molecule is described in the Examples section hereafter). In certain embodiments, a C-terminal sequence of about 25 amino acids or less from a G-protein gamma subunit containing a CAAX box motif sequence (e.g., about 5 to about 20 amino acids, about 10 to about 18 amino acids, or about 15 to about 18 amino acids of the native sequence with optional mutations) can be linked to the C-terminus of an Akt protein.

In some embodiments, an acyl moiety has a log p value of +1 to +6, and sometimes has a log p value of +3 to +4.5. Log p values are a measure of hydrophobicity and often are derived from octanol/water partitioning studies, in which molecules with higher hydrophobicity partition into octanol with higher frequency and are characterized as having a higher log p value. Log p values are published for a number of lipophilic molecules and log p values can be calculated using known partitioning processes (e.g., Chemical Reviews, Vol. 71, Issue 6, page 599, where entry 4493 shows lauric acid having a log p value of 4.2). Any acyl moiety can be linked to a peptide composition described above and tested for antimicrobial activity using known methods and those described hereafter. The acyl moiety sometimes is a C1-C20 alkyl, C2-C20 alkenyl, C2-C20 alkynyl, C3-C6 cycloalkyl, C1-C4 haloalkyl, C4-C12 cyclalkylalkyl, aryl, substituted aryl, or aryl (C1-C4) alkyl, for example. Any acyl-containing moiety sometimes is a fatty acid, and examples of fatty acid moieties are propyl (C3), butyl (C4), pentyl (C5), hexyl (C6), heptyl (C7), octyl (C8), nonyl (C9), decyl (C10), undecyl (C11), lauryl (C12), myristyl (C14), palmityl (C16), stearyl (C18), arachidyl (C20), behenyl (C22) and lignoceryl moieties (C24), and each moiety can contain 0, 1, 2, 3, 4, 5, 6, 7 or 8 unsaturations (i.e., double bonds). An acyl moiety sometimes is a lipid molecule, such as a phosphatidyl lipid (e.g., phosphatidyl serine, phosphatidyl inositol, phosphatidyl ethanolamine, phosphatidyl choline), sphingolipid (e.g., shingomyelin, sphigosine, ceramide, ganglioside, cerebroside), or modified versions thereof. In certain embodiments, one, two, three, four or five or more acyl moieties are linked to a membrane association region.

An Akt protein also may be linked to a single-pass or multiple pass transmembrane sequence (e.g., to the N-terminus or C-terminus of an Akt protein sequence). Single pass transmembrane regions are found in certain CD molecules, tyrosine kinase receptors, serine/threonine kinase receptors, TGFbeta, BMP, activin and phosphatases. Single pass transmembrane regions can include a signal peptide region and a transmembrane region of about 20 to about 25 amino acids, many of which are hydrophobic amino acids and can form an alpha helix. A short track of positively charged amino acids can follow the transmembrane span. Multiple pass proteins include ion pumps, ion channels, and transporters, and include two or more helices that span the membrane multiple times. All or substantially all of a multiple pass protein can be attached to an Akt molecule. Sequences for single pass and multiple pass transmembrane regions are known and can be selected for incorporation into an Akt molecule by the person of ordinary skill in the art.

Akt and Membrane Association Component Combinations

A membrane association region may be covalently linked to the N-terminus or C-terminus of an Akt protein or fragment, and such fusions sometimes are referred to herein as "chimeric proteins." Such chimeric proteins can be encoded by a nucleotide sequence in which the membrane association region-encoding sequence is adjacent to the Akt protein or fragment-encoding sequence, with or without an intervening linker sequence. Covalent linkages also can be generated by a chemically reactive binding pair, whereby a one member of the binding pair is linked to the Akt molecule and another member of the binding pair is linked to the membrane association region. Examples of chemically reactive binding pairs include without limitation sulfhydryl/maleimide, sulfhydryl/haloacetyl derivative, amine/isotriocyanate, amine/succinimidyl ester, and amine/sulfonyl halides. When binding pairs are utilized to generate a covalent linkage, it is possible to join the membrane association region to the N-terminus or C-terminus of the Akt molecule, or to a chemical moiety within the Akt molecule.

In certain embodiments, the membrane association portion may not be covalently attached and may non-covalently associate with the Akt molecule. Non-covalent linkages can be generated by interactive binding pairs, wherein one binding pair member is linked to the membrane association region and the other binding pair member is linked to the Akt molecule. Any suitable interactive binding pair can be utilized to effect a non-covalent linkage, including without limitation biotin/avidin, biotin/streptavidin, folic acid/folate binding protein, vitamin B12/intrinsic factor, nucleic acid/complementary nucleic acid (e.g., DNA, RNA, PNA), and may be antibody/antigen, antibody/antibody, antibody/antibody fragment, antibody/antibody receptor, antibody/protein A or protein G, or hapten/anti-hapten pairs.

Where the membrane association region and the Akt molecule are provided separately and then joined in a covalent or non-covalent manner, nucleotide sequences encoding each portion can be located on separate nucleic acids or the same nucleic acid. The nucleotide sequence encoding each portion often are under the control of the same regulatory sequences, and can be under the control of different regulatory sequences (e.g., promoter, internal ribosome entry sequence).

Multimerization regions also are known and can be utilized to inducibly join an Akt protein, fragment or variant with a membrane association region in a non-covalent manner. Such inducible systems are referred to herein as "chemically induced dimerization (CID)." In addition to being inducible, CID also is reversible, due to the degradation of the labile dimerizing agent or administration of a monomeric competitive inhibitor.

CID systems often involve synthetic bivalent ligands to rapidly crosslink signaling molecules that are fused to ligand-binding domains CID. This system has been used to trigger the oligomerization and activation of cell surface (Spencer et al., 1993; Spencer et al., 1996; Blau et al., 1997), or cytosolic proteins (Luo et al., 1996; MacCorkle et al., 1998), the recruitment of transcription factors to DNA elements to modulate transcription (Ho et al., 1996; Rivera et al., 1996) or the recruitment of signaling molecules to the plasma membrane to simulate signaling (Spencer et al., 1995; Holsinger et al., 1995).

CID systems often are based upon the notion that surface receptor aggregation effectively activates downstream signaling cascades. In one embodiment, the CID system uses a dimeric analog of the lipid permeable immunosuppressant drug, FK506, which loses its normal bioactivity while gaining the ability to crosslink molecules genetically fused to the FK506-binding protein, FKBP12. By fusing one or more FKBPs and a myristoylation sequence to the cytoplasmic signaling domain of a target receptor, one can stimulate signaling in a dimerizer drug-dependent, but ligand and ectodomain-independent manner. This approach provides the system with temporal control, reversibility using monomeric drug analogs, and enhanced specificity. The high affinity of third-generation AP20187/AP1903 CIDs for their binding domain (e.g., Pollock and Rivera, Methods Enzymol 306: 263-81 (1999)), FKBP12 permits specific activation of the recombinant receptor in vivo without the induction of non-specific side effects through endogenous FKBP12. In addition, the synthetic ligands are resistant to protease degradation, making them more efficient at activating receptors in vivo than most delivered protein agents.

In specific embodiments, rapamycin analogs crosslink endogenous FKBP12 with a 89 amino acid domain from FRAP/mTOR, called FRB (FRAP rapamycin binding domain, residues 2025-2113). Thus, in certain embodiments, activation of iAkt is based on ligand-dependent recruitment of chimeric Akt (first chimeric protein) to a membrane association protein (second chimeric protein).

Ligands utilized for CID are capable of binding to two or more of the ligand-binding domains. One skilled in the art realizes that the chimeric proteins may be able to bind to more than one ligand when they contain more than one ligand-binding domain. The ligand sometimes is a non-protein or a chemical. Exemplary ligands include, but are not limited to dimeric FK506 (e.g., FK1012), AP1903, rapamycin or a derivative thereof.

In specific embodiments, the ligand-binding region linked to the membrane association region is heterologous to the ligand-binding region linked to the Akt molecule. In certain embodiments, the ligand-binding region is a rapamycin-binding domain, FRB, from FRAP/mTOR. Representative sequences and methods of incorporating them into expression vectors are set forth in the Examples section hereafter.

Nucleic Acid Constructs

In certain immunotherapy procedures, antigen presenting cells are transfected or transformed with a nucleic acid having a polynucleotide sequence that encodes an Akt molecule described herein. The nucleic acid bearing such a nucleotide sequence can be transferred into the antigen presenting cell in a variety of manners, as described hereafter (e.g., delivery of a naked nucleic acid or encapsulation of the nucleic acid in a liposome or virus). Based on nucleotide sequences within the nucleic acid, a target nucleotide sequence encoding an Akt molecule and/or other target molecules may be stably integrated into the genomic DNA of the antigen presenting cell, in a random or non-random manner (e.g., knock-in), or may be transiently deposited to the antigen presenting cell.

Nucleic acids containing an Akt nucleotide sequence sometimes are referred to herein as "nucleic acid compositions." A nucleic acid composition can be from any source or composition, such as DNA, cDNA, RNA or mRNA, for example, and can be in any suitable form (e.g., linear, circular, supercoiled, single-stranded, double-stranded, and the like). A nucleic acid composition sometimes is a plasmid, phage, autonomously replicating sequence (ARS), centromere, artificial chromosome or other nucleic acid able to replicate or be replicated in vitro or in a host cell (e.g., dendritic cell). Such nucleic acid compositions are selected for their ability to guide production of the desired protein or nucleic acid molecule. When desired, the nucleic acid composition can be altered as known in the art such that codons encode for a different amino acid than is normal, including unconventional or unnatural amino acids (including detectably labeled amino acids).

A nucleic acid composition can comprise certain elements often selected according to the intended use of the nucleic acid. Any of the following elements can be included in or excluded from a nucleic acid composition. A nucleic acid composition, for example, may include one or more or all of the following nucleotide elements: one or more promoter elements, one or more 5' untranslated regions (5'UTRs), one or more regions into which a target nucleotide sequence may be inserted (an "insertion element"), one or more target nucleotide sequences, one or more 3' untranslated regions (3'UTRs), and a selection element. A nucleic acid composition is provided with one or more of such elements and other elements may be inserted into the nucleic acid before the template is contacted with a transcription and/or translation system. In some embodiments, a provided nucleic acid composition comprises a promoter, 5'UTR, optional 3'UTR and insertion element(s) by which a target nucleotide sequence is inserted (i.e., cloned) into the template. In certain embodiments, a provided nucleic acid composition comprises a promoter, insertion element(s) and optional 3'UTR, and a 5' UTR/target nucleotide sequence is inserted with an optional 3'UTR. The elements can be arranged in any order suitable for transcription and/or translation, and in some embodiments a nucleic acid composition comprises the following elements in the 5' to 3' direction: (1) promoter element, 5'UTR, and insertion element(s); (2) promoter element, 5'UTR, and target nucleotide sequence; (3) promoter element, 5'UTR, insertion element(s) and 3'UTR; and (4) promoter element, 5'UTR, target nucleotide sequence and 3'UTR.

A promoter element typically is required for DNA synthesis and/or RNA synthesis. A promoter often interacts with a RNA polymerase to generate message RNA suitable for translation of a protein, polypeptide or peptide. Promoter sequences are readily accessed and obtained by the artisan, and are readily adapted to nucleic acid compositions described herein. The particular promoter employed to control the expression of a polynucleotide sequence of interest is not believed to be important, so long as it is capable of directing the expression of the polynucleotide in the targeted cell. Thus, where a human cell is targeted, it is preferable to position the polynucleotide sequence-coding region adjacent to and under the control of a promoter that is capable of being expressed in a human cell. Generally speaking, such a promoter might include either a human or viral promoter. Examples of promoters include human cytomegalovirus (CMV) immediate early gene promoter, SV40 early promoter, Rous sarcoma virus long terminal repeat, .beta.-actin, elongation factor 1-alpha (EF-1.alpha.), rat insulin promoter and glyceraldehyde-3-phosphate dehydrogenase. The use of other viral or mammalian cellular or bacterial phage promoters which are well known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized.

In some circumstances, it is desirable to regulate expression of a transgene in an immunotherapy vector. For example, different viral promoters with varying strengths of activity are utilized depending on the level of expression desired. In mammalian cells, the CMV immediate early promoter can be used to provide strong transcriptional activation. Modified versions of the CMV promoter that are less potent have also been used when reduced levels of expression of the transgene are desired. When expression of a transgene in hematopoetic cells is desired, retroviral promoters such as the LTRs from MLV or MMTV can be used. Other viral promoters that are used depending on the desired effect include SV40, RSV LTR, HIV-1 and HIV-2 LTR, adenovirus promoters such as from the E1A, E2A, or MLP region, AAV LTR, HSV-TK, and avian sarcoma virus.

Tissue specific promoters sometimes are used to effect transcription in specific tissues or cells so as to reduce potential toxicity or undesirable effects to non-targeted tissues. For example, promoters such as the alpha myosin heavy chain (.alpha.MHC) promoter, directing expression to cardiac myocytes.

In certain indications, it is desirable to activate transcription at specific times after administration of an immunotherapy vector. Promoters that are hormone or cytokine regulatable often are utilized. Cytokine and inflammatory protein responsive promoters that can be used include K and T Kininogen (Kageyama et al., 1987), c-fos, TNF-alpha, C-reactive protein (Arcone et al., 1988), haptoglobin (Oliviero et al., 1987), serum amyloid A2, C/EBP alpha, IL-1, IL-6 (Poli and Cortese, 1989), Complement C3 (Wilson et al., 1990), IL-8, alpha-1 acid glycoprotein (Prowse and Baumann, 1988), alpha-1 antityrpsin, lipoprotein lipase (Zechner et al., 1988), angiotensinogen (Ron et al., 1991), fibrinogen, c-jun (inducible by phorbol esters, TNF-alpha, UV radiation, retinoic acid, and hydrogen peroxide), collagenase (induced by phorbol esters and retinoic acid), metallothionein (heavy metal and gluccocorticoid inducible), Stromelysin (inducible by phorbol ester, interleukin-1 and EGF), alpha-2 macroglobulin and alpha-1 antichymotrypsin. CID promoters also can be utilized (Ho et al., 1996; Rivera et al., 1996). Full citations of certain documents referenced herein are in U.S. 20030144204, published Jul. 31, 2003.

Other inducible promoters are known and can be utilized. An ecdysone system (Invitrogen, Carlsbad, Calif.) is one such system. This system is designed to allow regulated expression of a gene of interest in mammalian cells. It consists of a tightly regulated expression mechanism that allows virtually no basal level expression of the transgene, but over 200-fold inducibility. The system is based on the heterodimeric ecdysone receptor of *Drosophila*, and when ecdysone or an analog such as muristerone A binds to the receptor, the receptor activates a promoter to turn on expression of the downstream transgene high levels of mRNA transcripts are attained. In this system, both monomers of the heterodimeric receptor are constitutively expressed from one vector, whereas the ecdysone-responsive promoter, which drives expression of the gene of interest is on another plasmid. Engineering of this type of system into the gene transfer vector of interest would therefore be useful. Cotransfection of plasmids containing the gene of interest and the receptor monomers in the producer cell line would then allow for the production of the gene transfer vector without expression of a potentially toxic transgene. At the appropriate time, expression of the transgene could be activated with ecdysone or muristeron A. Another inducible system is the Tet-Off™ or Tet-On™ system (Clontech, Palo Alto, Calif.) originally developed by Gossen and Bujard (Gossen and Bujard, 1992; Gossen et al., 1995). This system also allows high levels of gene expression to be regulated in response to tetracycline or tetracycline derivatives such as doxycycline. In the Tet-On™ system, gene expression is turned on in the presence of doxycycline, whereas in the Tet-Off™ system, gene expression is turned on in the absence of doxycycline. These systems are based on two regulatory elements derived from the tetracycline resistance operon of *E. coli*. The tetracycline operator sequence to which the tetracycline repressor binds, and the tetracycline repressor protein. The gene of interest is cloned into a plasmid behind a promoter that has tetracycline-responsive elements present in it. A second plasmid contains a regulatory element called the tetracycline-controlled transactivator, which is composed, in the Tet-Off™ system, of the VP16 domain from the herpes simplex virus and the wild-type tertracycline repressor. Thus in the absence of doxycycline, transcription is constitutively on. In the Tet-On™ system, the tetracycline repressor is not wild type and in the presence of doxycycline activates transcription. For gene therapy vector production, the Tet-Offm system would be preferable so that the producer cells could be grown in the presence of tetracycline or doxycycline and prevent expression of a potentially toxic transgene, but when the vector is introduced to the patient, the gene expression would be induced constitutively.

It is envisioned that any of the above promoters alone or in combination with another can be useful according to the present invention depending on the action desired. In addition, this list of promoters should not be construed to be exhaustive or limiting, those of skill in the art will know of other promoters that are used in conjunction with the promoters and methods disclosed herein.

A 5' UTR may comprise one or more elements endogenous to the nucleotide sequence from which it originates, and sometimes includes one or more exogenous elements. A 5' UTR can originate from any suitable nucleic acid, such as genomic DNA, plasmid DNA, RNA or mRNA, for example, from any suitable organism (e.g., virus, bacterium, yeast, fungi, plant, insect or mammal). The artisan may select appropriate elements for the 5' UTR based upon the transcription and/or translation system being utilized. A 5' UTR sometimes comprises one or more of the following elements known to the artisan: enhancer sequence (e.g., Eukaryotic Promoter Data Base EPDB), translational enhancer sequence, transcription initiation site, transcription factor binding site, translation regulation site, translation initiation site, translation factor binding site, ribosome binding site, replicon, enhancer element, internal ribosome entry site (IRES), and silencer element.

A 5'UTR in the nucleic acid composition can comprise a translational enhancer nucleotide sequence. A translational enhancer nucleotide sequence often is located between the promoter and the target nucleotide sequence in a nucleic acid composition. A translational enhancer sequence often binds to a ribosome, sometimes is an 18S rRNA-binding ribonucleotide sequence (i.e., a 40S ribosome binding sequence) and sometimes is an internal ribosome entry sequence (IRES). An IRES generally forms an RNA scaffold with precisely placed RNA tertiary structures that contact a 40S ribosomal subunit via a number of specific intermolecular interactions. Examples of ribosomal enhancer sequences are known and can be identified by the artisan (e.g., Mignone et al., Nucleic Acids Research 33: D141-D146 (2005); Paulous et al., Nucleic Acids Research 31: 722-733 (2003); Akbergenov et al., Nucleic Acids Research 32: 239-247 (2004); Mignone et al., Genome Biology 3(3): reviews0004.1-0001.10 (2002); Gallie, Nucleic Acids Research 30: 3401-3411 (2002); Shaloiko et al., http address www.interscience.wiley.com, DOI: 10.1002/bit.20267; and Gallie et al., Nucleic Acids Research 15: 3257-3273 (1987)). A translational enhancer sequence sometimes is a eukaryotic sequence, such as a Kozak consensus sequence or other sequence (e.g., hydroid polyp sequence, GenBank accession no. U07128). A translational enhancer sequence sometimes is a prokaryotic sequence, such as a Shine-Dalgarno consensus sequence. In certain embodiments, the translational enhancer sequence is a viral nucleotide sequence. A translational enhancer sequence sometimes is from a 5'UTR of a plant virus, such as Tobacco Mosaic Virus (TMV), Alfalfa Mosaic Virus (AMV); Tobacco Etch Virus (ETV); Potato Virus Y (PVY); Turnip Mosaic (poty) Virus and Pea Seed Borne Mosaic Virus, for example. In certain embodiments, an omega sequence about 67 bases in length from TMV is included in the nucleic acid composition as a translational enhancer sequence (e.g., devoid of guanosine nucleotides and includes a 25 nucleotide long poly (CAA) central region). In some embodiments, a translational enhancer sequence comprises one or more ARC-1 or ARC-1 like sequence, such as one of the following nucleotide sequences GCCGGCGGAG (SEQ ID NO: 12), CUCAUAAGGU (SEQ ID NO: 13), GACUUUGAUU (SEQ ID NO: 14), CGGAACCCAA (SEQ ID NO: 15), AUACUCCCCC (SEQ ID NO: 16) and CCUUGCGACC (SEQ ID NO: 17), or a substantially identical sequence thereof. In certain embodiments, a translational enhancer sequence comprises an IRES sequence, such as one or more of EMBL nucleotide sequences J04513, X87949, M95825, M12783, AF025841, AF013263, AF006822, M17169, M13440, M22427, D14838 and M17446, or a substantially identical nucleotide sequence thereof. An IRES sequence may be a type I IRES (e.g., from enterovirus (e.g., poliovirus), rhinovirus (e.g., human rhinovirus)), a type II IRES (e.g., from cardiovirus (e.g., encephalomyocraditis virus), aphthovirus (e.g., foot-and-mouth disease virus)), a type III IRES (e.g., from Hepatitis A virus) or other picornavirus sequence (e.g., Paulos et al. supra, and Jackson et al., RNA 1:985-1000 (1995)).

A 3' UTR may comprise one or more elements endogenous to the nucleotide sequence from which it originates and sometimes includes one or more exogenous elements. A 3' UTR may originate from any suitable nucleic acid, such as genomic DNA, plasmid DNA, RNA or mRNA, for example, from any suitable organism (e.g., a virus, bacterium, yeast, fungi, plant, insect or mammal). The artisan can select appropriate elements for the 3' UTR based upon the transcription and/or translation system being utilized. A 3' UTR sometimes comprises one or more of the following elements known to the artisan: transcription regulation site, transcription initiation site, transcription termination site, transcription factor binding site, translation regulation site, translation termination site, translation initiation site, translation factor binding site, ribosome binding site, replicon, enhancer element, silencer element and polyadenosine tail. A 3'UTR can include a polyadenosine tail, and sometimes may not. If a polyadenosine tail is present, one or more adenosine moieties may be added or deleted from the native length (e.g., about 5, about 10, about 15, about 20, about 25, about 30, about 35, about 40, about 45 or about 50 adenosine moieties may be added or subtracted).

The term a "target nucleotide sequence" as used herein encodes a nucleic acid, peptide, polypeptide or protein of interest, and may be a ribonucleotide sequence or a deoxyribonucleotide sequence. An Akt nucleotide sequence (e.g., a chimeric sequence encoding an Akt sequence and a membrane-association sequence) may be incorporated into a nucleic acid composition as a target nucleotide sequence. The term "nucleic acid" as used herein is generic to polydeoxyribonucleotides (containing 2'-deoxy-D-ribose or modified forms thereof), to polyribonucleotides (containing D-ribose or modified forms thereof), and to any other type of polynucleotide which is an N-glycoside of a purine or pyrimidine bases, or modified purine or pyrimidine bases. A target nucleic acid can include an untranslated ribonucleic acid and sometimes is a translated ribonucleic acid. An untranslated ribonucleic acid may include, but is not limited to, a small interfering ribonucleic acid (siRNA), a short hairpin ribonucleic acid (shRNA), other ribonucleic acid capable of RNA interference (RNAi), an antisense ribonucleic acid, or a ribozyme. A translatable target nucleotide sequence (e.g., a target ribonucleotide sequence) sometimes encodes a peptide, polypeptide or protein, which are sometimes referred to herein as "target peptides," "target polypeptides" or "target proteins." The term "protein" as used herein refers to a molecule having a sequence of amino acids linked by peptide bonds. This term includes fusion proteins, oligopeptides, polypeptides, cyclic peptides, polypeptides and polypeptide derivatives. A protein or polypeptide sometimes is of intracellular origin (e.g., located in the nucleus, cytosol, or interstitial space of host cells in vivo) and sometimes is a cell membrane protein in vivo.

A translatable nucleotide sequence generally is located between a start codon (AUG in ribonucleic acids and ATG in deoxyribonucleic acids) and a stop codon (e.g., UAA (ochre), UAG (amber) or UGA (opal) in ribonucleic acids and TAA, TAG or TGA in deoxyribonucleic acids), and sometimes is referred to herein as an "open reading frame" (ORF). A nucleic acid composition sometimes comprises one or more ORFs. An ORF may be from any suitable source, sometimes from genomic DNA, mRNA, reverse transcribed RNA or complementary DNA (cDNA) or a nucleic acid library comprising one or more of the foregoing, and is from any organism species, such as human, insect, nematode, bovine, equine, canine, feline, rat or mouse, for example. An Akt nucleotide sequence often is utilized as an ORF herein, and sometimes a membrane association region-encoding nucleotide sequence is utilized as an ORF.

A nucleic acid composition sometimes comprises a nucleotide sequence adjacent to an ORF that is translated in conjunction with the ORF and encodes an amino acid tag. The tag-encoding nucleotide sequence is located 3' and/or 5' of an ORF in the nucleic acid composition, thereby encoding a tag at the C-terminus or N-terminus of the protein or peptide encoded by the ORF. Any tag that does not abrogate or substantially reduce transcription and/or translation may be utilized and may be appropriately selected by the artisan. A tag sometimes specifically binds a molecule or moiety of a solid phase or a detectable label, for example, thereby having utility for isolating, purifying and/or detecting a protein or peptide encoded by the ORF. In some embodiments, a tag comprises one or more of the following elements: FLAG (e.g., DYKDDDDKG, SEQ ID NO: 18), AU1 (e.g., DTYRYI, SEQ ID NO: 19), V5 (e.g., GKPIPNPLLGLDST, SEQ ID NO: 20), c-MYC (e.g., EQKLISEEDL, SEQ ID NO: 21), HSV (e.g., QPELAPEDPED, SEQ ID NO: 22), influenza hemaglutinin, HA (e.g., YPYDVPDYA, SEQ ID NO: 23), VSV-G (e.g., YTDIEMNRLGK, SEQ ID NO: 24), bacterial glutathione-S-transferase, maltose binding protein, a streptavidin- or avidin-binding tag (e.g., pcDNA™6 BioEase™ Gateway® Biotinylation System (Invitrogen)), thioredoxin, β-galactosidase, VSV-glycoprotein, a fluorescent protein (e.g., green fluorescent protein or one of its many color variants (e.g., yellow, red, blue)), a polylysine or polyarginine sequence, a polyhistidine sequence (e.g., $His_6$, SEQ ID NO: 25) or other sequence that chelates a metal (e.g., cobalt, zinc, copper) and/or a cysteine-rich sequence that binds to an arsenic-containing molecule. In certain embodiments, a cysteine-rich tag comprises the amino acid sequence CC—$X_n$—CC (SEQ ID NO: 26), wherein X is any amino acid and n is 1 to 3, and the cysteine-rich sequence sometimes is CCPGCC (SEQ ID NO: 27). In certain embodiments, the tag comprises a cysteine-rich element and a polyhistidine element (e.g., CCPGCC (SEQ ID NO: 27) and $His_6$ (SEQ ID NO: 25)).

A tag often conveniently binds to a binding partner. For example, some tags bind to an antibody (e.g., FLAG) and sometimes specifically bind to a small molecule. For example, a polyhistidine tag specifically chelates a bivalent metal, such as copper, zinc and cobalt; a polylysine or polyarginine tag specifically binds to a zinc finger; a glutathione S-transferase tag binds to glutathione; and a cysteine-rich tag specifically binds to an arsenic-containing molecule. Arsenic-containing molecules include LUMIO™ agents (Invitrogen, California), such as FlAsH™ ($EDT_2$[4',5'-bis(1,3, 2-dithioarsolan-2-yl)fluorescein-(1,2-ethanedithiol)$_2$]) and ReAsH reagents (e.g., U.S. Pat. No. 5,932,474 to Tsien et al., entitled "Target Sequences for Synthetic Molecules;" U.S. Pat. No. 6,054,271 to Tsien et al., entitled "Methods of Using Synthetic Molecules and Target Sequences;" U.S. Pat. Nos. 6,451,569 and 6,008,378; published U.S. Patent Application 2003/0083373, and published PCT Patent Application WO 99/21013, all to Tsien et al. and all entitled "Synthetic Molecules that Specifically React with Target Sequences"). Such antibodies and small molecules sometimes are linked to a solid phase for convenient isolation of the target protein or target peptide, as described in greater detail hereafter.

A tag sometimes comprises a sequence that localizes a translated protein or peptide to a component in a system, which is referred to as a "signal sequence" or "localization signal sequence" herein. A signal sequence often is incorporated at the N-terminus of a target protein or target peptide, and sometimes is incorporated at the C-terminus. Examples of signal sequences are known to the artisan, are readily incorporated into a nucleic acid composition, and often are selected according to the cells from which a cell-free extract is prepared. A signal sequence in some embodiments localizes a translated protein or peptide to a cell membrane. Examples of signal sequences include, but are not limited to, a nucleus targeting signal (e.g., steroid receptor sequence and N-terminal sequence of SV40 virus large T antigen); mitochondia targeting signal (e.g., amino acid sequence that forms an amphipathic helix); peroxisome targeting signal (e.g., C-terminal sequence in YFG from *S. cerevisiae*); and a secretion signal (e.g., N-terminal sequences from invertase, mating factor alpha, PHO5 and SUC2 in *S. cerevisiae*; multiple N-terminal sequences of *B. subtilis* proteins (e.g., Tjalsma et al., Microbiol. Molec. Biol. Rev. 64: 515-547 (2000)); alpha amylase signal sequence (e.g., U.S. Pat. No. 6,288,302); pectate lyase signal sequence (e.g., U.S. Pat. No. 5,846,818); precollagen signal sequence (e.g., U.S. Pat. No. 5,712,114); OmpA signal sequence (e.g., U.S. Pat. No. 5,470,719); lam beta signal sequence (e.g., U.S. Pat. No. 5,389,529); *B. brevis* signal sequence (e.g., U.S. Pat. No. 5,232,841); and *P. pastoris* signal sequence (e.g., U.S. Pat. No. 5,268,273)).

A tag sometimes is directly adjacent to the amino acid sequence encoded by an ORF (i.e., there is no intervening sequence) and sometimes a tag is substantially adjacent to a the ORF encoded amino acid sequence (e.g., an intervening sequence is present). An intervening sequence sometimes includes a recognition site for a protease, which is useful for cleaving a tag from a target protein or peptide. In some embodiments, the intervening sequence is cleaved by Factor Xa (e.g., recognition site I(E/D)GR), thrombin (e.g., recognition site LVPRGS, SEQ ID NO: 28), enterokinase (e.g., recognition site DDDDK, SEQ ID NO: 29), TEV protease (e.g., recognition site ENLYFQG, SEQ ID NO: 30) or PreScission™ protease (e.g., recognition site LEVLFQGP, SEQ ID NO: 31), for example.

An intervening sequence sometimes is referred to herein as a "linker sequence," and may be of any suitable length selected by the artisan. A linker sequence sometimes is about 1 to about 20 amino acids in length, and sometimes about 5 to about 10 amino acids in length. The artisan may select the linker length to substantially preserve target protein or peptide function (e.g., a tag may reduce target protein or peptide function unless separated by a linker), to enhance disassociation of a tag from a target protein or peptide when a protease cleavage site is present (e.g., cleavage may be enhanced when a linker is present), and to enhance interaction of a tag/target protein product with a solid phase. A linker can be of any suitable amino acid content, and often comprises a higher proportion of amino acids having relatively short side chains (e.g., glycine, alanine, serine and threonine).

A nucleic acid composition sometimes includes a stop codon between a tag element and an insertion element or ORF, which can be useful for translating an ORF with or without the tag. Mutant tRNA molecules that recognize stop codons (described above) suppress translation termination and thereby are designated "suppressor tRNAs." Suppressor tRNAs can result in the insertion of amino acids and continuation of translation past stop codons (e.g., U.S. Patent Application No. 60/587,583, filed Jul. 14, 2004, entitled "Production of Fusion Proteins by Cell-Free Protein Synthesis,"; Eggertsson, et al., (1988) Microbiological Review 52(3):354-374, and Engleerg-Kukla, et al. (1996) in *Escherichia coli* and *Salmonella* Cellular and Molecular Biology, Chapter 60, pps 909-921, Neidhardt, et al. eds., ASM, Washington, D.C.). A number of suppressor tRNAs are known, including but not limited to, supE, supP, supD, supF and supZ suppressors, which suppress the termination of translation of the amber stop codon; supB, glT, supL, supN, supC and supM suppressors, which suppress the function of the ochre stop codon and glyT, trpT and Su-9 suppressors, which suppress the function of the opal stop codon. In general, suppressor tRNAs contain one or more mutations in the anti-codon loop of the tRNA that allows the tRNA to base pair with a codon that ordinarily functions as a stop codon. The mutant tRNA is charged with its cognate amino acid residue and the cognate amino acid residue is inserted into the translating polypeptide when the stop codon is encountered. Mutations that enhance the efficiency of termination suppressors (i.e., increase stop codon read-through) have been identified. These include, but are not limited to, mutations in the uar gene (also known as the prfA gene), mutations in the ups gene, mutations in the sueA, sueB and sueC genes, mutations in the rpsD (ramA) and rpsE (spcA) genes and mutations in the rplL gene.

Thus, a nucleic acid composition comprising a stop codon located between an ORF and a tag can yield a translated ORF alone when no suppressor tRNA is present in the translation system, and can yield a translated ORF-tag fusion when a suppressor tRNA is present in the system. In some embodiments, the stop codon is located 3' of an insertion element or ORF and 5' of a tag, and the stop codon sometimes is an amber codon. Suppressor tRNA sometimes are within a cell-free extract (e.g., the cell-free extract is prepared from cells that produce the suppressor tRNA), sometimes are added to the cell-free extract as isolated molecules, and sometimes are added to a cell-free extract as part of another extract. A provided suppressor tRNA sometimes is loaded with one of the twenty naturally occurring amino acids or an unnatural amino acid (described herein). Suppressor tRNA can be generated in cells transfected with a nucleic acid encoding the tRNA (e.g., a replication incompetent adenovirus containing the human tRNA-Ser suppressor gene can be transfected into cells). Vectors for synthesizing suppressor tRNA and for translating ORFs with or without a tag are available to the artisan (e.g., Tag-On-Demand™ kit (Invitrogen Corporation, California); Tag-On-Demand™ Suppressor Supernatant Instruction Manual, Version B, 6 Jun. 2003, at http address www.invitrogen.com/content/sfs/manuals/tagondemand_supernatant_man.pdf; Tag-On-Demand™ Gateway® Vector Instruction Manual, Version B, 20 Jun., 2003 at http address www.invitrogen.com/content/sfs/manuals/tagondemand_vectors_man.pdf; and Capone et al., Amber, ochre and opal suppressor tRNA genes derived from a human serine tRNA gene. EMBO J. 4:213, 1985).

Any convenient cloning strategy known to the artisan may be utilized to incorporate an element, such as an ORF, into a nucleic acid composition. Known methods can be utilized to insert an element into the template independent of an insertion element, such as (1) cleaving the template at one or more existing restriction enzyme sites and ligating an element of interest and (2) adding restriction enzyme sites to the template by hybridizing oligonucleotide primers that include one or more suitable restriction enzyme sites and amplifying by polymerase chain reaction (described in greater detail herein). Other cloning strategies take advantage of one or more insertion sites present or inserted into the nucleic acid composition, such as an oligonucleotide primer hybridization site for PCR, for example, and others described hereafter.

In some embodiments, the nucleic acid composition includes one or more recombinase insertion sites. A recombinase insertion site is a recognition sequence on a nucleic acid molecule that participates in an integration/recombination reaction by recombination proteins. For example, the recombination site for Cre recombinase is loxP, which is a 34 base pair sequence comprised of two 13 base pair inverted repeats (serving as the recombinase binding sites) flanking an 8 base pair core sequence (e.g., FIG. 1 of Sauer, B., Curr. Opin. Biotech. 5:521-527 (1994)). Other examples of recombination sites include attB, attP, attL, and attR sequences, and mutants, fragments, variants and derivatives thereof, which are recognized by the recombination protein λ Int and by the auxiliary proteins integration host factor (IHF), FIS and excisionase (Xis) (e.g., U.S. Pat. Nos. 5,888,732; 6,143,557; 6,171,861; 6,270,969; 6,277,608; and 6,720,140; U.S. patent application Ser. No. 09/517,466, filed Mar. 2, 2000, and 09/732,914, filed Aug. 14, 2003, and in U.S. patent publication no. 2002-0007051-A1; Landy, Cuff. Opin. Biotech. 3:699-707 (1993)). Examples of recombinase cloning nucleic acids are in Gateway® systems (Invitrogen, California), which include at least one recombination site for cloning a desired nucleic acid molecules in vivo or in vitro. In some embodiments, the system utilizes vectors that contain at least two different site-specific recombination sites, often based on the bacteriophage lambda system (e.g., att1 and att2), and are mutated from the wild-type (att0) sites. Each mutated site has a unique specificity for its cognate partner att site (i.e., its binding partner recombination site) of the same type (for example attB1 with attP1, or attL1 with attR1) and will not cross-react with recombination sites of the other mutant type or with the wild-type att0 site. Different site specificities allow directional cloning or linkage of desired molecules thus providing desired orientation of the cloned molecules. Nucleic acid fragments flanked by recombination sites are cloned and subcloned using the Gateway® system by replacing a selectable marker (for example, ccdB) flanked by att sites on the recipient plasmid molecule, sometimes termed the Destination Vector. Desired clones are then selected by transformation of a ccdB sensitive host strain and positive selection for a marker on the recipient molecule. Similar strategies for negative selection (e.g., use of toxic genes) can be used in other organisms such as thymidine kinase (TK) in mammals and insects.

In certain embodiments, the nucleic acid composition includes one or more topoisomerase insertion sites. A topoisomerase insertion site is a defined nucleotide sequence recognized and bound by a site-specific topoisomerase. For example, the nucleotide sequence 5'-(C/T)CCTT-3' is a topoisomerase recognition site bound specifically by most poxvirus topoisomerases, including vaccinia virus DNA topoisomerase I. After binding to the recognition sequence, the topoisomerase cleaves the strand at the 3'-most thymidine of the recognition site to produce a nucleotide sequence comprising 5'-(C/T)CCTT-$PO_4$-TOPO, a complex of the topoisomerase covalently bound to the 3' phosphate via a tyrosine in the topoisomerase (e.g., Shuman, J. Biol. Chem. 266: 11372-11379, 1991; Sekiguchi and Shuman, Nucl. Acids Res. 22:5360-5365, 1994; U.S. Pat. No. 5,766,891; PCT/US95/16099; and PCT/US98/12372). In comparison, the nucleotide sequence 5'-GCAACTT-3' is a topoisomerase recognition site for type IA E. coli topoisomerase III. An element to be inserted often is combined with topoisomerase-reacted template and thereby incorporated into the nucleic acid composition (e.g., http address www.invitrogen.com/downloads/F-13512_Topo_Flyer.pdf; http address at www.invitrogen.com/content/sfs/brochures/710_021849%20_B_TOPO-Cloning_bro.pdf; TOPO TA Cloning® Kit and Zero Blunt® TOPO® Cloning Kit product information).

A nucleic acid composition sometimes contains one or more origin of replication (ORI) elements. In some embodiments, a template comprises two or more ORIs, where one functions efficiently in one organism (e.g., a bacterium) and another functions efficiently in another organism (e.g., a eukaryote). In some embodiments, an ORI may function efficiently in insect cells and another ORI may function efficiently in mammalian cells. A nucleic acid composition also sometimes includes one or more transcription regulation sites.

A nucleic acid composition often includes one or more selection elements. Selection elements often are utilized using known processes to determine whether a nucleic acid composition is included in a cell. In some embodiments, a nucleic acid composition includes two or more selection elements, where one functions efficiently in one organisms and another functions efficiently in another organism. Examples of selection elements include, but are not limited to, (1) nucleic acid segments that encode products that provide resistance against otherwise toxic compounds (e.g., antibiotics); (2) nucleic acid segments that encode products that are otherwise lacking in the recipient cell (e.g., essential products, tRNA genes, auxotrophic markers); (3) nucleic acid segments that encode products that suppress the activity of a gene product; (4) nucleic acid segments that encode products that can be readily identified (e.g., phenotypic markers such as antibiotics (e.g., β-lactamase), β-galactosidase, green fluorescent protein (GFP), yellow fluorescent protein (YFP), red fluorescent protein (RFP), cyan fluorescent protein (CFP), and cell surface proteins); (5) nucleic acid segments that bind products that are otherwise detrimental to cell survival and/or function; (6) nucleic acid segments that otherwise inhibit the activity of any of the nucleic acid segments described in Nos. 1-5 above (e.g., antisense oligonucleotides); (7) nucleic acid segments that bind products that modify a substrate (e.g., restriction endonucleases); (8) nucleic acid segments that can be used to isolate or identify a desired molecule (e.g., specific protein binding sites); (9) nucleic acid segments that encode a specific nucleotide sequence that can be otherwise non-functional (e.g., for PCR amplification of subpopulations of molecules); (10) nucleic acid segments that, when absent, directly or indirectly confer resistance or sensitivity to particular compounds; (11) nucleic acid segments that encode products that either are toxic (e.g., Diphtheria toxin) or convert a relatively non-toxic compound to a toxic compound (e.g., Herpes simplex thymidine kinase, cytosine deaminase) in recipient cells; (12) nucleic acid segments that inhibit replication, partition or heritability of nucleic acid molecules that contain them; and/or (13) nucleic acid segments that encode conditional replication functions, e.g., replication in certain hosts or host cell strains or under certain environmental conditions (e.g., temperature, nutritional conditions, and the like).

Certain nucleotide sequences sometimes are added to, modified or removed from one or more of the nucleic acid composition elements, such as the promoter, 5'UTR, target sequence, or 3'UTR elements, to enhance or potentially enhance transcription and/or translation before or after such elements are incorporated in a nucleic acid composition. In some embodiments, one or more of the following sequences may be modified or removed if they are present in a 5'UTR: a sequence that forms a stable secondary structure (e.g., quadruplex structure or stem loop stem structure (e.g., EMBL sequences X12949, AF274954, AF139980, AF152961, S95936, U194144, AF116649 or substantially identical sequences that form such stem loop stem structures)); a translation initiation codon upstream of the target nucleotide sequence start codon; a stop codon upstream of the target nucleotide sequence translation initiation codon; an ORF upstream of the target nucleotide sequence translation initiation codon; an iron responsive element (IRE) or like sequence; and a 5' terminal oligopyrimidine tract (TOP, e.g., consisting of 5-15 pyrimidines adjacent to the cap). A translational enhancer sequence and/or an internal ribosome entry site (IRES) sometimes is inserted into a 5'UTR (e.g., EMBL nucleotide sequences J04513, X87949, M95825, M12783, AF025841, AF013263, AF006822, M17169, M13440, M22427, D14838 and M17446 and substantially identical nucleotide sequences). An AU-rich element (ARE, e.g., AUUUA repeats) and/or splicing junction that follows a nonsense codon sometimes is removed from or modified in a 3'UTR. A polyadenosine tail sometimes is inserted into a 3'UTR if none is present, sometimes is removed if it is present, and adenosine moieties sometimes are added to or removed from a polyadenosine tail present in a 3'UTR. Thus, some embodiments are directed to a process comprising: determining whether any nucleotide sequences that reduce or potentially reduce translation efficiency are present in the elements, and removing or modifying one or more of such sequences if they are identified. Certain embodiments are directed to a process comprising: determining whether any nucleotide sequences that increase or potentially increase translation efficiency are not present in the elements, and incorporating such sequences into the nucleic acid composition.

An ORF sometimes is mutated or modified (for example, by point mutation, deletion mutation, insertion mutation, and the like) to alter, enhance or increase, reduce, substantially reduce or eliminate the activity of the encoded protein or peptide. The protein or peptide encoded by a modified ORF sometimes is produced in a lower amount or may not be produced at detectable levels, and in other embodiments, the product or protein encoded by the modified ORF is produced at a higher level (e.g., codons sometimes are modified so they are compatible with tRNA in cells used to prepare a cell-free extract). To determine the relative activity, the activity from the product of the mutated ORF (or cell containing it) can be compared to the activity of the product or protein encoded by the unmodified ORF (or cell containing it).

A stop codon at the end of an ORF sometimes is modified to another stop codon, such as an amber stop codon described above. In some embodiments, a stop codon is introduced within an ORF, sometimes by insertion or mutation of an existing codon. An ORF comprising a modified terminal stop codon and/or internal stop codon often is translated in a system comprising a suppressor tRNA that recognizes the stop codon. An ORF comprising a stop codon sometimes is translated in a system comprising a suppressor tRNA that incorporates an unnatural amino acid during translation of the target protein or target peptide. Methods for incorporating unnatural amino acids into a target protein or peptide are known, which include, for example, processes utilizing a heterologous tRNA/synthetase pair, where the tRNA recognizes an amber stop codon and is loaded with an unnatural amino acid (e.g., http address www.iupac.org/news/prize/2003/wang.pdf). Examples of unnatural amino acids are described above.

A nucleic acid composition is of any form useful for in vitro or in vivo transcription and/or translation. A nucleic acid sometimes is a plasmid, such as a supercoiled plasmid, sometimes is a linear nucleic acid (e.g., a linear nucleic acid produced by PCR or by restriction digest), sometimes is single-stranded and sometimes is double-stranded. A nucleic acid composition for transcription and/or translation can be prepared by any suitable process. A nucleic acid composition sometimes is prepared by an amplification process, such as a polymerase chain reaction (PCR) process or transcription-mediated amplification process (TMA). In TMA, two enzymes are used in an isothermal reaction to produce amplification products detected by light emission (see, e.g., Biochemistry 1996 Jun. 25; 35(25):8429-38 and http address www.devicelink.com/ivdt/archive/00/11/007.html). Standard PCR processes are known (e.g., U.S. Pat. Nos. 4,683,202; 4,683,195; 4,965,188; and 5,656,493), and generally are performed in cycles. Each cycle includes heat denaturation, in which hybrid nucleic acids dissociate; cooling, in which primer oligonucleotides hybridize; and extension of the oligonucleotides by a polymerase (i.e., Taq polymerase). An example of a PCR cyclical process is treating the sample at 95° C. for 5 minutes; repeating forty-five cycles of 95° C. for 1 minute, 59° C. for 1 minute, 10 seconds, and 72° C. for 1 minute 30 seconds; and then treating the sample at 72° C. for 5 minutes. Multiple cycles frequently are performed using a commercially available thermal cycler. PCR amplification products sometimes are stored for a time at a lower temperature (e.g., at 4° C.) and sometimes are frozen (e.g., at −20° C.) before analysis.

In some embodiments, a nucleic acid of other molecule described herein is isolated or purified. The term "isolated" as used herein refers to material removed from its original environment (e.g., the natural environment if it is naturally occurring, or a host cell if expressed exogenously), and thus is altered "by the hand of man" from its original environment. The term "purified" as used herein with reference to molecules does not refer to absolute purity. Rather, "purified" refers to a substance in a composition that contains fewer substance species in the same class (e.g., nucleic acid or protein species) other than the substance of interest in comparison to the sample from which it originated. "Purified," if a nucleic acid or protein for example, refers to a substance in a composition that contains fewer nucleic acid species or protein species other than the nucleic acid or protein of interest in comparison to the sample from which it originated. Sometimes, a protein or nucleic acid is "substantially pure," indicating that the protein or nucleic acid represents at least 50% of protein or nucleic acid on a mass basis of the composition. Often, a substantially pure protein or nucleic acid is at least 75% on a mass basis of the composition, and sometimes at least 95% on a mass basis of the composition.

Other nucleotide sequences not specifically described herein can be included in nucleic acid compositions, as selected for an application of the nucleic acid composition by the person of ordinary skill in the art. Certain sequences described in the section below entitled "Nucleic Acid Transfer to Antigen Presenting Cells," which include viral nucleotide sequences, sometimes are included in nucleic acid compositions.

Antigen Presenting Cells

Any antigen presenting cell (APC) can be used with the methods of the present invention. The term "APC" encompasses any cell capable of handling and presenting an antigen to lymphocytes. Typically, APCs include, e.g., macrophages, Langerhans dendritic cells and Follicular dendritic cells. In addition, B cells have also been shown to have an antigen presenting function and are thus contemplated by the present invention. The APCs often are dendritic cells. A "dendritic cell" (DC) is an APC with a characteristic morphology including lamellipodia extending from the dendritic cell body in several directions. Dendritic cells are able to initiate primary, antigen-specific T cell responses both in vitro and in vivo, and direct a strong mixed leukocyte reaction (MLR) compared to peripheral blood leukocytes, splenocytes, B cells and monocytes. DCs can be derived from a number of different hematopoietic precursor cells. For a general description of dendritic cells, including their differentiation and maturation, see, e.g. Steinman, Annu Rev Immunol. 9:271-96 (1991), and Lotze and Thomson, Dendritic Cells, 2nd Edition, Academic Press, 2001.

APCs can be isolated from any of the tissues where they reside and which are known to those of skill in the art. In particular, dendritic cells and their progenitors may be obtained from any tissue source comprising dendritic cell precursors that are capable of proliferating and maturing in vitro into dendritic cells, when cultured and induced to mature according to the methods of the present invention. Such suitable tissue sources include, e.g., peripheral blood, bone marrow, tumor-infiltrating cells, peritumoral tissues-infiltrating cells, lymph node biopsies, thymus, spleen, skin, umbilical cord blood, monocytes harvested from peripheral blood, CD34 or CD14 positive cells harvested from peripheral blood, blood marrow or any other suitable tissue or fluid. Dendritic cells sometimes are isolated from bone marrow or from peripheral blood mononuclear cells (PBMCs).

Peripheral blood can be collected using any standard apheresis procedure known in the art (see, e.g., Bishop et al., Blood 83:610:616 (1994)). PBMCs can then be prepared from whole blood samples by separating mononuclear cells from red blood cells. There are a number of methods for isolating PBMCs including, e.g., velocity sedimentation, isopyknic sedimentation, affinity purification, and flow cytometry. Typically, PBMCs are separated from red blood cells by density gradient (isopyknic) centrifugation, in which the cells sediment to an equilibrium position in the solution equivalent to their own density. For density gradient centrifugation, physiological media should be used, the density of the solution should be high, and the media should exert little osmotic pressure. Density gradient centrifugation uses solutions such as sodium ditrizoate-polysucrose, Ficoll, dextran, and Percoll (see, e.g., Freshney, Culture of Animal Cells, 3rd ed. (1994)). Such solutions are commercially available, e.g., HISTOPAQUE® (Sigma). Examples of methods for isolating dendritic cells from PBMCs are disclosed in, e.g., U.S. Pat. Nos. 6,017,527 and 5,851,756; and in O'Doherty et al., J. Exp. Med. 178:1067-1078 (1993); Young and Steinman, J. Exp. Med. 171:1315-1332 (1990); Freudenthal and Steinman, Proc. Natl. Acad. Sci. USA 57:7698-7702 (1990); Macatonia et al., Immunol. 67: 285-289 (1989); and Markowicz and Engleman, J. Clin. Invest. 85:955-961 (1990).

CD34+ PBMCs or CD14+ PBMCs can further be selected as a source of dendritic cells using a variety of selection techniques known to those of skill in the art. For example, monoclonal antibodies (or any protein-specific binding protein) can be used to bind to a cell surface antigen found on the surface of the PBMC sub-population of interest (e.g., CD34 or CD14 on the surface of CD34+ or CD 14+ PBMCs, respectively). Binding of such specific monoclonal antibodies allows the identification and isolation of the sub-group of PBMCs of interest from a total PBMC population by any of a number of immunoaffinity methods known to those of skill in the art. Examples of immunoaffinity methods for isolating sub-populations of PBMCs are described in, e.g., U.S. Pat. No. 6,017,527.

Alternatively, the dendritic cells of the present invention can be isolated from bone marrow. For a general description of methods for isolating dendritic cells from bone marrow see, e.g., U.S. Pat. No. 5,994,126; Dexter et al., in Long-Term Bone Marrow Culture, pages 57-96, Alan R. Liss, (1984); and Lutz et al., J. Immunol. Methods 223:77-92 (1999). Dendritic cells from bone marrow can typically be obtained from a number of different sources, including, for example, from aspirated marrow. Alternatively, bone marrow can be extracted from a sacrificed animal by dissecting out the femur, removing soft tissue from the bone and removing the bone marrow with a needle and syringe. Dendritic cells can be identified among the different cell types present in the bone marrow based on their morphological characteristics. For example, cultured immature dendritic cells in one or more phases of their development are loosely adherent to plastic, flattening out with a stellate shape.

Optionally, prior to culturing the cells, the tissue source can be pre-treated to remove cells that may compete with the proliferation and/or the survival of the dendritic cells or of their precursors. Examples of such pre-treatments are described, e.g., in U.S. Pat. No. 5,994,126.

Those of skill in the art will recognize that APCs can be cultured for any suitable amount of time. Antigen presenting cells often are cultured from 4 to 15 days, can be cultured for 10-12 days (Lutz et al., supra) and may be cultured for 5-7 days (Inaba et al., J. Exp. Med. 176:1693 (1992); Inaba et al., J. Exp. Med. 175:1157 (1992); Inaba et al., Current Protocols Immunol., Unit 3.7 (Coico et al., eds. 1998); Schneider et al., J. Immunol. Meth. 154:253 (1992)). Examples of cell culture conditions for dendritic cells and dendritic cell precursors are known to the person of ordinary skill in the art and are described in, e.g., U.S. Pat. Nos. 6,017,527 and 5,851,756; Inaba et al., J. Exp. Med. 176:1693 (1992); Inaba et al., J. Exp. Med. 175:1157 (1992); Inaba et al., Current Protocols Immunol., Unit 3.7 (Coico et al., eds. 1998); Schneider et al., J. Immunol. Meth. 154:253 (1992); and Lutz et al., supra.

In general, a cell culture environment includes consideration of such factors as the substrate for cell growth, cell density and cell contract, the gas phase, the medium, the temperature, and the presence of growth factors (see, e.g., Freshney et al., Culture of Animal Cells, 3rd ed. (1994)). Cells can be grown under conditions that provide for cell to cell contact, and may be grown in suspension as three dimensional aggregates. Suspension cultures can be achieved by using, e.g., a flask with a magnetic stirrer or a large surface area paddle, or on a plate that has been coated to prevent the cells from adhering to the bottom of the dish. For example, the cells may be grown in Costar dishes that have been coated with a hydrogel to prevent them from adhering to the bottom of the dish. For cells that grow in a monolayer attached to a substrate, plastic dishes, flasks, roller bottles, or microcarriers are typically used. Other artificial substrates can be used such as glass and metals. The substrate is often treated by etching, or by coating with substances such as collagen, chondronectin, fibronectin, laminin or poly-L-lysine. The type of culture vessel depends on the culture conditions, e.g., multi-well plates, petri dishes, tissue culture tubes, flasks, roller bottles, microcarriers, and the like. Cells are grown at optimal densities that are determined empirically based on the cell type.

Important constituents of the gas phase are oxygen and carbon dioxide. Typically, atmospheric oxygen tensions are used for dendritic cell cultures. Culture vessels are usually vented into the incubator atmosphere to allow gas exchange by using gas permeable caps or by preventing sealing of the culture vessels. Carbon dioxide plays a role in pH stabilization, along with buffer in the cell media, and is typically present at a concentration of 1-10% in the incubator. The $CO_2$ concentration for dendritic cell cultures often is 5%.

Cultured cells are normally grown in an incubator that provides a suitable temperature, e.g., the body temperature of the animal from which is the cells were obtained, accounting for regional variations in temperature. Generally, 37.degree. C. often is the temperature for dendritic cell culture. Most incubators are humidified to approximately atmospheric conditions.

Defined cell media are available as packaged, premixed powders or presterilized solutions. Examples of commonly used media include Iscove's media, RPMI 1640, DMEM, and McCoy's Medium (see, e.g., GibcoBRL/Life Technologies Catalogue and Reference Guide; Sigma Catalogue). Defined cell culture media are often supplemented with 5-20% serum, e.g., human, horse, calf, or fetal bovine serum. The culture medium is usually buffered to maintain the cells at a pH often from about 7.2 to about 7.4. Other supplements to the media include, e.g., antibiotics, amino acids, sugars, and growth factors (see, e.g., Lutz et al., supra). GM-CSF sometimes is in concentrations ranging from 5 ng/ml to about 20 ng/ml in a culture medium. Other factors described herein and known to stimulate growth of dendritic cells may be included in the culture medium. Some factors will have different effects that are dependent upon the stage of differentiation of the cells, which can be monitored by testing for differentiation markers specific for the cell's stage in the differentiation pathway. GM-CSF can be included in the medium throughout culturing. Other factors that may be included in a culture medium include granulocyte colony-stimulating factor (G-CSF), M-CSF, TNF-.alpha., IFN-.gamma., IL-1, IL-3, IL-6, SCF, LPS, and thrombopoietin. IL-4 may be present in the culture medium, sometimes at a concentration ranging from 1-100 ng/ml or about 5 ng/ml to about 20 ng/ml. Other factors and methods that can be utilized for DC cell culture are known to the person of ordinary skill in the art (e.g., U.S. 20040033213, published Feb. 19, 2004).

Dendritic cells can be recovered and used after cryogenic storage. Precultured DCs can be cryogenically stored, e.g., in liquid nitrogen, for several weeks or months or years. Dendritic cells may be cultured in the presence of GM-CSF, sometimes for about 10 days, prior to being stored cryogenically. The DCs can be stored either as immature cells or as matured APCs, following stimulation by suitable adjuvants, as described herein. Dendritic cells can be cryogenically stored before or following exposure to an antigen of interest. A variety of cryopreservation agents can be used and are described in, e.g., U.S. Pat. No. 5,788,963. Controlling the cooling rate, adding cryoprotective agents and/or limiting the heat of fusion phase where water turns to ice help preserve the function of the activated DCs. The cooling procedure can be carried out by use of, e.g., a programmable freezing device or a methanol bath procedure. After thorough freezing, cells can be rapidly transferred to a long-term cryogenic storage vessel. The samples can be cryogenically stored, for example, in liquid nitrogen (−196.degree. C.) or its vapor (−165.degree. C.). Such storage is facilitated by the availability of highly efficient liquid nitrogen refrigerators. For a general description of methods to store DCs cryogenically see, e.g., U.S. Pat. No. 5,788,963.

Certain factors may be contacted with dendritic cells to facilitate proliferation and maturation. GM-CSF has been found to promote the proliferation in vitro of both nonadherent immature dendritic cells and adherent macrophages (see, e.g., U.S. Pat. No. 5,994,126; and Lutz et al., supra). Precursor dendritic cells sometimes are cultured in the presence of GM-CSF at a concentration sufficient to promote survival and proliferation. The dose of GM-CSF depends, e.g., on the amount of competition from other cells (especially macrophages and granulocytes) for the GM-CSF, and on the presence of GM-CSF inactivators in the cell population (see, e.g., U.S. Pat. No. 5,994,126). GM-CSF concentration sometimes is of about 1 ng/ml to 100 ng/ml, and at times about 5 ng/ml to about 20 ng/ml. GM-CSF can be obtained from different sources well known to those of skill in the art (see, e.g., Lutz et al., supra; and U.S. Pat. No. 5,994,126).

In addition to GM-SCF, a variety of cytokines have been shown to induce proliferation and/or maturation of dendritic cells and other APCs (see, e.g., Caux et al., J. Exp. Med. 180:1263-1272 (1984); Allison, Archivum Immunologiae et Therapiae Experimentalis 45:141-147 (1997)). Cytokines that can be used to enhance maturation of dendritic cells ex vivo include, but are not limited to, TNF-alpha, stem cell factor (SCF; also named c-kit ligand, steel factor (SF), mast cell growth factor (MGF); see, e.g., EP 423,980; and U.S. Pat. No. 6,017,527), granulocyte colony-stimulating factor (G-CSF), monocyte-macrophage colony-stimulating factor (M-CSF), as well as a number of interleukins, such as, e.g., IL-1.alpha. and IL-1.beta., IL-3, IL-4, IL-6, and IL-13 (see, e.g., U.S. Pat. Nos. 6,017,527 and 5,994,126). In addition to promoting maturation of dendritic cells, some interleukins (e.g., IL-4) have been shown to suppresses the overall growth of macrophages and thus favors higher levels of pure DC growth. Cytokines are used in amounts which are effective in increasing the proportion of dendritic cells present in the culture by enhancing either the proliferation or the survival of dendritic cell precursors. In certain embodiments, dendritic cells and precursors are cultured in the presence of GM-CSF, and sometimes are cultured in the presence of GM-CSF and IL-4. When human dendritic precursor cells are cultured, the GM-CSF is sometimes is human GM-CSF (huGM-CSF).

Adjuvants also can be used to stimulate the maturation ex vivo of immature dendritic cells. Specifically, immature dendritic cells can be harvested from the induction cultures described supra and their maturation to end-stage antigen presenting cells can be induced by treating the cells with a variety of adjuvants. Adjuvants that promote maturation of dendritic cells include, but are not limited to, MPL® immunostimulant and selected synthetic lipid A analogs such as aminoalkyl glucosamide phosphate (AGP). Synthetic lipid A analogs include, for example, lipid A monosaccharide synthetics such as RC-529, RC-544 and RC-527, and the disaccharide mimetic, RC-511. These adjuvants can be used as 10% ethanol-in-water formulations, although any other formulation that promotes the maturation of dendritic cells is suitable for use with the methods of the present invention. Adjuvants can be synthesized or obtained from a variety of sources (see, e.g., Lutz et al., supra; Johnson et al., Bioorganic Medicinal Chemistry Letters 9:2273-2278 (1999)). Maturation of dendritic cells sometimes is induced using MPL or AGP in certain embodiments.

Maturation of DCs can be assessed by monitoring a number of molecular markers and cell surface phenotypic alterations. These changes can be analyzed, for example, using flow cytometry techniques. Maturation markers can be labeled using specific antibodies and DCs expressing a marker or a set of markers of interest can be separated from the total DC population using, for example, cell sorting FACS analysis. Markers of DC maturation include genes that are expressed at higher levels in mature DCs compared to immature DCs. Such markers include, but are not limited to, cell surface MHC Class II antigens (in particular HLA-DR), ICAM-1, B7-2, costimulating molecules such as CD40, CD80, CD86, CD83, cell trafficking molecules such as CD54, CD11b, CD18, and the like. Mature dendritic cells also can be identified based on their ability to stimulate the proliferation of naive allogeneic T cells in a mixed leukocyte reaction (MLR).

It has been shown that immature dendritic cells are efficient at antigen uptake but are poor antigen presenting cells, and mature dendritic cells are poor at antigen uptake but are very efficient antigen presenting cells. Accordingly, the antigen presenting function of dendritic cells can be used to determine the degree of maturation. The antigen presenting function of a dendritic cell can be measured using antigen-dependent, MHC-restricted T cell activation assays as described herein, as well as other standard assays well known to those of skill in the art. T cell activation can further be determined, e.g., by measuring the induction of cytokine production by the stimulated dendritic cells. Stimulation of cytokine production can be quantified using a variety of standard techniques, such as ELISA, known to those of ordinary skill in the art.

Thus, a DC utilized in a composition or process described herein can be a mature DC, an immature DC, a DC having one or more particular cell markers, a DC contacted with one or more cytokines, a DC contacted with an adjuvant, a DC from a particular source (e.g., bone marrow), a DC contacted with cell culture conditions, and/or a DC contacted with cryogenic conditions, for example, in certain embodiments.

Transferring Target Nucleotide Sequences Into Antigen Presenting Cells

Transgene expression in cells requires transfer of a nucleotide sequence encoding the transgene into the cell. Viral and non-viral methods of gene transfer are known to the person of ordinary skill in the art.

Several non-viral methods for transferring nucleic acids into cells are known. These transfer methods include, for example, calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979), cell sonication (Fechheimer et al., 1987), gene bombardment using high velocity microprojectiles (Yang et al., 1990), and receptor-mediated transfection (Wu and Wu, 1987; Wu and Wu, 1988).

In certain embodiments, the nucleic acid is complexed to a cationic polymer. Cationic polymers, which are water-soluble complexes, are known in the art and have been utilized in delivery systems for DNA plasmids. This strategy employs the use of a soluble system, which conveys nucleic acid into cells via receptor-mediated endocytosis (Wu & Wu 1988). Complexing nucleic acids with a cationic polymer can neutralize negative charge of the nucleic acid, which facilitates increased endocytic uptake. Examples of cationic polymers include, but are not limited to, polylysine, polyethyleneimine, polyhistidine, protamine, polyvinylamines, polyvinylpyridine, polymethacrylates, and polyornithine.

In some transfer embodiments, the nucleic acid is entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. Lipid components undergo self-rearrangement before the formation of closed structures and entrap water and dissolved solutes between the lipid bilayers (Ghosh and Bachhawat, 1991). Addition of nucleic acids to cationic liposomes causes a topological transition from liposomes to optically birefringent liquid-crystalline condensed globules (Radler et al., 1997). These DNA-lipid complexes are potential non-viral vectors for use in immunotherapy.

Liposome-mediated nucleic acid delivery and expression of foreign DNA in vitro has been very successful. Using the .beta.-lactamase gene, Wong et al., (1980) demonstrated the feasibility of liposome-mediated delivery and expression of foreign DNA in cultured chick embryo, HeLa, and hepatoma cells. Nicolau et al., (1987) accomplished successful liposome-mediated gene transfer in rats after intravenous injection. Also included are various commercial approaches involving "lipofection" technology.

In certain embodiments, the liposome is complexed with a hemagglutinating virus (HVJ). This has been shown to facilitate fusion with the cell membrane and promote cell entry of liposome-encapsulated DNA (Kaneda et al., 1989). In other embodiments, the liposome is complexed or employed in conjunction with nuclear nonhistone chromosomal proteins (HMG-1) (Kato et al., 1991). In yet further embodiments, the liposome is complexed or employed in conjunction with both HVJ and HMG-1. In that such expression constructs have been successfully employed in transfer and expression of nucleic acid in vitro and in vivo, then they are applicable for the present invention.

In other embodiments, the delivery vehicle may comprise a ligand and a liposome. For example, Nicolau et al., (1987) employed lactosyl-ceramide, a galactose-terminal asialganglioside, incorporated into liposomes and observed an increase in the uptake of the insulin gene by hepatocytes. Thus, it is feasible that a nucleic acid encoding a therapeutic gene also is specifically delivered into a cell type such as prostate, epithelial or tumor cells, by any number of receptor-ligand systems with or without liposomes. For example, the human prostate-specific antigen (Watt et al., 1986) is used as the receptor for mediated delivery of a nucleic acid in prostate tissue.

In another embodiment of the invention, the expression construct may simply consist of naked recombinant DNA or plasmids. Transfer of the construct is performed by any of the methods mentioned above which physically or chemically permeabilize the cell membrane. This is applicable particularly for transfer in vitro, however, it is applied for in vivo use as well. Dubensky et al., (1984) successfully injected polyomavirus DNA in the form of CaPO4 precipitates into liver and spleen of adult and newborn mice demonstrating active viral replication and acute infection. Benvenisty and Neshif (1986) also demonstrated that direct intraperitoneal injection of CaPO$_4$ precipitated plasmids results in expression of the transfected genes. It is envisioned that DNA encoding a CAM also is transferred in a similar manner in vivo and express CAM.

Another embodiment of the invention for transferring a naked DNA expression construct into cells may involve particle bombardment. This method depends on the ability to accelerate DNA coated microprojectiles to a high velocity by application of a propulsion force, allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Viral vectors also may be utilized to effect nucleic acid transfer to cells. In certain embodiments, a transgene is incorporated into a viral particle to mediate gene transfer to a cell. The resulting virus often is exposed to the appropriate host cell under physiologic conditions, permitting uptake of the virus. Such methods are advantageously employed using a variety of viral vectors, as discussed hereafter.

Adenovirus, sometimes referred to herein as "Ad," is particularly suitable for use as a gene transfer vector because of its mid-sized DNA genome, ease of manipulation, high titer, wide target-cell range, and high infectivity. The roughly 36 kB viral genome is bounded by 100-200 base pair (bp) inverted terminal repeats (ITR), in which are contained cis-acting elements necessary for viral DNA replication and packaging. The early (E) and late (L) regions of the genome that contain different transcription units are divided by the onset of viral DNA replication.

The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan, 1990). The products of the late genes (L1, L2, L3, L4 and L5), including the majority of the viral capsid proteins, are expressed only after significant processing of a single primary transcript issued by the major late promoter (MLP). The MLP (located at 16.8 map units) is particularly efficient during the late phase of infection, and all the mRNAs issued from this promoter possess a 5' tripartite leader (TL) sequence, which makes them often utilized mRNAs for translation.

Adenovirus often is optimized for immunotherapy by maximizing its carrying capacity so that large segments of DNA can be included. Large displacement of DNA is possible in adenovirus because the cis elements required for viral DNA replication all are localized in the inverted terminal repeats (ITR) (100-200 bp) at either end of the linear viral genome. Plasmids containing ITR's can replicate in the presence of a non-defective adenovirus (Hay et al., 1984). Therefore, inclusion of these elements in an adenoviral vector should permit replication.

Toxicity and immunologic reaction associated with certain adenoviral products also are minimized for immunotherapy applications. The two goals are, to an extent, coterminous in that elimination of adenoviral genes serves both ends. It is possible achieve both these goals while retaining the ability to manipulate the therapeutic constructs with relative ease.

In addition, the packaging signal for viral encapsidation is localized between 194-385 bp (0.5-1.1 map units) at the left end of the viral genome (Hearing et al., 1987). This signal mimics the protein recognition site in bacteriophage .lambda. DNA where a specific sequence close to the left end, but outside the cohesive end sequence, mediates the binding to proteins that are required for insertion of the DNA into the head structure. E1 substitution vectors of Ad have demonstrated that a 450 bp (0-1.25 map units) fragment at the left end of the viral genome could direct packaging in 293 cells (Levrero et al., 1991).

Previously, it has been shown that certain regions of the adenoviral genome can be incorporated into the genome of mammalian cells and the genes encoded thereby expressed. These cell lines are capable of supporting the replication of an adenoviral vector that is deficient in the adenoviral function encoded by the cell line. There also have been reports of complementation of replication deficient adenoviral vectors by "helping" vectors, e.g., wild-type virus or conditionally defective mutants.

Replication-deficient adenoviral vectors can be complemented, in trans, by helper virus. This observation alone does not permit isolation of the replication-deficient vectors, however, since the presence of helper virus, needed to provide replicative functions, would contaminate any preparation. Thus, an additional element was needed that would add specificity to the replication and/or packaging of the replication-deficient vector. That element, as provided for in the present invention, derives from the packaging function of adenovirus.

It has been shown that a packaging signal for adenovirus exists in the left end of the conventional adenovirus map (Tibbetts, 1977). Later studies showed that a mutant with a deletion in the E1A (194-358 bp) region of the genome grew poorly even in a cell line that complemented the early (E1A) function (Hearing and Shenk, 1983). When a compensating adenoviral DNA (0-353 bp) was recombined into the right end of the mutant, the virus was packaged normally. Further mutational analysis identified a short, repeated, position-dependent element in the left end of the Ad5 genome. One copy of the repeat was found to be sufficient for efficient packaging if present at either end of the genome, but not when moved towards the interior of the Ad5 DNA molecule (Hearing et al., 1987).

By using mutated versions of the packaging signal, it is possible to create helper viruses that are packaged with varying efficiencies. Typically, the mutations are point mutations or deletions. When helper viruses with low efficiency packaging are grown in helper cells, the virus is packaged, albeit at reduced rates compared to wild-type virus, thereby permitting propagation of the helper. When these helper viruses are grown in cells along with virus that contains wild-type packaging signals, however, the wild-type packaging signals are recognized preferentially over the mutated versions. Given a limiting amount of packaging factor, the virus containing the wild-type signals are packaged selectively when compared to the helpers. If the preference is great enough, stocks approaching homogeneity should be achieved.

Retrovirus also are useful for transferring Akt-encoding nucleotide sequences into cells. Retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes—gag, pol and env—that code for capsid proteins, polymerase enzyme, and envelope components, respectively. A sequence found upstream from the gag gene, termed .psi., functions as a signal for packaging of the genome into virions. Two long terminal repeat (LTR) sequences are present at the 5' and 3' ends of the viral genome. These contain strong promoter and enhancer sequences and also are required for integration in the host cell genome (Coffin, 1990).

In order to construct a retroviral vector, a nucleic acid encoding a promoter is inserted into the viral genome in the place of certain viral sequences to produce a virus that is replication-defective. In order to produce virions, a packaging cell line containing the gag, pol and env genes but without the LTR and .psi. components is constructed (Mann et al., 1983). When a recombinant plasmid containing a human cDNA, together with the retroviral LTR and .psi. sequences is introduced into this cell line (by calcium phosphate precipitation for example), the .psi. sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is collected, optionally concentrated, and used for gene transfer. Retroviral vectors are able to infect a broad variety of cell types. However, integration and stable expression of many types of retroviruses require the division of host cells (Paskind et al., 1975).

An approach designed to allow specific targeting of retrovirus vectors recently was developed based on the chemical modification of a retrovirus by the chemical addition of galactose residues to the viral envelope. This modification could permit the specific infection of cells such as hepatocytes via asialoglycoprotein receptors, should this be desired.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, the infection of a variety of human cells that bore those surface antigens was demonstrated with an ecotropic virus in vitro (Roux et al., 1989).

Adeno-associated virus, also referred to herein as "AAV," also may be utilized to transfer Akt-encoding nucleotide sequences into cells. AAV utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription.

The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42-46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low-level expression of AAV rep proteins is believed to hold AAV structural expression in check, and helper virus infection is thought to remove this block.

The terminal repeats of the AAV vector can be obtained by restriction endonuclease digestion of AAV or a plasmid such as p201, which contains a modified AAV genome (Samulski et al., 1987), or by other methods known to the skilled artisan, including but not limited to chemical or enzymatic synthesis of the terminal repeats based upon the published sequence of AAV. The ordinarily skilled artisan can determine, by well-known methods such as deletion analysis, the minimum sequence or part of the AAV ITRs which is required to allow function, i.e., stable and site-specific integration. The ordinarily skilled artisan also can determine which minor modifications of the sequence can be tolerated while maintaining the ability of the terminal repeats to direct stable, site-specific integration.

AAV-based vectors have proven to be safe and effective vehicles for gene delivery in vitro, and these vectors are being developed and tested in pre-clinical and clinical stages for a wide range of applications in potential gene therapy, both ex vivo and in vivo (Carter and Flotte, 1995; Chatterjee et al., 1995; Ferrari et al., 1996; Fisher et al., 1996; Flotte et al., 1993; Goodman et al., 1994; Kaplitt et al., 1994; 1996; Kessler et al., 1996; Koeberl et al., 1997; Mizukami et al., 1996).

AAV-mediated efficient gene transfer and expression in the lung has led to clinical trials for the treatment of cystic fibrosis (Carter and Flotte, 1995; Flotte et al., 1993). Similarly, the prospects for treatment of muscular dystrophy by AAV-mediated gene delivery of the dystrophin gene to skeletal muscle, of Parkinson's disease by tyrosine hydroxylase gene delivery to the brain, of hemophilia B by Factor IX gene delivery to the liver, and potentially of myocardial infarction by vascular endothelial growth factor gene to the heart, appear promising since AAV-mediated transgene expression in these organs has recently been shown to be highly efficient (Fisher et al., 1996; Flotte et al., 1993; Kaplitt et al., 1994; 1996; Koeberl et al., 1997; McCown et al., 1996; Ping et al., 1996; Xiao et al., 1996).

Other viral vectors also may be utilized for transfer of nucleic acids into cells. Vectors derived from viruses such as vaccinia virus (Ridgeway, 1988; Baichwal and Sugden, 1986; Coupar et al., 1988) canary pox virus, and herpes viruses are employed. These viruses offer several features for use in gene transfer into various mammalian cells. Several viral vectors are known and can be selected by the person of ordinary skill in the art (e.g., U.S. 20020123479, published on Sep. 5, 2002).

Once the construct has been delivered into the cell, the nucleic acid encoding the transgene are positioned and expressed at different sites. In certain embodiments, the nucleic acid encoding the transgene is stably integrated into the genome of the cell. This integration is in the cognate location and orientation via homologous recombination (gene replacement) or it is integrated in a random, non-specific location (gene augmentation). In yet further embodiments, the nucleic acid is stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

A nucleic acid may be targeted to a dendritic cell by associating a targeting molecule having affinity for a molecule present on the surface of a dendritic cell with the nucleic acid. A wide variety of targeting elements can be utilized to specifically direct a nucleic acid to a dendritic cell. As utilized herein, targeting elements are considered to be capable of interacting with a molecule present on the surface of a dendritic cell when a biological effect of the coupled targeting element may be seen in the cell, or, alternatively, when there is greater than at least about a 10-fold difference, and sometimes greater than at least about a 25, 50, or 100-fold difference, between the binding of the targeting element to dendritic cells as compared to non-dendritic cells. Generally, it is preferable that the targeting element interact with a molecule present on the surface of the selected cell type with a $K_D$ of less than about $10^{-5}$ M, preferably less than about $10^{-6}$ M, more preferably less than about $10^{-7}$ M, and most preferably less than about $10^{-8}$ M, as determined by Scatchard analysis (Scatchard, Ann. N.Y. Acad. Sci. 51:660, 1949). Suitable targeting elements are preferably non-immunogenic, not degraded by proteolysis, and not scavenged by the immune system. Particularly preferred targeting elements should have a half-life within an animal of between about 10 minutes and about 1 week.

Targeting elements often are proteins or peptides, although other non-proteinaceous molecules may also function as targeting elements. For example, antibodies (or the antigen binding domain thereof) can be utilized to target dendritic cells. Particularly useful antibodies are monoclonal antibodies which interact with the extracellular domains of integral membrane proteins found predominantly, or preferably exclusively, in the cell membranes of dendritic cells, (see generally, Wilchek and Bayer, Anal. Biochem 171:1-32, 1988). In some embodiments the Fc portion of such an antibody will serve as the targeting element, targeting the gene delivery vehicle to dendritic cells that express Fc receptor molecules. Suitable markers for antibody generation include CD11c, CD54, CD58, CD25, CD11a, CD23, CD32, CD40, CD1, CD45, MHC Class I, MHC Class II, Mac-1, Mac-2, and Mac-3. These and other lineage specific markers can be used to separate or purify dendritic cells from more diverse cell populations, in addition to those described above. Both positive and negative selection strategies may be employed. Techniques for conducting cell selection include FACS and affinity chromatography.

Other suitable targeting elements include hormones, immune accessory molecules (e.g., B7, IL-2, .alpha.-interferon, and .gamma.-interferon), cell adhesion molecules (e.g., ICAM-1, ICAM-2, and ICAM-3), integrins that bind to ICAMs and receptors known to be expressed on the surface of dendritic cells. Dendritic cell-specific ligands also may be selected from libraries created utilizing recombinant techniques (Scott and Smith, Science 249:386, 1990; Devlin et al., Science 249:404, 1990; Houghten et al., Nature 354:84 1991; Matthews and Wells, Science 260:1113, 1993; Nissim et al., EMBO J. 13(3):692-698, 1994), or equivalent techniques utilizing organic compound libraries.

Targeting molecules can be associated with a nucleic acid in a variety of manners. For example, a targeting molecule can be linked directly to a nucleic acid (e.g., when a nucleic acid is transferred to dendritic cell as naked DNA), can be incorporated into the lipid bilayer of a liposome that bears the nucleic acid, and can be expressed on the surface of a virus bearing the target nucleotide sequence.

A nucleic acid delivery vehicle sometimes is purified before it is contacted with an antigen presenting cell for transfer. Techniques utilized for purification are dependent on the type of vehicle used for nucleic acid delivery. If naked nucleic acid is delivered, there are a variety of techniques known in the art including, for example, purification by CsCl-ethidium bromide gradient, ion-exchange chromatography, gel-filtration chromatography, and differential precipitation with polyethylene glycol. Further description of nucleic acids purification is provided in Sambrook et. al., Molecular Cloning: A Laboratory Manual, 2d ed. (Cold Spring Harbor Laboratory Press, 1989). For viral delivery vehicles a sulfated oligosaccharide can be added directly to a virus-containing preparation for purification.

When the delivery vehicle is a liposome, a variety of purification methods known to those skilled in the art may be utilized and are described in more detail in Mannino and Gould-Fogerite (BioTechniques 6:682, 1988). Briefly, preparation of liposomes typically involves admixing solutions of one or more purified phospholipids and cholesterol in organic solvents and evaporating the solvents to dryness. An aqueous buffer containing the delivery vehicle then is added to the lipid film and the mixture is sonicated to create a fairly uniform dispersion of liposomes. In certain embodiments, dialysis, gel filtration, or ultracentrifugation is then be used to separate unincorporated components from the intact liposomes. (Stryer, L., Biochemistry, pp:236 1975 (W. H. Freeman, San Francisco): Szoka et al., Biochim. Biophys. Acta 600:1, 1980; Bayer et al., Biochim. Biophys. Acta. 550:464, 1979; Rivnay et al., Meth. Enzymol. 149: 119, 1987; Wang et al., PNAS 84: 7851, 1987 and, Plant et al., Anal. Biochem. 176:420, 1989.

Priming Modified Antigen Presenting Cells with Antigen

Loading APCs with antigen can be achieved by a variety of methods, including pulsing cells with antigenic peptides or infecting the cells with recombinant viral vectors, for example. Gene therapy techniques can be applied to dendritic cell vaccines. Such techniques use recombinant viral vectors incapable of replication to provide efficient and reliable means of gene transfer. Genetic material can be introduced into dendritic cells to provide them with a renewable source of antigen for presentation; this should lead to more sustained expression of antigen. The expression of viral (and therefore foreign) genes may boost the immune response, but this antiviral immunity primed by dendritic cells may cause the immune system to destroy dendritic cells rapidly in subsequent rounds of immunization. One solution can be to use viral vectors that do not result in the expression of viral genes, such as retroviruses or "gutless" adenoviral vectors.

Following expansion in culture and maturation, APCs can be pulsed with an antigen. Pulsing processes are known to and can be selected by the person of ordinary skill in the art, and cells may be pulsed with antigen one or more times in appropriate regular or variable cycles. APCs pulsed with an antigen of interest will process and present epitopes of the antigen. Antigens can be from any source, including, e.g., viruses, bacteria, parasites, etc. In one embodiment, the antigen is derived from *Mycobacterium sp, Chlamydia* sp., *Leishmania* sp., *Trypanosoma* sp., *Plasmodium* sp., or a *Candida* sp. APCs can be pulsed with either the entire peptide (antigen) or with a fragment thereof having immunogenic properties, e.g., an epitope.

Briefly, the antigen-activated APCs (e.g., antigen-activated dendritic cells) can be produced by exposing, ex vivo, an antigen to the APCs (e.g., the dendritic cells) prepared according to the methods known to the person of ordinary skill in the art. Dendritic cells, for example, can be plated in culture dishes and exposed to an antigen of interest in a sufficient amount and for a sufficient period of time to allow the antigen to bind to the dendritic cells. The amount and time necessary to achieve binding of the antigen to the dendritic cells may be determined by using standard immunoassays or binding assays. Any other method known to those of skill in the art may also be used to detect the presence of antigen on the dendritic cells following their exposure to the antigen. Methods for pulsing dendritic cells with an antigen of interest are described, e.g., in U.S. Pat. No. 6,017,527.

In general, antigens and fragments thereof may be prepared using any of a variety of procedures well known to those of skill in the art. For example, antigens can be naturally occurring and purified from a natural source. Alternatively, antigens and fragments thereof can be produced recombinantly using a DNA sequence that encodes the antigen, which has been inserted into an appropriate expression vector, i.e., a vector which contains the necessary elements for the transcription and translation of the inserted coding sequence, and expressed in an appropriate host. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., Molecular Cloning: A Laboratory Manual, Cold Spring Harbor Laboratories, Cold Spring Harbor, N.Y. (1989); and Ausubel et al., Current Protocols in Molecular Biology (1995 supplement). In addition, antigens and portions thereof may also be generated by synthetic means. Synthetic polypeptides having fewer than about 100 amino acids, and generally fewer than about 50 amino acids, may be generated using techniques well known in the art. For example, such polypeptides may be synthesized using any of the commercially available solid-phase techniques, such as the Merrifield solid-phase synthesis method, where amino acids are sequentially added to a growing amino acid chain (see Merrifield, J. Am. Chem. Soc. 85:2149-2146 (1963)). Equipment for automated synthesis of polypeptides is commercially available from suppliers such as Perkin Elmer/Applied Bio Systems Division, Inc., Foster City, Calif., and may be operated according to the manufacturer's instructions. Variants of a native antigen may generally be prepared using standard mutagenesis techniques, such as oligonucleotide-directed site-specific mutagenesis. Sections of the DNA sequence may also be removed using standard techniques to permit preparation of truncated polypeptides.

Within certain embodiments, the antigen of interest may be a fusion protein that comprises multiple polypeptides. A fusion protein may, for instance, include an antigen and a fusion partner which may, e.g., assist in providing T helper epitopes, and/or assist in expressing the protein at higher yields than the native recombinant protein. Other fusion partners may be selected so as to increase the solubility of the protein or to enable the protein to be targeted to desired intracellular compartments. Still further fusion partners include affinity tags, which facilitate the purification of the protein. Fusion proteins may generally be prepared using standard techniques, including chemical conjugation and as recombinant proteins.

An antigen often is a molecule associated with a disease or condition. For example, pathogen-associated antigens, such as viral antigens in virus-associated diseases (e.g., HIV-induced AIDS and HBV-induced liver disease), and portions thereof, can be utilized to prime modified APCs of the invention. Representative examples of pathogen associated antigens include antigens from bacteria (e.g., *E. coli, streptococcus, staphylococcus, mycobacteria*, and the like). fungi, parasites, and viruses (e.g., influenza virus, HIV, and Hepatitis A, B and C Virus ("HAV", "HBV" and "HCV", respectively), human papiloma virus ("HPV"), Epstein-Barr Virus ("EBV"), herpes simplex virus ("HSV"), hantavirus, HTLV I, HTLV II, cytomegalovirus ("CMV"), and feline leukemia virus). Antigens critical to the survival and proliferation of the cancer cell in vivo, and portions thereof, can be selected for priming modified APCs of the invention, and include, for example: (a) tissue-specific antigens that are elevated in cancer, such as carcinoembryonic antigen (CEA, colorectal cancer); .alpha.-fetoprotein (liver cancer); prostate cancer antigen (PSA, prostate cancer), mitochondrial creatine kinase (MCK, muscle cancers), myelin basic protein (MBP, oligodendrocyte specific), glial fibrillary acidic protein (GFAP, glial cell specific), tyrosinase (melanoma), and neuron cancer enolase (NSE, neuronal cancers); (b) mutated forms of tumor suppressor genes, such as K-ras (colorectal carcinomas), and p53 (J. L. Bos, Cancer Res. 49:4682, 1989; Chiba et al., Oncogene 5:1603, 1990; (c) viral proteins expressed by virally induced cancers, such as human papillomavirus 16/18 E6 and E7 proteins (cervical cancer) or Epstein Barr Virus peptides (EBV, B cell malignancies); (d) tumor-specific antigens such as MART-1 (melanoma), gp100 (melanoma), HER2/neu (breast and epithelial cancers); NY-ESO-1 (testes and various tumors), PSA or PSMA (prostate cancer), thymus-leukemia antigen (TL), and proteins of the MAGE family (hepatocellular cancer and other tumors); (e) survivin and other apoptosis inhibiting proteins expressed preferentially by tumor cells (M. Zeiss et al., J. Immunol. 170:5391, 2003); and (f) components involved in angiogenesis, such as vascular endothelia growth factor (VEGF, expressed in angiogenic stroma and tumor cells), VEGF receptor 2, Id1, Id3, and Tie-2 (preferentially expressed during neoangiogenesis) (US 2004/0115174 A1). These and other cancer-associated antigens can be selected by the person of ordinary skill in the art. General reviews for tumor related antigens useful as cancer vaccine targets include the text Tumor Antigens Recognized by T Cells and Antibodies by H. J. Stauss, Y. Kawakami, & G. Parmiani, CRC Press, 2003; and articles by Rosenberg, Immunity 10:281, 1999; Nestle et al., Nat. Med. 4:328, 1998; Dermime et al., Br. Med. Bull. 62:149, 2002; and Berzofsky et al., J. Clin. Invest. 113:1515, 2004. Methods for identifying additional cancer target antigens are described in Barnea et al., Eur J. Immunol. 32:213, 2002; Schirle et al., Eur J. Immunol. 30:2216, 2000; Vinals et al., Vaccine 19:2607, 2001; Perez-Diez et al., Cell. Mol. Life. Sci. 59:230, 2002; Radvanyi et al., Int. Arch. Allergy Immunol. 133:179, 2004. An antigen may be a protein, polypeptide, protein or polypeptide fragment, peptide, dominant epitope peptide that binds to an HLA class I or II molecule, a monosaccharide, a polysaccharide or nucleic acid.

Once an antigen is selected, one or more subfragments (i.e., portions) of the antigen having a dominant immunogenic epitope may be synthesized based upon the knowledge of the ordinary artisan for selecting epitope subsequences. Sequence motifs for dominant epitopes are known and can be selected based upon whether they are presented by specific MHC I (e.g., peptides of about 8-9 amino acids) and MHC II molecules (e.g., U.S. 20060093617, published on May 4, 2006, and U.S. 20050271676, published on Dec. 8, 2005). Some epitopes conform to "pan DR" motifs and are presented by multiple types of class II DR molecules (e.g., U.S. 20050049197 published on Mar. 3, 2005), and native epitopes may be modified into heteroclitic analogs having enhanced immunogenicity (e.g., U.S. 20030143672, published on Jul. 31, 2003).

Prior to loading, a polypeptide antigen may be covalently conjugated to an immunological partner that provides T cell help (e.g., a carrier molecule). Alternatively, an APC may be pulsed with a non-conjugated immunological partner, separately or in the presence of the antigen. Often, antigen presenting cells are primed with an antigen (e.g., a protein, polypeptide, protein or polypeptide fragment, peptide, dominant immunogenic epitope) for an hour or more before the cells are matured (e.g., contacted with a nucleic acid that encodes a membrane-targeted Akt molecule). The antigen presenting cells may be contacted with a full-length protein or polypeptide antigen, a fragment of the protein or polypeptide antigen or a dominant immunogenic epitope from the antigen that binds to a HLA class I or II molecule. An antigen may be linked to a cell surface receptor that facilitates uptake of the antigen by cells (e.g., DEC-205 or DC-sign receptor ligand).

APCs may be transfected with a polynucleotide sequence encoding an antigen of interest (e.g., a protein, polypeptide, protein or polypeptide fragment, peptide, dominant immunogenic epitope) such that the antigen, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In the latter embodiments, the antigen-encoding sequence and membrane-targeted Akt sequence may be expressed in cis (from the same nucleic acid) or in trans (from different nucleic acids). In vivo and ex vivo transfection of dendritic cells, for example, may generally be performed using any methods known in the art, such as those described in WO 97/24447, or the gene gun approach described by Mahvi et al., Immunology and cell Biology 75:456-460 (1997). Antigen loading of dendritic cells may be achieved by incubating dendritic cells or progenitor cells with the antigen, DNA (naked or within a plasmid vector) or RNA; or with antigen-expressing recombinant bacterium or viruses (e.g., vaccinia, fowlpox, adenovirus or lentivirus vectors). Vectors that express multiple antigenic epitopes in "minigenes" also may be utilized (e.g., U.S. 20060093617, published on May 4, 2006).

In the context of the present invention, the antigens, antigen fragments or fusion proteins used to pulse the dendritic cells are preferably immunogenic, i.e., they are able to elicit an immune response (e.g., cellular or humoral) in a patient, such as a human, and/or in a biological sample (in vitro). In particular, antigens that are immunogenic (and portions of such antigens that are immunogenic) comprise an epitope recognized by a B-cell and/or a T-cell surface antigen receptor. Antigens that are immunogenic (and immunogenic portions of such antigens) are capable of stimulating cell proliferation, interleukin-12 production and/or interferon-.gamma. production in biological samples comprising one or more cells selected from the group of T cells, NK cells, B cells and macrophages, where the cells have been previously stimulated with the antigen.

Immunomodulatory factors may be active in vivo and/or ex vivo, can enhance immunogenicity of an antigen, and may be co-administered (e.g., before, during or after administration of antigen(s)). Representative examples of immunomodulatory factors include, for example, cytokines, such as IL-1, IL-2 (Karupiah et al., J. Immunology 144:290, 1990: Weber et al., J. Exp. Med. 166:1716, 1987; Gansbacher et al., J. Exp. Med. 172:1217, 1990: U.S. Pat. No. 4,738,927). IL-3, IL-4 (Tepper et al., Cell 57:503, 1989, Golumbek et al., Science 254:713, 1991 and U.S. Pat. No. 5,017,691), IL-5, IL-6 (Brakenhof et al., J. Immunol. 139:4116, 1987, and WO 90/06370), IL-7 (U.S. Pat. No. 4,965,195), IL-8, IL-9, IL-10, IL-11, IL-12 (Wolf et al., J. Immuno. 46:3074, 1991 and Gubler et al., PNAS 88:4143, 1991), IL-13 (WO 94/04680), IL-14, IL-15, .alpha.-interferon (Finter et al., Drugs 42(5): 749, 1991, Nagata et al., Nature 284:316, 1980; Familletti et al., Methods in Enz. 78:387, 1981, Twu et al., PNAS USA 86:2046, 1989, Faktor et al., Oncogene 5:867, 1990, U.S. Pat. No. 4,892,743, U.S. Pat. No. 4,966,843, and WO 85/02862), .beta.-interferon (Seif et al., J. Vir. 65:664, 1991), .gamma.-interferons (Radford et al., The American Society of Hepatology 9:2008, 1991, Watanabe et al. PNAS 86:9456, 1989, Gansbacher et al., Cancer Research 50:7820, 1990, Maio et al., Can. Immunol. Immunother. 30:34, 1989, U.S. Pat. No. 4,762,791, and U.S. Pat. No. 4,727,138). G-CSF (U.S. Pat. Nos. 4,999,291 and 4,810,643), GM-CSF (WO 85/04188). tumor necrosis factors (TNFs) (Jayaraman et al., J. Immunology 144:942, 1990), CD3 (Krissanen et al., Immunogenetics 26:258, 1987), CD8, ICAM-1 (Altman et al., Nature 338:512, 1989; Simmons et al., Nature 331:624, 1988), ICAM-2 (Singer Science 255:1671, 1992), LFA-1 (Altmann et al., Nature 338:521, 1989), LFA-3 (Wallner et al., J. Exp. Med. 166(4):923, 1987), and other proteins such as HLA Class 1 molecules. HLA Class II molecules, B7 (Freeman et al., J. Immuno. 143:2714, 1989). B7-2, .beta.sub.2-microglubulin (Parnes et al., PNAS 78:2253, 1981), chaperones, and MHC linked transporter proteins or analogs thereof (Powis et al., Nature 354:528, 1991). The choice of which immunomodulatory factor(s) to employ is based upon the therapeutic effects of the factor. Immunomodulatory factors sometimes utilized include .alpha.-interferon, .gamma.-interferon, and IL-2.

A variety of standard assays for measuring the immunogenic properties of a polypeptide of interest or of a portion thereof are available and known to those of skill in the art (see, e.g., Paul, Fundamental Immunology, 3d ed., Raven Press, pp. 243-247 (1993), and references cited therein), and as described hereafter.

Assessing Modified Dendritic Cell Longevity and Induced Immune Response

In certain embodiments, modified antigen presenting cells described herein have a greater longevity (i.e., lifespan) than unmodified counterparts. Such longevity can be expressed in terms of hours, days weeks, number or fraction of surviving cells and number or fraction of dead cells (e.g., cells that have or are undergoing apoptosis), for example. Enhanced longevity can be expressed in terms of a fold-, fraction- or percentage-increase longevity of modified cells over the longevity of unmodified counterpart cells. In certain embodiments, Longevity or lifespan can be assessed in vitro, ex vivo or in vivo by a number of techniques know to the person of ordinary skill in the art. In certain embodiments, methods of observing cell staining (e.g., with Annexin, propidium iodide (PI), CFSE dyes), enzymatic activity (e.g., caspase activity), cell sorting (e.g., based upon cell markers associated with apoptosis or cell death) and/or cell morphology can be utilized. Representative methods for determining cell longevity and cell death are described in Examples 9 and 10 hereafter.

In one aspect of the invention, the modified antigen presenting cells (e.g., the modified dendritic cells) are used to generate an immune response to an antigen of interest. The modified antigen presenting cells described herein often induce a more intense immune response than unmodified counterparts. An enhanced immune response can be expressed in terms of a fold-, fraction- or percentage-increase of an immune response elicited by modified cells over the immune response elicited by unmodified counterpart cells. An immune response to an antigen of interest can be detected by a number of methods available to a person of ordinary skill in the art (e.g., ELISPOT assay described in Example 9). For example, an immune response can be assessed by examining the presence, absence, or enhancement of specific activation of CD4+ or CD8+ T cells or by antibodies. Typically, T cells isolated from an immunized individual by routine techniques (e.g., by Ficoll/Hypaque density gradient centrifugation of peripheral blood lymphocytes) are incubated with an antigen (e.g., such T cells often are incubated with APCs expressing antigen, since T cells generally are poor APCs). For example, T cells may be incubated in vitro for 2-9 days (typically 4 days) at 37.degree. C. with the antigen. It may be desirable to incubate another aliquot of a T cell sample in the absence of the antigen to serve as a control.

Specific activation of CD4+ or CD8+ T cells may be detected in a variety of ways. Methods for detecting specific T cell activation include detecting the proliferation of T cells, the production of cytokines, or the generation of cytolytic activity (i.e., generation of cytotoxic T cells specific for an antigen). For CD4+ T cells, an often utilized method for detecting specific T cell activation is the detection of the proliferation of T cells. For CD8+ T cells, and an often utilized method for detecting specific T cell activation is the detection of the generation of cytolytic activity.

Detection of the proliferation of T cells may be accomplished by a variety of known techniques. For example, T cell proliferation can be detected by measuring the rate of DNA synthesis. T cells which have been stimulated to proliferate exhibit an increased rate of DNA synthesis. A typical way to measure the rate of DNA synthesis is, for example, by pulse-labeling cultures of T cells with tritiated thymidine, a nucleoside precursor which is incorporated into newly synthesized DNA. The amount of tritiated thymidine incorporated can be determined using a liquid scintillation spectrophotometer. Other ways to detect T cell proliferation include measuring increases in interleukin-2 (IL-2) production, $Ca^{2+}$ flux, or dye uptake, such as 3-(4,5-dimethylthiazol-2-yl-)-2,5-diphenyltetrazolium. Alternatively, synthesis of lymphokines (e.g., interferon-gamma (IFN-.gamma.)) can be measured or the relative number of T cells that can respond to the antigen may be quantified.

Secretion of IL-2 or IFN-.gamma. can be measured by a variety of known techniques, including, but not limited to, the double monoclonal antibody sandwich immunoassay technique of David et al. (U.S. Pat. No. 4,376,110); monoclonal-polyclonal antibody sandwich assays (Wide et al., in Kirkham and Hunter, eds., Radioimmunoassay Methods, E. and S. Livingstone, Edinburgh (1970)); the "western blot" method of Gordon et al. (U.S. Pat. No. 4,452,901); immunoprecipitation of labeled ligand (Brown et al., J. Biol. Chem. 255: 4980-4983 (1980)); radioimmunoassays (RIA); enzyme-linked immunosorbent assays (ELISA) as described, for example, by Raines et al., J. Biol. Chem. 257:5154-5160 (1982); immunocytochemical techniques, including the use of fluorochromes (Brooks et al., Clin. Exp. Immunol. 39:477 (1980)); and neutralization of activity (Bowen-Pope et al., Proc. Natl. Acad. Sci. USA 81:2396-2400 (1984)). In addition to the immunoassays described above, a number of other immunoassays are available, including those described in U.S. Pat. Nos. 3,817,827; 3,850,752; 3,901,654; 3,935,074; 3,984,533; 3,996,345; 4,034,074; and 4,098,876.

CTLs that are produced ex vivo can be expanded by regular stimulation with APCs, which can be DCs or "non-professional" APCs that are modified (e.g., with MHC molecules, B7 and the like) to act as APCs. An advantage of artificial APCs is that they can be expanded to appropriate numbers as the T cell populations expand. Mature DCs are terminally differentiated and are utilized for initial T cell activation in certain embodiments. Expanded CTLs can be reinfused into patients by adoptive T cell therapy against virally infected cells or oncogene-transformed cells in certain embodiments and are especially useful for targeting comparatively weak antigens. (e.g., Dudley and Rosenberg, Nature Reviews 2: 666-678 (2003) and Savoldo et al., Blood 100(12): 4059-66 (2002)).

Administration and Immunotherapy

APCs can be isolated from a patient, modified with a membrane-associated AKT molecule described herein, cultured and exposed in vitro or ex vivo to an antigen of interest (e.g., isolated peptide epitope or nucleic acid-encoded epitope), and after expansion and/or cryogenic storage are administered back to the patient to stimulate an immune response, including T cell activation (see, e.g., Thurner et al., J. Immunol. Methods 223:1-15 (1999)), in vivo, in some embodiments. In certain embodiments, the modified APCs are utilized to generate a CTL response in vitro, the APCs optionally are separated from the CTLs, and the CTLs (sometimes in combination with the APCs) are administered to the subject in vivo.

In certain embodiments, modified DCs (e.g., obtained as described herein) are exposed ex vivo to an antigen, washed and administered to elicit an immune response or to augment an existing, albeit weak, response. As such, the DCs may constitute a vaccine and/or an immunotherapeutic agent. In addition, antigen presenting cells (APCs), and in particular dendritic cells, can be used as delivery vehicles for administering pharmaceutical compositions and vaccines. In this context, the APCs may, but need not, be genetically modified, e.g., to increase the capacity for presenting the antigen, to improve activation and/or maintenance of the T cell response and/or to be immunologically compatible with the receiver (i.e., matched HLA haplotype). APCs generally may be isolated from any of a variety of biological fluids and organs as described above, and may be autologous, allogeneic, syngeneic or xenogeneic cells.

Modified APCs primed with antigen may be administered by parenteral (e.g., intravenous, subcutaneous, and intramuscular) or other traditional direct routes, such as buccal/sublingual, rectal, oral, nasal, topical, (such as transdermal and ophthalmic), vaginal, pulmonary, intraarterial, intraperitoneal, intraocular, or intranasal routes or directly into a specific tissue, such as the liver, bone marrow, or into the tumor in the case of cancer therapy. Non-parenteral routes are discussed further in U.S. Appln. No. 08/366,788, filed Dec. 3, 1994. Dendritic cells modified ex vivo sometimes are administered in vivo by intradermal or subcutaneous injection, sometimes with 5-10 million cells administered per site. Modified DCs sometimes are administered interdermally or subcutaneously at between one to five sites in a subject. Methods for administering dendritic cells to a patient for eliciting an immune response in the patient are described, e.g., in U.S. Pat. Nos. 5,849,589; 5,851,756; 5,994,126; and 6,017,527. CTLs expanded by contact with modified APCs of the invention also may be administered to a subject via similar routes. Administration can be repeated at desired intervals based upon the patient's immune response.

A DC composition can be administered to a subject via a desired route and the subject may be tested for a desired biological response. Such testing may include immunological screening assays e.g., CTL assays, antibody assays. Other molecules may be detected after APCs or CTLs are administered to a subject, such as by assessing whether the amount of a disease-associated biological marker lowers over time. Administration by many of the routes of administration described herein or otherwise known in the art and may be accomplished simply by direct administration using a needle, catheter or related device, at a single time point or at multiple time points. Other routes and methods for administration include non-parenteral routes, such as are disclosed in U.S. Ser. No. 08/366,788, as well as administration via multiple sites, as disclosed in U.S. Ser. No. 08/366,784.

Pharmaceutical compositions described above can be utilized to elicit a "protective immune response" or "therapeutic immune response," which as used herein refer to a CTL and/or a T helper (e.g., "CD4+ T helper) response to an antigen derived from an infectious agent or a tumor antigen, which prevents or at least partially arrests or ameliorates disease symptoms or progression. An immune response may also include an antibody response which has been facilitated by the stimulation of helper T cells.

Pharmaceutical compositions described above can include components other than the modified APCs or CTLs produced from them. For example, pharmaceutical compositions may include the following types of proteins, fragments, peptides or nucleic acids, or nucleotide sequences (within or not within the APC) that encode such molecules: (a) Toll-like receptor (TLR) ligands that can increase DC activation locally, such as monophosphoryl lipid A (TLR4 ligand), imiquimod (TLR7/8 ligand), unmethylated CpG oligonucleotides (TLR9 ligand), and others, and additional activation ligands, such as those found in monocyte-conditioned media "maturation cocktail" also can be included; (b) targeting ligands; (c) one or more apoptosis-inhibiting factors, such as Bcl-2 or Bcl-xL, for example; (d) antisense, ribozyme or siRNA molecules that target apoptosis-inducing molecules (e.g., Bax, Bak, caspases) and/or molecules that block homeostatic feedback (e.g., SOCS-1, c-CBL, CBL-b, SHP-1). APCs also can be administered in conjunction with other therapeutic regimens. In the treatment of a cancer, for example, modified APCs described herein primed with a tumor-associated antigen (e.g., PSMA) can be administered in conjunction (e.g., before, during or after) with an anti-cancer therapeutic, including, but not limited to, radiation treatment (e.g., radioactive implant), chemotherapy or surgery. In the treatment of a virus infection, for example, modified APCs described herein primed with a virus-associated antigen (e.g., HIV antigen(s)) can be administered in conjunction with an antiviral drug (e.g., HIV protease inhibitor). The person of ordinary skill in the art can select other therapies in combination with administration of modified APCs described herein based upon the disease being treated.

A DC modified with a membrane-targeted Akt molecule also may be utilized in combination with one or more other agents. Such agents include, for example, a nucleic acid, a viral particle, an adjuvant and/or another modified DC, in some embodiments. For example, a DC may be may be contacted with a first polynucleotide sequence that encodes a membrane-targeted Akt described herein, and a second polynucleotide sequence that encodes an inducible CD40 molecule. Inducible CD40 molecule embodiments are described, for example, in US publication 20040209836 (published Oct. 21, 2004). The first and second polynucleotide sequences may be in one nucleic acid, in separate nucleic acids, in one viral particle or in separate viral particles. Thus, provided herein is a composition comprising (i) a first polynucleotide sequence that encodes a first chimeric protein comprising an Akt and a membrane-association region, and (ii) a second polynucleotide sequence that encodes a second chimeric protein comprising a membrane-association region, a multimeric ligand binding region and a CD40 cytoplasmic polypeptide region lacking the CD40 extracellular domain. The first and second polynucleotide sequences may be in one nucleic acid, or in separate nucleic acids, in certain embodiments. Also provided herein is a composition comprising the first chimeric protein and the second chimeric protein. The composition may comprise a DC that includes the first and second chimeric protein, in certain embodiments. Such a DC optionally may be contacted with an antigen or fragment thereof or a third polynucleotide sequence encoding the foregoing, and optionally may include an antigen or fragment thereof or a third polynucleotide sequence encoding the foregoing. Also provided are methods for using such polynucleotides, proteins and DCs.

Kits

Kits comprise one or more containers, which contain one or more of the compositions and/or components described herein. A kit comprises one or more of the components in any number of separate containers, packets, tubes, vials, microtiter plates and the like, or the components may be combined in various combinations in such containers. A kit in some embodiments includes a component described herein and provides instructions that direct the user to another component not included in the kit.

A kit can include components described herein in a variety of combinations. A kit may comprise one, two, three, four, five or more components described herein. For example, a kit can include a nucleic acid having a nucleotide sequence that encodes an Akt molecule.

A kit sometimes is utilized in conjunction with a method described herein, and sometimes includes instructions for performing one or more methods described herein and/or a description of one or more compositions described herein. Instructions and/or descriptions may be in printed form and may be included in a kit insert. A kit also may include a written description of an interne location that provides such instructions or descriptions.

Akt related components that may be provided in a kit include one or more adjuvants, one or more antigens or antigen-encoding nucleic acids, one or more types of cells (e.g., for producing a nucleic acid), one or more agents for transferring a nucleic acid to antigen presenting cells or another type of cell, one or more reagents or devices for isolating dendritic cells from a subject, one or more devices for transferring modified dendritic cells to a subject, and one or more agents or devices for assessing the presence or absence of an immune response, for example. A kit may include one or more other components described hereafter.

A component in a kit sometimes is a molecule that specifically interacts with (e.g., binds to) a nucleic acid, protein, polypeptide or peptide described above. The latter class of components sometimes are referred to herein as "specific interaction reagents" or "specific binding reagents." A specific binding reagent sometimes is in association with detectable label described in greater detail hereafter. Examples of specific binding reagents include antibodies and antibody fragments; binding partners; chemical compounds; and antisense, ribozyme and siRNA nucleic acids.

A variety of antibodies and antibody fragments are available to the artisan, and can be generated by the artisan, for use as a specific binding reagent. Antibodies sometimes are IgG, IgM, IgA, IgE, or an isotype thereof (e.g., IgG1, IgG2a, IgG2b or IgG3), sometimes are polyclonal or monoclonal, and sometimes are chimeric, humanized or bispecific versions of such antibodies. Polyclonal and monoclonal antibodies that bind specific antigens are commercially available, and methods for generating such antibodies are known. In general, polyclonal antibodies are produced by injecting an isolated antigen (e.g., an Akt protein or fragment) into a suitable animal (e.g., a goat or rabbit); collecting blood and/or other tissues from the animal containing antibodies specific for the antigen and purifying the antibody. Methods for generating monoclonal antibodies, in general, include injecting an animal with an isolated antigen (e.g., often a mouse or a rat); isolating splenocytes from the animal; fusing the splenocytes with myeloma cells to form hybridomas; isolating the hybridomas and selecting hybridomas that produce monoclonal antibodies which specifically bind the antigen (e.g., Kohler & Milstein, Nature 256:495 497 (1975) and StGroth & Scheidegger, J Immunol Methods 5:1 21 (1980)).

Methods for generating chimeric and humanized antibodies also are known (see, e.g., U.S. Pat. No. 5,530,101 (Queen, et al.), U.S. Pat. No. 5,707,622 (Fung, et al.) and U.S. Pat. Nos. 5,994,524 and 6,245,894 (Matsushima, et al.)), which generally involve transplanting an antibody variable region from one species (e.g., mouse) into an antibody constant domain of another species (e.g., human). Antigen-binding regions of antibodies (e.g., Fab regions) include a light chain and a heavy chain, and the variable region is composed of regions from the light chain and the heavy chain. Given that the variable region of an antibody is formed from six complementarity-determining regions (CDRs) in the heavy and light chain variable regions, one or more CDRs from one antibody can be substituted (i.e., grafted) with a CDR of another antibody to generate chimeric antibodies. Also, humanized antibodies are generated by introducing amino acid substitutions that render the resulting antibody less immunogenic when administered to humans.

A specific binding reagent sometimes is an antibody fragment, such as a Fab, Fab', F(ab)'2, Dab, Fv or single-chain Fv (ScFv) fragment, and methods for generating antibody fragments are known (see, e.g., U.S. Pat. Nos. 6,099,842 and 5,990,296 and PCT/GB00/04317). In some embodiments, a binding partner in one or more hybrids is a single-chain antibody fragment, which sometimes are constructed by joining a heavy chain variable region with a light chain variable region by a polypeptide linker (e.g., the linker is attached at the C-terminus or N-terminus of each chain) by recombinant molecular biology processes. Such fragments often exhibit specificities and affinities for an antigen similar to the original monoclonal antibodies. Bifunctional antibodies sometimes are constructed by engineering two different binding specificities into a single antibody chain and sometimes are constructed by joining two Fab' regions together, where each Fab' region is from a different antibody (e.g., U.S. Pat. No. 6,342, 221). Antibody fragments often comprise engineered regions such as CDR-grafted or humanized fragments. In certain embodiments the binding partner is an intact immunoglobulin, and in other embodiments the binding partner is a Fab monomer or a Fab dimer.

The artisan may select and prepare a binding partner of Akt as a specific binding reagent. Multiple binding partners of an Akt protein exist (e.g., CK2, IRAK1, MAP3K8, TNF11, MTTL7 (http address www.ncbi.nlm.nih.gov/entrez/query.fcgi?db=gene&cmd=Retrieve&dopt=full_report&list_uids=207)). The artisan may utilize a fragment of a binding partner that binds to an Akt protein or fragment as a specific binding reagent in specific embodiments. The artisan also may optimize a binding reagent for a specific use or identify new binding reagents using a variety of procedures. For example, binding partners may be identified by lysing cells and analyzing cell lysates by electrophoretic techniques. Alternatively, a two-hybrid assay or three-hybrid assay can be utilized (e.g., U.S. Pat. No. 5,283,317; Zervos et al., Cell 72:223-232 (1993); Madura et al., J. Biol. Chem. 268: 12046-12054 (1993); Bartel et al., Biotechniques 14: 920-924 (1993); Iwabuchi et al., Oncogene 8: 1693-1696 (1993); and Brent WO94/10300). A two-hybrid system is based on the modular nature of most transcription factors, which consist of separable DNA-binding and activation domains. The assay often utilizes two different DNA constructs. In one construct, an Akt nucleic acid (sometimes referred to as the "bait") is fused to a gene encoding the DNA binding domain of a known transcription factor (e.g., GAL-4). In another construct, a DNA sequence from a library of DNA sequences that encodes a potential binding partner (sometimes referred to as the "prey") is fused to a gene that encodes an activation domain of the known transcription factor. Sometimes, an Akt nucleic acid is linked to the activation domain. If the "bait" and the "prey" molecules interact in vivo, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to identify the potential binding partner.

The artisan of ordinary skill can select a chemical compound as a specific binding reagent. Compounds can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive (see, e.g., Zuckermann et al., J. Med. Chem.37: 2678-85 (1994)); spatially addressable parallel solid phase or solution phase libraries; synthetic library methods requiring deconvolution; "one-bead one-compound" library methods; and synthetic library methods using affinity chromatography selection. Biological library and peptoid library approaches are typically limited to peptide libraries, while the other approaches are applicable to peptide, non-peptide oligomer or small molecule libraries of compounds (Lam, Anticancer Drug Des. 12: 145, (1997)). Examples of methods for synthesizing molecular libraries are described, for example, in DeWitt et al., Proc. Natl. Acad. Sci. U.S.A. 90: 6909 (1993); Erb et al., Proc. Natl. Acad. Sci. USA 91: 11422 (1994); Zuckermann et al., J. Med. Chem. 37: 2678 (1994); Cho et al., Science 261: 1303 (1993); Carrell et al., Angew. Chem. Int. Ed. Engl. 33: 2059 (1994); Carell et al., Angew. Chem. Int. Ed. Engl. 33: 2061 (1994); and in Gallop et al., J. Med. Chem. 37: 1233 (1994). Libraries of compounds may be presented in solution (e.g., Houghten, Biotechniques 13: 412-421 (1992)), or on beads (Lam, Nature 354: 82-84 (1991)), chips (Fodor, Nature 364: 555-556 (1993)), bacteria or spores (Ladner, U.S. Pat. No. 5,223,409), plasmids (Cull et al., Proc. Natl. Acad. Sci. USA 89: 1865-1869 (1992)) or on phage (Scott and Smith, Science 249: 386-390 (1990); Devlin, Science 249: 404-406 (1990); Cwirla et al., Proc. Natl. Acad. Sci. 87: 6378-6382 (1990); Felici, J. Mol. Biol. 222: 301-310 (1991); Ladner supra.). A compound often is a small molecule. Small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

The artisan of ordinary skill can select and prepare a nucleic acid specific binding reagent for use. Nucleic acids may comprise or consist of analog or derivative nucleic acids, such as polyamide nucleic acids (PNA) and others exemplified in U.S. Pat. Nos. 4,469,863; 5,536,821; 5,541,306; 5,637,683; 5,637,684; 5,700,922; 5,717,083; 5,719,262; 5,739,308; 5,773,601; 5,886,165; 5,929,226; 5,977,296; 6,140,482; 5,614,622; 5,739,314; 5,955,599; 5,962,674; 6,117,992; WIPO publications WO 00/56746, WO 00/75372 and WO 01/14398, and related publications. An antisense nucleic acid sometimes is designed, prepared and/or utilized by the artisan to inhibit an Akt nucleic acid. An "antisense" nucleic acid refers to a nucleotide sequence complementary to a "sense" nucleic acid encoding an Akt protein or fragment (e.g., complementary to the coding strand of a double-stranded cDNA molecule or complementary to an mRNA sequence). The antisense nucleic acid can be complementary to an entire coding strand, or to a portion thereof or a substantially identical sequence thereof. In another embodiment, the antisense nucleic acid molecule is antisense to a "noncoding region" of the coding strand of a nucleotide sequence.

An antisense nucleic acid can be complementary to the entire coding region of an mRNA encoded by an Akt nucleotide sequence, and often the antisense nucleic acid is an oligonucleotide antisense to only a portion of a coding or noncoding region of the mRNA. For example, the antisense oligonucleotide can be complementary to the region surrounding the translation start site of the mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length. An antisense nucleic acid can be constructed using chemical synthesis or enzymatic ligation reactions using standard procedures. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids (e.g., phosphorothioate derivatives and acridine substituted nucleotides can be used). Antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

When utilized in subjects, antisense nucleic acids typically are administered to a subject (e.g., by direct injection at a tissue site) or generated in situ such that they hybridize with or bind to cellular mRNA and/or genomic DNA encoding a polypeptide and thereby inhibit expression of the polypeptide, for example, by inhibiting transcription and/or translation. Alternatively, antisense nucleic acid molecules can be modified to target selected cells and then are administered systemically. For systemic administration, antisense molecules can be modified such that they specifically bind to receptors or antigens expressed on a selected cell surface, for example, by linking antisense nucleic acid molecules to peptides or antibodies which bind to cell surface receptors or antigens. Antisense nucleic acid molecules can also be delivered to cells using the vectors described herein. Sufficient intracellular concentrations of antisense molecules are achieved by incorporating a strong promoter, such as a pol II or pol III promoter, in the vector construct. Antisense nucleic acid molecules sometimes are alpha-anomeric nucleic acid molecules. An alpha-anomeric nucleic acid molecule forms specific double-stranded hybrids with complementary RNA in which, contrary to the usual beta-units, the strands run parallel to each other (Gaultier et al., Nucleic Acids. Res. 15: 6625-6641 (1987)). Antisense nucleic acid molecules also can comprise a 2'-o-methylribonucleotide (Inoue et al., Nucleic Acids Res. 15: 6131-6148 (1987)) or a chimeric RNA-DNA analogue (Inoue et al., FEBS Lett. 215: 327-330 (1987)). Antisense nucleic acids sometimes are composed of DNA or PNA or any other nucleic acid derivatives described previously.

An antisense nucleic acid is a ribozyme in some embodiments. A ribozyme having specificity for an Aid nucleotide sequence can include one or more sequences complementary to such a nucleotide sequence, and a sequence having a known catalytic region responsible for mRNA cleavage (e.g., U.S. Pat. No. 5,093,246 or Haselhoff and Gerlach, Nature 334: 585-591 (1988)). For example, a derivative of a Tetrahymena L-19 IVS RNA is sometimes utilized in which the nucleotide sequence of the active site is complementary to the nucleotide sequence to be cleaved in a mRNA (e.g., Cech et al. U.S. Pat. No. 4,987,071; and Cech et al. U.S. Pat. No. 5,116,742). Akt mRNA sequences also may be utilized to select a catalytic RNA having a specific ribonuclease activity from a pool of RNA molecules (e.g., Bartel & Szostak, Science 261: 1411-1418 (1993)).

Specific binding reagents sometimes are nucleic acids that can form triple helix structures with an Aid nucleic acid. Akt expression can be inhibited by targeting nucleotide sequences complementary to the regulatory region of a nucleotide sequence referenced herein or a substantially identical sequence (e.g., promoter and/or enhancers) to form triple helical structures that prevent transcription of a gene in target cells (see e.g., Helene, Anticancer Drug Des. 6(6): 569-84 (1991); Helene et al., Ann. N.Y. Acad. Sci. 660: 27-36 (1992); and Maher, Bioassays 14(12): 807-15 (1992). Triple helix formation can be enhanced by generating a "switchback" nucleic acid molecule. Switchback molecules are synthesized in an alternating 5'-3',3'-5' manner, such that they base pair with first one strand of a duplex and then the other, eliminating the necessity for a sizeable stretch of purines or pyrimidines being present on one strand of a duplex.

An artisan may select an interfering RNA (RNAi) or siRNA specific binding reagent for use. The nucleic acid selected sometimes is the RNAi or siRNA or a nucleic acid that encodes such products. The term "RNAi" as used herein refers to double-stranded RNA (dsRNA) which mediates degradation of specific mRNAs, and can also be used to lower or eliminate gene expression. The term "short interfering nucleic acid", "siNA", "short interfering RNA", "siRNA", "short interfering nucleic acid molecule", "short interfering oligonucleotide molecule", or "chemically-modified short interfering nucleic acid molecule" as used herein refers to any nucleic acid molecule directed against a gene. For example, a siRNA is capable of inhibiting or down regulating gene expression or viral replication, for example by mediating RNA interference "RNAi" or gene silencing in a sequence-specific manner; see for example Zamore et al., 2000, Cell, 101, 25-33; Bass, 2001, Nature, 411, 428-429; Elbashir et al., 2001, Nature, 411, 494-498; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237; Hutvagner and Zamore, 2002, Science, 297, 2056-60; McManus et al., 2002, RNA, 8, 842-850; Reinhart et al., 2002, Gene & Dev., 16, 1616-1626; and Reinhart & Bartel, 2002, Science, 297, 1831). There is no particular limitation in the length of siRNA as long as it does not show toxicity. Examples of modified RNAi and siRNA include STEALTH™ forms (Invitrogen Corp., Carlsbad, Calif.), forms described in U.S. Patent Publication No. 2004/0014956 (application Ser. No. 10/357,529) and U.S. patent application Ser. No. 11/049,636, filed Feb. 2, 2005), and other forms described hereafter.

A siNA can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The siNA can be assembled from two separate oligonucleotides, where one strand is the sense strand and the other is the antisense strand, wherein the antisense and sense strands are self-complementary (i.e. each strand comprises nucleotide sequence that is complementary to nucleotide sequence in the other strand; such as where the antisense strand and sense strand form a duplex or double stranded structure, for example wherein the double stranded region is about 19 base pairs); the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof. Alternatively, the siNA is assembled from a single oligonucleotide, where the self-complementary sense and antisense regions of the siNA are linked by means of a nucleic acid based or non-nucleic acid-based linker(s). The siNA can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The siNA can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siNA molecule capable of mediating RNAi. The siNA can also comprise a single stranded polynucleotide having nucleotide sequence complementary to nucleotide sequence in a target nucleic acid molecule or a portion thereof (for example, where such siNA molecule does not require the presence within the siNA molecule of nucleotide sequence corresponding to the target nucleic acid sequence or a portion thereof), wherein the single stranded polynucleotide can further comprise a terminal phosphate group, such as a 5'-phosphate (see for example Martinez et al., 2002, Cell., 110, 563-574 and Schwarz et al., 2002, Molecular Cell, 10, 537-568), or 5',3'-diphosphate. In certain embodiments, the siNA molecule of the invention comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der waals interactions, hydrophobic interactions, and/or stacking interactions. In certain embodiments, the siNA molecules of the invention comprise nucleotide sequence that is complementary to nucleotide sequence of a target gene. In another embodiment, the siNA molecule of the invention interacts with nucleotide sequence of a target gene in a manner that causes inhibition of expression of the target gene.

The double-stranded RNA portions of siRNAs in which two RNA strands pair are not limited to the completely paired forms, and may contain non-pairing portions due to mismatch (the corresponding nucleotides are not complementary), bulge (lacking in the corresponding complementary nucleotide on one strand), and the like. Non-pairing portions can be contained to the extent that they do not interfere with siRNA formation. The "bulge" used herein often comprises 1 to 2 non-pairing nucleotides, and the double-stranded RNA region of siRNAs in which two RNA strands pair up sometimes contains 1 to 7, and at times 1 to 5 bulges. In addition, the "mismatch" used herein is contained in the double-stranded RNA region of siRNAs in which two RNA strands pair up, sometimes 1 to 7, and at times 1 to 5, in number. In an often utilized mismatch, one of the nucleotides is guanine, and the other is uracil. Such a mismatch is due to a mutation from C to T, G to A, or mixtures thereof in DNA coding for sense RNA, but not particularly limited to them. Furthermore, in the present invention, the double-stranded RNA region of siRNAs in which two RNA strands pair up may contain both bulge and mismatched, which sum up to, sometimes Ito 7, and at times Ito 5, in number. The terminal structure of siRNA may be either blunt or cohesive (overhanging) as long as siRNA enables to silence the target gene expression due to its RNAi effect.

As used herein, siRNA molecules need not be limited to those molecules containing only RNA, but further encompasses chemically-modified nucleotides and non-nucleotides. In addition, as used herein, the term RNAi is meant to be equivalent to other terms used to describe sequence specific RNA interference, such as post transcriptional gene silencing, translational inhibition, or epigenetics. For example, siRNA molecules of the invention can be used to epigenetically silence genes at both the post-transcriptional level or the pre-transcriptional level. In a non-limiting example, epigenetic regulation of gene expression by siRNA molecules of the invention can result from siRNA mediated modification of chromatin structure to alter gene expression (see, for example, Verdel et al., 2004, Science, 303, 672-676; Pal-Bhadra et al., 2004, Science, 303, 669-672; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237).

RNAi may be designed by those methods known to those of ordinary skill in the art. In one example, siRNA may be designed by classifying RNAi sequences, for example 1000 sequences, based on functionality, with a functional group being classified as having greater than 85% knockdown activity and a non-functional group with less than 85% knockdown activity. The distribution of base composition was calculated for entire the entire RNAi target sequence for both the functional group and the non-functional group. The ratio of base distribution of functional and non-functional group may then be used to build a score matrix for each position of RNAi sequence. For a given target sequence, the base for each position is scored, and then the log ratio of the multiplication of all the positions is taken as a final score. Using this score system, a very strong correlation may be found of the functional knockdown activity and the log ratio score. Once the target sequence is selected, it may be filtered through both fast NCBI blast and slow Smith Waterman algorithm search against the Unigene database to identify the gene-specific RNAi or siRNA. Sequences with at least one mismatch in the last 12 bases may be selected.

Nucleic acid reagents include those which are engineered, for example, to produce dsRNAs. Examples of such nucleic acid molecules include those with a sequence that, when transcribed, folds back upon itself to generate a hairpin molecule containing a double-stranded portion. One strand of the double-stranded portion may correspond to all or a portion of the sense strand of the mRNA transcribed from the gene to be silenced while the other strand of the double-stranded portion may correspond to all or a portion of the antisense strand. Other methods of producing dsRNAs may be used, for example, nucleic acid molecules may be engineered to have a first sequence that, when transcribed, corresponds to all or a portion of the sense strand of the mRNA transcribed from the gene to be silenced and a second sequence that, when transcribed, corresponds to all or portion of an antisense strand (i.e., the reverse complement) of the mRNA transcribed from the gene to be silenced.

Nucleic acid molecules which mediate RNAi may also be produced ex vivo, for example, by oligonucleotide synthesis. Oligonucleotide synthesis may be used for example, to design dsRNA molecules, as well as other nucleic acid molecules (e.g., other nucleic acid molecules which mediate RNAi) with one or more chemical modification (e.g., chemical modifications not commonly found in nucleic acid molecules such as the inclusion of 2'-O-methyl, 2'-O-ethyl, 2'-O-propyl, 2'-fluoro, etc. groups).

In some embodiments, a dsRNA to be used to silence a gene may have one or more (e.g., one, two, three, four, five, six, etc.) regions of sequence homology or identity to a gene to be silenced. Regions of homology or identity may be from about 20 bp (base pairs) to about 5 kbp (kilo base pairs) in length, 20 bp to about 4 kbp in length, 20 bp to about 3 kbp in length, 20 bp to about 2.5 kbp in length, from about 20 bp to about 2 kbp in length, 20 bp to about 1.5 kbp in length, from about 20 bp to about 1 kbp in length, 20 bp to about 750 bp in length, from about 20 bp to about 500 bp in length, 20 bp to about 400 bp in length, 20 bp to about 300 bp in length, 20 bp to about 250 bp in length, from about 20 bp to about 200 bp in length, from about 20 bp to about 150 bp in length, from about 20 bp to about 100 bp in length, from about 20 bp to about 90 bp in length, from about 20 bp to about 80 bp in length, from about 20 bp to about 70 bp in length, from about 20 bp to about 60 bp in length, from about 20 bp to about 50 bp in length, from about 20 bp to about 40 bp in length, from about 20 bp to about 30 bp in length, from about 20 bp to about 25 bp in length, from about 15 bp to about 25 bp in length, from about 17 bp to about 25 bp in length, from about 19 bp to about 25 bp in length, from about 19 bp to about 23 bp in length, or from about 19 bp to about 21 bp in length.

A hairpin containing molecule having a double-stranded region may be used as RNAi. The length of the double stranded region may be from about 20 bp (base pairs) to about 2.5 kbp (kilo base pairs) in length, from about 20 bp to about 2 kbp in length, 20 bp to about 1.5 kbp in length, from about 20 bp to about 1 kbp in length, 20 bp to about 750 bp in length, from about 20 bp to about 500 bp in length, 20 bp to about 400 bp in length, 20 bp to about 300 bp in length, 20 bp to about 250 bp in length, from about 20 bp to about 200 bp in length, from about 20 bp to about 150 bp in length, from about 20 bp to about 100 bp in length, 20 bp to about 90 bp in length, 20 bp to about 80 bp in length, 20 bp to about 70 bp in length, 20 bp to about 60 bp in length, 20 bp to about 50 bp in length, 20 bp to about 40 bp in length, 20 bp to about 30 bp in length, or from about 20 bp to about 25 bp in length. The non-base-paired portion of the hairpin (i.e., loop) can be of any length that permits the two regions of homology that make up the double-stranded portion of the hairpin to fold back upon one another.

Any suitable promoter may be used to control the production of RNA from the nucleic acid reagent, such as a promoter described above. Promoters may be those recognized by any polymerase enzyme. For example, promoters may be promoters for RNA polymerase II or RNA polymerase III (e.g., a U6 promoter, an H1 promoter, etc.). Other suitable promoters include, but are not limited to, T7 promoter, cytomegalovirus (CMV) promoter, mouse mammary tumor virus (MMTV) promoter, metalothionine, RSV (Rous sarcoma virus) long terminal repeat, SV40 promoter, human growth hormone (hGH) promoter. Other suitable promoters are known to those skilled in the art and are within the scope of the present invention.

Double-stranded RNAs used in the practice of the invention may vary greatly in size. Further the size of the dsRNAs used will often depend on the cell type contacted with the dsRNA. As an example, animal cells such as those of *C. elegans* and *Drosophila melanogaster* do not generally undergo apoptosis when contacted with dsRNAs greater than about 30 nucleotides in length (i.e., 30 nucleotides of double stranded region) while mammalian cells typically do undergo apoptosis when exposed to such dsRNAs. Thus, the design of the particular experiment will often determine the size of dsRNAs employed.

In many instances, the double stranded region of dsRNAs contained within or encoded by nucleic acid molecules used in the practice of the invention will be within the following ranges: from about 20 to about 30 nucleotides, from about 20 to about 40 nucleotides, from about 20 to about 50 nucleotides, from about 20 to about 100 nucleotides, from about 22 to about 30 nucleotides, from about 22 to about 40 nucleotides, from about 20 to about 28 nucleotides, from about 22 to about 28 nucleotides, from about 25 to about 30 nucleotides, from about 25 to about 28 nucleotides, from about 30 to about 100 nucleotides, from about 30 to about 200 nucleotides, from about 30 to about 1,000 nucleotides, from about 30 to about 2,000 nucleotides, from about 50 to about 100 nucleotides, from about 50 to about 1,000 nucleotides, or from about 50 to about 2,000 nucleotides. The ranges above refer to the number of nucleotides present in double stranded regions. Thus, these ranges do not reflect the total length of the dsRNAs themselves. As an example, a blunt ended dsRNA formed from a single transcript of 50 nucleotides in total length with a 6 nucleotide loop, will have a double stranded region of 23 nucleotides.

As suggested above, dsRNAs used in the practice of the invention may be blunt ended, may have one blunt end, or may have overhangs on both ends. Further, when one or more overhang is present, the overhang(s) may be on the 3' and/or 5' strands at one or both ends. Additionally, these overhangs may independently be of any length (e.g., one, two, three, four, five, etc. nucleotides). As an example, STEALTH™ RNAi is blunt at both ends. Also included are sets of RNAi and those which generate RNAi. Such sets include those which either (1) are designed to produce or (2) contain more than one dsRNA directed against the same target gene. As an example, the invention includes sets of STEALTH™ RNAi wherein more than one STEALTH™ RNAi shares sequence homology or identity to different regions of the same target gene.

A protein, fragment or nucleic acid described herein sometimes is in association with detectable label. The detectable label can be covalently linked to the reagent, and sometimes is in association with the reagent in a non-covalent linkage. Methods for attaching such binding pairs to reagents and effecting binding are known to the artisan. Any detectable label suitable for detection of an interaction or biological activity in a system can be appropriately selected and utilized by the artisan. Examples of detectable labels are fluorescent labels such as fluorescein, rhodamine, and others (e.g., Anantha, et al., Biochemistry (1998) 37:2709 2714; and Qu & Chaires, Methods Enzymol. (2000) 321:353 369); radioactive isotopes (e.g., $^{125}I$, $^{131}I$, $^{35}S$, $^{31}P$, $^{32}P$, $^{14}C$, $^{3}H$, $^{7}Be$, $^{28}Mg$, $^{57}Co$, $^{56}Zn$, $^{67}Cu$, $^{68}Ge$, $^{82}Sr$, $^{83}Rb$, $^{95}TC$, $^{96}TC$, $^{103}Pd$, $^{109}Cd$, and $^{127}Xe$); light scattering labels (e.g., U.S. Pat. No. 6,214,560, and commercially available from Genicon Sciences Corporation, CA); chemiluminescent labels and enzyme substrates (e.g., dioxetanes and acridinium esters), enzymic or protein labels (e.g., green fluorescence protein (GFP) or color variant thereof, luciferase, peroxidase); other chromogenic labels or dyes (e.g., cyanine), and labels described previously. Use of reagents in association with a detectable label are described in greater detail hereafter.

Cells also may be provided in a kit. A cell may over-express or under-express protein, fragment or nucleic acid or other molecule described herein. A cell can be processed in a variety of manners. For example, an artisan may prepare a lysate from a cell and optionally isolate or purify components, may transfect the cell with a nucleic acid reagent, may fix a cell reagent to a slide for analysis (e.g., microscopic analysis) and can immobilize a cell to a solid phase.

A cell that "over-expresses" an protein or fragment or nucleic acid described herein produces at least two, three, four or five times or more of the product as compared to a native cell from an organism that has not been genetically modified and/or exhibits no apparent symptom of a cell-proliferative disorder. Over-expressing cells may be stably transfected or transiently transfected with a nucleic acid a protein or fragment or nucleic acid described herein. A cell that "under-expresses" a protein or fragment or nucleic acid described herein produces at least five times less of the product as compared to a native cell from an organism that has not been genetically modified and/or exhibits no apparent symptom of a cell-proliferative disorder. In some embodiments, a cell that under-expresses a protein, fragment or nucleic acid contains no nucleic acid that can encode such a product (e.g., the cell is from a knock-out mouse) and no detectable amount of the product is produced. Methods for generating knock-out animals and using associated cells are known (e.g., Miller et al., J. Cell. Biol. 165: 407-419 (2004)). A cell that under-expresses a protein, fragment or nucleic acid described herein, for example, sometimes is in contact with a nucleic acid inhibitor that blocks or reduces the amount of the product produced by the cell in the absence of the inhibitor.

Cells include, but are not limited to, bacterial cells (e.g., *Escherichia* spp. cells (e.g., Expressway™ HTP Cell-Free *E. coli* Expression Kit, Invitrogen, California) such as DH10B, Stbl2, DH5-alpha, DB3, DB3.1 for example), DB4, DB5, JDP682 and ccdA-over (e.g., U.S. application Ser. No. 09/518,188), *Bacillus* spp. cells (e.g., *B. subtilis* and *B. megaterium* cells), *Streptomyces* spp. cells, *Erwinia* spp. cells, *Klebsiella* spp. cells, *Serratia* spp. cells (particularly *S. marcessans* cells), *Pseudomonas* spp. cells (particularly *P. aeruginosa* cells), and *Salmonella* spp. cells (particularly *S. typhimurium* and *S. typhi* cells); photosynthetic bacteria (e.g., green non-sulfur bacteria (e.g., *Choroflexus* spp. (e.g., *C. aurantiacus*), *Chloronema* spp. (e.g., *C. gigateum*)), green sulfur bacteria (e.g., *Chlorobium* spp. (e.g., *C. limicola*), *Pelodictyon* spp. (e.g., *P. luteolum*), purple sulfur bacteria (e.g., *Chromatium* spp. (e.g., *C. okenii*)), and purple non-sulfur bacteria (e.g., *Rhodospirillum* spp. (e.g., *R. rubrum*), *Rhodobacter* spp. (e.g., *R. sphaeroides, R. capsulatus*), *Rhodomicrobium* spp. (e.g., *R. vanellii*)); yeast cells (e.g., *Saccharomyces cerevisiae* cells and *Pichia pastoris* cells); insect cells (e.g., *Drosophila* (e.g., *Drosophila melanogaster*), *Spodoptera* (e.g., *Spodoptera frugiperda* Sf9 and Sf21 cells) and *Trichoplusa* (e.g., High-Five cells); nematode cells (e.g., *C. elegans* cells); avian cells; amphibian cells (e.g., *Xenopus laevis* cells); reptilian cells; and mammalian cells (e.g., NIH3T3, 293, CHO, COS, VERO, C127, BHK, Per-C6, Bowes melanoma and HeLa cells). These and other suitable cells are available commercially, for example, from Invitrogen Corporation, (Carlsbad, Calif.), American Type Culture Collection (Manassas, Va.), and Agricultural Research Culture Collection (NRRL; Peoria, Ill.).

EXAMPLES

The examples set forth below illustrate but do not limit the invention. The maturation state and lifespan of dendritic cells (DCs) are critical for the regulation of immunity. However, current DC preparations based on ex vivo treatment with differentiation and maturation factors can lead to transiently active DCs that may curtail T cell responses following re-infusion. Here, it is shown that Akt1 levels drop rapidly following growth factor withdrawal and are critical for pro-inflammatory signal-mediated DC survival and maturation. Conversely, LPS or CD40 signaling stabilizes Akt1 and promotes both DC activation and survival. Also, it is shown that Akt1-mediated survival depends on Bcl-2, but not Bcl-xL. Adenoviral-mediated overexpression of a novel, lipid-raft targeted Akt allele, MF-ΔAkt, is sufficient for murine bone marrow-derived DC maturation and survival, resulting in enhanced T cell proliferation and activation, and eradication of large pre-established thymoma as well as B 16 melanoma. In addition, transduction of human DCs with an adenovirus expressing human Akt1, MF-ΔhAkt, also significantly improves DC survival, antigen-specific T cell proliferation and CD8+ T cell responses. These data demonstrate that Akt1 is a critical regulator of DC lifespan and can significantly improve the efficacy of DC-based tumor vaccines. Results presented herein also is presented in Park et al., Nat. Biotechnol. 2006 Dec. 24(12):1581-90.

Example 1

Rapid Down-Regulation of Akt Following Cytokine Withdrawal is Prevented by Signals of Innate and Acquired Immune Responses To investigate pathways involved in DC survival following inflammatory stimuli, signaling proteins induced by LPS that have been previously implicated in cell survival were assessed. In addition to the NF-kappaB pathway, a variety of signaling molecules, such as MAPK30, JAK31, PI3K24 and Src family kinases32, are activated by LPS treatment of DCs and macrophages. Therefore, LPS-treated bone marrow-derived DCs (BMDCs) were incubated with effective concentrations of specific inhibitors for 48 hr to substantially block these proteins. Treatment with PI3K and Src kinase inhibitors significantly antagonized LPS-mediated survival, whereas JAK and MAPK inhibitors had almost no effect (FIG. 1A).

To further study the role of PI3K in DC survival, kinetics of Akt expression, a key down-stream effector of PI3K signaling were determined, during GM-CSF deprivation-mediated DC death. Within 24 hours of GM-CSF deprivation, prior to DC death, total Akt protein levels were rapidly down regulated. In addition down-regulation of Akt closely correlated with decreases in the protein level of Bcl-2, known to be down-regulated during DC maturation (FIG. 1B). To test whether innate and adaptive immune response-triggering molecules modulate Akt protein level, leading to DC survival, it first was confirmed that anti-CD40 mAb and LPS both protect DCs against GM-CSF deprivation-mediated death (FIG. 1C). While GM-CSF deprivation consistently down-regulated AU protein levels, LPS or anti-CD40 treatment prevented this down-regulation of Akt. Like previous reports, it was determined that minimal manipulation of DCs, such as re-plating, contributed to DC activation, reflected by DC maturation markers (data not shown) and the increase in Akt phosphorylation at day 2 after GM-CSF withdrawal. By contrast, LPS and CD40 signals induced high Akt phosphorylation and protein levels on day 4, suggesting that LPS and CD40 stimulation regulate not only the phosphorylation state but also the steady-state protein level of Akt, thereby promoting DC survival (FIG. 1D).

To further test the hypothesis that PI3K and Akt are common regulators for immune response-mediated DC survival, we evaluated effects of various concentrations (0.05 µM-5 µM) of another PI3K inhibitor, wortmannin, on DCs treated with LPS or anti-CD40. Even low wortmannin concentrations (0.05-0.5 µM), having little effect on other cell types (data not shown), led to death of both LPS- and anti-CD40-treated DCs, implicating an essential role for PI3K for DC survival (FIG. 1E). Anti-apoptotic molecules Bcl-x and Bcl-2 are essential in preventing DC death and are purportedly differentially regulated during innate and acquired immune responses 12. Therefore, Bcl-2 and Bcl-xL protein levels were determined in wortmannin-treated DCs pre-exposed to LPS or anti-CD40. Consistent with previous findings, GM-CSF deprivation down-regulated Bcl-xL as well as Bcl-2, but LPS and anti-CD40 treatment reversed this effect. In the presence of wortmannin with LPS or anti-CD40, only Bcl-2 protein was rapidly down regulated, whereas protein levels of Bcl-xL were stable for at least 3 days (FIG. 1F). By contrast, LPS and anti-CD40-induced Bcl-xL did not prevent DC death triggered by PI3K inhibition, suggesting that Akt and Bcl-2 were critical effectors of PI3K-dependent DC survival, and Bcl-xL was regulated independently.

A description of FIGS. 1A to 1F follows. FIG. 1A shows PI3K and Src kinase are involved in LPS-mediated DC survival. Bone marrow-derived CD11c+DCs were incubated for 16 hr with LPS (1 µg/ml) along with the indicated concentrations (µM) of PI3K inhibitor Ly294002, JAK inhibitor AG490, MAPK inhibitor PD98059 or Src kinase inhibitor PP2. Cell viability was assessed 2 days later using propidium iodide (PI) staining. FIG. 1B shows down-regulation of Akt and Bcl-2 following GM-CSF withdrawal. Total Akt and Bcl-2 protein levels of BMDCs were determined after incubation for 1-4 days without GM-CSF. FIG. 1C shows following GM-CSF withdrawal, BMDCs were treated for 16 hr with 1 µg/ml of LPS (●), 10 µg/ml of anti-CD40 antibody (▲) or neither (■) before incubation for indicated times, and cell viability was assessed by PI staining. FIG. 1D shows LPS and anti-CD40 prevent the down-regulation in BMDCs of phospho-Akt and total AU, as determined by Western blotting using anti-pAkt-S473 and anti-AU Abs, respectively. FIG. 1E shows PI3K is essential for both LPS and anti-CD40-mediated DC survival. DC viability was assessed by PI staining at indicated time points after LPS or alpha-CD40 treatment along with 0 (■), 0.05 (•), 0.5 (○) or 5 (□)µM wortmannin. FIG. 1F shows down-regulation of Akt correlates with Bcl-2, but not Bcl-xL, expression levels. Protein levels were determined by Western blotting at indicated time points. The amount of loaded proteins was normalized to actin. All data represent two (FIGS. 1B, 1D and 1F) or three (FIGS. 1A, 1C and 1E) independent experiments with similar results. Error bars represent S.D. of duplicate measurements (FIGS. 1A and 1E).

Example 2

Activation and Maintenance of DC Survival Requires Akt1

Despite an essential role for PI3K in DC survival and the commonly pivotal position of Akt in PI3K signaling, it was also possible that the observed Akt down-regulation following GM-CSF withdrawal was a secondary outcome of DC death. Therefore, to directly evaluate the role of Akt, it was determined whether endogenous Akt activity was essential for LPS or CD40-mediated DC survival. First, expression pattern of Akt subtypes was assessed in DCs. Of the two Akt isoforms commonly found in hematopoietic cells, Akt1 was identified as the predominant isoform in BMDCs (FIG. 2A). Based on these results, LPS or CD40-mediated survival of DCs was tested from Akt1+/+ and Akt1-/- mice. Although the total protein level of Akt is much less in Akt1-deficient BMDCs (FIG. 2B), Akt1-/- DCs showed comparable numbers and viability relative to Akt1+/+DCs after BMDC isolation (data not shown). However, GM-CSF withdrawal for 48 hr reduced the survival of Akt1-/- DCs relative to Akt1+/+ DCs. In addition, the protective effect of LPS and CD40 was completely abolished in Aka1-/- DCs, indicating that innate (LPS) and acquired (CD40) immune response-related DC survival requires Akt1 (FIG. 2C).

To further confirm the role of Akt1 in LPS-mediated DC survival from cytokine deprivation, growth factor-starved BMDCs were treated with moderate concentrations (5 µM) of Akt specific inhibitor Akt-I (IC50=5 µM) along with LPS for 16 hr, followed by incubation for an additional 48 hr in GM-CSF-free DC medium. Consistently, Akt-I significantly reduced LPS-mediated DC survival (FIG. 9C). Moreover, transfection of Akt-RNAi (100 nM), a synthetic Akt1-specific siRNA36, into BMDCs suppressed Akt expression and significantly (P<0.005) increased DC death even in the presence of LPS compared with control RNAi (FIG. 9A, 9B). Therefore, it was determined Akt1 is a critical mediator of DC survival signals, and down-regulation of Akt1 is a major regulatory mechanism to control DC longevity.

Figure 9:
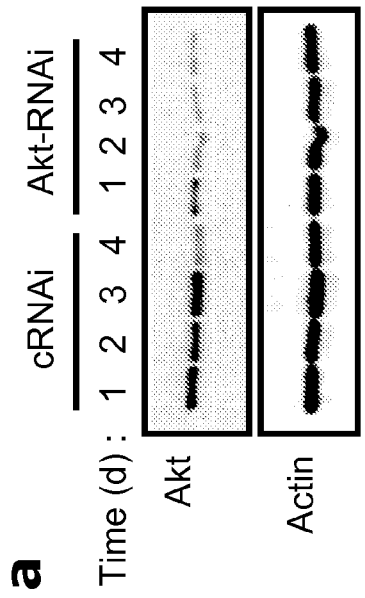
FIGS. 9A-9C show effects of Akt inhibitors on DC survival.
Figure 9:
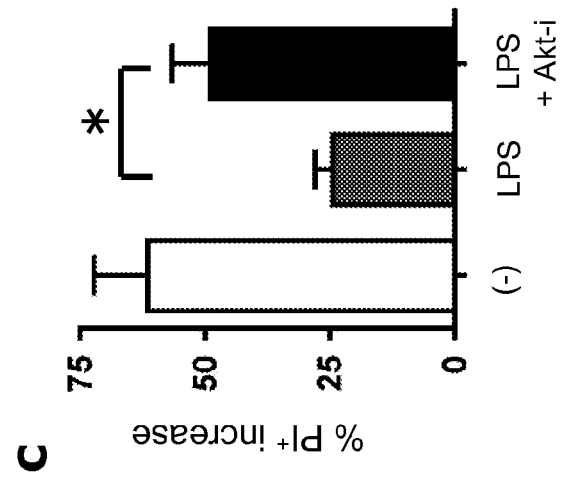
Figure 9:
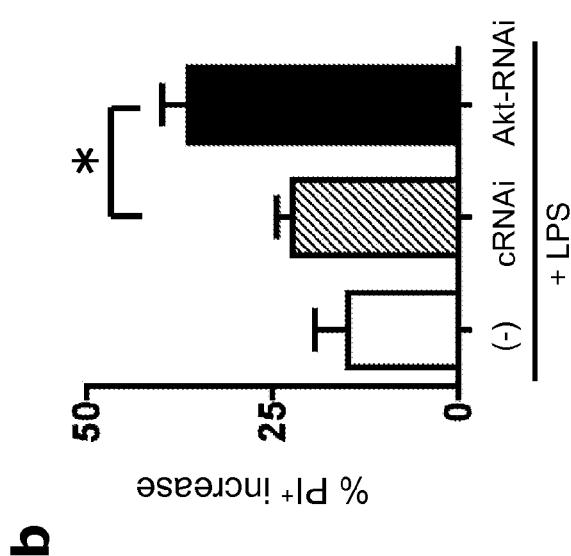

In addition to promoting DC survival, Akt can induce NF-kappaB activity through IKKbeta phosphorylation, critical for DC activation and maturation. However, the role of Akt in DC differentiation from bone marrow precursors has not been tested. Therefore, to investigate the effects of Akt1 on DC differentiation and activation, surface expression of several MHC and costimulatory molecules was assessed in Akt1+/+ and Aka1-/- BMDCs, including CD40, CD80, MHC class I Kb and MHC class II I-Ab. Although there was no difference in viability, the surface expression of lineage markers, CD11b and CD11c, and several MHC and costimulatory molecules on day 0 and 2 after DC differentiation, Akt1-/- BMDCs showed significantly reduced expression of maturation markers, CD40 (P<0.01), CD80 (P<0.005) and MHC class I Kb (P<0.01), relative to Akt1+/+ DCs on day 6 (FIG. 2D, FIG. 9). In addition, Akt1−/− BMDCs revealed a large defect in the further enhancement of maturation markers, such as CD40 and MHC class I Kb (FIG. 2F), as well as CD80 and MHC class II I-Ab (data not shown), even after LPS and CD40 stimulation, suggesting that Aka plays a critical role in DC differentiation and activation.

To further investigate the physiological effects of Akt1 deficiency in DCs, size and cellularity of lymph nodes and spleen were examined in Akt1−/− and Akt1+/+ mice. Although the relative distribution of T cell, B cell and CD11c+ cells was normal with only a partial decrease of CD8+ T cells (data not shown), the total cell number of inguinal lymph nodes and spleen was dramatically reduced (86% and 43%, respectively) in Akt1−/− mice when compared to Akt1+/+ littermates (FIG. 2E, FIG. 11), supporting the tenet that reduced survival and activation defects in Akt1−/− DCs results in reduction of size, cellularity and likely functions of secondary lymphoid organs.

A description of FIGS. 2A-2F follows. FIG. 2A shows analysis of Akt isoforms in BMDCs. BMDC (DC) or control (A431) cell lysates were immunoblotted with specific antibodies against Akt1 and Akt2. Protein level of total Akt was determined by reprobing with anti-Akt Ab. FIG. 2B shows analysis of Akt1 and total Akt protein level in Akt1−/− DCs. Cell lysates from Akt1+/+ or Akt1−/− BMDCs were immunoblotted with antibodies against Akt1 or total Akt. Protein loading was normalized by actin immunoblotting. FIG. 1C shows comparison of LPS- or anti-CD40-mediated survival in Akt1+/+ or Akt−/− DCs. BMDCs from Akt1+/+ or Akt1−/− mice were untreated (open bars) or treated with LPS (1 μg/ml, gray bars) or anti-CD40 (10 μg/ml, filled bars) and further incubated in the presence of wortmannin (0.5 μM) for 48 hrs. Background % PI+ at day 0 was subtracted from each data point. FIG. 2D shows expression of surface markers in Akt1+/+ or Akt1−/− DCs. On day 6 after DC differentiation, surface expression of MHC and costimulatory molecules in Akt1+/+ or Akt1−/− BMDCs was assessed by CD40, CD80, MHC class I Kb and MHC class II I-Ab staining along with CD11c. MFI, is mean fluorescence intensity. FIG. 2E shows a comparison of lymph nodes from Akt1+/+ or Akt−/− mice. Size of inguinal lymph nodes isolated from Akt1+/+ or Akt1−/− littermates was measured (bottom scale bar, 1 mm gap) and trypan blue staining assessed total cell numbers within each lymph node. FIG. 2F shows reduced maturation of Akt1−/− DCs. After 6 days of BMDC differentiation, BMDCs in the starting wells were further treated with indicated stimuli as above in FIG. 2C for 48 hr. DC maturation was assessed by CD40 and MHC class I Kb staining. Numbers indicate percentage of cells in that quadrant. Data represent two (FIGS. 2B and 2F), three (FIGS. 2C and 2D) or six (FIG. 2E) independent experiments. Error bars indicate mean±S.D. of results derived from three (FIGS. 2D and 2E) independent littermates. *, P<0.01, **, P<0.005, . . . , P<0.0005.

Example 3

Figure 3:
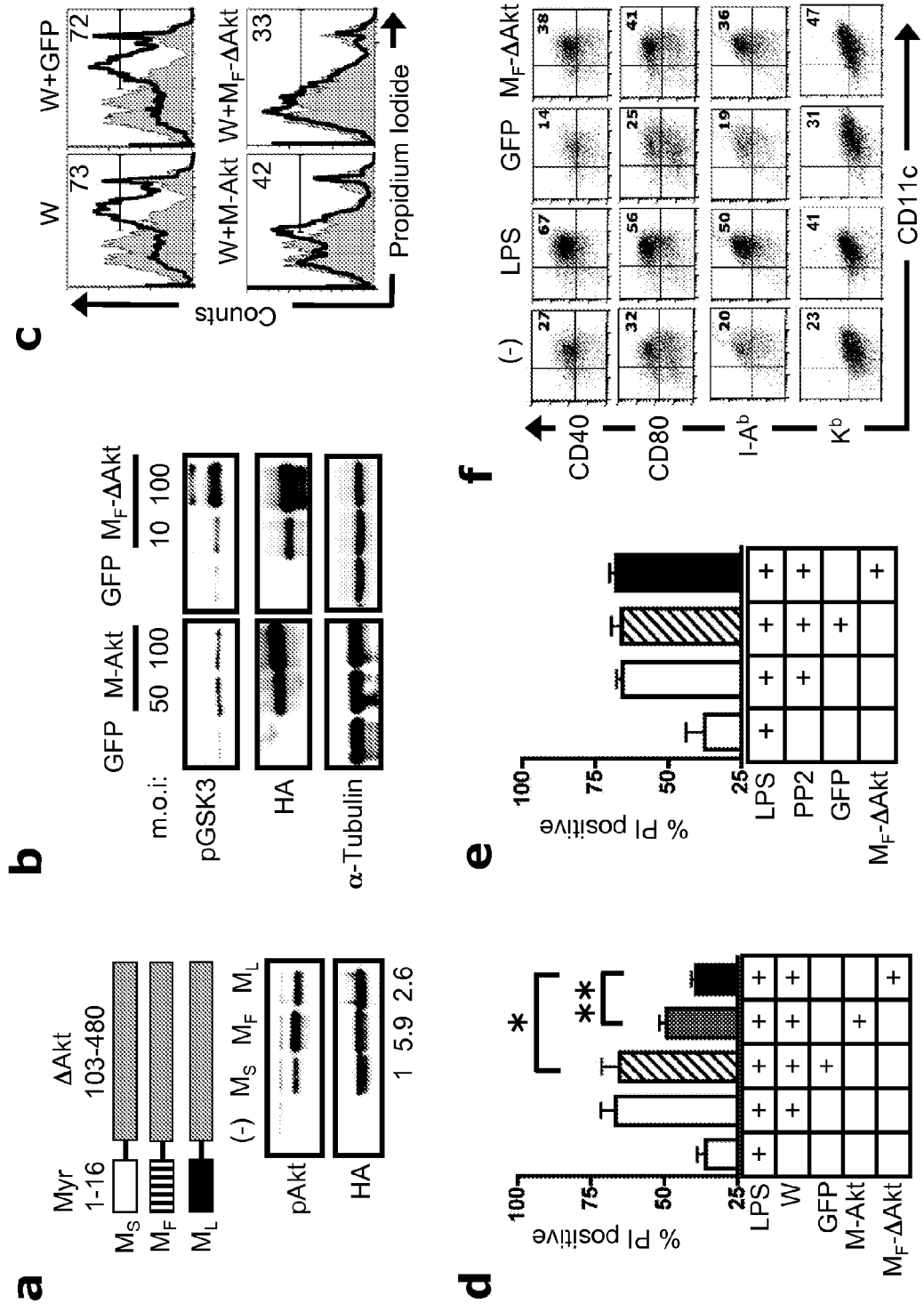
FIGS. 3A-3F show functionally optimized Akt induces DC activation and protects DCs from PI3K inhibition.
Figure 12:
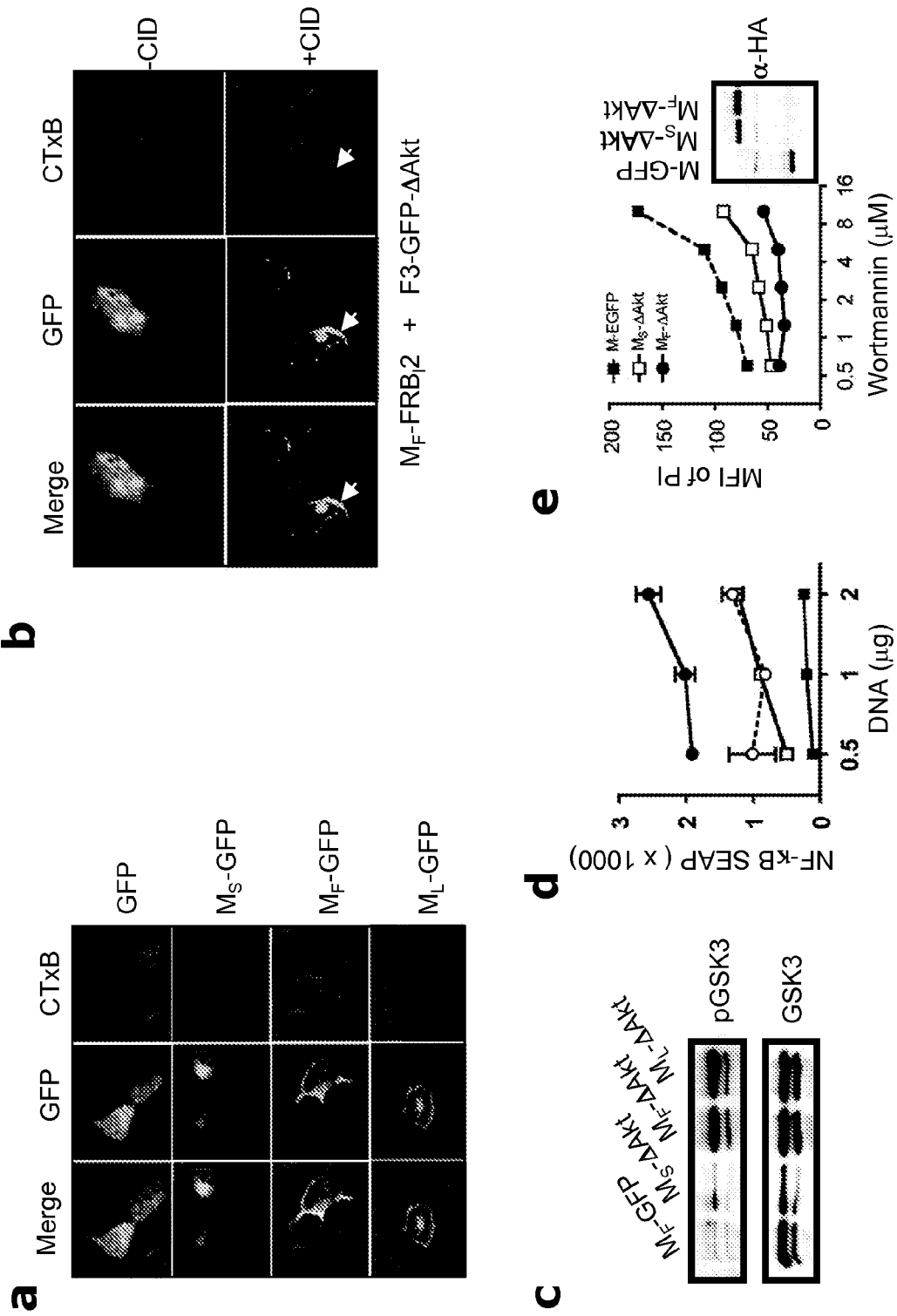
FIGS. 12A-12E show effects of different acylation regions.

Akt1 is Sufficient for Activation and Maintenance of LPS-Mediated DC Survival To further study the molecular mechanism of Akt in PI3K- and Src kinase-mediated DC survival, we initially utilized a previously described constitutively active Akt (M-Akt) allele, consisting of full length Akt, targeted to intracellular membranes with a myristoylation-targeting sequence from c-Src. However, because dual acylation, such as palmitoylation and myristoylation, is important for lipid raft localization of Src family kinases, c-Src, which is only myristoylated, may be excluded from lipid rafts (FIG. 12A). Therefore, to test the possibility that efficient lipid raft localization of Akt improves its function, this construct was compared to several distinct Akt constructs, containing myristoylation-targeting sequences from Src family kinases Src, Fyn and Lck fused to a truncated (denoted "Δ") Akt (FIG. 3A). The pleckstrin homology (PH) domain (residues 1-102) was removed to improve Akt activity, important when PI3K activity is low. Among the three membrane-targeting sequences, the Fyn myristoylation-targeting sequence (MF) showed the most efficient lipid raft localization, 2-3-fold NF-kappaB induction, about a 6-fold-increased Akt-S473 and GSK3 phosphorylation, and enhanced viability of transfected Jurkat cells following treatment with PI3K inhibitors (FIG. 3A and FIG. 12). To further enhance Akt activity, Fyn myristoylated ΔAkt (MF-ΔAkt) was generated, which carried point mutations at both key phosphorylation sites (E308 and D473). However, these mutations failed to further improve reporter gene activity (data not shown). Therefore, MF-ΔAkt is referred to as "functionally optimized" Akt and was used in most subsequent experiments. For improved expression in BMDCs, we generated replication-defective adenovirus (Ad), Ad-MF-ΔAkt.

To evaluate the functional activity of Ad-MF-ΔAkt in BMDCs, phosphorylation of GSK3alpha/beta was examined in transduced cells. Consistently, Ad-MF-ΔAkt led to higher GSK3alpha/beta phosphorylation in BMDCs, compared with Ad-M-Akt39 (FIG. 3B). It was next tested whether DCs transduced with either Ad-M-Akt or Ad-MF-ΔAkt escaped death triggered by PI3K inhibition. In vitro DC survival assays indicated that both constructs, unlike Ad-GFP, significantly inhibited wortmannin-mediated lethality in BMDCs (P<0.005). In addition, Ad-MF-ΔAkt protected DCs better than Ad-M-Akt (FIG. 3c, d, P<0.01). Meanwhile, over-expression of functionally optimized Akt had no effect on PP2-mediated DC death (FIG. 3E). These findings indicated that functionally optimized Akt almost completely suppressed DC death initiated by PI3K, but not Src, inhibition, suggesting that PI3K and Src kinase likely control DC survival by distinct pathways.

To directly investigate the effects of Akt1 on DC phenotype, BMDCs were treated with either Ad-MF-ΔAkt or LPS and Ad-GFP as positive and negative controls, respectively. Flow cytometry analysis after 48 hr of treatment at about 50% transduction efficiency, revealed that Ad-MF-ΔAkt-transduced DCs had consistently enhanced expression of DC activation markers, including I-Ab, CD40, CD80 and Kb compared with Ad-GFP-transduced DCs, implicating that Akt activity is sufficient to induce DC activation and maturation (FIG. 3F).

A description of FIGS. 3A-3F follows. FIG. 3A shows a schematic of distinct Akt alleles comprised of myristoylation-targeting sequences (residues 1-16) from Src (MS), Fyn (MF) or Lck (ML) fused to PH domain-deleted Akt (ΔAkt 103-408). Activation state and expression of Ms-ΔAkt (MS), MF-ΔAkt (MF), and ML-ΔAkt (ML) were determined using anti-pAkt-S473 and anti-HA antibodies, respectively. FIG. 3B shows phosphorylation of substrate GSK3alpha/beta in BMDCs transduced by adenovectors expressing constitutive AU. Activity and expression of Ad-MF-ΔAkt (MF-ΔAkt) or Ad-MS-Akt (M-Akt) were determined using anti-phospho-GSK3 (pGSK3) and anti-HA antibodies respectively. Protein loading was normalized by alpha-tubulin immunoblotting. FIGS. 3C and 3D show MF-ΔAkt protects BMDCs from wortmannin-mediated death in vitro. BMDCs transduced with adenoviruses expressing GFP, M-Akt or MF-ΔAkt at 100 m.o.i. were further incubated with LPS (1 μg/ml) and wortmannin (W, 0.5 nM) for 2 days. In FIG. 3C cell death was assessed by PI staining under indicated treatment conditions (open diagrams) compared to LPS alone (filled reference histogram). Numbers represent %-gated region of open diagrams. FIG. 3D is a graphical representation of FIG. 3C. FIG. 3E shows Src and PI3K have independent roles in DC survival. Viability of BMDCs was assessed as above in FIG. 3D except for replacement of wortmannin with Src kinase inhibitor, PP2 (20 μM). FIG. 4F shows MF-ΔAkt induces BMDC activation. Two days after indicated treatments of BMDCs, CD11c+ DC activation was assessed by CD40, CD80, Kb and I-Ab staining. Numbers indicate percentage of cells in upper right quadrant. Data represent at least two independent experiments. Error bars represent S.D. of triplicate (FIGS. 3D and 3E) measurements. *, P<0.005, **, P<0.01.

Example 4

Bcl-2 is Required for Akt-Mediated DC Survival

Figure 4:
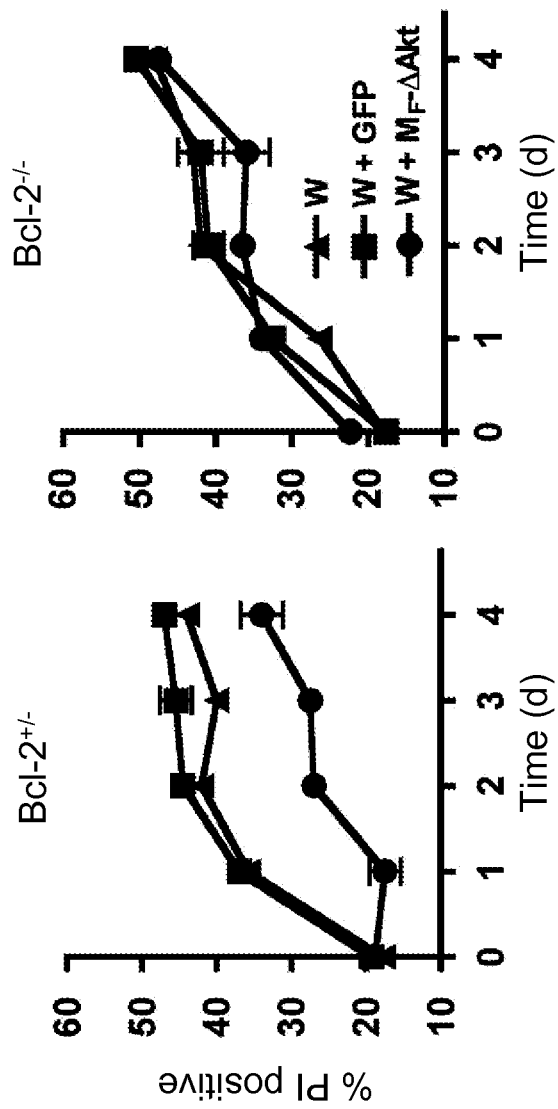
FIG. 4 shows AU-mediated DC longevity requires Bcl-2.

Since the kinetics of Akt protein down-regulation following cytokine withdrawal correlated with Bcl-2 protein levels (FIG. 1B), it was hypothesized that Bcl-2 might be a critical downstream effector of PI3K/Akt. To test this hypothesis, Akt-mediated survival of DCs was compared in Bcl-2+/− and Bcl-2−/− mice. Overall viability of Bcl-2−/− DCs was similar to that of Bcl-2+/−DCs in complete DC medium (data not shown). Consistent with previous results, treatment of DCs with the PI3K inhibitor, wortmannin, rapidly induced cell death both in Bcl-2+/− and Bcl-2−/− DCs. Ad-MF-ΔAkt transduction prior to wortmannin treatment, however, overcame the deleterious effects of PI3K inhibition, leading to enhanced survival of Bcl-2+/−DCs (FIG. 4, left). By contrast, the protective effect of Ad-MF-ΔAkt-transduction was completely abolished in Bcl-2−/− DCs, indicating that Akt mediated DC survival requires Bcl-2 (FIG. 4, right). In FIG. 4, BMDCs from Bcl2+/− or Bcl2−/− mice were left untreated (▲) or transduced with Ad-GFP (■) or Ad-MF-ΔAkt (●) and further incubated in the presence of wortmannin (W, 0.5 μM) for indicated times. Viability was assayed by flow cytometry based on PI uptake in triplicate. Data represent three independent experiments with similar results. Error bars represent the mean±S.D. of triplicate measurements.

Example 5

Akt-Transduced DCs Show Prolonged Longevity In Vitro and In Vivo

Figure 5:
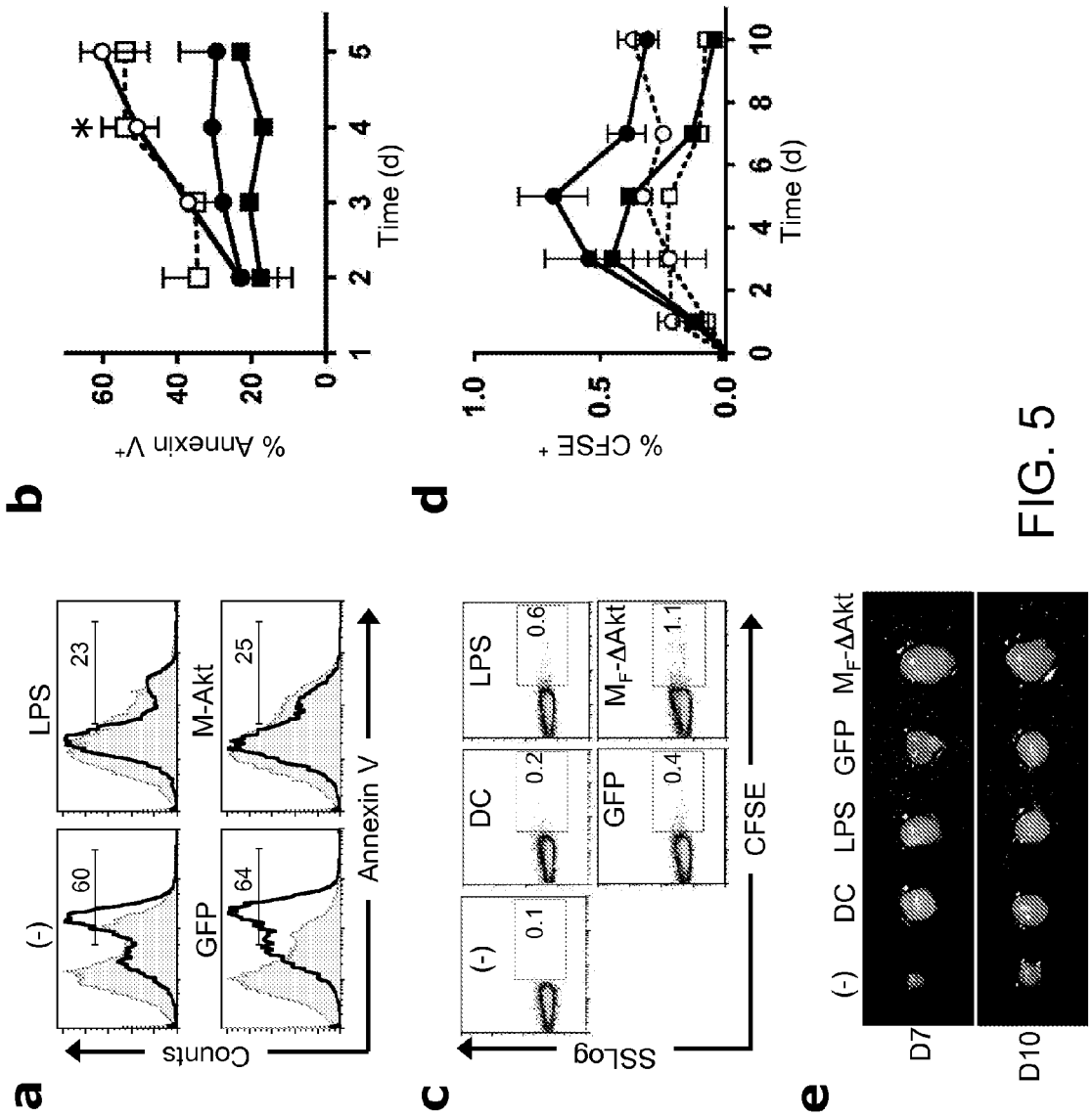
FIGS. 5A-5E show MF-ΔAkt and M-Akt induce BMDC longevity in vitro and in vivo.

Previous reports demonstrated a correlation between prolonging DC lifespan and the adjuvant potency of DC-based vaccines and T cell dependent immunity. Therefore, whether the induction of Akt activity promoted the survival of BMDCs under various conditions was tested. Initially, effects of Ad-M-Akt and LPS on DC survival were compared following growth factor deprivation. As shown in FIGS. 5A and 5B, DCs pre-incubated with LPS (1 μg/ml) or infected with Ad-M-Akt maintained viability for at least 5 days after GM-CSF withdrawal, whereas untreated or Ad-GFP-transduced DCs underwent significant cell death by day 4, suggesting that the induction of Akt inhibits cell death signals mediated by GM-CSF withdrawal in vitro.

To further investigate AU-mediated survival of DCs in vivo, the viability of Ad-MF-ΔAkt-transduced DCs with LPS-treated or Ad-GFP-transduced DCs was compared in draining lymph nodes. DCs were stained with the fluorescent dye CFSE followed by subcutaneous (s.c.) delivery into the hind legs of syngeneic mice (FIG. 5C). On day 5 after delivery, the quantity of CFSE+MF-ΔAkt-DCs residing in the draining popliteal lymph nodes was ~1% of total lymph node cells, which was a 2-3-fold higher percentage than control Ad-GFP-DC-treated mice. Consistent with previous findings, the percentage of CFSE+ DCs from control mice injected with untreated or LPS-treated DCs rapidly decreased at later time points, whereas Akt-transduced DCs sustained their disproportionate representation for at least 10 days post-delivery (FIG. 5D). Prolonged survival of Ad-GFP-transduced DCs at day 10 may be due to transfer of long-lived EGFP to resident phagocytes. In addition, the average volume of draining lymph nodes exposed to MF-ΔAkt-DCs was approximately 4-8-fold more than control mice, indicating that Ad-MF-ΔAkt transduction enhances the number of lymph node resident leukocytes compared to all negative control groups as well as LPS-treated DCs (FIG. 5E). Because the arrival of CFSE+ DCs does not apparently differ significantly among the groups in the first 24 hr after injection, these data strongly suggest that ex vivo transduction of DCs with Ad-MF-ΔAkt promotes their prolonged lifespan, which results in sustained immunity by overcoming various DC death signals in lymphoid tissues.

A description of FIGS. 5A-5E follows. FIGS. 5A and 5B show the anti-apoptotic effect of Ad-M-Akt on DC death, in vitro. BMDCs were left untreated (□), or treated with LPS (■), Ad-GFP (○) or Ad-M-Akt (●) at 100 m.o.i. and further incubated for 2 to 5 days without GM-CSF. In vitro DC apoptosis was examined by Annexin V-PE staining. Histograms of Day 5 (open histogram) were compared to that of Day 2 (filled histogram). In FIG. 5A, numbers represent %-gated region of open histograms. In FIG. 5B, error bars indicate mean±S.D. of results pooled from three independent experiments. *, P<0.05 between Ad-EGFP and Ad-M-Akt. FIGS. 5C, 5D and 5E show effects of Ad-MF-ΔAkt on BMDC longevity, in vivo. CFSE-stained BMDCs were left untreated (□), or treated with LPS (■), Ad-GFP (○) or Ad-MF-ΔAkt (•) for 2 hr before injection into the hind legs of syngeneic mice (n=2-4 per time point). After indicated times, cells from draining LNs (popliteal) were stained with PI. Within PI-populations, CFSE+ cells were analyzed by flow cytometry. FIG. 5C shows representative dot plots of CFSE+ populations at day 5 (P<0.05, between Ad-M-Akt and all controls). Boxed numbers indicate CFSE+ populations. In FIG. 5D background CFSE+ from PBS control (−) was subtracted for each value. Error bars indicate mean±S.E.M. Data represent three independent experiments with similar results. FIG. 5E shows representative LNs isolated from indicated mice on day 7 and 10.

Example 6

Akt Improves DC Ability to Stimulate T Cell Functions

Figure 6:
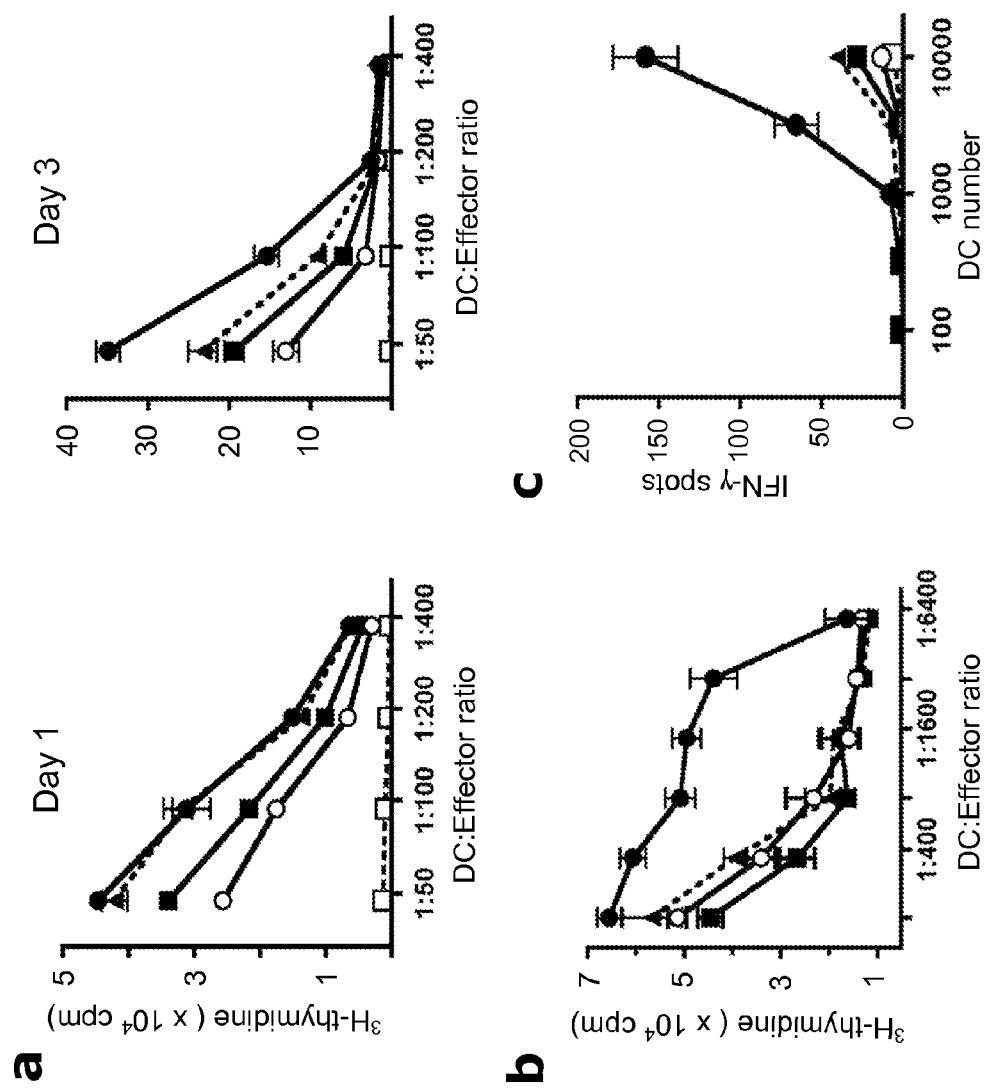
FIGS. 6A-6C show MF-ΔAkt and M-Akt-expressing BMDCs reveal improved T cell activation and proliferation.

In addition to promoting DC survival, optimal maturation and DC activation, accompanied by IL-12 production, are important for naïve T cell priming, leading to T cell proliferation and IFN-gamma production. However, it has been suggested that PI3K negatively regulates IL-12 production in DCs. Therefore, to test whether enhanced survival and activation of MF-ΔAkt-DCs promotes T cell function, the proliferative response of allogeneic (BALB/c) and syngeneic OT-1 T cells (expressing transgenic TCRs specific for Kb-restricted OVA257-264 peptide (SIINFEKL, SEQ ID NO: 32)) to peptide-pulsed, Akt-transduced DCs was examined. After 24-hr incubation of DCs with syngeneic splenocytes from OT-1 mice, Ad-MF-ΔAkt-transduced DCs induced more T cell proliferation than Ad-GFP-transduced DCs, which was similar to LPS-treated DCs. Moreover, after ~72 hr incubation, MF-ΔAkt-DCs induced about two-fold higher T cell proliferation than DCs activated with LPS (FIG. 6A). Ad-M-Akt-transduced DCs also consistently showed 5-7-fold higher allogeneic T cell proliferation than DCs pulsed with LPS or Ad-GFP at low DC:effector ratios after 72 hours (FIG. 6B). These data support a model in which Akt induces DC maturation and survival, leading to robust T cell proliferation.

To further determine whether upregulated Akt improves DC-mediated activation of T cells, secretion of IFN-gamma by OT-1 splenocytes incubated with Ad-MF-ΔAkt- or control virus-pulsed DCs was examined. Peptide-pulsed and Akt or GFP virus-transduced DCs were cultured with pooled spleen cells from OT-1 mice for 24 hr or 72 hr. Then, the OVA peptide-specific splenocyte response was measured ex vivo by IFN-gamma ELISPOT assay. LPS- or Ad-GFP-transduced DCs showed approximately the same numbers of IFN-gamma-producing cells, relative to untreated DCs. In contrast, MF-ΔAkt-DCs induced at least 7-fold higher IFN-gamma production by splenocytes (on both day 1 and day 3 (not shown)) than DCs treated with LPS or Ad-GFP (FIG. 6C). Therefore, in this experimental model, MF-ΔAkt-DCs elicit relatively persistent immunity by stimulating proliferation and activation of antigen specific CD8+ T cells.

A description of FIGS. 6A-6C follows. FIGS. 6A and 6B show MF-ΔAkt induces DC function to stimulate antigen-specific and allogeneic T cell proliferation. BMDCs alone (□) or pulsed with SIINFEKL peptide (SEQ ID NO: 32) for 2 hr (FIG. 6A) were left untreated (■) or treated with LPS (▲), Ad-EGFP (○) or Ad-$M_F$-μAkt (FIG. 6A, ●) and Ad-M-Akt (FIG. 6B, ●) for 16 hr. DCs were mixed in various dilutions with $1\times10^5$ splenocytes from syngeneic OT-1 (FIG. 6A) or allogeneic Balb/c (FIG. 6B) mice and incubated for an additional 1 to 3 days. T cell proliferative responses were measured by 3H-thymidine uptake (1 mCi/well) for 16 hr. FIG. 6C shows the effect of Ad-MF-ΔAkt transduction of BMDCs on CD8+ T cell activation. DCs as treated in FIG. 6A were incubated with splenocytes from syngeneic OT-1 mice for 3 days. IFN-gamma+ spots were assessed. All data represent two to three independent experiments.

Example 7

Figure 13:
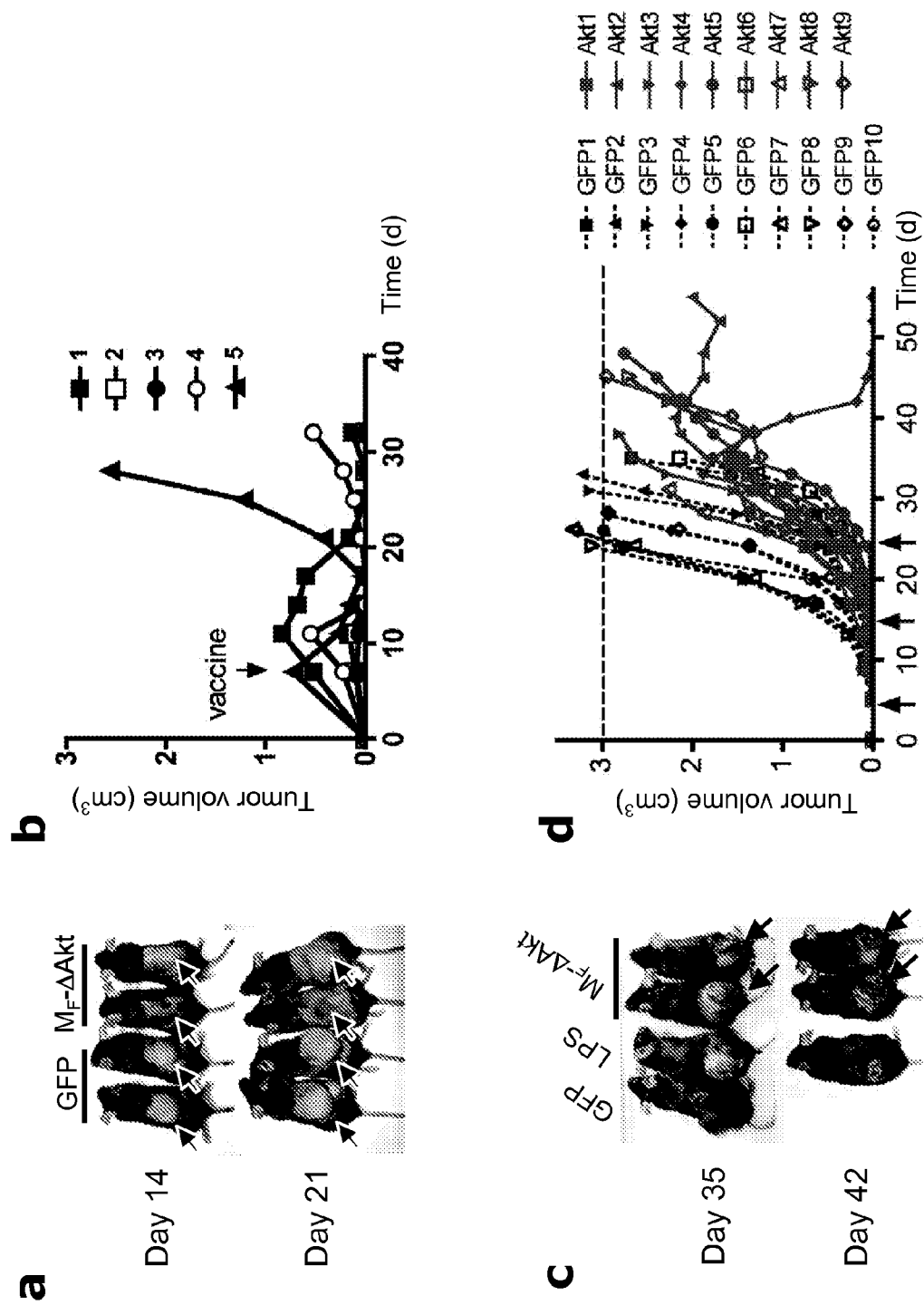
FIGS. 13A-13D show effects of modified DCs described herein on tumor growth and animal survival.

MF-ΔAkt Enhances the Efficacy of DC Vaccines to Eradicate Pre-Established Tumors To better evaluate the clinical relevance of MF-ΔAkt-DCs, anti-tumor efficacy was tested against two distinct models. Initially, the induction of antitumor immunity by Ad-MF-ΔAkt-transduced DC vaccines was monitored after immunization of C57BL/6 mice bearing large (about 0.4 cm³) subcutaneous EG.7-OVA thymomas. While control or LPS-treated and SIINFEKL-pulsed (SEQ ID NO: 32) DC vaccines failed to inhibit tumor growth or increase survival in most animals, immunization with a single intraperitoneal dose of peptide-pulsed MF-ΔAkt-DCs led to significant tumor growth inhibition (P<0.05) (FIG. 7A, FIG. 13). At early time points, MF-ΔAkt-DCs successfully suppressed all pre-established EG.7-OVA tumors, although 2 of 5 tumors eventually relapsed (FIG. 13B). To measure sustained antigen-specific T cell responses in tumor-bearing mice, H-2 Kb OVA257-264 tetramer analysis was performed on peripheral blood CD8+ T cells harvested 14 days after vaccination. Consistent with tumor suppression, this analysis showed that vaccination with peptide-pulsed MF-ΔAkt-DCs led to an expanded population of OVA257-264 antigen-specific CD8+ T cells (FIG. 7B). Anti-tumor effects of MF-ΔAkt-DCs against a "natural" tumor associated antigen, tyrosinase-related protein (TRP)$_2$, that is expressed in poorly immunogenic B 16 melanoma, next was tested. Once again, peptide-pulsed LPS-treated mature DCs were not significantly better than control DCs. However, immunization with a single or triple intraperitoneal dose of TRP-2 peptide-pulsed MF-ΔAkt-DCs significantly reduced the growth of pre-established B16 melanoma, leading to increased survival of tumor-bearing mice relative to vaccination with control DCs (p=0.003) or LPS-DCs (p=0.006). (FIG. 7C, FIG. 7D). In addition, it was observed that only mice vaccinated with MF-ΔAkt-DCs (5 out of 9) showed clinical responses, such as extended reduction of tumor growth associated with tumor necrosis and frequently severe central ulceration. Among those 5 mice, one mouse exhibited stable tumor size and one mouse bearing an ~2 cm³ peak tumor size completely rejected its tumor without relapse up to 55 days (FIG. 13C and FIG. 13D).

Figure 14:
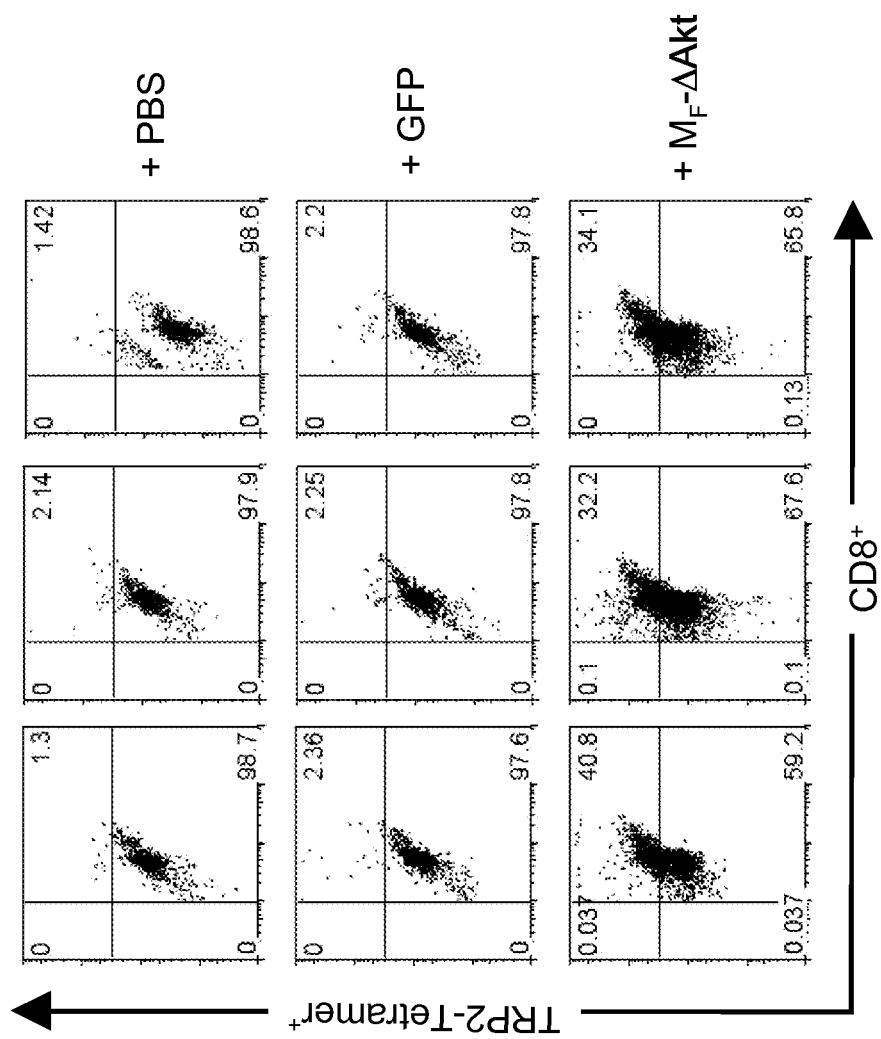
FIG. 14 shows representative memory recall responses for particular antigens.

To further assess the induction of recall memory responses in MF-ΔAkt-BMDC-treated mice, long-lived CD8+ memory responses to TRP-2 were tested in tumor naïve mice 1 week after a booster DC vaccination that followed two months after three initial biweekly vaccinations. Up to 30% of all peripheral blood CD8+ T cells were TRP-2-specific from MF-ΔAkt-DC-vaccinated mice, whereas only 1-3% of all peripheral blood CD8+ T cells from control DC-treated mice were TRP-2-specific (P<0.0005) (FIG. 7E, FIG. 14). Concomitantly, up to 3 months after the initiation of DC treatment, no evidence of autoimmunity-induced depigmentation (i.e. vitiligo) or toxicity was observed, including measurements of body weight, complete blood cell counts and serum biochemistry (e.g. AST, ALT, glucose, blood urea nitrogen, creatine kinase, etc) (data not shown). These findings support the hypothesis that upregulation of Akt activity in DCs improves DC function, producing enhanced long-term anti-tumor effects even in the aggressive, poorly immunogenic B16 tumor model without apparent autoimmunity and toxicity.

A description of FIGS. 7A-7E follows. FIG. 7A shows growth of pre-established EG.7-OVA tumors following single vaccinations with Akt-transduced DCs. Syngeneic C57BL/6 mice (n=5 per group) challenged with $2\times10^6$ EG.7-OVA thymoma cells at day 0 were treated at day 7 with PBS (▲) or vaccinated with $2\times10^6$ BMDCs pulsed SIINFEKL peptide (SEQ ID NO: 32) (20 μg/ml) alone (○) or treated with LPS (1 μg/ml) (●), 100 m.o.i. Ad-GFP (□) or Ad-$M_F$-ΔAkt (■), and tumor sizes were estimated as $w^2*1*0.5236$ and recorded biweekly. Numbers indicate fraction of mice bearing palpable tumors (>0.1 cm³). ♦, P<0.05; MF-ΔAkt-DCs versus GFP-DCs. FIG. 7B shows Ad-MF-ΔAkt-transduced BMDCs significantly increased numbers of tumor antigen-specific CD8+ T cells. For the left portion of FIG. 7B, PBMCs from indicated group at day 21 were isolated and stained with PE-conjugated KbSIINFEKL (SEQ ID NO: 32) tetramer and FITC-conjugated CD8. The right portion of FIG. 7B shows the mean percentage of CD8+ and KbSIINFEKL (SEQ ID NO: 32) tetramer positive population in PBMCs from two to three mice per group. ♦♦, P<0.005. FIG. 7C shows tumor growth and FIG. 7D shows animal survival regarding pre-established B16 melanoma tumors following vaccinations with Akt-transduced DCs. B16 melanoma cells were injected subcutaneously into syngeneic C57BL/6 mice ($1\times10^5$ cells/mouse, n=9 or 10 per group) at day 0. Treatment with indicated DC vaccines ($2\times10^6$ DCs/mouse) pulsed with TRP2 peptide (10 μg/ml) was done 4 (or 5), 15 and 25 days after tumor injection (arrow). Two tumor measurements were recorded every 3-4 days. Mice which had about 3 cm³ tumors were euthanized and plotted with the last recorded volume. ♦, P<0.05 based on one-way ANOVA test. In FIG. 7D, P<0.005, MF-ΔAkt-DCs versus control DCs and GFP-DCs; P<0.01, MF-ΔAkt-DCs versus LPS-DCs based on log rank test. Similar trends were observed for single dosing and triple dosing of DC vaccine and tumors established with $0.5 \times 10^5$ B16 melanoma cells, and for single dosing of DC vaccine and tumors established with $1 \times 10^5$ B16 melanoma cells. Controls with (1) LPS and CD40 ligand, and (2) MF-ΔAkt with LPS and CD40 ligand also were tested. The trend for the latter control followed the trend for the MF-ΔAkt alone, indicating that LPS and CD40 ligand did not further enhance DC effectiveness. FIG. 7E shows a memory CD8+ T Cell response by peptide-pulsed Akt-transduced DCs. Long-lived CD8+ memory responses were monitored two months after the third vaccination and 1-week after a booster DC vaccine following the initial three biweekly vaccinations of tumor naive animals with TRP-2-pulsed, PBS, Ad-GFP- or Ad-MF-ΔAkt-transduced BMDCs ($2 \times 10^6$ DCs/mouse, 6 mice/group). Recall response of antigen-specific CD8+ T cell was measured by the percentage of the CD8+ and H-2 Kb/TRP2 tetramer positive population in PBMCs using flow cytometry. Data shown is gated on CD8+ T cells. *, P<0.0005. Data represent two (FIGS. 7A and 7B) or three (FIGS. 7C and 7D) independent experiments with comparable results. Error bars represent mean±S.E.M.

Example 8

MF-ΔhAkt is a Potent Adjuvant to Induce Human MoDC Longevity and CTL Function

Figure 8:
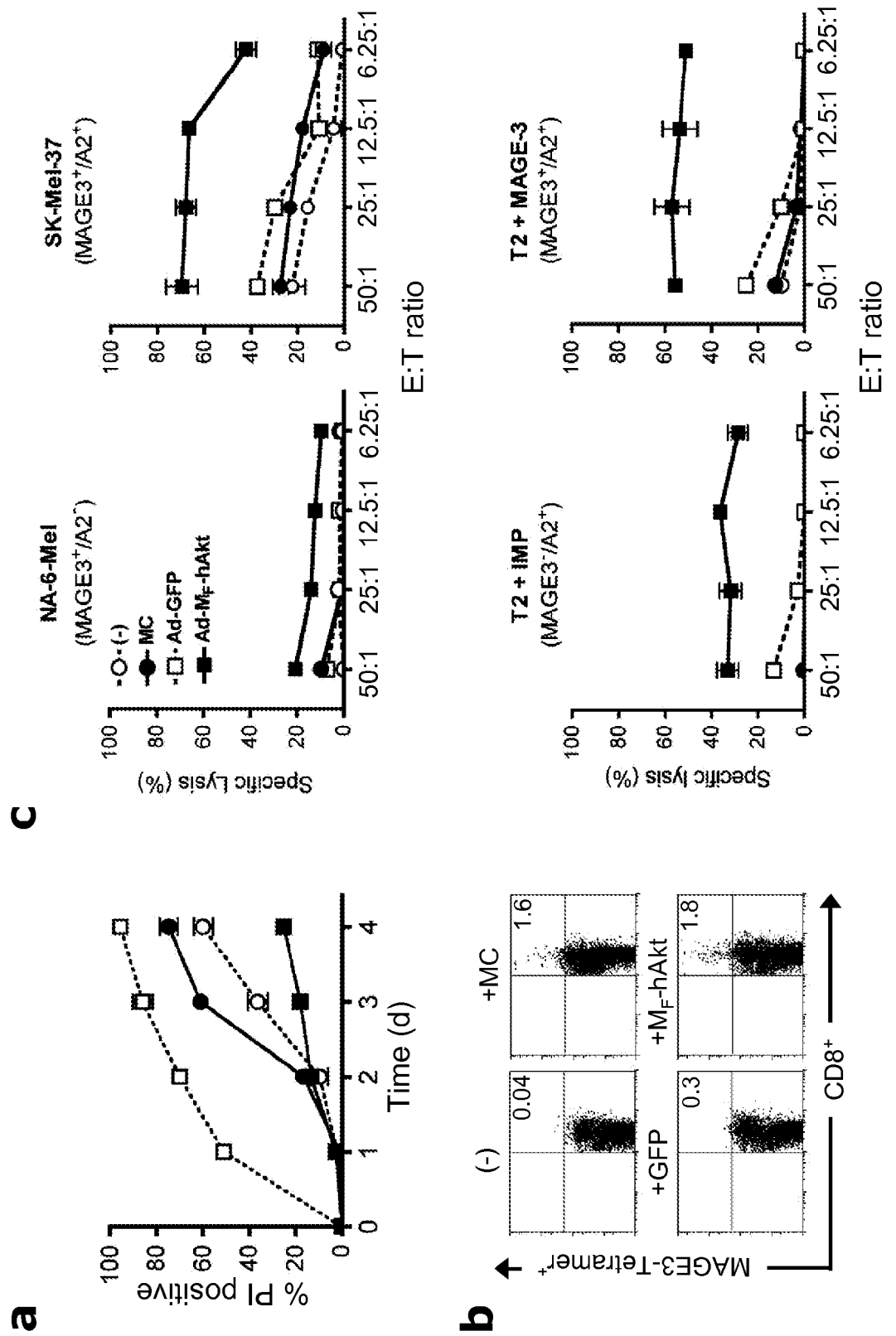
FIGS. 8A-8C show MF-ΔhAkt induces human MoDC longevity leading to improved antigen-specific CTL activation and proliferation.

To test whether upregulation of Akt can also enhance human monocyte-derived DC (MoDC) function, a "humanized" MF-ΔhAkt was developed, and subcloned it into an Ad5f35 vector to improve transduction of human DCs. First, viability of Ad-MF-ΔhAkt-transduced MoDCs was compared with Ad-GFP-transduced MoDCs and DCs treated with standard maturation cocktail (MC)(i.e. IL-1, IL-6, TNF, and PGE2). As shown in FIG. 8A, MoDCs pre-incubated with Ad-MF-ΔhAkt maintained viability up to 4 days after GM-CSF withdrawal, whereas Ad-GFP and MC-treated MoDCs showed extensive cell death by day 3, suggesting that targeted upregulation of Akt also inhibits death signals in human MoDCs and is more anti-apoptotic than standard MC. In addition, we observed that Ad-MF-ΔhAkt-transduced MoDCs consistently enhanced expression of DC activation markers, including CD80, CD86 and CCR7 compared with Ad-GFP-transduced MoDCs.

To further determine whether upregulated Akt also improves MoDC-mediated activation of antigen-specific human T cells, we performed HLA-A2/MAGE-3271-279 tetramer analysis on peripheral blood CD8+ T cells from healthy volunteers. Consistent with the proliferative responses observed for allogeneic (BALB/c) and syngeneic OT-1 T cells to Ad-MF-ΔAkt-transduced DCs, vaccination with MF-ΔhAkt-transduced and peptide-pulsed DCs led to an expanded population of MAGE-3271-279 antigen-specific CD8+ T cells with higher IFN-gamma production (FIG. 8B). Moreover, MF-ΔhAkt-DC-mediated proliferative responses were closely correlated with robust MAGE-3-specific CTL responses against T2 cells pulsed with MAGE-3271-279 peptide and SK-Me1-37 (HLA-A2+/MAGE3+) target cells but not against control target cells, lacking HLA-A2 or MAGE3 (FIG. 8C). Taken together, these data clearly showed that administration of activated Akt into human MoDCs is a more potent adjuvant than conventional cytokine maturation cocktail and is attractive for clinical applications.

MoDCs also can be primed with other antigens, such as a prostate cancer specific antigen, PSMA (e.g., SEQ ID NO: 10). Isolated MoDCs are incubated with the antigen for a period of time (e.g., approximately 1-2 hours) and infected with MF-ΔhAkt adenovirus described above. After administration of the resulting MoDCs into human subjects, the proliferation response of antigen-specific CD8+ T cells is determined. The immune response against this antigen sometimes is compared against the immune response of control cells (e.g., cells lacking the antigen or a particular HLA molecule).

A description of FIGS. 8A-8C follows. FIG. 8A shows an anti-apoptotic effect of Ad-MF-ΔhAkt on human MoDC death. MoDCs from two donors were left untreated (○), or treated with maturation cocktail (MC) (●), Ad5f35-GFP (□) or Ad5f35-$M_F$-ΔhAkt (■) at 100 m.o.i. and further incubated for 1 to 4 days without hGM-CSF. In vitro DC apoptosis was examined by PI staining. FIG. 8B shows enhanced MAGE3-specific CD8+ T cells after stimulation with MF-ΔhAkt-transduced MoDCs. Blood CD8+ T cells from a HLA-A2-positive healthy volunteer were stimulated with DCs untreated (−), or treated with maturation cocktail (+MC), Ad5f35-GFP (+GFP) or Ad5f35-MF-ΔhAkt (+MF-hAkt) and stained with PE-conjugated HLA-A2/MAGE-3271-279 tetramer and FITC-conjugated CD8. The percentages indicate the fraction of tetramer-positive cells within the entire populations of T cells. FIG. 8C shows MF-ΔhAkt transduced DCs enhance antigen specific CTL killing activity. Human MoDCs were pulsed with MAGE3 peptide and adenoviruses (Ad-GFP, □, and Ad-$M_F$-ΔhAkt, ■) or MC (●) as indicated. After three serial stimulations of autologous T cells with DCs at day 7 and 8, antigen-specific CTL activity was evaluated with $^{51}$Cr release assay. Labeled target cells included melanoma cell lines SK-Me1-37 (MAGE3+, A2+), NA-6-Mel (MAGE3+, A2−), as well as T2 cells (MAGE3−, A2+) loaded with either MAGE3 (positive control) or influenza M1 (IM A2.1) peptides (as negative control). Data represent average of two donors (FIG. 8A) or three independent experiments with similar results (FIGS. 8B and 8C). Error bars represent mean±S.D.

A description of FIGS. 9 to 14 are described hereafter. FIG. 9A shows specificity of small interfering RNA for Akt-1 (Akt-RNAi). BMDCs were transfected with 100 nM of control RNAi (c-RNAi) or Akt-RNAi and further incubated for indicated times. Akt protein level was assessed by Akt immunobloting. FIG. 9B shows an effect of Akt-RNAi on LPS-mediated DC survival. BMDCs (−) and BMDCs transfected with c-RNAi or Akt-RNAi were incubated with LPS (1 μg/ml) for 3 days. Loaded proteins were normalized by actin immunobloting (FIG. 9A). (c) Effect of Akt inhibitor on LPS-mediated DC survival. BMDCs were left untreated (−) or treated with LPS with or without Akt inhibitor (Akt-i) and further incubated for 3 days. Cell viability was assayed by PI staining. Data represent three independent experiments with triplicate measurements (9FIGS. 9B and 9C). Error bars represent mean±S.D. *, P<0.005.

Figure 10:
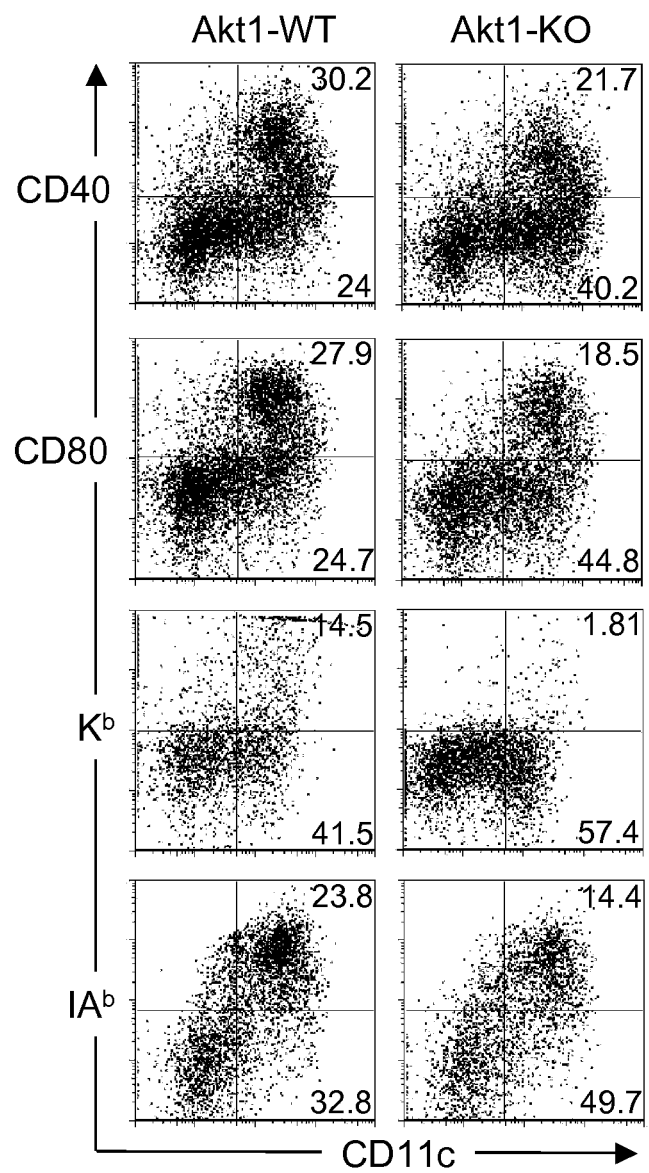
FIG. 10 shows a representative analysis of surface markers of Akt1$^{+/+}$ or Akt1$^{-/-}$ DCs.

FIG. 10 shows a representative analysis of surface markers of Akt1$^{+/+}$ or Akt1$^{−/−}$ DCs. After 6 days of DC differentiation, surface expression of MHC and costimulatory molecules in Akt1$^{+/+}$ or Akt1$^{−/−}$ BMDCs was assessed by CD40, CD80, MHC class I K$^b$ and MHC class III-Abstaining along with CD11c. Numbers indicate percentage of cells in that area.

Figure 11:
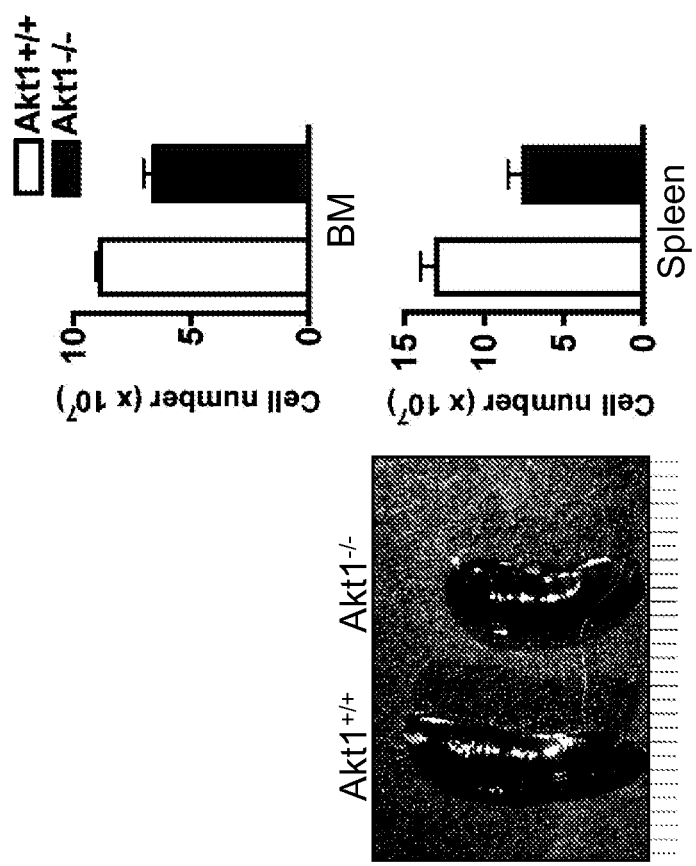
FIG. 11 shows a comparison of bone marrow and spleens isolated from Akt1$^{+/+}$ or Akt1$^{-/-}$ mice.

FIG. 11 shows a comparison of bone marrow and spleens isolated from Akt1$^{+/+}$ or Akt$^{−/−}$ mice. Size of spleens isolated form Akt1 or Aka littermates was measured (bottom scale bar, 1 mm gap) and total cell numbers of bone marrow (pooled from two femurs and tibias) and spleens were assessed by trypan blue staining.

FIG. 12A shows a comparison of lipid raft localization of myristoylation-targeting sequences (Myr 1-16) from Src (MS), Fyn (MF) or Lck (ML) fused to GFP in 293 cells. Membrane lipid rafts were stained with cholera toxin B (CTxB-TRITC). FIG. 12B shows inducible lipid raft localization of Akt. 293 cells were transfected with membrane docking protein with Fyn myristoylation sequence (M F-FRB12) and three tandem FKBP domains fused with ΔAkt (F3-GFP-ΔAkt), followed by chemically induced dimerization (CID, AP22783, L1, B. et al. Gene Therapy (2001) 9: 2 33-244). FIG. 12C shows induced phosphorylation of substrate GSK3 bp MS-ΔAkt, MF-ΔAkt, and ML-ΔAkt in 293 cells. FIG. 12D shows activation of NF-kappaB in Jurkat TAg cells transiently transfected with indicated amounts of control plasmid (■) or plasmids encoding MS-ΔAkt (□), MF-ΔAkt (●), or ML-ΔAkt (○) along with NF-kappaB SEAP reporter. FIG. 12E shows protection of wortmannin-mediated cell death by MS-ΔAkt (□) or MF-ΔAkt (●) in Jurkat TAg cells. Viability was assayed by flow cytometry of PI uptake in triplicate (MFI; mean fluorescent intensity).

FIG. 13A shows representative examples of EG.7-OVA tumor-bearing mice vaccinated with Ad-GFP or Ad-MF-ΔAkt BMDCs. Tumors were compared on day 7 and 14 after vaccination (day 14 and day 21 respectively). FIGS. 13B and 13D show growth of individual pre-established EG.7-OVA tumors following single vaccinations with Akt-transduced DCs (FIG. 13B) or individual pre-established B16 tumors following triple vaccination with GFP- or Akt-transduced DCs (FIG. 13D). Numbers indicate individual tumor-bearing mice vaccinated with Akt-transduced DCs (FIG. 13B). FIG. 13C shows representative examples of B16 melanoma tumor-bearing mice vaccinated with Ad-GFP (GFP), LPS or Ad-MF-ΔAkt (MF-ΔAkt) BMDCs. Tumors were compared on day 35 and 42 after tumor cell challenge.

FIG. 14 shows three representative animals of memory recall response of antigen-specific CD8+ T cells by PBS (+PBS), Ad-GFP (+GFP) or Ad-MF-Akt (+MF-ΔAkt)-treated BMDCs. Long-lived CD8+ memory responses were quantified by the percentage of the CD8+ and H-2 Kb/TRP2 tetramer positive population in PBMCs one week after a booster vaccination that followed two months after the initial three biweekly vaccinations. Numbers indicate percentage of cells in that area.

Provided hereafter is a discussion of results presented in this Example and previous Examples. DCs are the most potent antigen-presenting cells capable of initiating an immune response by activating rare, naïve antigen-specific T cells. The outcome of immune responses depends on DC longevity and abundance at the site of T cell priming. Although previous studies suggested that pro-inflammatory signals increase life span of DCs through NF-kappaB and Bcl-2 family members, the molecular mechanism of DC survival is still not clearly defined. Here, we show that the PI3K/Akt pathway is an essential mediator of LPS- and CD40-triggered survival signals that occur at the initiation of innate and adaptive immunity, Bcl-2 is a critical down-stream effector of Akt-mediated DC survival. A recent report showed that pathogen-derived pro-inflammatory signals induce in bone marrow-derived DCs both a conserved, Bcl-xL-dependent DC survival pathway and a Bim-dependent DC apoptotic pathway, which is transiently suppressed by Bcl-2, serving as a "molecular timer". It was determined by the studies reported in these Examples that the protein levels of Bcl-2 and Bcl-xL were independently regulated by pro-inflammatory signals. In addition, it was determined that Akt acts as a "life switch" to control Bcl-2 levels and regulates both DC lifespan and their ability to stimulate an immune response. Furthermore, it was demonstrated that DC death correlated with a rapid down-regulation of Akt following GM-CSF withdrawal. Withdrawal of other growth factors, like IL-3, insulin, and VEGF, has also been shown to trigger rapid down-regulation of Akt, mediated, in part, by its degradation. For example, caspase and proteasome inhibitors have a protective effect on Akt protein level following VEGF removal and promote endothelial cell viability. Therefore, it is possible that proteasome and/or caspase-targeted degradation of Akt regulate the PI3K/Akt signaling pathway to control DC lifespan.

Although the activity of Akt is dependent on PI3K function, the precise role of PI3K in DC function is controversial. One group observed that the reduction of class IA PI3K activity by disruption of p85-alpha along with wortmannin treatment enhanced IL-12 production in DCs, suggesting that PI3K may have a negative role in IL-12 production by DCs43. However, an independent report showed that defective DC migration and subsequent down-regulation of adaptive immunity occurs in PI3 Kgamma-deficient mice, indicating complex, non-redundant roles of PI3K isoforms in DC function. In addition, other reports have shown that CD40L-induced human DC survival is mediated by PI3K signaling, and inhibition of PI3K significantly reduces CD40L and CpG-mediated IL-12 production by BMDCs. A more recent study showed that tyrosine phosphorylation of TLR3 initiated by double-strand RNA recruits and activates PI3K and Akt, leading to full phosphorylation and activation of IRF-3, suggesting also an essential role of PI3K/Akt in TLR3-mediated gene expression.

Figure 2:
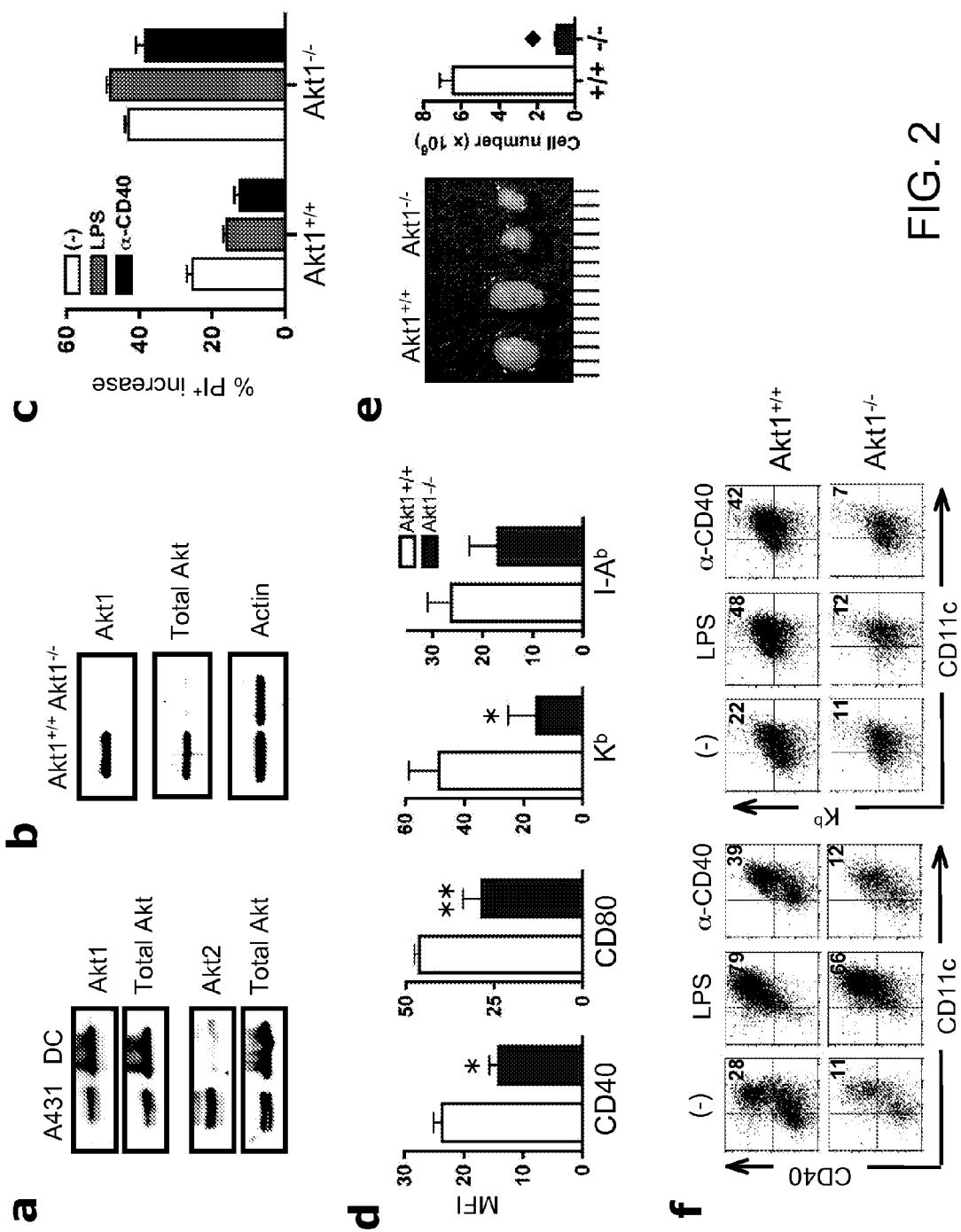
FIGS. 2A-2F show Akt1 is critical for LPS and CD40-mediated DC survival and activation.

Consistent with a largely stimulatory role for PI3K, it was observed that expression of PI3K substrate Akt, via Ad-MF-ΔAkt, induces DC maturation and activation, leading to enhanced T cell proliferation and IFN-gamma production by activated T cells. Moreover, it was observed that Akt deficiency reduces BMDC differentiation following GM-CSF treatment. Although expression of lineage markers CD11b and CD11c are similar in immature BMDCs from both Akt1+/+ and Akt1−/− mice, expression of some DC markers, such as MHC class I molecules, was clearly reduced. In addition, Akt1−/− BMDCs showed a large defect in the enhancement of DC activation and maturation markers even after LPS and CD40 stimulation (FIG. 2). Consistently, overexpression of Akt1 itself was sufficient to enhance the expression of DC activation markers (FIG. 3F). In addition, induced surface expression of CCR7 in MF-ΔhAkt-transduced DCs supports a model in which Akt1 plays a positive role in DC migration. Together, these observations demonstrate that Akt is involved in both DC activation and maturation.

While Akt activation plays a critical role in preventing cell death in various cell types and contexts in vitro, only a few studies have reported that constitutively active Akt promotes survival of target cells in vivo. Because the Src myristoylation sequence, used in other Akt constructs, does not target proteins efficiently to lipid rafts, where Akt is most active, their efficacy may have been reduced. The optimization studies described herein led to development of MF-ΔAkt, comprised of the Fyn myristoylation sequence ("MF") fused to truncated Akt, ΔAkt, lacking a partially inhibitory pleckstrin homology domain. MF-ΔAkt functions better than M-Akt in vitro and sustains DC lifespan for at least 10 days post-delivery in vivo, indicating that the described Akt improvements translate to improved DC function. In an independent study, MF-ΔAkt also appeared to regulate neurite morphology as well as the survival of cultured sensory neurons. Therefore, in addition to potentiating DC vaccine efficacy, functionally optimized Akt may have numerous applications. Targeting other signaling molecules directly to lipid rafts with the myristoylation-targeting sequence from Fyn, rather than Src, would likely improve many so-called "constitutive" alleles.

Figure 7:
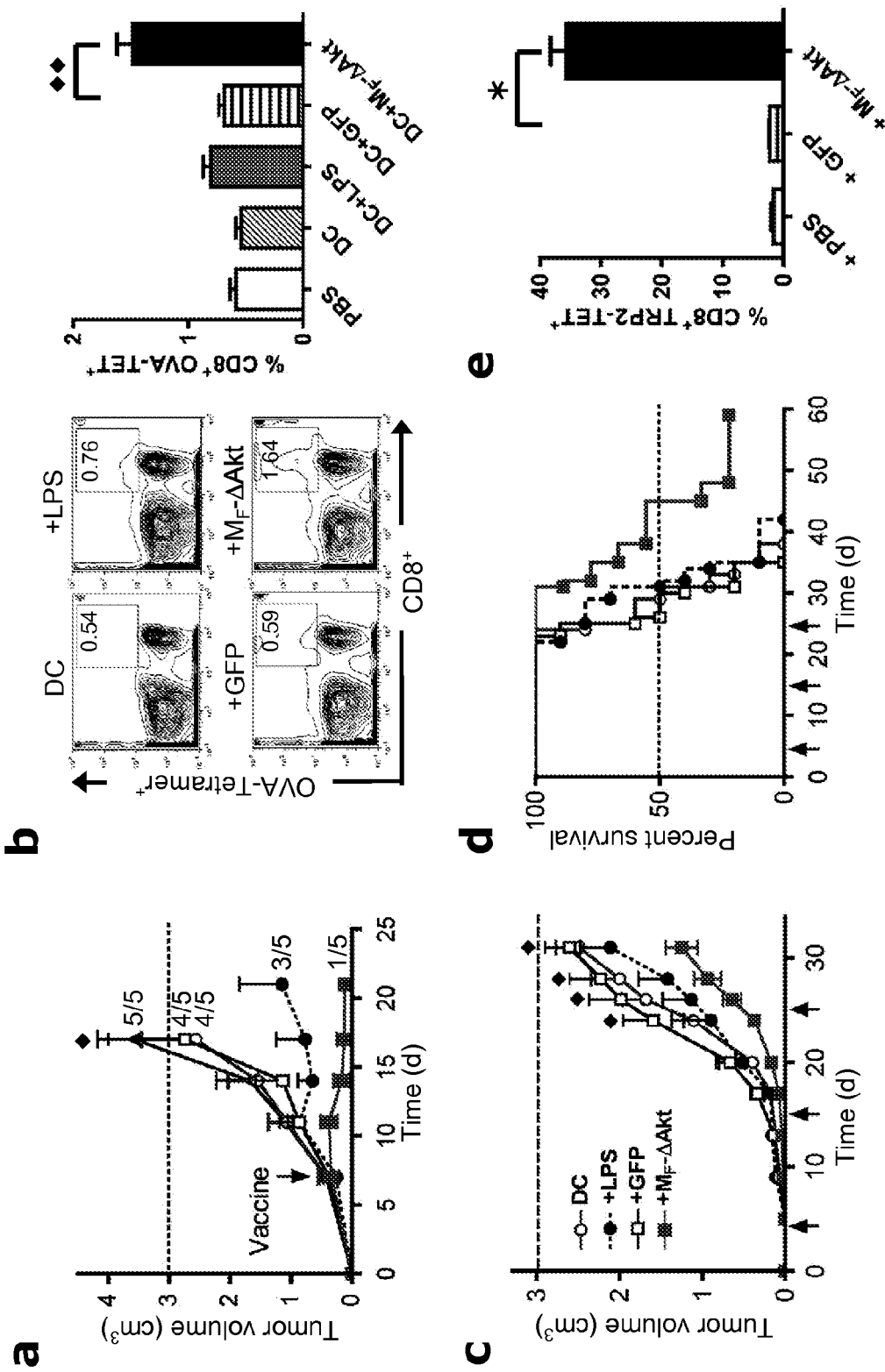
FIGS. 7A-7E show MF-ΔAkt expression enhances the efficacy of DC-based therapeutic tumor vaccines.

Studies provided herein also showed that overexpressing Aka in BMDCs led to improved vaccination against both immunogenic tumors and poorly immunogenic B16 tumors (FIG. 7). In addition, adenoviral administration of MF-ΔAkt provides a more robust and extended activation of DCs relative to the potent adjuvants such as LPS in mouse and maturation cocktails in human. Although LPS and cytokine cocktails appeared more effective than Akt in maturing a higher percentage of DCs in vitro, most likely due to incomplete transduction of target cells by adenovirus, MF-ΔAkt transduced DCs achieved higher T cell proliferation, IFN-gamma production and cytolytic activity than DCs treated with LPS (mouse BMDCs) or maturation cocktails (human MoDCs). MF-ΔAkt-DCs also efficiently induced long-lived CD8+ memory responses without detectable signs of autoimmunity (FIG. 7E, FIG. 14). Furthermore, in vivo, Ad-MF-ΔAkt led to a significantly improved DC-based tumor vaccine compared to antigen-loaded and LPS-treated DCs, which have been reported to efficiently retard tumor growth via supra-physiological T cell expansion in C57BL/6 mice bearing poorly immunogenic B16-F10 melanoma cells55. It is proposed that the anti-tumor effects are due to the ability of functionally optimized Akt to evade negative feedback mechanisms of DC activation and survival, such as pro-inflammatory receptor desensitization or downregulation 13-15 and TLR-mediated upregulation of pro-apoptotic molecules12 which can limit the survival signaling capacity of pro-inflammatory signals to maintain homeostasis. In addition, in vitro transduction of DCs with Ad-MF-ΔAkt provides an alternative way to overcome some of the toxicity associated with in vivo administration of microbial adjuvant or systemic administration of soluble CD40L or CD40 specific monoclonal antibody.

In summary, the role of Akt1 was characterized in dendritic cell survival and therapeutic applications were evaluated. Previously, it has been shown that a synthetic dimerizing drug-inducible allele of CD40 (called iCD40) leads to increased lifespan and prolonged activation of DCs, resulting in more potent T cell-mediated immune responses. The studies presented herein suggest that at least a subset of the signals provided by iCD40 in vivo may be attainable independently of pharmacological reagents. Use of enhanced DCs should complement previous efforts to identify tumor-associated antigens and apply in vitro expanded and matured DCs to tumor immunotherapy.

Example 9

Materials and Methods Utilized in Examples 1-8

Mice and Cell Lines.

Six to eight-week-old female C57BL/6 mice were purchased from the Center for Comparative Medicine (Baylor College of Medicine, Houston, Tex.). BALB/c mice, Akt1+/−, Bcl-2+/− and OT-1 TCR transgenic mice, responsive to OVA257-264 peptide (Kb-restricted SIINFEKL, SEQ ID NO: 32), were purchased from Jackson laboratory. Akt1−/− and Bcl-2−/− mice were obtained by inbreeding. OVA-expressing EG7 thymoma cells were purchased from American Tissue Culture Collection and maintained in RPMI 1640 medium containing 10% FBS, 0.4 mg/ml G418, 50 μM beta-mercaptoethanol, 1 mM sodium pyruvate, and antibiotics. All mice were housed in the pathogen-free units of Texas Mouse Facility at Baylor College of Medicine.

Reagents.

Recombinant murine GM-CSF and IL-4 were purchased from RDI Research Diagnostics. *E. Coli* LPS and anti-mouse CD40 mAb (3/23) were purchased from Sigma and BD Pharmingen respectively. The PI3-Kinase inhibitors LY294002 and wortmannin, ERK inhibitor PD98059, Src kinase inhibitor PP2, JNK inhibitor AG490 and Akt inhibitor were purchased from Calbiochem. The following antibodies were used for Western blotting: anti-Aid, anti-phospho-Akt (Ser473) and anti-phospho-GSK3alpha/beta (Ser21/9) (Cell Signaling Technology), anti-Akt1 and anti-Akt2 (Upstate cell signaling solutions), anti-Bcl-2 and anti-Bcl-XL (BD Biosciences), anti-actin (1-19) and anti-alpha-tubulin (Santa Cruz Biotechnology), and anti-mouse hemagglutinin (HA) epitope (HA-11, Covance). CFSE was purchased from Molecular Probes (Eugene). DC death was assessed using Propidium Iodide (PI; Sigma) and PE-conjugated Annexin V (BD Pharmingen). OVA257-264 peptide (SIINFEKL, SEQ ID NO: 32) and MAGE-3271-279 (FLWGPRALV, SEQ ID NO: 33) were purchased from (Tetramer Core Facility, Baylor College of Medicine). TRP2 peptide (VYDFFVWL, SEQ ID NO: 34) was utilized in the studies.

Preparation of Plasmids and Recombinant Adenoviruses.

The recombinant adenovirus encoding constitutively active Akt (Ad-M-Akt) is described in Guha, M. et al., Lipopolysaccharide activation of the MEK-ERK½ pathway in human monocytic cells mediates tissue factor and tumor necrosis factor alpha expression by inducing Elk-1 phosphorylation and Egr-1 expression. Blood 98, 1429-39 (2001). Preparation of plasmids and generation of recombinant adenovirus encoding myristoylation-targeting sequences from Fyn kinase fused to a PH domain truncated murine Aka (Ad-MF-ΔAkt) or human Aka (Ad5f35-MF-ΔhAkt) are described hereafter. Large-scale expansion of adenoviruses expressing M-Akt (Ad-M-Akt), MF-ΔAkt (Ad-MF-ΔAkt), MF-ΔhAkt (Ad5f35-MF-ΔhAkt) and control adenovirus encoding EGFP (Ad-GFP for mouse DCs and Ad5f35-GFP for human DCs) was carried out in the Viral Vector Core Facility (Baylor College of Medicine).

For the construction of Src-, Fyn- or Lck-myristoylated ΔAkt or EGFP, annealed oligonucleotide duplexes encoding Src, Fyn or Lck myristoylation targeting sequences (Src; 5MyrS17: 5'-ggccaccatgggtagcaacaagag-caagcccaaggatgccagccag cggcgccgcagcc-3' (SEQ ID NO: 35), 3MyrS17: 5'-tcgaggctgcggcgccgctggctg-gcatccttgggcttgctcttgttgctacccatggtggccgc-3' (SEQ ID NO: 36), Fyn; 5MyrL17: 5'-ggccaccatgggctgtgtctgcagct-caaaccctgaagatgactggatggagaacattc-3' (SEQ ID NO: 37), 3MyrL17: 5'-tcgagaatgttctccatccagtcatct-tcagggttttgagctgcagacacagcccatggtggccgc-3' (SEQ ID NO: 38), Lck; 5MyrF17: 5'-ggccaccatgggctgtgtgcaatgtaag-gataaagaagcaacaaaactgacggaggagc-3' (SEQ ID NO: 39), 3MyrF17: 5'-tcgagctcctccgtcagttttgttgct-tctttatccttacattgcacacagcccatggtggccgc-3' (SEQ ID NO: 40)) were subcloned into expression vector, pBJ5(Spencer '93) at Sst II and Xho I. Fragments encoding Sal I-linkered EGFP or Sal I linkered ΔAkt (lacking its PH domain), which were removed from plasmids pSH1/M-ΔAkt-E (L1, B. et al. Gene Therapy (2001) 9: 233-244), were subcloned in-frame into the Xho I and Sal I sites downstream of each myristoylation-targeting sequence. To generate adenovirus, Ad-MF-ΔAkt, expressing doubly acylated ΔAkt, MF-ΔAkt fragments were isolated from pBJ5-MF-ΔAkt by Not I/Klenow and EcoR I digestion and subcloned into SmaI/EcoRI-digested shuttle vector pDNR-CMV to create pDNR-MF-ΔAkt. Finally, recombinant adenoviral vector, pLP-Adeno-X-MF-ΔAkt, encoding MF-ΔAkt, was generated by Cre-loxP-mediated recombination according to the Adeno-X-Expression System 2 (BD Biosciences) protocol. To generate adenovirus expressing MF-ΔhAkt (Ad5f35-MF-human ΔAkt1), human ΔAkt1 (lacking its PH domain) fused with myristoylation targeting sequence (MF) was subcloned into shuttle vector, pShuttle-X, sequenced, I-CeuI/PI-SceI-digested and transferred into similarly digested Ad5f35 (BCM Gene Vector Lab). Generation, purification and titration of recombinant adenoviruses expressing MF-ΔAkt (Ad-MF-ΔAkt) and MF-hΔAkt (Ad5f35-MF-hΔAkt) were performed as described in the manufacturer's protocol (BD Biosciences).

Mouse and Human DC Preparation.

Bone marrow derived dendritic cells (BMDCs) from six to eight-week-old wild type C57BL/6 mice and Aka1-/- (C57BL/6) mice or two to three-week-old Bcl-2+/- and Bcl-2-/- mice were generated as described previously with minor modifications (Inaba, K. et al. Generation of large numbers of dendritic cells from mouse bone marrow cultures supplemented with granulocyte/macrophage colony-stimulating factor. J Exp Med 176, 1693-702 (1992)). Briefly, bone marrow cells were isolated from mouse femurs and tibias and cultured in DC medium (RPMI 1640 medium containing 10% FBS, 50 μM beta-mercaptoethanol, and antibiotics in the presence of 10 ng/ml each of mouse GM-CSF and IL-4). Half the culture medium was replaced every other day. On day 6, BMDCs were collected and enriched with CD11c microbeads (Miltenyi Biotec). For the generation of human monocyte-derived DCs (MoDCs) from healthy donors, peripheral blood mononuclear cells (PBMCs) were isolated by Lymphoprep (Nycomed Pharma AS, Oslo, Norway) and allowed to adhere in culture plates for 2 hr. Nonadherent cells were removed by extensive washes and adherent cells were cultured for 5 days in serum free DC medium (CellGenix) with 500 U/ml of hIL-4 and 800 U/ml hGM-CSF (R&D Systems). For cell survival experiments, MoDCs precursors were purified by positive sorting using CD14 microbeads (Miltenyi Biotec) from PBMCs and cultured as described above.

In Vitro Mouse and Human DC Survival Assay.

Purified mouse BMDCs (2×106 cells/ml) were incubated with combinations of LPS (1 μg/ml), anti-CD40 (10 μg/ml) and chemical inhibitors as indicated in the Results section or transduced with Ad-GFP, Ad-M-Akt or Ad-MF-Akt vectors at 100 m.o.i. under GM-CSF-free conditions. For human DC survival assays, purified human MoDCs (2×106 cells/ml) were transduced with adenoviruses (Ad5f35-GFP or Ad5f35-MF-ΔhAkt) at 100 m.o.i. or stimulated with maturation cocktail (MC) containing 10 ng/ml TNF-alpha, 10 ng/ml IL-1beta, 150 ng/ml IL-6 (R&D Systems) and 1 μg/ml of PGE2 (Cayman Chemicals). After 16-20 hr, DCs were washed and further incubated in 96-well plates (2×105 cells/well) in complete DC medium without GM-CSF and IL-4. DC death was assessed by loss of propidium iodide exclusion (PI+) and by binding of PE-conjugated Annexin-V (Annexin-V+) using flow cytometry (Epics® XL-MCL).

In Vivo DC Survival Assay.

To analyze DC survival in vivo, BMDCs were treated with LPS (1 μg/ml), Ad-GFP or Ad-MF-ΔAkt for 2 hr, labeled with CFSE dye and injected subcutaneously into hind legs below knees of syngeneic C57BL/6 mice (1×106 cells per mouse) as described previously (Nopora, A. & Brocker, T. Bcl-2 controls dendritic cell longevity in vivo. J Immunol 169, 3006-14 (2002)). The draining popliteal lymph nodes were harvested at various time points after injection, and percentage CFSE-positive cells among live LN cells (based on propidium iodide staining) were analyzed by flow cytometry.

Flow Cytometry Analysis.

Prior to staining with labeled antibodies, BMDCs were pretreated with Fc blocking antibody (anti-CD16/CD32 mAb; BD Pharmingen) to avoid nonspecific binding. DCs were then stained with FITC-conjugated anti-mouse CD11c and PE-conjugated anti-mouse CD40, CD80, MHC class 1 Kb, or MHC class II I-Ab (BD Pharmingen). For counting ovalbumin-specific or TRP2-specific CD8+ T cells, peripheral blood lymphocytes were stained with FITC-conjugated anti-mouse CD8alpha (BD Pharmingen) and PE-conjugated H-2 Kb/OVA257-264 tetramer or H-2 Kb/TRP2181-188 (VYDFFVWL, SEQ ID NO: 34) respectively (Tetramer Core Facility, Baylor College of Medicine). To detect MAGE-3-specific CD8+ T cells, presensitized CD8+ T cells were stained with PE-labeled HLA-A2/MAGE-3271-279 (FLWG-PRALV, SEQ ID NO: 33) tetramer (Tetramer Core Facility, Baylor College of Medicine) for 15 min at 37° C. before addition of FITC-conjugated anti-human CD8 mAb (BD Biosciences). Stained cells were analyzed by flow cytometry and FlowJo (TreeStar, Inc., Ashland, Oreg.) software.

Allogeneic and Autologous T Cell Proliferation Assays.

Purified BMDCs (C57BL/6) were incubated with LPS (1 μg/ml), Ad-GFP or Ad-MF-ΔAkt virus at 100 m.o.i. For autologous T cell proliferation assays, BMDCs were pulsed with SIINFEKL peptide (SEQ ID NO: 32) (OVA257-264, Protein Chemistry Core Facility, Baylor College of Medicine) prior to incubation with LPS or recombinant adenoviruses. After 16-hr incubation, BMDCs were co-cultured with syngeneic (C57BL/6) or allogeneic (BALB/c) splenocytes at different ratios (1:50-1:6400) in 96-well round-bottom plates for 1 to 3 days. Thereafter, cells were pulsed with 1 μCi of [$^3$H]thymidine (New England Nuclear) per well for 12 hr, and thymidine incorporation was measured by liquid scintillation (1205 BS Betaplate). All experiments were conducted in triplicate and expressed as mean±S.D.

IFN-Gamma ELISPOT Assay.

BMDC-mediated T cell activation was assessed by IFN-gamma ELISPOT assay as described previously with minor modifications (Nikitina, E. Y. et al. Versatile prostate cancer treatment with inducible caspase and interleukin-12. Cancer Res 65, 4309-19 (2005)). Briefly, 2×105 OT-1 splenocytes and syngeneic BMDCs treated with SIINFEKL peptide (SEQ ID NO: 32) and LPS or adenoviruses were cultured for 24 or 72 hours in 96-well Multi-Screen-HA plates (Millipore) coated with 10 μg/mL of purified rat anti-mouse IFN-gamma monoclonal antibody (clone R4-6A2; PharMingen). Plates were then incubated overnight at 4° C. with 5 μg/mL biotinylated rat anti-mouse IFN-gamma monoclonal antibody (clone XMG1.2; PharMingen). Spots were visualized with 5-bromo-4-chloro-3-indolylphosphate/nitro blue tetrazolium alkaline phosphatase substrate (Sigma) reaction and counted per triplicate well using a stereomicroscope.

In Vivo Tumor Vaccination Studies.

EG.7-OVA thymoma or B16 melanoma cells (ATCC) were expanded in culture and injected subcutaneously into C57BL/6 mice (2×10$^6$ EG.7-OVA cells/mouse or 0.5×10$^5$ or 1×10$^5$ B16 melanoma cells/mouse). For therapeutic DC vaccines, BMDCs were pulsed with SIINFEKL peptide (SEQ ID NO: 32) (20 μg/ml) for EG.7-OVA cells or tyrosinase-related protein (TRP)-2 peptide (10 sequence VYDFFVWL, SEQ ID NO: 34) for B16 cells, transduced with or without adenoviruses or LPS and injected intraperitoneally (2×10$^6$ DCs/mouse). Single DC vaccine treatment was done 7 days after EG.7-OVA tumor injection (tumor sizes reached approximately 0.4 cm$^3$) or triple DC vaccination was done 4 (or 5), 15 and 25 days after B16 tumor injection. Two tumor measurements were recorded every 3-4 days. Tumor volumes were estimated as (m12×m2×0.5236) $w^2 \ast 1 \ast 0.5236$.

MAGE3-Specific CTL Activity Assay.

For T cell assays, DCs were purified from HLA-A2-positive healthy volunteers, after HLA typing by flow cytometry with FITC-conjugated anti-HLA-A2 specific antibody (BD Biosciences, San Diego, Calif.). DCs were pulsed with MAGE3271-279 (FLWGPRALV, SEQ ID NO: 33) peptide (Genemed Synthesis Inc, San Francisco, Calif.) and transduced with adenoviruses (Ad5f35-GFP or Ad5f35-MF-ΔhAkt, 10,000 vp/cell). Cytolytic assays were performed by coculturing DCs with autologous T cells (isolated using a Pan T cell isolation kit (Miltenyi Biotec)) at 1:10 ratio. T cells were restimulated twice in the presence of IL-2 (10 U/ml). After 20 days of culture, effector cells were harvested and analyzed by cytolytic assays. Target cells including melanoma cell lines SK-Me1-37 (MAGE3 positive, A2 positive), NA-6-Mel (MAGE3 positive, A2 negative) and T2 cells (MAGE3 negative, A2 positive) loaded with MAGE3271-279 peptide were labeled with 100 μCi 51Cr-sodium chromate (Amersham Pharmacia Biotech) and cocultured for 6 hours with effector cells at the indicated cell ratios. The percentage of specific lysis was calculated as: 100*[(experimental−spontaneous release)/(maximum−spontaneous release)]. For control purposes, T2 cells were pulsed with flu matrix peptide (IMP) p58-66 GILGFVFT (SEQ ID NO: 41) (Genemed Synthesis Inc).

Statistical Analysis.

Statistical significance was determined based on the student t-test between indicated groups or one-way ANOVA with a multiple comparison test. Animal survival was analyzed using Kaplan-Meier survival curves with log rank test (Prism v4, GraphPad Software, Inc.).

Preparation of siRNAs.

The previously identified small interfering RNA (siRNA) for Akt-1, matching closely all isoforms (siAKTc; Katome, T., et al. J. Biol. Chem. (2003) 278: 28312), was synthesized from Integrated DNA Technologies (Coralville, Iowa), and negative control siRNA was purchased from Ambion (Austin, Tex.). Transfection of siRNAs into BMDCs was done by GeneSilencer™ siRNA Transfection (GTS, San Diego, Calif.) or nucleofection using the Human Dendritic Cell Nucleofector Kit (Amaxa Biosystems, Gaithersburg, Md.).

NF-kappaB Secreted Alkaline Phosphatase (SEAP) Reporter Assay.

Jurkat TAg cells were transfected with indicated amounts of plasmids along with NF-kappaB SEAP reporter plasmid by electroporation. The following day, cells were plated with suboptimal concentrations of phorbol ester PMA (0.5 nM) and further incubated for about 24 hr. Thereafter, supernatants were collected and analyzed for SEAP activity as described previously (L1, B. et al. Gene Therapy (2001) 9: 233-244).

Fluorescent Confocal Microscopy.

293 cells cultured on poly-L-lysine-coated coverslips were transfected with indicated plasmids in 6-well plates and further incubated for 24 hr. For drug-dependent lipid-raft localization, 100 nM of Rapalog (Rapa-B) was added for an additional 4 hr. After fixation with 4% paraformaldehyde for 30 min, cells were labeled with cholera toxin B (CTx-B-TRITC) to detect glycosphingolipid in membrane lipid-rafts (List Biological Laboratories, Campbell, Calif.), and analyzed by LSM 430 confocal microscopy.

Example 10

Inducible Akt (iAkt) Membrane Targeting

Inducible Akt (iAkt) membrane targeting was effected by (a) linking a modified Akt with a polypeptide that binds to a bifunctional compound, and (b) linking a membrane association component to a another polypeptide that binds to the same bifunctional compound. Adding the bifunctional compound to a system in which component (a) and (b) are present can induce the two components to join with one another and the complex can be recruited to the cell membrane in an inducible manner. In the example below, the bifunctional compound, a rapamycin derivative, binds to (a) a derivative of FK binding protein linked to an Akt protein lacking a PH domain, and (b) a rapamycin binding domain from mTOR/FRAP/RAFT linked to a N-terminal myristoylation region from the protein kinase Src. Constructs and methods for generating and using these components are described in U.S. patent application publication US2003/0144204 published on Jul. 31, 2003 and filed on Dec. 19, 2002, entitled "Akt-Based Inducible Survival Switch," which can be consulted by the person of ordinary skill in the art for any details not presented below. Alternative embodiments include substituting the Src N-terminal myristoylation region with a dual acylation region from a different protein (e.g., from Fyn or Lck) or with another membrane protein or membrane protein fragment, as can be accomplished by the person of ordinary skill in the art using standard techniques.

Plasmid Construction.

To generate F3-Akt, F3-DPH.Akt, F3-AktKM and variants, Akt and .DELTA.PH. Akt were Pfu (Stratagene)-amplified from pCMV6-HA-Akt or pCMV6-HA-AktK179M using SalI-linkered 5' primers, mAkt5SPH (full-length): 5'-agagcgacaacgacgtagccattgtgaaggag-3' (SEQ ID NO: 42) or mAkt5S (truncated .DELTA.PH): 5'-agagtcgacaccgccattcagactgtggcc-3' (SEQ ID NO: 43); and 3' primer, mAkt3 S: 5'-agagtcgacggctgtgccactggctgagtag-3' (SEQ ID NO: 44). PCR products were subcloned into pCR-Blunt (Invitrogen) or pKSII+ (Stratagene) and sequence verified, to createpSH5/mAkt, pSH5/m.DELTA.PH.Akt, and pKS/mAkt.KM. The 1440-bp full-length Akt and 1130-bp .DELTA.PH.Akt fragments were removed with SalI and subcloned into XhoI/SalI-digested M-Fpk 3-E, or XhoI or SalI-digested S-F.sub.pk 3-E (MacCorkle et al., 1998), to create M-Akt (and Akt variants), Akt-F3 (and variants) and F3-Akt (and variants). All chimeric proteins contain the HA epitope (E), but the "E" is left off (along with "pk" subscripts) for simplicity. The heterodimeric rapalog/CID.sub.HED can effect the crosslinking of FRB1 and FKPB12 (called F). In these experiments, the non-toxic variant of FKBP12, Fpk (FKBP12(G89P, 190K)), was used to eliminate background toxicity.

To generate myristoylated rapalogue-binding domains, the rapamycin binding domain (FRB) from human FRAP (res. 2025-2113; T2098L) was PfuI-amplified from FRAP*-AD using primers SEQ ID NO: 9 (5'-cgatctcgaggagatgtggcatgaaggcctgg-3', SEQ ID NO: 45) and 3FRBS: SEQ ID NO: 10 (5'-cgatgtcgacctttgagattcgtcggaacacatg-3', SEQ ID NO: 46) and subcloned into pCR-Blunt to produce pSH5/FRB.sub.1. One or two copies of the XhoI/SalI FRB1 domain were subcloned into XhoI/SalI-digested M-F.sub.pk 3-E to create M-FRB.sub.1 and M-FRB.sub.1 2. Also, the NF-.kappa.B-SEAP reporter plasmid was produced. Thus, a constitutively active, myristoylated Akt (M-Akt) or M-.DELTA.PH.Akt and kinase-dead mutant versions (i.e. Akt.K179M, named AktKM) of chimeric Akt constructs were developed.

To make the bicistronic iAkt constructs, two different internal ribosome entry sequence (IRES) elements from EMCV or poliovirus were used to link M-FRB.sub.12 and F3-.DELTA.PH.Akt on the same transcript. The poliovirus IRES sequence (IRESp) was PfuI-amplified from pTPOV-3816 with primers, 5pIRES/Mn: 5'-atacaattgccgcggttcgaattctgttttatactcccttcccgtaac-3' (SEQ ID NO: 47) and 3pIRES/Mun; 5'-tatcaattggtttaaacagcaaacagatagataatgagtctcac-3' (SEQ ID NO: 48). The resulting PCR products were subcloned into pCR-Blunt to create pSH5/IRESp-Mun. The 615-bp IRESp MunI fragment was ligated into EcoRI-digested pSH1/M-FRB.sub.12-E to create pSH1/M-FRB.sub.12-E-IRESp. Finally, the NotI/EcoRI F3-.DELTA.PH.Akt fragment from pSH1/F3-.DELTA.PH.Akt was blunt-ligated into the PmeI site to create pSH1/M-FRB.sub.1 2-E-IRESp-F3.DELTA.PH.Akt, renamed as iAkt.sub.b. The bicistronic vector iAkt.sub.a utilizes the EMCV IRES and was made by a comparable strategy.

For establishing Jurkat.iAkt cell lines, the bicistronic NotI/MunI fragment from iAkt.sub.b was subcloned into NotI/EcoRI-digested pBJ5-neo to create pBJ5-neo/iAkt.sub.b.

To generate inducible Akt (iAkt) molecules, three tandem FKBP domains (F3) were fused to the N- or C-termini of wild-type Akt or a variant.DELTA.PH.Akt), lacking the pleckstrin homology (PH) domain to reduce natural membrane association.

Cell Culture.

293T human embryonic kidney cells (ATCC) and Jurkat (ATCC), Jurkat-TAg and Jurkat.iAkt were maintained in DMEM or RPMI-1640, respectively, containing 10% fetal bovine serum (FBS) and antibiotics. The Jurkat.iAkt line was derived by transfecting Jurkat cells with NdeI-linearized pBJ5-neo/iAkt.sub.b plasmid followed by G418 (1 mg/ml) selection. Clones were screened by anti-HA immunoblotting.

Electroporation and SEAP Assay.

Jurkat-TAg cells in logarithmic-phase growth were electroporated (950 mF, 250 V; Gene Pulser II (BIO-RAD)) with expression plasmids and the NF-.kappa.B-SEAP reporter plasmid. After 24 hours, transfected cells were stimulated with sub-optimal levels of the phorbol ester PMA (5 ng/ml) along with log dilutions of the heterodimerizing CID, AP22783, and additional treatments. After an additional 24 hours, supernatants were assayed for SEAP activity.

Western Blots.

293T cells seeded in 6-well plates were transiently transfected with 2.mu.g of different expression constructs in 6.mu.l FuGENE6 (Boehringer-Mannheim, Indianapolis, Ind.) in Opti-MEM-I medium for 24 hours followed by serum starvation for an additional 24 hours. Cells were then treated with different agents and harvested at different time points. After washing (2.times) in ice-cold PBS, cell pellets were lysed in RIPA buffer containing protease inhibitors (CytoSignal, Irvine, Calif.). Equal amounts of protein from each sample were separated on 10% SDS-PAGE gels and transferred to PVDF membrane (Amersham Pharmacia Biotech, Piscataway, N.J.). Phospho-specific antibodies against Akt (T308 or 5473 site) (Cell Signaling, Beverly, Mass.) were used for measuring Akt phosphorylation, and the signal was detected by AP-conjugated secondary antibodies (NEB, Beverly, Mass.) and CDP-Star chemiluminescence reagent (NEN life science, Boston, Mass.).

Immunoprecipitation and In Vitro Akt Kinase Assay.

Jurkat.iAkt.sub.b were serum starved for 24 hours followed by treatment with AP22783 or serum for 30 min. Cells were then lysed in a lysis buffer provided with the Akt Kinase Assay kit (Cell Signaling, Beverly, Mass.), and F.sub.pk3-.DELTA.PH.Akt-E was immunoprecipitated with polyclonal anti-HA antibody. Antibody-antigen complexes were washed three times in lysis buffer and once in kinase buffer. In vitro kinase assays for Akt were performed using a GSK3.alpha./.beta. "crosstide". The extent of crosstide phosphorylation was determined by anti-GSK.alpha./.beta. immunoblotting according to the manufacturer's protocol. Apoptosis and Flow Cytometry. Jurkat.iAkt were serum starved for 24 hours followed by pre-treatment with AP22783 in 0, 2 or 10% FBS for 40 min. After incubation with apoptosis-inducing stimuli for the periods indicated, cells were harvested and washed twice in ice-cold PBS and fixed in 70% ethanol. Cells were stained in 50.mu.g/ml propidium iodide and 100.mu.g/mlR-Nase A for 30 min at 37.degree. C., and hypodiploid cells were quantitated by flow cytometry using a Beckman-Coulter EPICS XL-MCL.

For determination of caspase-3 activation and PARP cleavage after staurosporine treatment, cell pellets were lysed in Laemmli sample buffer containing 5% (v/v).beta.-mercaptoethanol (Bio-Rad, Hercules, Calif.), and equal amounts of protein were separated on 6 (for PARP) or 12% (for caspase3) SDS-PAGE followed by immunoblotting with anti-caspase-3 and anti-PARP antibodies.

Inducible Membrane Recruitment of iAkt.

Two key requirements for efficient synthetic regulation of a biological event are highly specific conditional dependency and low background. NF-kappaB induction is a major target of Akt following growth factor signaling, and multiple reports show that a constitutively active myristoylated Akt (M-Akt) can enhance protein kinase C (PKC)-mediated NF-.kappa.B induction by either phosphorylation of IKK.alpha., the activation domain of p65/RelA, or both. Therefore, in order to optimize iAkt, an NF-.kappa.B-responsive secreted alkaline phosphatase (SEAP) reporter plasmid was used as an assay for Akt activation.

Briefly, the human T cell line, Jurkat-TAg, was cotransfected with reporter plasmid, NF-.kappa.B/SEAP, along with constitutively active M-Akt expression vector or empty control vector. Twenty-four hours after transfection, cells were divided into aliquots that were stimulated with sub-optimal levels (5 ng/ml) of the phorbol ester, PMA, or were untreated. After an additional 24 hours, SEAP activity was measured. Although Akt activity alone was insufficient to induce measurable NF-.kappa.B activity, M-Akt expression potentiated (by 3-4 fold) PKC-induced NF-.kappa.B activity, consistent with multiple reports. Furthermore, inhibition of PI3K by LY294002 (5.mu.M) or wortmannin (1.mu.M) did not prevent NF-.kappa.B activation by M-Akt plus PKC, although inhibition of "typical" PKC isoforms with R0318220 (1.mu.M) led to complete inhibition of NF-.kappa.B as expected (FIG. 2).

Since the constitutively active Akt (T308) kinase, PDK1, is primarily membrane-associated following growth factor stimulation, membrane recruitment of Akt via its PH domain is necessary for its activation. Furthermore, although the PH domain has been shown to suppress basal phosphorylation of T308 and Akt activation when not bound by its lipid ligand, PIP2, this initial phosphorylation should still require interaction with membrane-localized PDK1.

Basal Akt activity and activation following membrane recruitment of full length and truncated Akt, lacking the PH domain, was compared using a NF-.kappa.B reporter assay. Both full length and .DELTA.PH.Akt were fused to a tandem trimer of the CID-binding domain, F3, at both the amino and carboxyl termini. As before Jurkat-TAg cells were cotransfected with reporter plasmid NF-.kappa.B/SEAP along with the membrane docking molecule, M-FRB.sub.12, alone, various F3-Akt chimeras, alone, or both together. Twenty-four hours after transfection, cells were stimulated with 5 ng/ml PMA along with log dilutions of heterodimerizing CID, AP22783. After additional 24 hr incubation, SEAP activity was assayed. Wild type Akt showed significant CID-independent NF-.kappa.B induction that was only slightly increased by crosslinking to the membrane, via M-FRB12. This was true regardless of whether F3 was fused to the N- or C-terminus of Akt. As expected, membrane recruitment or overexpression of kinase-deficient Akt.KM (K179M) had no detectable effect on NF-.kappa.B induction over PMA alone. Thus, membrane recruitment of full-length Akt only slightly increases its activity due to the high basal activity from its overexpression. In contrast, membrane recruitment of F3-.DELTA.PH.Akt showed a very clear CID-dependent induction of NF-.kappa.B with undetectable CID-independent activity. Moreover, myristoylated M.DELTA.PH.Akt was more active than M-Akt in augmenting NF-.kappa.B activation, consistent with an inhibitory function for the PH domain. Again, M-FRB.sub.1 2 alone or recruitment of kinase dead F3-.DELTA.PH.AktKM did not influence NF-.kappa.B induction.

These results indicated that the chimeric F3-.DELTA.PH.Akt allele is strongly CID-inducible with very low basal activity. Also, these results are consistent with previous reports that the PH domain of Akt kinase is responsible for its translocation to the plasma membrane and also has an inhibitory function. Since most applications of CID technology have been based partly, at least, on empirically designed inducible chimeric proteins, CID-mediated targeting or crosslinking might not always faithfully reflect physiological signaling. Further, CID-binding domains, like FKBP12, could potentially sterically hinder an essential target protein domain(s). Therefore, .DELTA.PH.Akt with F3 fused to both termini of .DELTA.PH.Akt was tested. The N-terminal fusion chimera, F3-.DELTA.PH.Akt, potentiated NF-.kappa.B transactivation somewhat better than the C-terminal chimera, .DELTA.PH.Akt-F3. Since both molecules were expressed at similar levels, membrane recruitment of F3-.DELTA.PH.Akt may place Akt in a more favorable orientation for interacting with PDK1 or other interacting proteins. In either orientation, however, both iAkt versions were devoid of detectable basal NF-.kappa.B signaling.

Since M-FRB.sub.1 2 could potentially recruit two chimeric Akt molecules simultaneously, it was determine if membrane recruitment of one Akt molecule was sufficient for optimal activation or whether oligomerization of multiple Akt molecules might enhance activation. Therefore, CID-mediated iAkt activity was compared when the membrane docking molecule, contained one or two FRB.sub.1 domains (FRB-.sub.1 vs FRB.sub.1 2, respectively). There was no significant difference in NF-.kappa.B induction by iAkt whether one or two tandem FRB.sub.1 domains were used for the docking site, indicating that forced Akt oligomerization is not a prerequisite for its activation. It was also shown that CID dependent membrane targeting of Akt resulted in rapid phosphorylation and activation of endogenous Akt.

Example 12

Combination Immunotherapeutics

Figure 15:
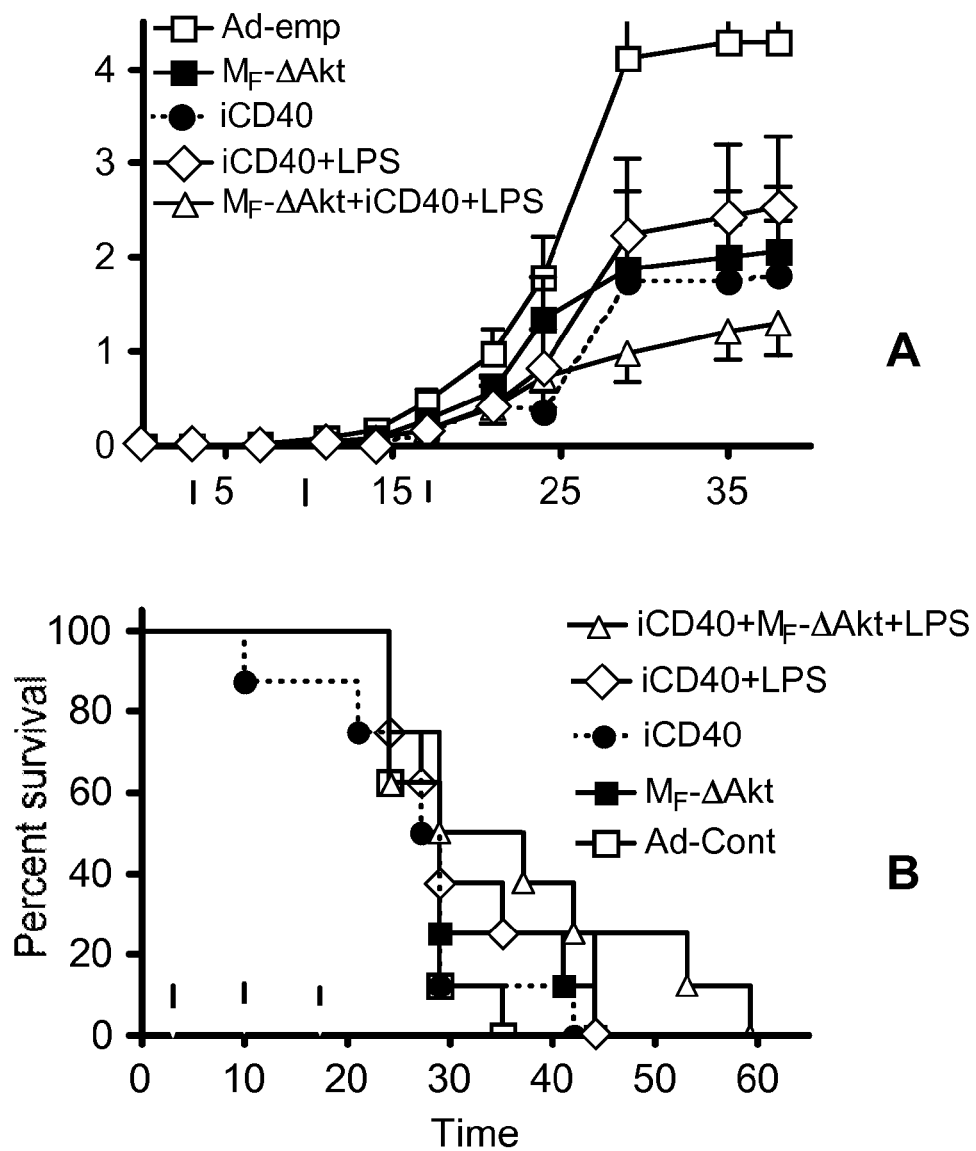
FIGS. 15A-15B show effects of a combination immunotherapy.

Tumor challenges similar to those described in Example 7 and reported in FIGS. 7C and 7D were performed to determine effects of combination immunotherapies. The combined effects of $M_F$-ΔAkt and an inducible CD40 (iCD40, described in US publication 20040209836 (published Oct. 21, 2004)) were assessed. Briefly, adenoviral particles having a polynucleotide sequence encoding the $M_F$-ΔAkt molecule and adenoviral particles having a polynucleotide sequence encoding the iCD40 construct were utilized to transduce dendritic cells (DCs). DCs were pulsed with TRP-$2_{181-188}$ peptide (10 micrograms/ml; VYDFFVWL, SEQ ID NO: 34) for about 3 hours and treated with the adenoviruses (about 10,000 viral particles/DC for iCD40 particles and control adenoviral particles (Ad-emp) and about 500 viral particles/DC for $M_F$-ΔAkt particles) plus or minus LPS (1 ug/ml) as indicated for 2 hours. The transduced DCs were utilized in a triple intraperitoneal vaccination ($2\times10^6$ CD11c$^+$ DCs/100 ul PBS) on days 3, 10 and 17. Host animals were C57BL/6 (6-8 wks) female mice (8 mice/group), and tumors were established by subcutaneous injection of B16 melanoma cells (100,000/100 ul) on the back of each mouse (day 0). Inducer was administered to the mice intraperitoneally at a dose of 2 mg/kg AP20187/100 ul/mouse on days 4, 11, 18. Results are shown in FIGS. 15A and 15B. The combination yielded effects that were at least additive and may be synergistic. Effects of the combination are under additional investigation.

Example 13

Immunotherapeutic Effect on Human Tumors

Six to eight week-old athymic male Balb/c nu/nu mice (NCI at Frederick, Md.) are used as hosts for human xenografts (e.g., Xie et al. Cancer Research 61: 6795-6804 (2001)). Mice are maintained in a specific pathogen-free environment, in compliance with standard guidelines. Cells in logarithmic-phase growth are lightly trypsinized and washed twice with OPTI-medium (GIBCO). Cell suspensions ($1\times10^6$-cells/200 ul) of modified DCs primed with antigen, as described herein (e.g., in Example 8), are subcutaneously injected into the right flank of the mice. To establish LNCaP tumors, a 1:4 mix of 100-ul cell suspension ($1\times10^6$ cells) with Matrigel™ (Becton Dickinson, Bedford, Mass.) is injected before, contemporaneously or after, injection of the modified DCs. The effect of the modified DCs described herein on tumor growth is determined according to standard measurements and procedures.

Example 13

Representative Sequences

Provided hereafter are examples of representative sequences.
SEQ ID NO: 1 (Accession no. NM_009652: mouse Akt1)

```
  1 ccgggaccag cggacggacc gagcagcgtc ctgcggccgg caccgcggcg gcccagatcc
 61 ggccagcagc gcgcgcccgg acgccgctgc cttcagccgg ccccgcccag cgcccgcccg
121 cgggatgcgg agcggcgggc gcccgaggcc gcggcccggc taggcccagt cgcccgcacg
181 cggcggcccg acgctgcggc caggccggct gggctcagcc taccgagaag agactctgat
```

-continued

```
 241 catcatccct gggttacccc tgtctctggg ggccacggat accatgaacg acgtagccat
 301 tgtgaaggag ggctggctgc acaaacgagg ggaatatatt aaaacctggc ggccacgcta
 361 cttcctcctc aagaacgatg cacctttat tggctacaag aacggcctc aggatgtgga
 421 tcagcgagag tccccactca acaacttctc agtggcacaa tgccagctga tgaagacaga
 481 gcggccaagg cccaacacct ttatcatccg ctgcctgcag tggaccacag tcattgagcg
 541 caccttccat gtggaaacgc ctgaggagcg ggaagaatgg gccaccgcca ttcagactgt
 601 ggccgatgga ctcaagaggc aggaagaaga gacgatggac ttccgatcag gctcacccag
 661 tgacaactca ggggctgaag atggaggt gtccctggcc aagcccaagc ccgtgtgac
 721 catgaacgag tttgagtacc tgaaactact gggcaagggc acctttggga aagtgattct
 781 ggtgaaagag aaggccacag gccgctacta tgccatgaag atcctcaaga aggaggtcat
 841 cgtcgccaag gatgaggttg cccacacgct tactgagaac cgtgtcctgc agaactctag
 901 gcatcccttc cttacggccc tcaagtactc attccagacc cacgaccgcc tctgctttgt
 961 catggagtat gccaacgggg gcgagctctt cttccacctg tctcgagagc gcgtgttctc
1021 cgaggaccgg gcccgcttct atggtgcgga gattgtgtct gccctggact acttgcactc
1081 cgagaagaac gtggtgtacc gggacctgaa gctggagaac ctcatgctgg acaaggacgg
1141 gcacatcaag ataacggact cgggctgtg caaggagggg atcaaggatg gtgccactat
1201 gaagacattc tgcggaacgc cggagtacct ggcccctgag gtgctggagg acaacgacta
1261 cggccgtgca gtggactggt gggggctggg cgtggtcatg tatgagatga tgtgtggccg
1321 cctgcccttc tacaaccagg accacgagaa gctgttcgag ctgatcctca tggaggagat
1381 ccgcttcccg cgcacactcg gccctgaggc caagtccctg ctctccgggc tgctcaagaa
1441 ggaccctaca cagaggctcg gtggggctc tgaggatgcc aaggagatca tgcagcaccg
1501 gttctttgcc aacatcgtgt ggcaggatgt gtatgagaag aagctgagcc cacctttcaa
1561 gcccaggtc acctctgaga ctgacaccag gtatttcgat gaggagttca cagctcagat
1621 gatcaccatc acgccgcctg atcaagatga cagcatggag tgtgtggaca gtgagcggag
1681 gccgcacttc ccccagttct cctactcagc cagtggcaca gcctgaggcc tggggcagcg
1741 gctggcagct ccacgctcct ctgcattgcc gagtccagaa gccccgcatg atcatctga
1801 acctgatgtt ttgtttctcg gatgcgctgg ggaggaacct tgccagcctc caggaccagg
1861 ggaggatgtt tctactgtgg gcagcagcct acctcccagc caggtcagga ggaaaactat
1921 cctggggttt ttcttaattt atttcatcca gtttgagacc acacatgtgg cctcagtgcc
1981 cagaacaatt agattcatgt agaaaactat taaggactga cgcgaccatg tgcaatgtgg
2041 gctcatgggt ctgggtgggt cccgtcactg cccccattgg cctgtccacc ctggccgcca
2101 cctgtctcta gggtccaggg ccaaagtcca gcaagaaggc accagaagca cctccctgtg
2161 gtatgctaac tggccctctc cctctggggcg gggagaggtc acagctgctt cagccctagg
2221 gctggatggg atggccaggg ctcaagtgag gttgacagag gaacaagaat ccagtttgtt
2281 gctgtgtccc atgctgttca gagacattta ggggatttta atcttggtga caggagagcc
2341 cctgccctcc cgctcctgcg tggtggctct tagcgggtac cctgggagcc cctgcctcac
2401 gtgagccctc tcctagcact tgtccttta gatgctttcc ctctcccgct gtccgtcacc
2461 ctggcctgtc ccctcccgcc agacgctggc cattgctgca ccatgtcgtt ttttacaaca
2521 ttcagcttca gcatttttac tattataata agaaactgtc cctccaaatt caataaaaat
2581 tgcttttcaa gcttgaaaaa aaaaaaaaaa aaaaaaaaaa aaaaaa
```

SEQ ID NO: 2 (Accession no. NM_001014431: human Akt1 mRNA)

```
   1  cggcaggacc gagcgcggca ggcggctggc ccagcgcagc cagcgcggcc cgaaggacgg
  61  gagcaggcgg ccgagcaccg agcgctgggc accgggcacc gagcggcggc ggcacgcgag
 121  gcccggcccc gagcagcgcc cccgcccgcc gcggcctcca gcccggcccc gcccagcgcc
 181  ggcccgcggg gatgcggagc ggcgggcgcc ggaggccgcg gcccggctag gcccgcgctc
 241  gcgcccggac gcggcggccc gaggctgtgg ccaggccagc tgggctcggg gagcgccagc
 301  ctgagaggag cgcgtgagcg tcgcgggagc ctcgggcacc atgagcgacg tggctattgt
 361  gaaggagggt tggctgcaca acgagggga gtacatcaag acctggcggc acgctactt
 421  cctcctcaag aatgatggca ccttcattgg ctacaaggag cggccgcagg atgtggacca
 481  acgtgaggct cccctcaaca acttctctgt ggcgcagtgc cagctgatga gacggagcg
 541  gccccggccc aacaccttca tcatccgctg cctgcagtgg accactgtca tcgaacgcac
 601  cttccatgtg gagactcctg aggagcggga ggagtggaca accgccatcc agactgtggc
 661  tgacggcctc aagaagcagg aggaggagga gatggacttc cggtcgggct cacccagtga
 721  caactcaggg gctgaagaga tggaggtgtc cctggccaag cccaagcacc gcgtgaccat
 781  gaacgagttt gagtacctga agctgctggg caagggcact ttcggcaagg tgatcctggt
 841  gaaggagaag gccacaggcc gctactacgc catgaagatc ctcaagaagg aagtcatcgt
 901  ggccaaggac gaggtggccc acacactcac cgagaaccgc gtcctgcaga actccaggca
 961  ccccttcctc acagccctga gtactctttt ccagacccac gaccgcctct gctttgtcat
1021  ggagtacgcc aacggggggcg agctgttctt ccacctgtcc cgggagcgtg tgttctccga
1081  ggaccgggcc cgcttctatg cgctgagat tgtgtcagcc ctggactacc tgcactcgga
1141  gaagaacgtg gtgtaccggg acctcaagct ggagaacctc atgctggaca aggacgggca
1201  cattaagatc acagacttcg ggctgtgcaa ggaggggatc aaggacggtg ccaccatgaa
1261  gaccttttgc ggcacacctg agtacctggc ccccgaggtg ctggaggaca tgactacgg
1321  ccgtgcagtg gactggtggg ggctgggcgt ggtcatgtac gagatgatgt gcggtcgcct
1381  gcccttctac aaccaggacc atgagaagct ttttgagctc atcctcatgg aggagatccg
1441  cttcccgcgc acgcttggtc ccgaggccaa gtccttgctt tcagggctgc tcaagaagga
1501  ccccaagcag aggcttggcg ggggctccga ggacgccaag gagatcatgc agcatcgctt
1561  ctttgccggt atcgtgtggc agcacgtgta cgagaagaag ctcagcccac ccttcaagcc
1621  ccaggtcacg tcggagactg acaccaggta ttttgatgag gagttcacgg cccagatgat
1681  caccatcaca ccacctgacc aagatgacag catggagtgt gtggacagcg agcgcaggcc
1741  ccacttcccc cagttctcct actcggccag cggcacggcc tgaggcggcg gtggactgcg
1801  ctggacgata gcttggaggg atggagaggc ggcctcgtgc catgatctgt atttaatggt
1861  ttttatttct cgggtgcatt tgagagaagc cacgctgtcc tctcgagccc agatggaaag
1921  acgttttgt gctgtgggca gcaccctccc ccgcagcggg gtagggaaga aaactatcct
1981  gcgggttta atttatttca tccagtttgt tctccgggtg tggcctcagc cctcagaaca
2041  atccgattca cgtagggaaa tgttaaggac ttctgcagct atgcgcaatg tggcattggg
2101  gggccgggca ggtcctgccc atgtgtcccc tcactctgtc agccagccgc cctgggctgt
2161  ctgtcaccag ctatctgtca tctctctggg gccctgggcc tcagttcaac ctggtggcac
2221  cagatgcaac ctcactatgg tatgctggcc agcaccctct cctgggggtg gcaggcacac
2281  agcagccccc cagcactaag gccgtgtctc tgaggacgtc atcggaggct gggcccctgg
```

-continued

```
2341 gatgggacca gggatggggg atgggccagg gtttacccag tgggacagag gagcaaggtt 2401 taaatttgtt attgtgtatt atgttgttca aatgcatttt gggggttttt aatctttgtg 2461 acaggaaagc cctcccccct cccctctgt gtcacagttc ttggtgactg tcccaccggg 2521 agcctccccc tcagatgatc tctccacggt agcacttgac cttttcgacg cttaaccttt 2581 ccgctgtcgc cccaggccct ccctgactcc ctgtgggggt ggccatccct gggcccctcc 2641 acgcctcctg gccagacgct gccgctgccg ctgcaccacg gcgttttttt acaacattca 2701 actttagtat ttttactatt ataatataat atggaacctt ccctccaaat tcttcaataa 2761 aagttgcttt tcaaaaaaaa aaaaaaaaa aaaa
```

SEQ ID NO: 3 (Accession no. NM_001626: human Akt2 mRNA)

```
   1 gaattccagc ggcggcgccg ttgccgctgc cgggaaacac aaggaaaggg aaccagcgca 61 gcgtggcgat gggcgggggt agagccccgc cggagaggct gggcggctgc cggtgacaga 121 ctgtgccctg tccacggtgc ctcctgcatg tcctgctgcc ctgagctgtc ccgagctagg 181 tgacagcgta ccacgctgcc accatgaatg aggtgtctgt catcaaagaa ggctggctcc 241 acaagcgtgg tgaatacatc aagacctgga ggccacggta cttcctgctg aagagcgacg 301 gctccttcat tgggtacaag gagaggcccg aggcccctga tcagactcta ccccccttaa 361 acaacttctc cgtagcagaa tgccagctga tgaagaccga gaggccgcga cccaacacct 421 ttgtcatacg ctgcctgcag tggaccacag tcatcgagag gaccttccac gtggattctc 481 cagacgagag ggaggagtgg atgcgggcca tccagatggt cgccaacagc ctcaagcagc 541 gggccccagg cgaggacccc atggactaca agtgtggctc ccccagtgac tcctccacga 601 ctgaggagat ggaagtggcg gtcagcaagg cacgggctaa agtgaccatg aatgacttcg 661 actatctcaa actccttggc aagggaacct ttggcaaagt catcctggtc cgggagaagg 721 ccactggccg ctactacgcc atgaagatcc tgcgaaagga agtcatcatt gccaaggatg 781 aagtcgctca cacagtcacc gagagccggg tcctccagaa caccaggcac ccgttcctca 841 ctgcgctgaa gtatgccttc cagacccacg accgcctgtg ctttgtgatg gagtatgcca 901 acgggggtga gctgttcttc cacctgtccc gggagcgtgt cttcacagag gagcgggccc 961 ggttttatgg tgcagagatt gtctcggctc ttgagtactt gcactcgcgg gacgtggtat 1021 accgcgacat caagctggaa aacctcatgc tggacaaaga tggccacatc aagatcactg 1081 actttggcct ctgcaaagag ggcatcagtg acggggccac catgaaaacc ttctgtggga 1141 ccccggagta cctggcgcct gaggtgctgg aggacaatga ctatggccgg gccgtggact 1201 ggtgggggct gggtgtggtc atgtacgaga tgatgtgcgg ccgcctgccc ttctacaacc 1261 aggaccacga gcgcctcttc gagctcatcc tcatggaaga gatccgcttc ccgcgcacgc 1321 tcagccccga ggccaagtcc ctgcttgctg ggctgcttaa gaaggacccc aagcagaggc 1381 ttggtggggg gcccagcgat gccaaggagg tcatggagca caggttcttc ctcagcatca 1441 actggcagga cgtggtccag aagaagctcc tgccaccctt caaacctcag gtcacgtccg 1501 aggtcgacac aaggtacttc gatgatgaat ttaccgccca gtccatcaca atcacacccc 1561 ctgaccgcta tgacagcctg ggcttactgg agctggacca gcggaccac ttcccccagt 1621 tctcctactc ggccagcatc cgcgagtgag cagtctgccc acgcaggagga cgcacgctcg 1681 ctgccatcac cgctgggtgg ttttttaccc ctgcc
```

SEQ ID NO: 4 (Accession no. NM_005465: human Akt3 mRNA)

```
   1  gcagcagcag agaatccaaa ccctaaagct gatatcacaa agtaccattt ctccaagttg
  61  ggggctcaga ggggagtcat catgagcgat gttaccattg tgaaagaagg ttgggttcag
 121  aagagggag  aatatataaa aaactggagg ccaagatact tccttttgaa gacagatggc
 181  tcattcatag gatataaaga gaaacctcaa gatgtggatt taccttatcc cctcaacaac
 241  ttttcagtgg caaaatgcca gttaatgaaa acagaacgac aaagccaaa  cacatttata
 301  atcagatgtc tccagtggac tactgttata gagagaacat ttcatgtaga tactccagag
 361  gaaagggaag aatggacaga agctatccag gctgtagcag acagactgca gaggcaagaa
 421  gaggagagaa tgaattgtag tccaacttca caaattgata atataggaga ggaagagatg
 481  gatgcctcta caacccatca taaaagaaag acaatgaatg attttgacta tttgaaacta
 541  ctaggtaaag gcacttttgg gaaagttatt ttggttcgag agaaggcaag tggaaaatac
 601  tatgctatga agattctgaa gaaagaagtc attattgcaa aggatgaagt ggcacacact
 661  ctaactgaaa gcagagtatt aaagaacact agacatccct ttttaacatc cttgaaatat
 721  tccttccaga caaaagaccg tttgtgtttt gtgatggaat atgttaatgg gggcgagctg
 781  ttttcccatt tgtcgagaga gcgggtgttc tctgaggacc gcacgcgttt ctatggtgca
 841  gaaattgtct ctgccttgga ctatctacat tccggaaaga ttgtgtaccg tgatctcaag
 901  ttggagaatc taatgctgga caaagatggc cacataaaaa ttacagattt tggactttgc
 961  aaagaaggga tcacagatgc agccaccatg aagacattct gtggcactcc agaatatctg
1021  gcaccagagg tgttagaaga taatgactat ggccgagcag tagactggtg gggcctaggg
1081  gttgtcatgt atgaaatgat gtgtgggagg ttacctttct acaaccagga ccatgagaaa
1141  cttttgaat  taatattaat ggaagacatt aaatttcctc gaacactctc ttcagatgca
1201  aaatcattgc tttcagggct cttgataaag gatccaaata aacgccttgg tggaggacca
1261  gatgatgcaa aagaaattat gagacacagt ttcttctctg gagtaaactg gcaagatgta
1321  tatgataaaa agcttgtacc tccttttaaa cctcaagtaa catctgagac agatactaga
1381  tattttgatg aagaatttac agctcagact attacaataa caccacctga aaatatgat
1441  gaggatggta tggactgcat ggacaatgag aggcggccgc atttccctca attttcctac
1501  tctgcaagtg gacgagaata agtctctttc attctgctac ttcactgtca tcttcaattt
1561  attactgaaa atgattcctg gacatcacca gtcctagctc ttacacatag caggggcacc
1621  ttccgacatc ccagaccagc caagggtcct caccccctcgc cacctttcac cctcatgaaa
1681  acacacatac acgcaaatac actccagttt ttgtttttgc atgaaattgt atctcagtct
1741  aaggtctcat gctgttgctg ctactgtctt actattatag caactttaag aagtaatttt
1801  ccaacctttg gaagtcatga gcccaccatt gttcatttgt gcaccaatta tcatcttttg
1861  atctttagt  ttttccctca gtgaaggcta aatgagatac actgattcta ggtacatttt
1921  ttaactttct agaagagaaa aactaactag actaagaaga tttagtttat aaattcagaa
1981  caagcaattg tggaagggtg gtggcgtgca tatgtaaagc acatcagatc cgtgcgtgaa
2041  gtaggcatat atcactaagc tgtggctgga attgattagg aagcatttgg tagaaggact
2101  gaacaactgt tgggatatat atatatatat ataatttttt ttttttaaat tcctggtgga
2161  tactgtagaa gaagcccata tcacatgtgg atgtcgagac ttcacgggca atcatgagca
2221  agtgaacact gttctaccaa gaactgaagg catatgcaca gtcaaggtca cttaaagggt
2281  cttatgaaac aatttgagcc agagagcatc tttcccctgt gcttggaaac cttttttcct
```

```
2341 tcttgacatt tatcacctct gatggctgaa gaatgtagac aggtataatg atactgcttt 2401 tcaccaaaat ttctacacca aggtaaacag gtgtttgcct tatttaattt tttactttca 2461 gttctacgtg aattagcttt ttctcagatg ttgaaacttt gaatgtcctt ttatgatttt 2521 gtttatattg cagtagtatt tattttttag tgatgagaat tgtatgtcat gttagcaaac 2581 gcagctccaa cttatataaa atagacttac tgcagttact tttgacccat gtgcaaggat 2641 tgtacacgct gatgagaatc atgcactttt tctcctctgt taaaaaaaat gataaggctc 2701 tgaaatggaa tatattggtt agaatttggc tttgggagaa gagatgctgc catttaaccc 2761 cttggtactg aaaatgagaa aatccccaac tatgcatgcc aaggggttaa tgaaacaaat 2821 agctgttgac gtttgctcat ttaagaattt gaaacgttat gatgacctgg caacaaaaag 2881 taatgaagaa aattgagacc tgagtgaaga taagaaatga tctttacgtg gcaaaatgaa 2941 cacatcttga gtatttagga aatgggcagt gaaggctaag aacctggtgt gtttcttggg 3001 atcatggtac atttatcact gaattaagcc atcagggaaa aaacaacaaa aaaagagaac 3061 acctccagct tttctttttc tgtatatact catgtccccc agattccaac atttctcact 3121 gaaagggggc atgtatgcaa acctcatctt tctccttcat taatgatgat cttcagatta 3181 aacccttttgg tgctaggagc tgacaatttc caaagcagcc tgtgaagtcc taggggctgg 3241 gggccactct tgcggcaagc agaaggccat cctactccgc ggagtgatca tggaaatgta 3301 ttttagttaa actctgacag ctcccaaacg gaagactaca gcatgacgta gtattatgat 3361 tgcattgtat gaaagagcaa gtgactttct aagtaggatg aatcatattc atatgcagat 3421 gtcttagcct cttgacgctg gaagtgtgga tttatagcta tgaaaccact gctggcagtg 3481 ggtgggccac tgggactgac gggggttaaa gggcatttta ctaaggcagc taagacatat 3541 tcagacatca acgttatcct tctttttcat atttctacct gagtgaag
```

Amino acid sequences of the forgoing mRNA sequences can be obtained by a person of ordinary skill in the art by consulting standard interne resources. Amino acid sequences encoded by SEQ ID NO: 1-4 are designated by Accession nos. NP_033782, NP_001014432, NP_001617 and NP_005456, respectively. Other cloned sequences for each of these Akt forms also are available and accessed by the person of ordinary skill in the art.

SEQ ID NO: 5 (mRNA of human Akt1 lacking a PH domain; ΔPHAkt-1 (starting at position 101 of the encoded amino acid sequence)):

```
accgccatccagactgtggctgacggcctcaagaagcaggaggaggaggagatggacttccggtcgggctcacccagtgacaactc aggggctgaagagatggaggtgtccctggccaagcccaagcaccgcgtgaccatgaacgagtttgagtacctgaagctgctgggca agggcactttcggcaaggtgatcctggtgaaggagaaggccacaggccgctactacgccatgaagatcctcaagaaggaagtcatc gtggccaaggacgaggtggcccacacactcaccgagaaccgcgtcctgcagaactccaggcacccctcctcacagccctgaagta ctcttccagacccacgaccgcctctgctttgtcatggagtacgccaacggggcgagctgttcttccacctgtcccgggagcgtg tgttctccgaggaccgggcccgcttctatggcgctgagattgtgtcagccctggactacctgcactcggagaagaacgtggtgtac cgggacctcaagctggagaacctcatgctggacaaggacgggcacattaagatcacagacttcgggctgtgcaaggagggatcaa ggacggtgccaccatgaagacctttttgcggcacacctgagtacctggcccccgaggtgctggaggacaatgactacggccgtgcag tggactggtgggggctgggcgtggtcatgtacgagatgatgtgcggtcgcctgcccttctacaaccaggaccatgagaagcttttt gagctcatcctcatggaggagatccgcttcccgcgcacgcttggtcccgaggccaagtccttgctttcagggctgctcaagaagga ccccaagcagaggcttggcggggctccgaggacgccaaggagatcatgcagcatcgcttctttgccggtatcgtgtggcagcacg tgtacgagaagaagctcagcccaccccttcaagcccaggtcacgtcggagactgacaccaggtattttgatgaggagttcacggcc cagatgatcaccatcacaccacctgaccaagatgacagcatggagtgtgtggacagcgagcgcaggccccacttcccccagttctc ctactcggccagcgcgacggcctga
```

SEQ ID NO: 6 (amino acid sequence encoded by SEQ ID NO: 5)

ThrAlaIleGlnThrValAlaAspGlyLeuLysLysGlnGluGluGluGluMetAspPheArgSerGlySerProSerAspAsnSerGlyAlaGluGluMetGluValSerLeuAlaLysProLysHisArgValThrMetAsnGluPheGluTyrLeuLysLeuLeuGlyLysGlyThrPheGlyLysValIleLeuValLysGluLysAlaThrGlyArgTyrTyrAlaMetLysIleLeuLysLysGluValIleValAlaLysAspGluValAlaHisThrLeuThrGluAsnArgValLeuGlnAsnSerArgHisProPheLeuThrAlaLeuLysTyrSerPheGlnThrHisAspArgLeuCysPheValMetGluTyrAlaAsnGlyGlyGluLeuPhePheHisLeuSerArgGluArgValPheSerGluAspArgAlaArgPheTyrGlyAlaGluIleValSerAlaLeuAspTyrLeuHisSerGluLysAsnValValTyrArgAspLeuLysLeuGluAsnLeuMetLeuAspLysAspGlyHisIleLysIleThrAspPheGlyLeuCysLysGluGlyIleLysAspGlyAlaThrMetLysThrPheCysGlyThrProGluTyrLeuAlaProGluValLeuGluAspAsnAspTyrGlyArgAlaValAspTrpTrpGlyLeuGlyValValMetTyrGluMetMetCysGlyArgLeuProPheTyrAsnGlnAspHisGluLysLeuPheGluLeuIleLeuMetGluGluIleArgPheProArgThrLeuGlyProGluAlaLysSerLeuLeuSerGlyLeuLeuLysLysAspProLysGlnArgLeuGlyGlyGlySerGluAspAlaLysGluIleMetGlnHisArgPhePheAlaGlyIleValTrpGlnHisValTyrGluLysLysLeuSerProProPheLysProGlnValThrSerGluThrAspThrArgTyrPheAspGluGluPheThrAlaGlnMetIleThrIleThrProProAspGlnAspAspSerMetGluCysValAspSerGluArgArgProHisPheProGlnPheSerTyrSerAlaSerAlaThrAla

SEQ ID NO: 7 (membrane association region from human c-Fyn)

atgggctgtgtgcaatgtaaggataaagaagcaacaaaactgacggaggag-ctcgag    30

SEQ ID NO: 8 (amino acid sequence encoded by SEQ ID NO: 7)

MetGlyCysValGlnCysLysAspLys-GluAlaThrLysLeuThrGluGlu-LeuGlu    35

SEQ ID NO: 9 (nucleotide sequence encoding PSMA)

gcggatccgcatcatcatcatcatcacagctccggaatcgagggacgtggtaaatcctccaatgaagctactaacattactccaaa
gcataatatgaaagcattttttggatgaattgaaagctgagaacatcaagaagttcttatataattttacacagataccacatttag
caggaacagaacaaaactttcagcttgcaaagcaaattcaatcccagtggaaagaatttggcctggattctgttgagctagcacat
tatgatgtcctgttgtcctacccaaataagactcatcccaactacatctcaataattaatgaagatggaaatgagattttcaacac
atcattatttgaaccacctcctccaggatatgaaaatgtttcggatattgtaccacctttcagtgctttctctcctcaaggaatgc
cagagggcgatctagtgtatgttaactatgcacgaactgaagacttctttaaattggaacgggacatgaaaatcaattgctctggg
aaaattgtaattgccagatatgggaaagttttcagaggaaataaggttaaaaatgcccagctggcaggggccaaaggagtcattct
ctactccgaccctgctgactactttgctcctggggtgaagtcctatccagatggttggaatcttcctggaggtggtgtccagcgtg
gaaatatcctaaatctgaatggtgcaggagaccctctcacaccaggttacccagcaaatgaatatgcttataggcgtggaattgca
gaggctgttggtcttccaagtattcctgttcatccaattggatactatgatgcacagaagctcctagaaaaaatgggtggctcagc
accaccagatagcagctggagaggaagtctcaaagtgccctacaatgttggacctggctttactggaaactttttctacacaaaaag
tcaagatgcacatccactctaccaatgaagtgacaagaatttacaatgtgataggtactctcagaggagcagtggaaccagacaga
tatgtcattctgggaggtcaccgggactcatgggtgtttggtggtattgaccctcagagtggagcagctgttgttcatgaaattgt
gaggagctttggaacactgaaaaaggaagggtggagacctagaagaacaattttgtttgcaagctgggatgcagaagaatttggtc
ttct tggttctactgagtgggcagaggagaattcaagactccttcaagagcgtggcgtggcttaattaatgctgactcatctata
gaaggaaactacactctgagagttgattgtacaccgctgatgtacagcttggtacacaacctaacaaaagagctgaaaagccctga
tgaaggctttgaaggcaaatctctttatgaaagttggactaaaaaaagtccttccccagagttcagtggcatgcccaggataagca -continued

```
aattgggatctggaaatgattttgaggtgttcttccaacgacttggaattgcttcaggcagagcacggtatactaaaaattgggaa acaaacaaattcagcggctatccactgtatcacagtgtctatgaaacatatgagttggtggaaaagttttatgatccaatgtttaa atatcacctcactgtggcccaggttcgaggagggatggtgtttgagctagccaattccatagtgctccttttgattgtcgagatt atgctgtagttttaagaaagtatgctgacaaaatctacagtatttctatgaaacatccacaggaaatgaagacatacagtgtatca tttgattcacttttttctgcagtaaagaattttacagaaattgcttccaagttcagtgagagactccaggactttgacaaaagcaa gcatgtcatctatgctccaagcagccacaacaagtatgcaggggagtcattcccaggaatttatgatgctctgtttgatattgaaa gcaaagtggaccettccaaggcctggggagaagtgaagagacagatttatgttgcagccttcacagtgcaggcagctgcagagact ttgagtgaagtagcctaagcggccgcatagca
```

15
SEQ ID NO: 10 (PSMA amino acid sequence encoded by SEQ ID NO: 9)

```
MWNLLHETDSAVATARRPRWLCAGALVLAGGFFLLGFLFGWFIKSSNEATNITPKHNMKAFLDELKAENIKKFLYNFTQIPHLAGT

EQNFQLAKQIQSQWKEFGLDSVELAHYDVLLSYPNKTHPNYISIINEDGNEIFNTSLFEPPPPGYENVSDIVPPFSAFSPQGMPEG

DLVYVNYARTEDFFKLERDMKINCSGKIVIARYGKVFRGNKVKNAQLAGAKGVILYSDPADYFAPGVKSYPDGWNLPGGGVQRGNI

LNLNGAGDPLTPGYPANEYAYRRGIAEAVGLPSIPVHPIGYYDAQKLLEKMGGSAPPDSSWRGSLKVPYNVGPGFTGNFSTQKVKM

HIHSTNEVTRIYNVIGTLRGAVEPDRYVILGGHRDSWVFGGIDPQSGAAVVHEIVRSFGTLKKEGWRPRRTILFASWDAEEFGLLG

STEWAEENSRLLQERGVAYINADSSIEGNYTLRVDCTPLMYSLVHNLTKELKSPDEGFEGKSLYESWTKKSPSPEFSGMPRISKLG

SGNDFEVFFQRLGIASGRARYTKNWETNKFSGYPLYHSVYETYELVEKFYDPMFKYHLTVAQVRGGMVFELANSIVLPFDCRDYAV

VLRKYADKIYSISMKHPQEMKTYSVSFDSLFSAVKNFTEIASKFSERLQDFDKSKHVIYAPSSHNKYAGESFPGIYDALFDIESKV

DPSKAWGEVKRQIYVAAFTVQAAAETLSEVA
```

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following claims.

What is claimed is:

1. A method for preparing a modified dendritic cell, which comprises:
transferring a polynucleotide into a dendritic cell, wherein the polynucleotide encodes a membrane-targeted Akt protein comprising a dual acylation region and a mammalian Akt region, wherein the mammalian Akt region comprises the amino acid sequence of SEQ ID NO: 6, wherein the membrane-targeted Akt protein is expressed in the dendritic cell and the modified dendritic cell survives longer than dendritic cells that do not express the protein.

2. A method for preparing a modified dendritic cell, which comprises:
transferring a polynucleotide into a dendritic cell, wherein the polynucleotide encodes a membrane-targeted Akt protein comprising a dual acylation region and a mammalian Akt region, wherein the mammalian Akt region consists of the amino acid sequence of SEQ ID NO: 6, wherein the membrane-targeted Akt protein is expressed in the dendritic cell and the modified dendritic cell survives longer than dendritic cells that do not express the protein.

3. The method of claim 1, wherein the acylation region comprises the amino acid sequence of SEQ ID NO: 8.

4. The method of claim 1, wherein the acylation region consists of the amino acid sequence of SEQ ID NO: 8.

5. The method of claim 1, wherein the polynucleotide is from a virus.

6. The method of claim 5, wherein the dendritic cell is contacted with a virus that contains the polynucleotide.

7. The method of claim 1, wherein the polynucleotide comprises a constitutively active promoter operably linked to the polynucleotide that encodes the membrane-targeted Akt protein.

8. The method of claim 1, wherein the polynucleotide is transferred into the dendritic cell by a method selected from the group consisting of calcium phosphate precipitation, electroporation, direct microinjection, liposome transfer, gene bombardment, receptor-mediated transfection, receptor-mediated endocytosis, and viral transfer.

9. The method of claim 1, wherein the polynucleotide is transferred into the dendritic cell using an adenoviral vector.

10. The method of claim 1, wherein the dual acylation region is a Fyn myristoylation sequence.

11. The method of claim 2, wherein the acylation region comprises the amino acid sequence of SEQ ID NO: 8.

12. The method of claim 2, wherein the acylation region consists of the amino acid sequence of SEQ ID NO: 8.

13. The method of claim 12, wherein the modified dendritic cell is loaded with antigen and wherein the modified dendritic cell presents a greater amount of the antigen than dendritic cells that do not include the polynucleotide.

14. The method of claim 12, wherein the modified dendritic cell is more immunogenic than dendritic cells that do not include the polynucleotide.

15. The method of claim 12, which comprises contacting the modified dendritic cell with an antigen.

16. The method of claim 15, wherein the antigen is prostate specific membrane antigen.

17. The method of claim 16, wherein the antigen has a sequence of SEQ ID NO: 10, or an immunogenic fragment thereof.

18. The method of claim 12, wherein the dendritic cell is a human cell.

19. The method of claim 1, wherein the modified dendritic cell is loaded with antigen and wherein the modified dendritic cell presents a greater amount of the antigen than dendritic cells that do not include the polynucleotide.

20. The method of claim 1, wherein the modified dendritic cell is more immunogenic than dendritic cells that do not include the polynucleotide.

21. The method of claim 1, which comprises contacting the modified dendritic cell with an antigen.

22. The method of claim 19, wherein the antigen is prostate specific membrane antigen.

23. The method of claim 20, wherein the antigen comprises a sequence of SEQ ID NO: 10, or an immunogenic fragment thereof.

24. The method of claim 1, wherein the dendritic cell is a human cell.

* * * * *

SEQUENCE LISTING

```
<160> NUMBER OF SEQ ID NOS: 48

<210> SEQ ID NO 1
<211> LENGTH: 2626
<212> TYPE: DNA
<213> ORGANISM: Mus musculus

<400> SEQUENCE: 1
ccgggaccag cggacggacc gagcagcgtc ctgcggccgg caccgcggcg gcccagatcc      60
ggccagcagc gcgcgcccgg acgccgctgc cttcagccgg ccccgcccag cgcccgcccg     120
cgggatgcgg agcggcgggc gcccgaggcc gcggcccggc taggcccagt cgcccgcacg     180
cggcggcccg acgctgcggc caggccggct gggctcagcc taccgagaag agactctgat     240
```

```
catcatccct gggttacccc tgtctctggg ggccacggat accatgaacg acgtagccat    300
tgtgaaggag ggctggctgc acaaacgagg ggaatatatt aaaacctggc ggccacgcta    360
cttcctcctc aagaacgatg gcacctttat tggctacaag gaacggcctc aggatgtgga    420
tcagcgagag tccccactca acaacttctc agtggcacaa tgccagctga tgaagacaga    480
gcggccaagg cccaacacct ttatcatccg ctgcctgcag tggaccacag tcattgagcg    540
caccttccat gtggaaacgc ctgaggagcg ggaagaatgg gccaccgcca ttcagactgt    600
ggccgatgga ctcaagaggc aggaagaaga gacgatggac ttccgatcag gctcacccag    660
tgacaactca ggggctgaag agatggaggt gtccctggcc aagcccaagc accgtgtgac    720
catgaacgag tttgagtacc tgaaactact gggcaagggc acctttggga aagtgattct    780
ggtgaaagag aaggccacag gccgctacta tgccatgaag atcctcaaga aggaggtcat    840
cgtcgccaag gatgaggttg cccacacgct tactgagaac cgtgtcctgc agaactctag    900
gcatcccttc cttacggccc tcaagtactc attccagacc cacgaccgcc tctgctttgt    960
catggagtat gccaacgggg gcgagctctt cttccacctg tctcgagagc gcgtgttctc   1020
cgaggaccgg gcccgcttct atggtgcgga gattgtgtct gccctggact acttgcactc   1080
cgagaagaac gtggtgtacc gggacctgaa gctggagaac ctcatgctgg acaaggacgg   1140
gcacatcaag ataacggact cgggctgtgt caaggagggg atcaaggatg gtgccactat   1200
gaagacattc tgcggaacgc cggagtacct ggcccctgag gtgctggagg acaacgacta   1260
cggccgtgca gtggactggt gggggctggg cgtggtcatg tatgagatga tgtgtggccg   1320
cctgcccttc tacaaccagg accacgagaa gctgttcgag ctgatcctca tggaggagat   1380
ccgcttcccg cgcacactcg gccctgaggc caagtccctg ctctccgggc tgctcaagaa   1440
ggaccctaca cagaggctcg gtgggggctc tgaggatgcc aaggagatca tgcagcaccg   1500
gttctttgcc aacatcgtgt ggcaggatgt gtatgagaag aagctgagcc cacctttcaa   1560
gccccaggtc acctctgaga ctgacaccag gtatttcgat gaggagttca cagctcagat   1620
gatcaccatc acgccgcctg atcaagatga cagcatggag tgtgtggaca gtgagcggag   1680
gccgcacttc ccccagttct cctactcagc cagtggcaca gcctgaggcc tggggcagcg   1740
gctggcagct ccacgctcct ctgcattgcc gagtccagaa gccccgcatg gatcatctga   1800
acctgatgtt ttgtttctcg gatgcgctgg ggaggaacct tgccagcctc caggaccagg   1860
ggaggatgtt tctactgtgg gcagcagcct acctcccagc caggtcagga ggaaaactat   1920
cctggggttt ttcttaattt atttcatcca gtttgagacc acacatgtgg cctcagtgcc   1980
cagaacaatt agattcatgt agaaaactat taaggactga cgcgaccatg tgcaatgtgg   2040
gctcatgggt ctgggtgggt cccgtcactg ccccattgg cctgtccacc ctggccgcca   2100
cctgtctcta gggtccaggg ccaaagtcca gcaagaaggc accagaagca cctccctgtg   2160
gtatgctaac tggccctctc cctctgggcg gggagaggtc acagctgctt cagccctagg   2220
gctggatggg atgccagggg ctcaagtgag gttgacagag gaacaagaat ccagtttgtt   2280
gctgtgtccc atgctgttca gagacattta ggggatttta atcttggtga caggagagcc   2340
cctgccctcc cgctcctgcg tggtggctct tagcgggtac cctgggagcg cctgcctcac   2400
gtgagccctc tcctagcact tgtccttta tgatgctttcc ctctcccgct gtccgtcacc   2460
ctggcctgtc ccctcccgcc agacgctggc cattgctgca ccatgtcgtt ttttacaaca   2520
ttcagcttca gcattttac tattataata agaaactgtc cctccaaatt caataaaaat   2580
tgcttttcaa gcttgaaaaa aaaaaaaaaa aaaaaaaaaa aaaaa           2626
```

<210> SEQ ID NO 2
<211> LENGTH: 2794
<212> TYPE: DNA
<213> ORGANISM: Homo sapiens

<400> SEQUENCE: 2

```
cggcaggacc gagcgcggca ggcggctggc ccagcgcagc cagcgcggcc cgaaggacgg      60
gagcaggcgg ccgagcaccg agcgctgggc accgggcacc gagcggcggc ggcacgcgag     120 gccccggcccc gagcagcgcc cccgcccgcc gcggcctcca gcccggcccc gcccagcgcc    180
ggcccgcggg gatgcggagc ggcgggcgcc ggaggccgcg gccccggctag gcccgcgctc     240 gcgcccggac gcggcggccc gaggctgtgg ccaggccagc tgggctcggg gagcgccagc      300
ctgagaggag cgcgtgagcg tcgcgggagc ctcgggcacc atgagcgacg tggctattgt      360
gaaggagggt tggctgcaca acgagggga gtacatcaag acctggcggc acgctactt      420 cctcctcaag aatgatggca ccttcattgg ctacaaggag cggccgcagg atgtggacca     480
acgtgaggct cccctcaaca acttctctgt ggcgcagtgc cagctgatga agacggagcg     540
gccccggccc aacaccttca tcatccgctg cctgcagtgg accactgtca tcgaacgcac     600
cttccatgtg gagactcctg aggagcggga ggagtggaca accgccatcc agactgtggc     660
tgacggcctc aagaagcagg aggaggagga gatggacttc cggtcgggct caccccagtga    720 caactcaggg gctgaagaga tggaggtgtc cctggccaag cccaagcacc gcgtgaccat     780
gaacgagttt gagtacctga gctgctggg caagggcact ttcggcaagg tgatcctggt     840
gaaggagaag gccacaggcc gctactacgc catgaagatc ctcaagaagg aagtcatcgt    900
ggccaaggac gaggtggccc acacactcac cgagaaccgc gtcctgcaga actccaggca     960 cccccttcctc acagccctga gtactctt ccagacccac gaccgcctct gctttgtcat    1020
ggagtacgcc aacggggggcg agctgttctt ccacctgtcc cgggagcgtg tgttctccga   1080
ggaccgggcc cgcttctatg gcgctgagat tgtgtcagcc ctggactacc tgcactcgga    1140
gaagaacgtg gtgtaccggg acctcaagct ggagaacctc atgctggaca aggacgggca    1200
cattaagatc acagacttcg gcctgtgcaa ggaggggatc aaggacggtg ccaccatgaa    1260 gacctttgc ggcacacctg agtacctggc ccccgaggtg ctggaggaca atgactacgg    1320
ccgtgcagtg gactggtggg ggctgggcgt ggtcatgtac gagatgatgt gcggtcgcct    1380
gcccttctac aaccaggacc atgagaagct ttttgagctc atcctcatgg aggagatccg    1440
cttcccgcgc acgcttggtc ccgaggccaa gtccttgctt tcagggctgc tcaagaagga    1500
ccccaagcag aggcttggcg ggggctccga ggacgccaag gagatcatgc agcatcgctt    1560 cttttgccggt atcgtgtggc agcacgtgta cgagaagaag ctcagcccac ccttcaagcc    1620
ccaggtcacg tcggagactg acaccaggta ttttgatgag gagttcacgg cccagatgat    1680
caccatcaca ccacctgacc aagatgacag catggagtgt gtggacagcg agcgcaggcc    1740
ccacttcccc cagttctcct actcggccag cggcacggcc tgaggcggcg gtggactgcg    1800
ctggacgata gcttggaggg atggagaggc ggcctcgtgc catgatctgt atttaatggt    1860
ttttatttct cgggtgcatt tgagagaagc cacgctgtcc tctcgagccc agatggaaag    1920
acgtttttgt gctgtgggca gcaccctccc ccgcagcggg gtagggaaga aaactatcct    1980 gcgggttttta atttatttca tccagtttgt tctccgggtg tggcctcagc cctcagaaca    2040
atccgattca cgtagggaaa tgttaaggac ttctgcagct atgcgcaatg tggcattggg    2100
gggccgggca ggtcctgccc atgtgtcccc tcactctgtc agccagccgc cctgggctgt    2160
```

| | |
|---|---|
| ctgtcaccag ctatctgtca tctctctggg gccctgggcc tcagttcaac ctggtggcac | 2220 |
| cagatgcaac ctcactatgg tatgctggcc agcaccctct cctggggtg gcaggcacac | 2280 |
| agcagccccc cagcactaag gccgtgtctc tgaggacgtc atcggaggct gggcccctgg | 2340 |
| gatgggacca gggatggggg atgggccagg gtttacccag tgggacagag gagcaaggtt | 2400 |
| taaatttgtt attgtgtatt atgttgttca aatgcatttt gggggttttt aatctttgtg | 2460 |
| acaggaaagc cctccccctt cccttctgt gtcacagttc ttggtgactg tcccaccggg | 2520 |
| agcctcccc tcagatgatc tctccacggt agcacttgac cttttcgacg cttaaccttt | 2580 |
| ccgctgtcgc cccaggccct ccctgactcc ctgtgggggt ggccatccct gggcccctcc | 2640 |
| acgcctcctg gccagacgct gccgctgccg ctgcaccacg gcgttttttt acaacattca | 2700 |
| actttagtat ttttactatt ataatataat atggaacctt ccctccaaat tcttcaataa | 2760 |
| aagttgcttt tcaaaaaaaa aaaaaaaaaa aaaa | 2794 |

<210> SEQ ID NO 3
<211> LENGTH: 1715
<212> TYPE: DNA
<213> ORGANISM: Homo sapiens

<400> SEQUENCE: 3

| | |
|---|---|
| gaattccagc ggcggcgccg ttgccgctgc cgggaaacac aaggaaaggg aaccagcgca | 60 |
| gcgtggcgat gggcggggt agagccccgc cggagaggct gggcggctgc cggtgacaga | 120 |
| ctgtgccctg tccacggtgc ctcctgcatg tcctgctgcc ctgagctgtc ccgagctagg | 180 |
| tgacagcgta ccacgctgcc accatgaatg aggtgtctgt catcaaagaa ggctggctcc | 240 |
| acaagcgtgg tgaatacatc aagacctgga ggccacggta cttcctgctg aagagcgacg | 300 |
| gctccttcat tgggtacaag gagaggcccg aggccctga tcagactcta ccccccttaa | 360 |
| acaacttctc cgtagcagaa tgccagctga tgaagaccga gaggccgcga cccaacacct | 420 |
| ttgtcatacg ctgcctgcag tggaccacag tcatcgagag gaccttccac gtggattctc | 480 |
| cagacgagag ggaggagtgg atgcgggcca tccagatggt cgccaacagc ctcaagcagc | 540 |
| gggccccagg cgaggacccc atggactaca agtgtggctc ccccagtgac tcctccacga | 600 |
| ctgaggagat ggaagtggcg gtcagcaagg cacgggctaa agtgaccatg aatgacttcg | 660 |
| actatctcaa actccttggc aagggaacct ttggcaaagt catcctggtg cgggagaagg | 720 |
| ccactggccg ctactacgcc atgaagatcc tgcgaaagga agtcatcatt gccaaggatg | 780 |
| aagtcgctca cacagtcacc gagagccggg tcctccagaa caccaggcac ccgttcctca | 840 |
| ctgcgctgaa gtatgccttc cagacccacg accgcctgtg ctttgtgatg gagtatgcca | 900 |
| acggggtga gctgttcttc cacctgtccc gggagcgtgt cttcacagag gagcgggccc | 960 |
| ggttttatgg tgcagagatt gtctcggctc ttgagtactt gcactcgcgg gacgtggtat | 1020 |
| accgcgacat caagctggaa aacctcatgc tggacaaaga tggccacatc aagatcactg | 1080 |
| actttggcct ctgcaaagag ggcatcagtg acggggccac catgaaaacc ttctgtggga | 1140 |
| ccccggagta cctggcgcct gaggtgctgg aggacaatga ctatggccgg gccgtggact | 1200 |
| ggtgggggct gggtgtggtc atgtacgaga tgatgtgcgg ccgcctgccc ttctacaacc | 1260 |
| aggaccacga gcgcctcttc gagctcatcc tcatggaaga gatccgcttc ccgcgcacgc | 1320 |
| tcagccccga ggccaagtcc ctgcttgctg ggctgcttaa gaaggacccc aagcagaggc | 1380 |
| ttggtggggg gccagcgat gccaaggagg tcatggagca caggttcttc ctcagcatca | 1440 |
| actggcagga cgtggtccag aagaagctcc tgccacccctt caaacctcag gtcacgtccg | 1500 |

-continued

| | |
|---|---|
| aggtcgacac aaggtacttc gatgatgaat ttaccgccca gtccatcaca atcacacccc | 1560 |
| ctgaccgcta tgacagcctg ggcttactgg agctggacca gcggacccac ttcccccagt | 1620 |
| tctcctactc ggccagcatc cgcgagtgag cagtctgccc acgcagagga cgcacgctcg | 1680 |
| ctgccatcac cgctgggtgg ttttttaccc ctgcc | 1715 |

<210> SEQ ID NO 4
<211> LENGTH: 3588
<212> TYPE: DNA
<213> ORGANISM: Homo sapiens

<400> SEQUENCE: 4

| | |
|---|---|
| gcagcagcag agaatccaaa ccctaaagct gatatcacaa agtaccattt ctccaagttg | 60 |
| ggggctcaga ggggagtcat catgagcgat gttaccattg tgaaagaagg ttgggttcag | 120 |
| aagagggag aatatataaa aaactggagg ccaagatact tcctttttgaa gacagatggc | 180 |
| tcattcatag gatataaaga gaaacctcaa gatgtggatt taccttatcc cctcaacaac | 240 |
| ttttcagtgg caaaatgcca gttaatgaaa acagaacgac caaagccaaa cacatttata | 300 |
| atcagatgtc tccagtggac tactgttata gagagaacat tcatgtaga tactccagag | 360 |
| gaaagggaag aatggacaga agctatccag gctgtagcag acagactgca gaggcaagaa | 420 |
| gaggagagaa tgaattgtag tccaacttca caaattgata atataggaga ggaagagatg | 480 |
| gatgcctcta caacccatca taaaagaaag acaatgaatg attttgacta tttgaaacta | 540 |
| ctaggtaaag gcacttttgg gaaagttatt ttggttcgag agaaggcaag tggaaaatac | 600 |
| tatgctatga agattctgaa gaaagaagtc attattgcaa aggatgaagt ggcacacact | 660 |
| ctaactgaaa gcagagtatt aaagaacact agacatccct ttttaacatc cttgaaatat | 720 |
| tccttccaga caaaagaccg tttgtgtttt gtgatggaat atgttaatgg gggcgagctg | 780 |
| ttttttccatt tgtcgagaga gcgggtgttc tctgaggacc gcacacgttt ctatggtgca | 840 |
| gaaattgtct ctgccttgga ctatctacat tccggaaaga ttgtgtaccg tgatctcaag | 900 |
| ttggagaatc taatgctgga caaagatggc cacataaaaa ttacagattt tggacttttgc | 960 |
| aaagaaggga tcacagatgc agccaccatg aagacattct gtggcactcc agaatatctg | 1020 |
| gcaccagagg tgttagaaga taatgactat ggccgagcag tagactggtg gggcctaggg | 1080 |
| gttgtcatgt atgaaatgat gtgtgggagg ttacctttct acaaccagga ccatgagaaa | 1140 |
| cttttttgaat taatattaat ggaagacatt aaatttcctc gaacactctc ttcagatgca | 1200 |
| aaatcattgc tttcagggct cttgataaag gatccaaata aacgccttgg tggaggacca | 1260 |
| gatgatgcaa agaaattat gagacacagt ttcttctctg gagtaaactg gcaagatgta | 1320 |
| tatgataaaa agcttgtacc tccttttaaa cctcaagtaa catctgagac agatactaga | 1380 |
| tattttgatg aagaatttac agctcagact attacaataa caccacctga aaaatatgat | 1440 |
| gaggatggta tggactgcat ggacaatgag aggcggccgc atttccctca atttttcctac | 1500 |
| tctgcaagtg gacgagaata agtctctttc attctgctac ttcactgtca tcttcaattt | 1560 |
| attactgaaa atgattcctg gacatcacca gtcctagctc ttacacatag caggggcacc | 1620 |
| ttccgacatc ccagaccagc caagggtcct caccccctcgc cacctttcac cctcatgaaa | 1680 |
| acacacatac acgcaaatac actccagttt ttgttttttgc atgaaattgt atctcagtct | 1740 |
| aaggtctcat gctgttgctg ctactgtctt actattatag caactttaag aagtaatttt | 1800 |
| ccaacctttg gaagtcatga gcccaccatt gttcatttgt gcaccaatta tcatcttttg | 1860 |
| atctttttagt ttttcccctca gtgaaggcta aatgagatac actgattcta ggtacatttt | 1920 |

| | |
|---|---:|
| ttaactttct agaagagaaa aactaactag actaagaaga tttagtttat aaattcagaa | 1980 |
| caagcaattg tggaagggtg gtggcgtgca tatgtaaagc acatcagatc cgtgcgtgaa | 2040 |
| gtaggcatat atcactaagc tgtggctgga attgattagg aagcatttgg tagaaggact | 2100 |
| gaacaactgt tgggatatat atatatatat ataattttt ttttttaaat tcctggtgga | 2160 |
| tactgtagaa gaagcccata tcacatgtgg atgtcgagac ttcacgggca atcatgagca | 2220 |
| agtgaacact gttctaccaa gaactgaagg catatgcaca gtcaaggtca cttaaagggt | 2280 |
| cttatgaaac aatttgagcc agagagcatc tttcccctgt gcttggaaac cttttttcct | 2340 |
| tcttgacatt tatcacctct gatggctgaa gaatgtagac aggtataatg atactgcttt | 2400 |
| tcaccaaaat ttctacacca aggtaaacag gtgtttgcct tatttaattt tttactttca | 2460 |
| gttctacgtg aattagcttt ttctcagatg ttgaaacttt gaatgtcctt ttatgatttt | 2520 |
| gtttatattg cagtagtatt tatttttttag tgatgagaat tgtatgtcat gttagcaaac | 2580 |
| gcagctccaa cttatataaa atagacttac tgcagttact tttgacccat gtgcaaggat | 2640 |
| tgtacacgct gatgagaatc atgcactttt tctcctctgt taaaaaaaat gataaggctc | 2700 |
| tgaaatggaa tatattggtt agaatttggc tttgggagaa gagatgctgc catttaaccc | 2760 |
| cttggtactg aaaatgagaa atcccccaac tatgcatgcc aaggggttaa tgaaacaaat | 2820 |
| agctgttgac gtttgctcat ttaagaattt gaaacgttat gatgacctgg caacaaaaag | 2880 |
| taatgaagaa aattgagacc tgagtgaaga taagaaatga tctttacgtg gcaaaatgaa | 2940 |
| cacatcttga gtatttagga aatgggcagt gaaggctaag aacctggtgt gtttcttggg | 3000 |
| atcatggtac atttatcact gaattaagcc atcagggaaa aaacaacaaa aaaagagaac | 3060 |
| acctccagct tttctttttc tgtatatact catgtccccc agattccaac atttctcact | 3120 |
| gaaaggggggc atgtatgcaa acctcatctt tctccttcat taatgatgat cttcagatta | 3180 |
| aacccttttgg tgctaggagc tgacaatttc caaagcagcc tgtgaagtcc taggggctgg | 3240 |
| gggccactct tgcggcaagc agaaggccat cctactccgc ggagtgatca tggaaatgta | 3300 |
| ttttagttaa actctgacag ctcccaaacg gaagactaca gcatgacgta gtattatgat | 3360 |
| tgcattgtat gaaagagcaa gtgactttct aagtaggatg aatcatattc atatgcagat | 3420 |
| gtcttagcct cttgacgctg gaagtgtgga tttatagcta tgaaaccact gctggcagtg | 3480 |
| ggtgggccac tgggactgac gggggttaaa gggcatttta ctaaggcagc taagacatat | 3540 |
| tcagacatca acgttatcct tctttttcat atttctacct gagtgaag | 3588 |

<210> SEQ ID NO 5
<211> LENGTH: 1143
<212> TYPE: DNA
<213> ORGANISM: Homo sapiens

<400> SEQUENCE: 5

| | |
|---|---:|
| accgccatcc agactgtggc tgacggcctc aagaagcagg aggaggagga gatggacttc | 60 |
| cggtcgggct cacccagtga caactcaggg gctgaagaga tggaggtgtc cctggccaag | 120 |
| cccaagcacc gcgtgaccat gaacgagttt gagtacctga gctgctggg caagggcact | 180 |
| ttcggcaagg tgatcctggt gaaggagaag gccacaggcc gctactacgc catgaagatc | 240 |
| ctcaagaagg aagtcatcgt ggccaaggac gaggtggccc acacactcac cgagaaccgc | 300 |
| gtcctgcaga actccaggca ccccttcctc acagccctga agtactcttt ccagacccac | 360 |
| gaccgcctct gctttgtcat ggagtacgcc aacgggggcg agctgttctt ccacctgtcc | 420 |
| cgggagcgtg tgttctccga ggaccgggcc cgcttctatg gcgctgagat tgtgtcagcc | 480 |

-continued

```
ctggactacc tgcactcgga gaagaacgtg gtgtaccggg acctcaagct ggagaacctc      540
atgctggaca aggacgggca cattaagatc acagacttcg ggctgtgcaa ggaggggatc      600
aaggacggtg ccaccatgaa gaccttttgc ggcacacctg agtacctggc ccccgaggtg      660
ctggaggaca tgactacggg ccgtgcagtg gactggtggg gctgggcgt ggtcatgtac       720 gagatgatgt gcggtcgcct gcccttctac aaccaggacc atgagaagct ttttgagctc      780
atcctcatgg aggagatccg cttcccgcgc acgcttggtc ccgaggccaa gtccttgctt      840
tcagggctgc tcaagaagga ccccaagcag aggcttggcg ggggctccga ggacgccaag      900
gagatcatgc agcatcgctt ctttgccggt atcgtgtggc agcacgtgta cgagaagaag      960
ctcagcccac ccttcaagcc ccaggtcacg tcggagactg acaccaggta ttttgatgag     1020
gagttcacgg cccagatgat caccatcaca ccacctgacc aagatgacag catggagtgt     1080
gtggacagcg agcgcaggcc ccacttcccc cagttctcct actcggccag cgcgacggcc     1140
tga                                                                   1143
```

<210> SEQ ID NO 6
<211> LENGTH: 380
<212> TYPE: PRT
<213> ORGANISM: Homo sapiens

<400> SEQUENCE: 6

```
Thr Ala Ile Gln Thr Val Ala Asp Gly Leu Lys Lys Gln Glu Glu Glu
 1               5                  10                  15

Glu Met Asp Phe Arg Ser Gly Ser Pro Ser Asp Asn Ser Gly Ala Glu
            20                  25                  30

Glu Met Glu Val Ser Leu Ala Lys Pro Lys His Arg Val Thr Met Asn
        35                  40                  45

Glu Phe Glu Tyr Leu Lys Leu Leu Gly Lys Gly Thr Phe Gly Lys Val
    50                  55                  60

Ile Leu Val Lys Glu Lys Ala Thr Gly Arg Tyr Tyr Ala Met Lys Ile
65                  70                  75                  80

Leu Lys Lys Glu Val Ile Val Ala Lys Asp Glu Val Ala His Thr Leu
                85                  90                  95

Thr Glu Asn Arg Val Leu Gln Asn Ser Arg His Pro Phe Leu Thr Ala
            100                 105                 110

Leu Lys Tyr Ser Phe Gln Thr His Asp Arg Leu Cys Phe Val Met Glu
        115                 120                 125

Tyr Ala Asn Gly Gly Glu Leu Phe Phe His Leu Ser Arg Glu Arg Val
    130                 135                 140

Phe Ser Glu Asp Arg Ala Arg Phe Tyr Gly Ala Glu Ile Val Ser Ala
145                 150                 155                 160

Leu Asp Tyr Leu His Ser Glu Lys Asn Val Val Tyr Arg Asp Leu Lys
                165                 170                 175

Leu Glu Asn Leu Met Leu Asp Lys Asp Gly His Ile Lys Ile Thr Asp
            180                 185                 190

Phe Gly Leu Cys Lys Glu Gly Ile Lys Asp Gly Ala Thr Met Lys Thr
        195                 200                 205

Phe Cys Gly Thr Pro Glu Tyr Leu Ala Pro Glu Val Leu Glu Asp Asn
    210                 215                 220

Asp Tyr Gly Arg Ala Val Asp Trp Trp Gly Leu Gly Val Val Met Tyr
225                 230                 235                 240

Glu Met Met Cys Gly Arg Leu Pro Phe Tyr Asn Gln Asp His Glu Lys
                245                 250                 255
```

```
Leu Phe Glu Leu Ile Leu Met Glu Glu Ile Arg Phe Pro Arg Thr Leu
                260                 265                 270
Gly Pro Glu Ala Lys Ser Leu Leu Ser Gly Leu Leu Lys Lys Asp Pro
            275                 280                 285
Lys Gln Arg Leu Gly Gly Ser Glu Asp Ala Lys Glu Ile Met Gln
        290                 295                 300
His Arg Phe Phe Ala Gly Ile Val Trp Gln His Val Tyr Glu Lys Lys
305                 310                 315                 320
Leu Ser Pro Pro Phe Lys Pro Gln Val Thr Ser Glu Thr Asp Thr Arg
                325                 330                 335
Tyr Phe Asp Glu Glu Phe Thr Ala Gln Met Ile Thr Ile Thr Pro Pro
                340                 345                 350
Asp Gln Asp Asp Ser Met Glu Cys Val Asp Ser Glu Arg Arg Pro His
                355                 360                 365
Phe Pro Gln Phe Ser Tyr Ser Ala Ser Ala Thr Ala
                370                 375                 380

<210> SEQ ID NO 7
<211> LENGTH: 57
<212> TYPE: DNA
<213> ORGANISM: Homo sapiens

<400> SEQUENCE: 7
atgggctgtg tgcaatgtaa ggataaagaa gcaacaaaac tgacggagga gctcgag       57

<210> SEQ ID NO 8
<211> LENGTH: 19
<212> TYPE: PRT
<213> ORGANISM: Homo sapiens

<400> SEQUENCE: 8

Met Gly Cys Val Gln Cys Lys Asp Lys Glu Ala Thr Lys Leu Thr Glu
  1               5                  10                  15

Glu Leu Glu

<210> SEQ ID NO 9
<211> LENGTH: 2096
<212> TYPE: DNA
<213> ORGANISM: Homo sapiens

<400> SEQUENCE: 9
gcggatccgc atcatcatca tcatcacagc tccggaatcg agggacgtgg taaatcctcc      60
aatgaagcta ctaacattac tccaaagcat aatatgaaag cattttttgga tgaattgaaa    120 gctgagaaca tcaagaagtt cttatataat tttacacaga taccacattt agcaggaaca    180
gaacaaaact ttcagcttgc aaagcaaatt caatcccagt ggaaagaatt tggcctggat    240
tctgttgagc tagcacatta tgatgtcctg ttgtcctacc caaataagac tcatcccaac    300
tacatctcaa taattaatga agatggaaat gagattttca acacatcatt atttgaacca    360
cctcctccag gatatgaaaa tgtttcggat attgtaccac cttttcagtgc tttctctcct    420 caaggaatgc cagagggcga tctagtgtat gttaactatg cacgaactga agacttcttt    480
aaattggaac gggacatgaa aatcaattgc tctgggaaaa ttgtaattgc cagatatggg    540
aaagttttca gaggaaataa ggttaaaaat gcccagctgg cagggggccaa aggagtcatt    600 ctctactccg accctgctga ctactttgct cctgggggtga agtcctatcc agatggttgg    660
aatcttcctg gaggtggtgt ccagcgtgga aatatcctaa atctgaatgg tgcaggagac    720
cctctcacac caggttaccc agcaaatgaa tatgcttata ggcgtggaat tgcagaggct    780
```

```
gttggtcttc caagtattcc tgttcatcca attggatact atgatgcaca gaagctccta    840
gaaaaaatgg gtggctcagc accaccagat agcagctgga gaggaagtct caaagtgccc    900
tacaatgttg gacctggctt tactggaaac ttttctacac aaaaagtcaa gatgcacatc    960
cactctacca atgaagtgac aagaatttac aatgtgatag gtactctcag aggagcagtg   1020
gaaccagaca gatatgtcat tctgggaggt caccgggact catgggtgtt tggtggtatt   1080
gaccctcaga gtggagcagc tgttgttcat gaaattgtga ggagctttgg aacactgaaa   1140
aaggaagggt ggagacctag aagaacaatt ttgtttgcaa gctgggatgc agaagaattt   1200
ggtcttcttg gttctactga gtgggcagag agaattcaa gactccttca agagcgtggc    1260
gtggcttata ttaatgctga ctcatctata gaaggaaact acactctgag agttgattgt   1320
acaccgctga tgtacagctt ggtacacaac ctaacaaaag agctgaaaag ccctgatgaa   1380
ggctttgaag gcaaatctct ttatgaaagt tggactaaaa aaagtccttc cccagagttc   1440
agtggcatgc ccaggataag caaattggga tctggaaatg atttttgaggt gttcttccaa   1500 cgacttggaa ttgcttcagg cagagcacgg tatactaaaa attgggaaac aaacaaattc   1560
agcggctatc cactgtatca cagtgtctat gaaacatatg agttggtgga aaagttttat   1620
gatccaatgt ttaaatatca ccctcactgtg gcccaggttc gaggagggat ggtgtttgag   1680
ctagccaatt ccatagtgct cccttttgat tgtcgagatt atgctgtagt tttaagaaag   1740
tatgctgaca aaatctacag tatttctatg aaacatccac aggaaatgaa gacatacagt   1800
gtatcatttg attcactttt ttctgcagta aagaattta cagaaattgc ttccaagttc     1860
agtgagagac tccaggactt tgacaaaagc aagcatgtca tctatgctcc aagcagccac   1920
aacaagtatg caggggagtc attcccagga atttatgatg ctctgtttga tattgaaagc   1980
aaagtggacc cttccaaggc tggggagaa gtgaagagac agatttatgt tgcagccttc    2040
acagtgcagg cagctgcaga gactttgagt gaagtagcct aagcggccgc atagca       2096
```

<210> SEQ ID NO 10
<211> LENGTH: 719
<212> TYPE: PRT
<213> ORGANISM: Homo sapiens

<400> SEQUENCE: 10

```
Met Trp Asn Leu Leu His Glu Thr Asp Ser Ala Val Ala Thr Ala Arg
  1               5                  10                  15

Arg Pro Arg Trp Leu Cys Ala Gly Ala Leu Val Leu Ala Gly Gly Phe
             20                  25                  30

Phe Leu Leu Gly Phe Leu Phe Gly Trp Phe Ile Lys Ser Ser Asn Glu
         35                  40                  45

Ala Thr Asn Ile Thr Pro Lys His Asn Met Lys Ala Phe Leu Asp Glu
     50                  55                  60

Leu Lys Ala Glu Asn Ile Lys Lys Phe Leu Tyr Asn Phe Thr Gln Ile
 65                  70                  75                  80

Pro His Leu Ala Gly Thr Glu Gln Asn Phe Gln Leu Ala Lys Gln Ile
                 85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140
```

-continued

```
Glu Pro Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
            165                 170                 175

Val Asn Tyr Ala Arg Thr Glu Asp Phe Phe Lys Leu Glu Arg Asp Met
        180                 185                 190

Lys Ile Asn Cys Ser Gly Lys Ile Val Ile Ala Arg Tyr Gly Lys Val
    195                 200                 205

Phe Arg Gly Asn Lys Val Lys Asn Ala Gln Leu Ala Gly Ala Lys Gly
210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Val Gln Arg Gly
            245                 250                 255

Asn Ile Leu Asn Leu Asn Gly Ala Gly Asp Pro Leu Thr Pro Gly Tyr
        260                 265                 270

Pro Ala Asn Glu Tyr Ala Tyr Arg Arg Gly Ile Ala Glu Ala Val Gly
    275                 280                 285

Leu Pro Ser Ile Pro Val His Pro Ile Gly Tyr Tyr Asp Ala Gln Lys
290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
            325                 330                 335

Phe Ser Thr Gln Lys Val Lys Met His Ile His Ser Thr Asn Glu Val
        340                 345                 350

Thr Arg Ile Tyr Asn Val Ile Gly Thr Leu Arg Gly Ala Val Glu Pro
    355                 360                 365

Asp Arg Tyr Val Ile Leu Gly Gly His Arg Asp Ser Trp Val Phe Gly
370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
            405                 410                 415

Leu Phe Ala Ser Trp Asp Ala Glu Glu Phe Gly Leu Leu Gly Ser Thr
        420                 425                 430

Glu Trp Ala Glu Glu Asn Ser Arg Leu Leu Gln Glu Arg Gly Val Ala
    435                 440                 445

Tyr Ile Asn Ala Asp Ser Ser Ile Glu Gly Asn Tyr Thr Leu Arg Val
450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
            485                 490                 495

Trp Thr Lys Lys Ser Pro Ser Pro Glu Phe Ser Gly Met Pro Arg Ile
        500                 505                 510

Ser Lys Leu Gly Ser Gly Asn Asp Phe Glu Val Phe Phe Gln Arg Leu
    515                 520                 525

Gly Ile Ala Ser Gly Arg Ala Arg Tyr Thr Lys Asn Trp Glu Thr Asn
530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
            565                 570                 575
```

```
Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
            595                 600                 605

Asp Lys Ile Tyr Ser Ile Ser Met Lys His Pro Gln Glu Met Lys Thr
            610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
            645                 650                 655

Lys His Val Ile Tyr Ala Pro Ser Ser His Asn Lys Tyr Ala Gly Glu
            660                 665                 670

Ser Phe Pro Gly Ile Tyr Asp Ala Leu Phe Asp Ile Glu Ser Lys Val
            675                 680                 685

Asp Pro Ser Lys Ala Trp Gly Glu Val Lys Arg Gln Ile Tyr Val Ala
            690                 695                 700

Ala Phe Thr Val Gln Ala Ala Ala Glu Thr Leu Ser Glu Val Ala
705                 710                 715

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide motif
<220> FEATURE:
<221> NAME/KEY: MOD_RES
<222> LOCATION: (4)
<223> OTHER INFORMATION: Variable amino acid

<400> SEQUENCE: 11

Met Gly Cys Xaa Cys
  1               5

<210> SEQ ID NO 12
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
gccggcggag                                                          10

<210> SEQ ID NO 13
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
cucauaaggu                                                          10

<210> SEQ ID NO 14
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 14
gacuuugauu                                                          10

<210> SEQ ID NO 15
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
cggaacccaa                                                          10

<210> SEQ ID NO 16
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
auacuccccc                                                          10

<210> SEQ ID NO 17
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
ccuugcgacc                                                          10

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asp Tyr Lys Asp Asp Asp Asp Lys Gly
  1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Thr Tyr Arg Tyr Ile
  1               5

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 20

Gly Lys Pro Ile Pro Asn Pro Leu Leu Gly Leu Asp Ser Thr
 1               5                  10

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Glu Gln Lys Leu Ile Ser Glu Glu Asp Leu
 1               5                  10

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Pro Glu Leu Ala Pro Glu Asp Pro Glu Asp
 1               5                  10

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Tyr Pro Tyr Asp Val Pro Asp Tyr Ala
 1               5

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Tyr Thr Asp Ile Glu Met Asn Arg Leu Gly Lys
 1               5                  10

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 25

His His His His His His
 1               5

<210> SEQ ID NO 26
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: This region may encompass 1 to 3 variable amino
      acids

<400> SEQUENCE: 26

Cys Cys Xaa Xaa Xaa Cys Cys
 1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Cys Cys Pro Gly Cys Cys
 1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Leu Val Pro Arg Gly Ser
 1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asp Asp Asp Asp Lys
 1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Glu Asn Leu Tyr Phe Gln Gly
 1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 31

Leu Glu Val Leu Phe Gln Gly Pro
 1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ser Ile Ile Asn Phe Glu Lys Leu
 1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Phe Leu Trp Gly Pro Arg Ala Leu Val
 1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Val Tyr Asp Phe Phe Val Trp Leu
 1               5

<210> SEQ ID NO 35
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ggccaccatg ggtagcaaca agagcaagcc caaggatgcc agccagcggc gccgcagcc      59

<210> SEQ ID NO 36
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
tcgaggctgc ggcgccgctg gctggcatcc ttgggcttgc tcttgttgct acccatggtg      60
gccgc                                                                  65

<210> SEQ ID NO 37
<211> LENGTH: 59
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 37
ggccaccatg gctgtgtct gcagctcaaa ccctgaagat gactggatgg agaacattc      59

<210> SEQ ID NO 38
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
tcgagaatgt tctccatcca gtcatcttca gggtttgagc tgcagacaca gcccatggtg   60
gccgc                                                                65

<210> SEQ ID NO 39
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ggccaccatg gctgtgtgc aatgtaagga taaagaagca acaaaactga cggaggagc      59

<210> SEQ ID NO 40
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tcgagctcct ccgtcagttt tgttgcttct ttatccttac attgcacaca gcccatggtg   60
gccgc                                                                65

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Ile Leu Gly Phe Val Phe Thr
 1               5

<210> SEQ ID NO 42
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
agagcgacaa cgacgtagcc attgtgaagg ag                                  32

<210> SEQ ID NO 43
```

```
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
agagtcgaca ccgccattca gactgtggcc                                          30

<210> SEQ ID NO 44
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
agagtcgacg gctgtgccac tggctgagta g                                        31

<210> SEQ ID NO 45
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
cgatctcgag gagatgtggc atgaaggcct gg                                       32

<210> SEQ ID NO 46
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
cgatgtcgac ctttgagatt cgtcggaaca catg                                     34

<210> SEQ ID NO 47
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
atacaattgc cgcggttcga attctgtttt atactcccct cccgtaac                      48

<210> SEQ ID NO 48
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tatcaattgg tttaaacagc aaacagatag ataatgagtc tcac                          44
```